US012697327B2

(12) United States Patent
Sanzone et al.

(10) Patent No.: US 12,697,327 B2
(45) Date of Patent: Aug. 4, 2026

(54) PHARMACOLOGICAL CORRECTORS OF RHODOPSIN AND USES THEREOF

(71) Applicant: Octant, Inc., Emeryville, CA (US)

(72) Inventors: Jillian R. Sanzone, San Francisco, CA (US); Tao Zheng, Richmond, CA (US); Stacie S. Kim, Emeryville, CA (US); Christopher Sinz, Walnut Creek, CA (US); Jean-François Fournier, Mont-Royal (CA); Alexandre Larivee, Montreal (CA); David Tong, Dollard-des-Ormeaux (CA); Brandon Groves, Candiac (CA); Ludovic Deny, Montreal (CA); Kenneth Matthew Whitmore, Boucherville (CA)

(73) Assignee: Octant, Inc., Emeryville, CA (US)

( * ) Notice: Subject to any disclaimer, the term of this patent is extended or adjusted under 35 U.S.C. 154(b) by 0 days.

(21) Appl. No.: 19/370,579

(22) Filed: Oct. 27, 2025

(65) Prior Publication Data

US 2026/0115174 A1 Apr. 30, 2026

Related U.S. Application Data

(60) Provisional application No. 63/712,970, filed on Oct. 28, 2024.

(51) Int. Cl.

| | |
|---|---|
| ***A61K 31/4375*** | (2006.01) |
| ***A61K 31/437*** | (2006.01) |
| ***A61K 31/4985*** | (2006.01) |
| ***C07D 471/04*** | (2006.01) |
| ***C07D 487/04*** | (2006.01) |
| ***C07D 498/04*** | (2006.01) |
| ***C07D 513/04*** | (2006.01) |

(52) U.S. Cl.

CPC ........ *A61K 31/4375* (2013.01); *A61K 31/437* (2013.01); *A61K 31/4985* (2013.01); *C07D 471/04* (2013.01); *C07D 487/04* (2013.01); *C07D 498/04* (2013.01); *C07D 513/04* (2013.01)

(58) Field of Classification Search

CPC .............. A61K 31/4375; A61K 31/437; A61K 31/4985; C07D 471/04; C07D 487/04; C07D 498/04; C07D 513/04

USPC .......................................................... 514/249

See application file for complete search history.

(56) References Cited

U.S. PATENT DOCUMENTS

| | | | |
|---|---|---|---|
| 2007/0238771 A1 | 10/2007 | Edwards et al. |
| 2008/0275052 A1 | 11/2008 | Dhar et al. |
| 2019/0127380 A1 | 5/2019 | Gunaga et al. |

FOREIGN PATENT DOCUMENTS

| | | |
|---|---|---|
| WO | WO-2021173929 A1 | 9/2021 |
| WO | WO-2025101780 A1 | 5/2025 |
| WO | WO-2025217213 A2 | 10/2025 |

OTHER PUBLICATIONS

Amidon, Seth. et al. Colon-Targeted Oral Drug Delivery Systems: Design Trends and Approaches. AAPS PharmSciTech 16(4):731-741 (2015).

Berge, Stephen M. et al. Pharmaceutical Salts. Journal of Pharmaceutical Sciences 66(1):1-19 (1977).

Chourasia et al. Pharmaceutical approaches to colon targeted drug delivery systems. J Pharm Pharm Sci. 6(1):33-66 (2003).

Kumar P. et al. Colon Targeted Drug Delivery Systems—an Overview. Current Drug Delivery 5(3):186-198 (2008).

Patel, Mayur et al. Therapeutic Opportunities In Colon-specific Drug-delivery Systems. Critical Reviews in Therapeutic Drug Carrier Systems 24(2):147-202 (2007).

PCT/US2024/054963 International Search Report and Written Opinion dated Jan. 22, 2025.

PubChem SID: 296105184, (1H-benzimidazol-2-yl(3,4-dihydro-1H-isoquinolin-2-yl)methanone). Created on Jan. 27, 2016. [retrieved o n Nov. 17, 2025]. Available at URL: https://pubchem.ncbi.nlm.nih.gov/substance/296105184 pp. 1-5.

PubChem SID: 337426846, (6,8-dihydro-5H-[1,2,4]triazolo[1,5-a]pyrazin-7-yl-(3-methyl-1H-indol-2-yl)methanone). Created on Jun. 18, 2017. [retrieved o n Nov. 17, 2025]. Available at URL: https://pubchem.ncbi.nlm.nih.gov/substance/337426846 pp. 1-5.

Van Den Mooter, Guy. Colon Drug Delivery. Expert Opinion on Drug Delivery 3(1):111-125 (2006).

Ortega et al.: Rhodopsin as a Molecular Target to Mitigate Retinitis Pigmentosa. Protein Reviews. Adv Exp Med Biol. 1371:61-77 (2022).

PCT/US2025/052690 International Search Report and Written Opinion dated Feb. 12, 2026.

PCT/US2025/052690 Invitation to Pay Additional Fees dated Dec. 16, 2025.

*Primary Examiner* — Kristin A Vajda

(74) *Attorney, Agent, or Firm* — Wilson Sonsini Goodrich & Rosati

(57) ABSTRACT

Described herein are pharmacologic correctors of rhodopsin, methods of making such compounds, pharmaceutical compositions and medicaments comprising such compounds, and methods of using such compounds in treating disease.

28 Claims, No Drawings

PHARMACOLOGICAL CORRECTORS OF RHODOPSIN AND USES THEREOF

CROSS-REFERENCE

This application claims benefit of U.S. Provisional Patent Application No. 63/712,970 filed on Oct. 28, 2024, which is incorporated herein by reference in its entirety.

BACKGROUND OF THE INVENTION

Autosomal dominant retinitis pigmentosa (adRP) is a progressive blindness disease with over 10,000 patients in the U.S. and Europe alone. Misfolding mutations of Rhodopsin constitute the most common cause of adRP. There is currently no approved pharmacologic treatment for rhodopsin-mediated autosomal dominant retinitis pigmentosa (RHO-adRP). Therefore, an approved RHO-adRP therapy would address an important unmet medical need.

SUMMARY OF THE INVENTION

In one aspect, described herein is a compound of Formula (I), or a pharmaceutically acceptable salt or solvate thereof:

Formula (I)

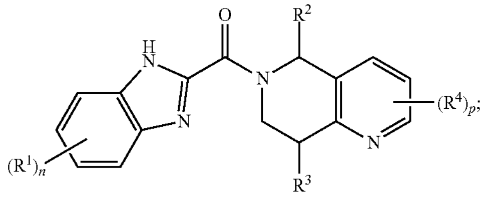

wherein:

each $R^1$ is independently selected from halogen, —CN, —OH, $C_{1-6}$alkyl, $C_{1-6}$haloalkyl, and $C_{1-6}$alkoxy;

$R^2$ is $C_{1-6}$alkyl or $C_{1-6}$haloalkyl;

$R^3$ is hydrogen, —CN, or $C_{1-6}$alkoxy, wherein if $R^3$ is hydrogen, then $R^2$ is $C_{1-6}$haloalkyl;

each $R^4$ is independently selected from halogen, —CN, $C_{1-6}$alkyl, and $C_{1-6}$haloalkyl;

n is 2, 3, or 4; and p is 0, 1, 2, or 3.

In some embodiments is a compound of Formula (I), or a pharmaceutically acceptable salt or solvate thereof, wherein $R^2$ is $C_{1-6}$haloalkyl. In some embodiments is a compound of Formula (I), or a pharmaceutically acceptable salt or solvate thereof, wherein $R^2$ is $—CF_2H$. In some embodiments is a compound of Formula (I), or a pharmaceutically acceptable salt or solvate thereof, wherein $R^2$ is $C_{1-6}$alkyl. In some embodiments is a compound of Formula (I), or a pharmaceutically acceptable salt or solvate thereof, wherein $R^2$ is $—CH_3$. In some embodiments is a compound of Formula (I), or a pharmaceutically acceptable salt or solvate thereof, wherein $R^3$ is hydrogen. In some embodiments is a compound of Formula (I), or a pharmaceutically acceptable salt or solvate thereof, wherein $R^3$ is $C_{1-6}$alkoxy. In some embodiments is a compound of Formula (I), or a pharmaceutically acceptable salt or solvate thereof, wherein $R^3$ is $—OCH_3$. In some embodiments is a compound of Formula (I), or a pharmaceutically acceptable salt or solvate thereof, wherein $R^3$ is —CN. In some embodiments is a compound of Formula (I), or a pharmaceutically acceptable salt or solvate thereof, wherein p is 0.

In another aspect, described herein is a compound of Formula (II), or a pharmaceutically acceptable salt or solvate thereof:

Formula (II)

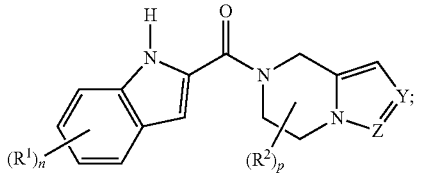

wherein:

Y and Z are each independently $C(R^3)$ or N, wherein one of Y and Z is N;

each $R^1$ is independently selected from halogen, —CN, —OH, $C_{1-6}$alkyl, $C_{1-6}$haloalkyl, and $C_{1-6}$alkoxy;

each $R^2$ is independently selected from —CN, $C_{1-6}$alkyl, $C_{1-6}$haloalkyl, $C_{3-6}$cycloalkyl, and $C_{1-6}$alkoxy;

$R^3$ is hydrogen, halogen, —CN, $C_{1-6}$alkyl, $—C_{1-6}$alkyl-$OR^4$, $—N(R^4)(R^5)$, $C_{3-6}$cycloalkyl, or $C_{1-6}$alkoxy;

$R^4$ and $R^5$ are independently selected from hydrogen and $C_{1-6}$alkyl;

n is 2, 3, or 4; and p is 0, 1, 2, 3, or 4.

In some embodiments is a compound of Formula (II), or a pharmaceutically acceptable salt or solvate thereof, wherein Y is N and Z is $C(R^3)$. In some embodiments is a compound of Formula (II), or a pharmaceutically acceptable salt or solvate thereof, wherein Y is $C(R^3)$ and Z is N. In some embodiments is a compound of Formula (II), or a pharmaceutically acceptable salt or solvate thereof, wherein $R^3$ is hydrogen, halogen, or —CN. In some embodiments is a compound of Formula (II), or a pharmaceutically acceptable salt or solvate thereof, wherein $R^3$ is hydrogen. In some embodiments is a compound of Formula (II), or a pharmaceutically acceptable salt or solvate thereof, wherein each $R^2$ is $C_{1-6}$alkyl. In some embodiments is a compound of Formula (II), or a pharmaceutically acceptable salt or solvate thereof, wherein $R^2$ is $—CH_3$. In some embodiments is a compound of Formula (II), or a pharmaceutically acceptable salt or solvate thereof, wherein p is 1. In some embodiments is a compound of Formula (I) or (II), or a pharmaceutically acceptable salt or solvate thereof, wherein each $R^1$ is independently selected from halogen, $C_{1-6}$alkyl, and $C_{1-6}$alkoxy. In some embodiments is a compound of Formula (I) or (II), or a pharmaceutically acceptable salt or solvate thereof, wherein each $R^1$ is independently selected from halogen and $C_{1-6}$alkyl. In some embodiments is a compound of Formula (I) or (II), or a pharmaceutically acceptable salt or solvate thereof, wherein n is 2. In some embodiments is a compound of Formula (I) or (II), or a pharmaceutically acceptable salt or solvate thereof, wherein n is 3.

In another aspect, described herein is a compound of Formula (III), or a pharmaceutically acceptable salt or solvate thereof:

Formula (III)

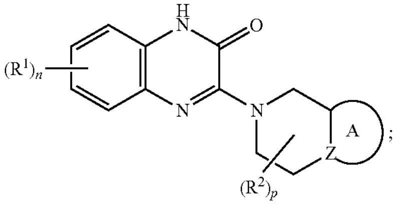

wherein:

ring A is a 5- or 6-membered heteroaryl ring optionally substituted with 1-3 $R^{5c}$ groups;

Z is C or N;

$R^1$ is selected from halogen, —CN, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$N(R^{12})C(O)R^{13}$, —$S(O)_2R^{13}$, —$S(O)_2N(R^{10})(R^{11})$—, —S(═O)(═NH)$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5a}$ groups;

each $R^2$ is independently selected from halogen, —CN, —$OR^{10}$, —$SR^{10}$, —$N(R^{10})(R^{11})$, $C_{1-6}$alkyl, $C_{1-6}$halo alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5b}$ groups;

each $R^{5a}$, $R^{5b}$, and $R^{5c}$ is each independently selected from halogen, oxo, —CN, $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$ heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —S(═O)(═NH)$N(R^{10})(R^{11})$, —C(═$NOR^{11}$)$R^{13}$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$ heterocycloalkyl, $C_{6-10}$aryl, —$CH_2$—$C_{6-10}$aryl, $C_{1-9}$heteroaryl, —$CH_2$—$C_{1-9}$heteroaryl are optionally substituted with one, two, or three groups selected from halogen, —CN, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, —$OR^{10}$, and —$N(R^{10})(R^{11})$;

each $R^{10}$ is independently selected from hydrogen, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

n is 0, 1, 2, 3, or 4; and p is 0, 1, 2, 3, or 4.

In some embodiments is a compound of Formula (III), or a pharmaceutically acceptable salt or solvate thereof, wherein Z is C. In some embodiments is a compound of Formula (III), or a pharmaceutically acceptable salt or solvate thereof, wherein Z is N. In some embodiments is a compound of Formula (III), or a pharmaceutically acceptable salt or solvate thereof, wherein ring A is a 6-membered heteroaryl ring optionally substituted with 1-3 $R^{5c}$ groups.

In some embodiments is a compound of Formula (III), or a pharmaceutically acceptable salt or solvate thereof, having the structure of Formula (IIIa):

Formula (IIIa)

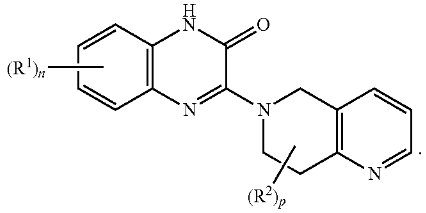

In some embodiments is a compound of Formula (III), or a pharmaceutically acceptable salt or solvate thereof, wherein ring A is a 5-membered heteroaryl ring optionally substituted with 1-2 $R^{5c}$ groups.

In some embodiments is a compound of Formula (III), or a pharmaceutically acceptable salt or solvate thereof, having the structure of Formula (IIIb):

Formula (IIIb)

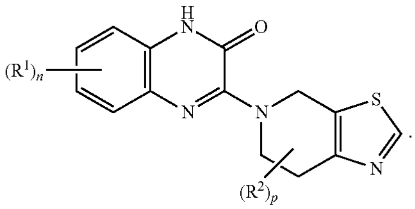

In some embodiments is a compound of Formula (III), or a pharmaceutically acceptable salt or solvate thereof, having the structure of Formula (IIIc):

Formula (IIIc)

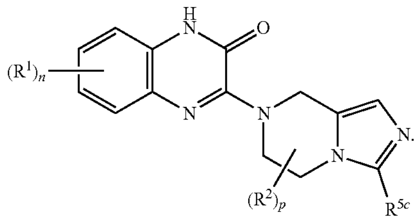

In another aspect, described herein is a compound of Formula (IVa), Formula (IVb), or Formula (IVc), or a pharmaceutically acceptable salt or solvate thereof:

Formula (IVa)

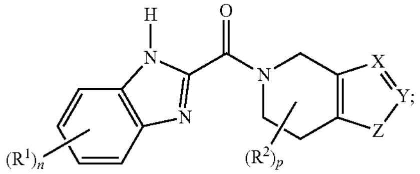

Formula (IVb)

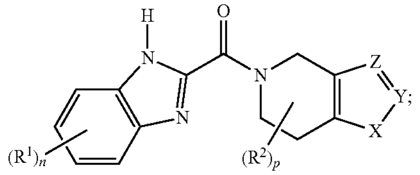

Formula (IVc)

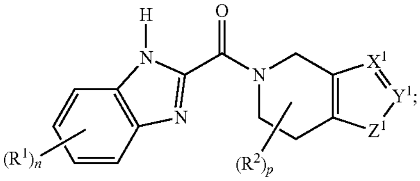

wherein:

X is $C(R^{3a})$;

Y is selected from $C(R^3)$ and N;

Z is selected from O, S, and $N(R^4)$;

$X^1$ is selected from $C(R^3)$ and N;

$Y^1$ is selected from O, S, and $N(R^4)$;

$Z^1$ is selected from $C(R^3)$ and N;

$R^1$ is selected from halogen, —CN, —$OR^{10}$, —$SR^{10}$, —$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{6-10}$aryl, and $C_{1-9}$heteroaryl are optionally substituted with 1-5 $R^{5a}$ groups;

each $R^2$ is independently selected from halogen, —CN, —$OR^{10}$, —$SR^{10}$, —$N(R^{10})(R^{11})$, $C_{1-6}$alkyl, $C_{1-6}$halo alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5b}$ groups;

each $R^3$ is independently selected from hydrogen, halogen, —CN, $C_{1-6}$alkyl, $C_{1-6}$haloalkyl, $C_{3-6}$cycloalkyl, $C_{2-9}$heterocycloalkyl, —$OR^{10}$, —$SR^{10}$, —$N(R^{10})(R^{11})$, —$C(O)OR^{10}$, —$C(O)R^{13}$, —$C(O)N(R^{10})(R^{11})$, —$N(R^{12})C(O)R^{13}$, —$S(O)_2R^{13}$, and —$S(O)_2N(R^{10})(R^{11})$—, wherein $C_{1-6}$alkyl, $C_{3-6}$cycloalkyl, and $C_{2-9}$heterocycloalkyl are optionally substituted with 1-5 $R^{5c}$ groups;

$R^{3a}$ is selected from hydrogen, halogen, —CN, $C_{1-6}$alkyl, $C_{1-6}$haloalkyl, $C_{3-6}$cycloalkyl, $C_{2-9}$heterocycloalkyl, —$OR^{10}$, —$SR^{10}$, —$N(R^{10})(R^{11})$, —$C(O)OR^{10}$, —$C(O)R^{13}$, —$C(O)N(R^{10})(R^{11})$, —$N(R^{12})C(O)R^{13}$, —$S(O)_2R^{13}$, and —$S(O)_2N(R^{10})(R^{11})$—, wherein $C_{1-6}$alkyl, $C_{3-6}$cycloalkyl, and $C_{2-9}$heterocycloalkyl are optionally substituted with 1-5 $R^{5c}$ groups;

$R^4$ is selected from hydrogen, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, and —$C(O)R^{13}$, wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with 1-5 $R^{5d}$ groups;

each $R^{5a}$, $R^{5b}$, $R^{5c}$, and $R^{5d}$ is each independently selected from halogen, oxo, —CN, $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$S(=O)(=NH)N(R^{10})(R^{11})$, —$C(=NOR^{11})R^{13}$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl are optionally substituted with one, two, or three groups selected from halogen, —CN, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, —$OR^{10}$, and —$N(R^{10})(R^{11})$;

each $R^{10}$ is independently selected from hydrogen, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and n is 0, 1, 2, 3, or 4; and p is 0, 1, 2, 3, or 4.

In some embodiments is a compound of Formula (IV), or a pharmaceutically acceptable salt or solvate thereof, having the structure of Formula (IVa):

Formula (IVa)

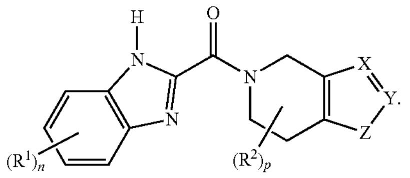

In some embodiments is a compound of Formula (IV), or a pharmaceutically acceptable salt or solvate thereof, having the structure of Formula (IVb):

Formula (IVb)

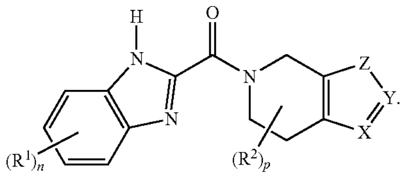

In some embodiments is a compound of Formula (IVa) or (IVb), or a pharmaceutically acceptable salt or solvate thereof, wherein X is $C(R^{3a})$ and $R^{3a}$ is selected from hydrogen, unsubstituted $C_{1-6}$alkyl, and unsubstituted $C_{1-6}$haloalkyl. In some embodiments is a compound of Formula (IVa) or (IVb), or a pharmaceutically acceptable salt or solvate thereof, wherein Y is N. In some embodiments is a compound of Formula (IVa) or (IVb), or a pharmaceutically acceptable salt or solvate thereof, wherein Y is $C(R^3)$. In some embodiments is a compound of Formula (IVa) or (IVb), or a pharmaceutically acceptable salt or solvate thereof, wherein Y is $C(R^3)$ and $R^3$ is selected from hydrogen, unsubstituted $C_{1-6}$alkyl, unsubstituted $C_{1-6}$haloalkyl, and —$N(R^{12})C(O)R^{13}$. In some embodiments is a compound of Formula (IVa) or (IVb), or a pharmaceutically acceptable salt or solvate thereof, wherein Z is S. In some embodiments is a compound of Formula (IVa) or (IVb), or a pharmaceutically acceptable salt or solvate thereof, wherein Z is O. In some embodiments is a compound of Formula (IVa) or (IVb), or a pharmaceutically acceptable salt or solvate thereof, wherein Z is $N(R^4)$. In some embodiments is a compound of Formula (IVa) or (IVb), or a pharmaceutically acceptable salt or solvate thereof, wherein Z is $N(R^4)$ and $R^4$ is selected from hydrogen and $C_{1-6}$alkyl.

In some embodiments is a compound of Formula (IV), or a pharmaceutically acceptable salt or solvate thereof, having the structure of Formula (IVc):

Formula (IVc)

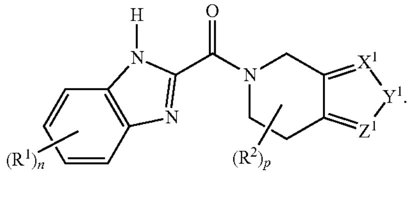

In some embodiments is a compound of Formula (IVc), or a pharmaceutically acceptable salt or solvate thereof, wherein $X^1$ is selected from $C(R^3)$. In some embodiments is a compound of Formula (IVc), or a pharmaceutically acceptable salt or solvate thereof, wherein $R^3$ is selected from hydrogen and $C_{1-6}$alkyl. In some embodiments is a compound of Formula (IVc), or a pharmaceutically acceptable salt or solvate thereof, wherein $Y^1$ is S. In some embodiments is a compound of Formula (IVc), or a pharmaceutically acceptable salt or solvate thereof, wherein $Y^1$ is O. In some embodiments is a compound of Formula (IVc), or a pharmaceutically acceptable salt or solvate thereof, wherein $Z^1$ is N.

In some embodiments is a compound of Formula (III), (IIIa), (IIIb), (IIIc), (IVa), (IVb), or (IVc), or a pharmaceutically acceptable salt or solvate thereof, wherein each $R^1$ is independently selected from halogen, —CN, —$OR^{10}$, unsubstituted $C_{1-6}$alkyl, and unsubstituted $C_{1-6}$haloalkyl. In some embodiments is a compound of Formula (III), (IIIa), (IIIb), (IIIc), (IVa), (IVb), or (IVc), or a pharmaceutically acceptable salt or solvate thereof, wherein each $R^1$ is independently selected from halogen, —CN, —OH, —$OCH_3$, —$CH_3$, and —$CF_3$. In some embodiments is a compound of Formula (III), (IIIa), (IIIb), (IIIc), (IVa), (IVb), or (IVc), or a pharmaceutically acceptable salt or solvate thereof, wherein each $R^1$ is independently selected from halogen and —$CH_3$. In some embodiments is a compound of Formula (III), (IIIa), (IIIb), (IIIc), (IVa), (IVb), or (IVc), or a pharmaceutically acceptable salt or solvate thereof, wherein n is 2. In some embodiments is a compound of Formula (III), (IIIa), (IIIb), (IIIc), (IVa), (IVb), or (IVc), or a pharmaceutically acceptable salt or solvate thereof, wherein n is 3. In some embodiments is a compound of Formula (III), (IIIa), (IIIb), (IIIc), (IVa), (IVb), or (IVc), or a pharmaceutically acceptable salt or solvate thereof, wherein n is 1.

In another aspect, described herein is a compound of Formula (V), or a pharmaceutically acceptable salt or solvate thereof:

Formula (V)

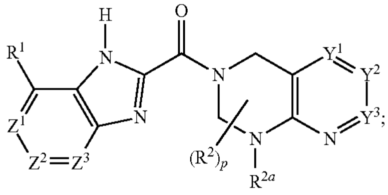

wherein:

$Y^1$, $Y^2$, and $Y^3$ are each independently $C(R^3)$ or N, wherein at least one of $Y^2$ and $Y^3$ is $C(R^3)$;

$Z^1$, $Z^2$, and $Z^3$ are each independently $C(R^4)$ or N, wherein at least one of $Z^1$, $Z^2$, and $Z^3$ is $C(R^4)$;

$R^1$ is selected from hydrogen, halogen, —CN, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$N(R^{12})C(O)R^{13}$, —$S(O)_2R^{13}$, —$S(O)_2N(R^{10})(R^{11})$—, —S(=O)(=NH)$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5a}$ groups;

each $R^2$ is independently selected from halogen, —CN, —$OR^{10}$, —$SR^{10}$, —$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5b}$ groups;

$R^{2a}$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —C(O)OR$^{10}$, —C(O)R$^{13}$, —S(O)R$^{13}$, —C(O)N(R$^{10}$)(R$^{11}$), and —S(O)$_2$R$^{13}$, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5b}$ groups;

each $R^3$ is independently selected from hydrogen, halogen, —CN, —SR$^{10}$, —N(R$^{10}$)(R$^{11}$), $C_{1-6}$alkyl, $C_{1-6}$haloalkyl, $C_{1-6}$alkoxy, $C_{2-6}$alkenyl, $C_{2-6}$alkynyl, $C_{3-6}$ cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{1-6}$alkoxy, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5c}$ groups;

each $R^4$ is independently selected from hydrogen, halogen, —CN, —OR$^{10}$, —SR$^{10}$, —N(R$^{10}$)(R$^{11}$), $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5d}$ groups;

each $R^{5a}$, $R^{5b}$, $R^{5c}$, and $R^{5d}$ is each independently selected from halogen, oxo, —CN, $C_{1-6}$alkyl, $C_{1-6}$haloalkyl, $C_{2-6}$alkenyl, $C_{2-6}$alkynyl, $C_{3-6}$cycloalkyl, —CH$_2$—$C_{3-6}$ cycloalkyl, $C_{2-9}$heterocycloalkyl, —CH$_2$—$C_{2-9}$ heterocycloalkyl, $C_{6-10}$aryl, —CH$_2$—$C_{6-10}$aryl, $C_{1-9}$heteroaryl, —CH$_2$—$C_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —S(=O)(=NH)N(R$^{10}$)(R$^{11}$), —C(=NOR$^{11}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$), wherein $C_{1-6}$alkyl, $C_{1-6}$haloalkyl, $C_{2-6}$alkenyl, $C_{2-6}$alkynyl, $C_{3-6}$cycloalkyl, —CH$_2$—$C_{3-6}$ cycloalkyl, $C_{2-9}$heterocycloalkyl, —CH$_2$—$C_{2-9}$ heterocycloalkyl, $C_{6-10}$aryl, —CH$_2$—$C_{6-10}$aryl, $C_{1-9}$heteroaryl, —CH$_2$—$C_{1-9}$heteroaryl are optionally substituted with one, two, or three groups selected from halogen, —CN, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, —OR$^{10}$, and —N(R$^{10}$)(R$^{11}$);

each $R^{10}$ is independently selected from hydrogen, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and p is 0, 1, 2, 3, or 4.

In some embodiments is a compound of Formula (V), or a pharmaceutically acceptable salt or solvate thereof, having the structure of Formula (Va):

Formula (Va)

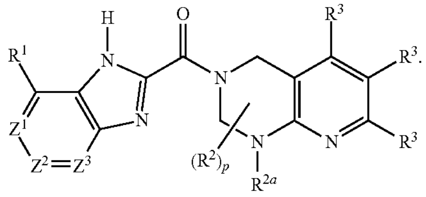

In some embodiments is a compound of Formula (V) or (Va), or a pharmaceutically acceptable salt or solvate thereof, wherein $R^{2a}$ is selected from hydrogen, $C_{1-6}$alkyl, and —S(O)$_2$R$^{13}$ wherein $C_{1-6}$alkyl is optionally substituted with 1-5 $R^{5b}$ groups. In some embodiments is a compound of Formula (V) or (Va), or a pharmaceutically acceptable salt or solvate thereof, wherein $R^{2a}$ is selected from hydrogen, unsubstituted $C_{1-6}$alkyl, and —S(O)$_2$R$^{13}$, wherein $R^{13}$ is unsubstituted $C_{1-6}$alkyl.

In another aspect, described herein is a compound of Formula (VI), or a pharmaceutically acceptable salt or solvate thereof:

Formula (VI)

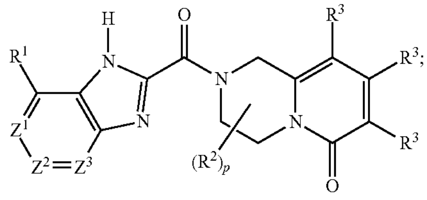

wherein:

$Z^1$, $Z^2$, and $Z^3$ are each independently C(R$^4$) or N, wherein at least one of $Z^1$, $Z^2$, and $Z^3$ is C(R$^4$);

$R^1$ is selected from hydrogen, halogen, —CN, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —S(=O)(=NH)N(R$^{10}$)(R$^{11}$), $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5a}$ groups;

each $R^2$ is independently selected from halogen, —CN, —OR$^{10}$, —SR$^{10}$, —N(R$^{10}$)(R$^{11}$), $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5b}$ groups;

each $R^3$ is independently selected from hydrogen, halogen, —CN, —$SR^{10}$, —$N(R^{10})(R^{11})$, $C_{1-6}$alkyl, $C_{1-6}$haloalkyl, $C_{1-6}$alkoxy, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{1-6}$alkoxy, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5c}$ groups;

each $R^4$ is independently selected from hydrogen, halogen, —CN, —$OR^{10}$, —$SR^{10}$, —$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5d}$ groups;

each $R^{5a}$, $R^{5b}$, $R^{5c}$, and $R^{5d}$ is each independently selected from halogen, oxo, —CN, $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$ heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$S(=O)(=NH)N(R^{10})(R^{11})$, —$C(=NOR^{11})R^{13}$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl are optionally substituted with one, two, or three groups selected from halogen, —CN, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, —$OR^{10}$, and —$N(R^{10})(R^{11})$;

each $R^{10}$ is independently selected from hydrogen, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and p is 0, 1, 2, 3, or 4.

In some embodiments is a compound of Formula (V), (Va), or (VI), or a pharmaceutically acceptable salt or solvate thereof, wherein each $R^3$ is independently selected from hydrogen, halogen, $C_{1-6}$alkyl, and $C_{1-6}$haloalkyl, wherein $C_{1-6}$alkyl and $C_{1-6}$haloalkyl are optionally substituted with 1-5 $R^{5c}$ groups. In some embodiments is a compound of Formula (V), (Va), or (VI), or a pharmaceutically acceptable salt or solvate thereof, wherein each $R^3$ is hydrogen. In some embodiments is a compound of Formula (V), (Va), or (VI), or a pharmaceutically acceptable salt or solvate thereof, wherein $R^1$ is selected from halogen, —CN, —$OR^{10}$, unsubstituted $C_{1-6}$alkyl, and unsubstituted $C_{1-6}$haloalkyl. In some embodiments is a compound of Formula (V), (Va), or (VI), or a pharmaceutically acceptable salt or solvate thereof, wherein $R^1$ is selected from halogen, —CN, —OH, —$OCH_3$, —$CH_3$, and —$CF_3$. In some embodiments is a compound of Formula (V), (Va), or (VI), or a pharmaceutically acceptable salt or solvate thereof, wherein $R^1$ is halogen. In some embodiments is a compound of Formula (V), (Va), or (VI), or a pharmaceutically acceptable salt or solvate thereof, wherein $Z^1$, $Z^2$, and $Z^3$ are each independently $C(R^4)$. In some embodiments is a compound of Formula (V), (Va), or (VI), or a pharmaceutically acceptable salt or solvate thereof, wherein each $R^4$ is independently selected from hydrogen, halogen, —CN, —$OR^{10}$, $C_{1-6}$alkyl, $C_{1-6}$haloalkyl, and $C_{3-6}$cycloalkyl, wherein $C_{1-6}$alkyl, $C_{1-6}$haloalkyl, and $C_{3-6}$cycloalkyl are optionally substituted with 1-5 $R^{5d}$ groups. In some embodiments is a compound of Formula (V), (Va), or (VI), or a pharmaceutically acceptable salt or solvate thereof, wherein each $R^4$ is independently selected from hydrogen, halogen, and unsubstituted $C_{1-6}$alkyl. In some embodiments is a compound of Formula (V), (Va), or (VI), or a pharmaceutically acceptable salt or solvate thereof, wherein each $R^4$ is independently selected from hydrogen and halogen.

In some embodiments is a compound of Formula (III), (IIIa), (IIIb), (IIIc), (IVa), (IVb), (IVc), (V), (Va), or (VI), or a pharmaceutically acceptable salt or solvate thereof, wherein each $R^2$ is $C_{1-6}$alkyl optionally substituted with 1-5 $R^{5b}$ groups. In some embodiments is a compound of Formula (III), (IIIa), (IIIb), (IIIc), (IVa), (IVb), (IVc), (V), (Va), or (VI), or a pharmaceutically acceptable salt or solvate thereof, wherein each $R^2$ is —$CH_3$. In some embodiments is a compound of Formula (III), (IIIa), (IIIb), (IIIc), (IVa), (IVb), (IVc), (V), (Va), or (VI), or a pharmaceutically acceptable salt or solvate thereof, wherein p is 1.

In another aspect, described herein is a pharmaceutical composition comprising a compound of Formula (I), (II), (III), (IIIa), (IIIb), (IIIc), (IVa), (IVb), (IVc), (V), (Va), or (VI), or a pharmaceutically acceptable salt or solvate thereof, and at least one pharmaceutically acceptable excipient.

In another aspect, described herein is a method of treating autosomal dominant retinitis pigmentosa (adRP) in a patient in need thereof comprising administering to the patient a compound of Formula (I), (II), (III), (IIIa), (IIIb), (IIIc), (IVa), (IVb), (IVc), (V), (Va), or (VI), or a pharmaceutically acceptable salt or solvate thereof.

Any combination of the groups described above for the various variables is contemplated herein. Throughout the specification, groups and substituents thereof are chosen by one skilled in the field to provide stable moieties and compounds.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Autosomal dominant retinitis pigmentosa (adRP) is a progressive blindness disease with no standard of care or approved therapies. Misfolding mutations of Rhodopsin (RHO) constitute the most common cause of adRP. Mutations have toxic gain-of-function effects and most frequently result in RHO misfolding and mistrafficking. Misfolded RHO accumulation causes cellular stress, which leads to death of photoreceptor cells (rods) and ultimately loss of central vision (cones).

Described herein are small molecule correctors which prevent or mitigate RHO misfolding, directly addressing the underlying mechanism of disease to restore Rhodopsin trafficking. Properly folded RHO is trafficked to the rod outer segment preventing photoreceptor cell death and preserving vision.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ . . . $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, 4 carbon atoms, 5 carbon atoms, 6 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect, the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_6$alkylene. In other embodiments, an alkylene is a $C_1$-$C_4$alkylene. In certain embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises two carbon atoms (e.g., $C_2$ alkylene). In other embodiments, an alkylene comprises two to four carbon atoms (e.g., $C_2$-$C_4$ alkylene). Typical alkylene groups include, but are not limited to, $-CH_2-$, $-CH(CH_3)-$, $-C(CH_3)_2-$, $-CH_2CH_2-$, $-CH_2CH(CH_3)-$, $-CH_2C(CH_3)_2-$, $-CH_2CH_2CH_2-$, $-CH_2CH_2CH_2CH_2-$, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula $-C(R)=CR_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include $-CH=CH_2$, $-C(CH_3)=CH_2$, $-CH=CHCH_3$, $-C(CH_3)=CHCH_3$, and $-CH_2CH=CH_2$.

The term "alkynyl" refers to a type of alkyl group in which at least one carbon-carbon triple bond is present. In one embodiment, an alkenyl group has the formula $-C≡C-R$, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include $-C≡CH$, $-C≡CCH_3-C≡CCH_2CH_3$, $-CH_2C≡CH$.

An "alkoxy" group refers to a (alkyl)O— group, where alkyl is as defined herein.

The term "alkylamine" refers to the $-N(alkyl)_xH_y$ group, where x is 0 and y is 2, or where x is 1 and y is 1, or where x is 2 and y is 0.

The term "aromatic" refers to a planar ring having a delocalized R-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon or nitrogen atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicyclo[1.1.1]pentyl. In some embodiments, a cycloalkyl is a $C_3$-$C_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.2]octyl and bicyclo[2.2.1]heptanyl), norbornenyl, decalinyl, 7,7-dimethyl-bicyclo[2.2.1]heptanyl, and the like.

The term "halo" or, alternatively, "halogen" or "halide" means fluoro, chloro, bromo or iodo. In some embodiments, halo is fluoro, chloro, or bromo.

The term "haloalkyl" refers to an alkyl in which one or more hydrogen atoms are replaced by a halogen atom. In one aspect, a fluoroalkyl is a $C_1$-$C_6$fluoroalkyl.

The term "fluoroalkyl" refers to an alkyl in which one or more hydrogen atoms are replaced by a fluorine atom. In one aspect, a fluoroalkyl is a $C_1$-$C_6$fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heteroalkylene" refers to a divalent heteroalkyl radical.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. In some embodiments, heterocycles are monocyclic, bicyclic, polycyclic, spirocyclic or bridged compounds. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 2-azabicyclo[2.2.2]octanyl, 3-azabicyclo[3.2.1]octanyl, 5-azabicyclo[2.1.1]hexanyl, 6-azabicyclo[3.1.1]heptanyl, 7-azabicyclo[2.2.1]heptanyl, 8-azabicyclo[3.2.1]octanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "oxo" refers to the =O radical.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from D, halogen, —CN, $—NH_2$, —NH(alkyl), $—N(alkyl)_2$, —OH, $—CO_2H$, $—CO_2alkyl$, $—C(=O)NH_2$, —C(=O)NH(alkyl), $—C(=O)N(alkyl)_2$, $—S(=O)_2NH_2$, $—S(=O)_2NH(alkyl)$, $—S(=O)_2N(alkyl)_2$, alkyl, alkenyl, alkynyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, $—NH_2$, $—NH(CH_3)$, $—N(CH_3)_2$, —OH, $—CO_2H$, $—CO_2(C_1\text{-}C_4alkyl)$, $—C(=O)NH_2$, $—C(=O)NH(C_1\text{-}C_4alkyl)$, $—C(=O)N(C_1\text{-}C_4alkyl)_2$, $—S(=O)_2NH_2$, $—S(=O)_2NH(C_1\text{-}C_4alkyl)$, $—S(=O)_2N(C_1\text{-}C_4alkyl)_2$, $C_1\text{-}C_4alkyl$, $C_3\text{-}C_6cycloalkyl$, $C_1\text{-}C_4fluoroalkyl$, $C_1\text{-}C_4heteroalkyl$, $C_1\text{-}C_4alkoxy$, $C_1\text{-}C_4fluoroalkoxy$, $—SC_1\text{-}C_4alkyl$, $—S(=O)C_1\text{-}C_4alkyl$, and $—S(=O)_2C_1\text{-}C_4alkyl$. In some embodiments, optional substituents are independently selected from D, halogen, —CN, $—NH_2$, —OH, $—NH(CH_3)$, $—N(CH_3)_2$, $—CH_3$, $—CH_2CH_3$, $—CF_3$, $—OCH_3$, and $—OCF_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of a corrector, an agonist, partial agonist, an inverse agonist, antagonist, degrader, or combinations thereof. In some embodiments, a modulator is a corrector.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Compounds

Compounds described herein, including pharmaceutically acceptable salts, active metabolites and pharmaceutically acceptable solvates thereof, are small molecule correctors of rhodopsin.

In some embodiments, described herein is a compound of Formula (I), or a pharmaceutically acceptable salt or solvate thereof:

Formula (I)

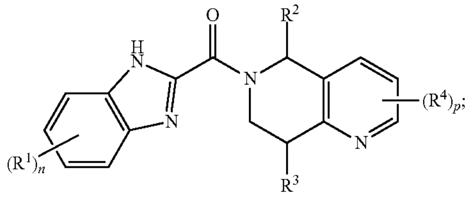

wherein:

each $R^1$ is independently selected from halogen, —CN, —OH, $C_{1-6}$alkyl, $C_{1-6}$haloalkyl, and $C_{1-6}$alkoxy;

$R^2$ is $C_{1-6}$alkyl or $C_{1-6}$haloalkyl;

$R^3$ is hydrogen, —CN, or $C_{1-6}$alkoxy, wherein if $R^3$ is hydrogen, then $R^2$ is $C_{1-6}$haloalkyl;

each $R^4$ is independently selected from halogen, —CN, $C_{1-6}$alkyl, and $C_{1-6}$haloalkyl;

n is 2, 3, or 4; and p is 0, 1, 2, or 3.

In some embodiments is a compound of Formula (I), or a pharmaceutically acceptable salt or solvate thereof, wherein $R^2$ is $C_{1-6}$alkyl. In some embodiments is a compound of Formula (I), or a pharmaceutically acceptable salt or solvate thereof, wherein $R^2$ is —$CH_3$. In some embodiments is a compound of Formula (I), or a pharmaceutically acceptable salt or solvate thereof, wherein $R^2$ is $C_{1-6}$ alkyl and $R^3$ is —CN. In some embodiments is a compound of Formula (I), or a pharmaceutically acceptable salt or solvate thereof, wherein $R^2$ is —$CH_3$ and $R^3$ is —CN. In some embodiments is a compound of Formula (I), or a pharmaceutically acceptable salt or solvate thereof, wherein $R^2$ is $C_{1-6}$ alkyl and $R^3$ is $C_{1-6}$alkoxy. In some embodiments is a compound of Formula (I), or a pharmaceutically acceptable salt or solvate thereof, wherein $R^2$ is $C_{1-6}$alkyl and $R^3$ is —$OCH_3$. In some embodiments is a compound of Formula (I), or a pharmaceutically acceptable salt or solvate thereof, wherein $R^2$ is $C_{1-6}$alkyl and $R^3$ is —$OCH_2CH_3$. In some embodiments is a compound of Formula (I), or a pharmaceutically acceptable salt or solvate thereof, wherein $R^2$ is —$CH_3$ and $R^3$ is $C_{1-6}$alkoxy. In some embodiments is a compound of Formula (I), or a pharmaceutically acceptable salt or solvate thereof, wherein $R^2$ is —$CH_3$ and $R^3$ is —$OCH_3$. In some embodiments is a compound of Formula (I), or a pharmaceutically acceptable salt or solvate thereof, wherein $R^2$ is —$CH_3$ and $R^3$ is —$OCH_2CH_3$.

In some embodiments is a compound of Formula (I), or a pharmaceutically acceptable salt or solvate thereof, wherein $R^2$ is $C_{1-6}$haloalkyl. In some embodiments is a compound of Formula (I), or a pharmaceutically acceptable salt or solvate thereof, wherein $R^2$ is —$CF_2H$. In some embodiments is a compound of Formula (I), or a pharmaceutically acceptable salt or solvate thereof, wherein $R^2$ is —$CH_2F$. In some embodiments is a compound of Formula (I), or a pharmaceutically acceptable salt or solvate thereof, wherein $R^2$ is —$CF_3$. In some embodiments is a compound of Formula (I), or a pharmaceutically acceptable salt or solvate thereof, wherein $R^2$ is $C_{1-6}$haloalkyl and $R^3$ is hydrogen. In some embodiments is a compound of Formula (I), or a pharmaceutically acceptable salt or solvate thereof, wherein $R^2$ is —$CF_2H$ and $R^3$ is hydrogen. In some embodiments is a compound of Formula (I), or a pharmaceutically acceptable salt or solvate thereof, wherein $R^2$ is —$CH_2F$ and $R^3$ is hydrogen. In some embodiments is a compound of Formula (I), or a pharmaceutically acceptable salt or solvate thereof, wherein $R^2$ is —$CF_3$ and $R^3$ is hydrogen. In some embodiments is a compound of Formula (I), or a pharmaceutically acceptable salt or solvate thereof, wherein $R^2$ is $C_{1-6}$haloalkyl and $R^3$ is —CN. In some embodiments is a compound of Formula (I), or a pharmaceutically acceptable salt or solvate thereof, wherein $R^2$ is —$CF_2H$ and $R^3$ is —CN. In some embodiments is a compound of Formula (I), or a pharmaceutically acceptable salt or solvate thereof, wherein $R^2$ is —$CH_2F$ and $R^3$ is —CN. In some embodiments is a compound of Formula (I), or a pharmaceutically acceptable salt or solvate thereof, wherein $R^2$ is —$CF_3$ and $R^3$ is —CN. In some embodiments is a compound of Formula (I), or a pharmaceutically acceptable salt or solvate thereof, wherein $R^2$ is $C_{1-6}$ haloalkyl and $R^3$ is $C_{1-6}$alkoxy. In some embodiments is a compound of Formula (I), or a pharmaceutically acceptable salt or solvate thereof, wherein $R^2$ is —$CF_2H$ and $R^3$ is $C_{1-6}$alkoxy. In some embodiments is a compound of Formula (I), or a pharmaceutically acceptable salt or solvate thereof, wherein $R^2$ is —$CF_2H$ and $R^3$ is —$OCH_3$. In some embodiments is a compound of Formula (I), or a pharmaceutically acceptable salt or solvate thereof, wherein $R^2$ is —$CF_2H$ and $R^3$ is —$OCH_2CH_3$. In some embodiments is a compound of Formula (I), or a pharmaceutically acceptable salt or solvate thereof, wherein $R^2$ is —$CH_2F$ and $R^3$ is $C_{1-6}$alkoxy. In some embodiments is a compound of Formula (I), or a pharmaceutically acceptable salt or solvate thereof, wherein $R^2$ is —$CH_2F$ and $R^3$ is —$OCH_3$. In some embodiments is a compound of Formula (I), or a pharmaceutically acceptable salt or solvate thereof, wherein $R^2$ is —$CH_2F$ and $R^3$ is —$OCH_2CH_3$. In some embodiments is a compound of Formula (I), or a pharmaceutically acceptable salt or solvate thereof, wherein $R^2$ is —$CF_3$ and $R^3$ is $C_{1-6}$alkoxy. In some embodiments is a compound of Formula (I), or a pharmaceutically acceptable salt or solvate thereof, wherein $R^2$ is —$CF_3$ and $R^3$ is —$OCH_3$. In some embodiments is a compound of Formula (I), or a pharmaceutically acceptable salt or solvate thereof, wherein $R^2$ is —$CF_3$ and $R^3$ is —$OCH_2CH_3$.

In some embodiments is a compound of Formula (I), or a pharmaceutically acceptable salt or solvate thereof, wherein each $R^4$ is independently selected from halogen, $C_{1-6}$alkyl, and $C_{1-6}$ haloalkyl. In some embodiments is a compound of Formula (I), or a pharmaceutically acceptable salt or solvate thereof, wherein each $R^4$ is independently selected from halogen and $C_{1-6}$alkyl, each $R^4$ is independently selected from halogen. In some embodiments is a compound of Formula (I), or a pharmaceutically acceptable salt or solvate thereof, wherein each $R^4$ is independently selected from $C_{1-6}$alkyl. In some embodiments is a compound of Formula (I), or a pharmaceutically acceptable salt or solvate thereof, wherein each $R^4$ is independently selected from $C_{1-6}$haloalkyl.

In some embodiments is a compound of Formula (I), or a pharmaceutically acceptable salt or solvate thereof, wherein p is 1, 2, or 3. In some embodiments is a compound of Formula (I), or a pharmaceutically acceptable salt or solvate thereof, wherein p is 1. In some embodiments is a compound of Formula (I), or a pharmaceutically acceptable salt or solvate thereof, wherein p is 2. In some embodiments is a compound of Formula (I), or a pharmaceutically acceptable salt or solvate thereof, wherein p is 3.

In some embodiments is a compound of Formula (I), or a pharmaceutically acceptable salt or solvate thereof, wherein p is 0.

In some embodiments is a compound of Formula (I), or a pharmaceutically acceptable salt or solvate thereof, wherein each $R^1$ is independently selected from halogen, —CN, $C_{1-6}$alkyl, $C_{1-6}$haloalkyl, and $C_{1-6}$alkoxy. In some embodiments is a compound of Formula (I), or a pharmaceutically acceptable salt or solvate thereof, wherein each $R^1$ is independently selected from halogen, $C_{1-6}$alkyl, $C_{1-6}$haloalkyl, and $C_{1-6}$alkoxy. In some embodiments is a compound of Formula (I), or a pharmaceutically acceptable salt or solvate thereof, wherein each $R^1$ is independently selected from halogen, $C_{1-6}$alkyl, and $C_{1-6}$alkoxy. In some embodiments is a compound of Formula (I), or a pharmaceutically acceptable salt or solvate thereof, wherein each $R^1$ is independently selected from halogen and $C_{1-6}$alkyl. In some embodiments is a compound of Formula (I), or a pharmaceutically acceptable salt or solvate thereof, wherein each $R^1$ is independently selected from halogen. In some embodiments is a compound of Formula (I), or a pharmaceutically acceptable salt or solvate thereof, wherein each $R^1$ is independently selected $C_{1-6}$alkyl.

In some embodiments is a compound of Formula (I), or a pharmaceutically acceptable salt or solvate thereof, wherein n is 2 or 3. In some embodiments is a compound of Formula (I), or a pharmaceutically acceptable salt or solvate thereof, wherein n is 2. In some embodiments is a compound of Formula (I), or a pharmaceutically acceptable salt or solvate thereof, wherein n is 3. In some embodiments is a compound of Formula (I), or a pharmaceutically acceptable salt or solvate thereof, wherein n is 4.

In some embodiments, described herein is a compound of Formula (II), or a pharmaceutically acceptable salt or solvate thereof:

Formula (II)

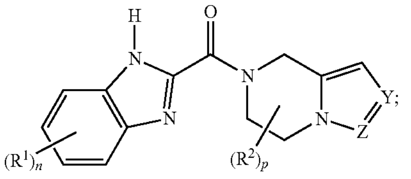

wherein:

Y and Z are each independently $C(R^3)$ or N, wherein one of Y and Z is N;

each $R^1$ is independently selected from halogen, —CN, —OH, $C_{1-6}$alkyl, $C_{1-6}$haloalkyl, and $C_{1-6}$alkoxy;

each $R^2$ is independently selected from —CN, $C_{1-6}$alkyl, $C_{1-6}$haloalkyl, $C_{3-6}$cycloalkyl, and $C_{1-6}$alkoxy;

$R^3$ is hydrogen, halogen, —CN, $C_{1-6}$alkyl, —$C_{1-6}$alkyl-$OR^4$, —$N(R^4)(R^5)$, $C_{3-6}$cycloalkyl, or $C_{1-6}$alkoxy;

$R^4$ and $R^5$ are independently selected from hydrogen and $C_{1-6}$alkyl;

n is 2, 3, or 4; and p is 0, 1, 2, 3, or 4.

In some embodiments is a compound of Formula (II), or a pharmaceutically acceptable salt or solvate thereof, wherein Y is $C(R^3)$ and Z is N. In some embodiments is a compound of Formula (II), or a pharmaceutically acceptable salt or solvate thereof, wherein Y is N and Z is $C(R^3)$.

In some embodiments is a compound of Formula (II), or a pharmaceutically acceptable salt or solvate thereof, wherein $R^3$ is hydrogen, halogen, —CN, $C_{1-6}$alkyl, or —$C_{1-6}$alkyl-$OR^4$. In some embodiments is a compound of Formula (II), or a pharmaceutically acceptable salt or solvate thereof, wherein $R^3$ is hydrogen, halogen, —CN, or —$C_{1-6}$alkyl-$OR^4$. In some embodiments is a compound of Formula (II), or a pharmaceutically acceptable salt or solvate thereof, wherein $R^3$ is hydrogen, halogen, or —CN. In some embodiments is a compound of Formula (II), or a pharmaceutically acceptable salt or solvate thereof, wherein $R^3$ is hydrogen. In some embodiments is a compound of Formula (II), or a pharmaceutically acceptable salt or solvate thereof, wherein $R^3$ is halogen. In some embodiments is a compound of Formula (II), or a pharmaceutically acceptable salt or solvate thereof, wherein $R^3$ is —CN. In some embodiments is a compound of Formula (II), or a pharmaceutically acceptable salt or solvate thereof, wherein $R^3$ is —$C_{1-6}$alkyl-$OR^4$. In some embodiments is a compound of Formula (II), or a pharmaceutically acceptable salt or solvate thereof, wherein $R^3$ is —$C_{1-6}$alkyl-$OR^4$ and $R^4$ is $C_{1-6}$alkyl. In some embodiments is a compound of Formula (II), or a pharmaceutically acceptable salt or solvate thereof, wherein $R^3$ is $C_{1-6}$alkyl.

In some embodiments is a compound of Formula (II), or a pharmaceutically acceptable salt or solvate thereof, wherein each $R^2$ is independently selected from $C_{1-6}$alkyl, $C_{1-6}$haloalkyl, and $C_{3-6}$cycloalkyl. In some embodiments is a compound of Formula (II), or a pharmaceutically acceptable salt or solvate thereof, wherein each $R^2$ is independently selected from $C_{1-6}$alkyl and $C_{1-6}$haloalkyl. In some embodiments is a compound of Formula (II), or a pharmaceutically acceptable salt or solvate thereof, wherein each $R^2$ is independently selected from $C_{1-6}$alkyl. In some embodiments is a compound of Formula (II), or a pharmaceutically acceptable salt or solvate thereof, wherein each $R^2$ is independently selected from —$CH_3$. In some embodiments is a compound of Formula (II), or a pharmaceutically acceptable salt or solvate thereof, wherein each $R^2$ is independently selected from $C_{1-6}$haloalkyl. In some embodiments is a compound of Formula (II), or a pharmaceutically acceptable salt or solvate thereof, wherein each $R^2$ is —$CF_2H$. In some embodiments is a compound of Formula (II), or a pharmaceutically acceptable salt or solvate thereof, wherein each $R^2$ is —$CH_2F$. In some embodiments is a compound of Formula (II), or a pharmaceutically acceptable salt or solvate thereof, wherein each $R^2$ is —$CF_3$.

In some embodiments is a compound of Formula (II), or a pharmaceutically acceptable salt or solvate thereof, wherein p is 1, 2, or 3. In some embodiments is a compound of Formula (II), or a pharmaceutically acceptable salt or solvate thereof, wherein p is 1. In some embodiments is a compound of Formula (II), or a pharmaceutically acceptable salt or solvate thereof, wherein p is 2. In some embodiments is a compound of Formula (II), or a pharmaceutically acceptable salt or solvate thereof, wherein p is 3. In some embodiments is a compound of Formula (II), or a pharmaceutically acceptable salt or solvate thereof, wherein p is 4.

In some embodiments is a compound of Formula (II), or a pharmaceutically acceptable salt or solvate thereof, wherein p is 0.

In some embodiments is a compound of Formula (II), or a pharmaceutically acceptable salt or solvate thereof, wherein each $R^1$ is independently selected from halogen, —CN, $C_{1-6}$alkyl, $C_{1-6}$ haloalkyl, and $C_{1-6}$alkoxy. In some embodiments is a compound of Formula (II), or a pharmaceutically acceptable salt or solvate thereof, wherein each $R^1$ is independently selected from halogen, $C_{1-6}$alkyl, $C_{1-6}$haloalkyl, and $C_{1-6}$alkoxy. In some embodiments is a compound of Formula (II), or a pharmaceutically acceptable salt or solvate thereof, wherein each $R^1$ is independently selected from halogen, $C_{1-6}$alkyl, and $C_{1-6}$alkoxy. In some embodiments is a compound of Formula (II), or a pharmaceutically acceptable salt or solvate thereof, wherein each $R^1$ is independently selected from halogen and $C_{1-6}$alkyl. In some embodiments is a compound of Formula (II), or a pharmaceutically acceptable salt or solvate thereof, wherein each $R^1$ is independently selected from halogen. In some embodiments is a compound of Formula (II), or a pharmaceutically acceptable salt or solvate thereof, wherein each $R^1$ is independently selected $C_{1-6}$alkyl.

In some embodiments is a compound of Formula (II), or a pharmaceutically acceptable salt or solvate thereof, wherein n is 2 or 3. In some embodiments is a compound of Formula (II), or a pharmaceutically acceptable salt or solvate thereof, wherein n is 2. In some embodiments is a compound of Formula (II), or a pharmaceutically acceptable salt or solvate thereof, wherein n is 3. In some embodiments is a compound of Formula (II), or a pharmaceutically acceptable salt or solvate thereof, wherein n is 4.

In some embodiments, described herein is a compound of Formula (III), or a pharmaceutically acceptable salt or solvate thereof:

Fomula (III)

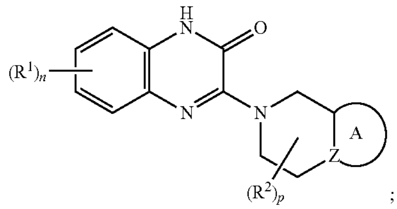

;

wherein:

ring A is a 5- or 6-membered heteroaryl ring optionally substituted with 1-3 $R^{5c}$ groups;

Z is C or N;

$R^1$ is selected from halogen, —CN, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$N(R^{12})C(O)R^{13}$, —$S(O)_2R^{13}$, —$S(O)_2N(R^{10})(R^{11})$—, —$S(=O)(=NH)N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5a}$ groups;

each $R^2$ is independently selected from halogen, —CN, —$OR^{10}$, —$SR^{10}$, —$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5b}$ groups;

each $R^{5a}$, $R^{5b}$, and $R^{5c}$ is each independently selected from halogen, oxo, —CN, $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$ heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$S(=O)(=NH)N(R^{10})(R^{11})$, —$C(=NOR^{11})R^{13}$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl are optionally substituted with one, two, or three groups selected from halogen, —CN, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, —$OR^{10}$, and —$N(R^{10})(R^{11})$;

each $R^{10}$ is independently selected from hydrogen, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

n is 0, 1, 2, 3, or 4; and p is 0, 1, 2, 3, or 4.

In some embodiments is a compound of Formula (III), or a pharmaceutically acceptable salt or solvate thereof, wherein Z is C. In some embodiments is a compound of Formula (III), or a pharmaceutically acceptable salt or solvate thereof, wherein Z is N. In some embodiments is a compound of Formula (III), or a pharmaceutically acceptable salt or solvate thereof, wherein ring A is a 6-membered heteroaryl ring optionally substituted with 1-3 $R^{5c}$ groups. In some embodiments is a compound of Formula (III), or a pharmaceutically acceptable salt or solvate thereof, wherein ring A is a pyridyl ring optionally substituted with 1-3 $R^{5c}$ groups. In some embodiments is a compound of Formula (III), or a pharmaceutically acceptable salt or solvate thereof, wherein ring A is a 5-membered heteroaryl ring optionally substituted with 1-2 $R^{5c}$ groups. In some embodiments is a compound of Formula (III), or a pharmaceutically acceptable salt or solvate thereof, wherein ring A is an imidazolyl ring optionally substituted with 1-2 $R^{5c}$ groups. In some embodiments is a compound of Formula (III), or a pharmaceutically acceptable salt or solvate thereof, wherein ring A is a thiazolyl ring optionally substituted with an $R^{5c}$ group. In some embodiments is a compound of Formula (III), or a pharmaceutically acceptable salt or solvate thereof, wherein ring A is an oxazolyl ring optionally substituted with an $R^{5c}$ group. In some embodiments is a compound of Formula (III), or a pharmaceutically acceptable salt or solvate thereof, wherein each $R^{5c}$ is independently selected from halogen, $C_{1-6}$alkyl, and $C_{1-6}$haloalkyl. In some embodiments is a compound of Formula (III), or a pharmaceutically acceptable salt or solvate thereof, wherein each $R^{5c}$ is independently selected from halogen. In some embodiments is a compound of Formula (III), or a pharmaceutically acceptable salt or solvate thereof, wherein each $R^{5c}$ is independently selected from $C_{1-6}$alkyl. In some embodiments is a compound of Formula (III), or a pharmaceutically acceptable salt or solvate thereof, wherein each $R^{5c}$ is independently selected from $C_{1-6}$haloalkyl.

In some embodiments is a compound of Formula (III), or a pharmaceutically acceptable salt or solvate thereof, having the structure of Formula (IIIa):

Formula (IIIa)

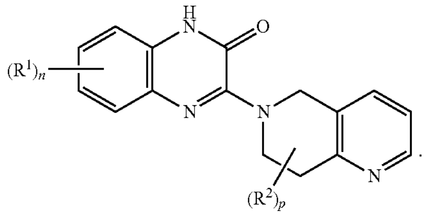

In some embodiments is a compound of Formula (III), or a pharmaceutically acceptable salt or solvate thereof, having the structure of Formula (IIIb):

Formula (IIIb)

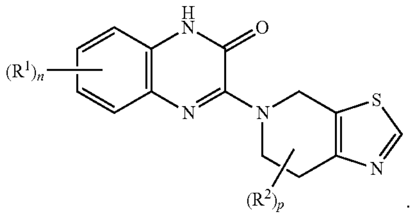

In some embodiments is a compound of Formula (III), or a pharmaceutically acceptable salt or solvate thereof, having the structure of Formula (IIIc):

Formula (IIIc)

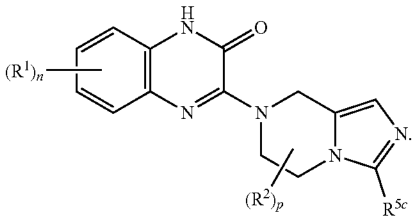

In some embodiments is a compound of Formula (III), (IIIa), (IIIb), or (IIIc), or a pharmaceutically acceptable salt or solvate thereof, wherein each $R^2$ is independently selected from $C_{1-6}$alkyl, $C_{1-6}$haloalkyl, and $C_{3-6}$cycloalkyl, wherein $C_{1-6}$alkyl, $C_{1-6}$haloalkyl, and $C_{3-6}$cycloalkyl are optionally substituted with 1-5 $R^{5b}$ groups. In some embodiments is a compound of Formula (III), (IIIa), (IIIb), or (IIIc), or a pharmaceutically acceptable salt or solvate thereof, wherein each $R^2$ is $C_{1-6}$alkyl optionally substituted with 1-5 $R^{5b}$ groups. In some embodiments is a compound of Formula (III), (IIIa), (IIIb), or (IIIc), or a pharmaceutically acceptable salt or solvate thereof, wherein each $R^2$ is independently selected from unsubstituted $C_{1-6}$alkyl and unsubstituted $C_{1-6}$ haloalkyl. In some embodiments is a compound of Formula (III), (IIIa), (IIIb), or (IIIc), or a pharmaceutically acceptable salt or solvate thereof, wherein each $R^2$ is independently selected from unsubstituted $C_{1-6}$alkyl. In some embodiments is a compound of Formula (III), (IIIa), (IIIb), or (IIIc), or a pharmaceutically acceptable salt or solvate thereof, wherein each $R^2$ is independently selected from —$CH_3$. In some embodiments is a compound of Formula (III), (IIIa), (IIIb), or (IIIc), or a pharmaceutically acceptable salt or solvate thereof, wherein each $R^2$ is independently selected from unsubstituted $C_{1-6}$haloalkyl. In some embodiments is a compound of Formula (III), (IIIa), (IIIb), or (IIIc), or a pharmaceutically acceptable salt or solvate thereof, wherein each $R^2$ is —$CF_2H$. In some embodiments is a compound of Formula (III), (IIIa), (IIIb), or (IIIc), or a pharmaceutically acceptable salt or solvate thereof, wherein each $R^2$ is —$CH_2F$. In some embodiments is a compound of Formula (III), (IIIa), (IIIb), or (IIIc), or a pharmaceutically acceptable salt or solvate thereof, wherein each $R^2$ is —$CF_3$.

In some embodiments is a compound of Formula (III), (IIIa), (IIIb), or (IIIc), or a pharmaceutically acceptable salt or solvate thereof, wherein p is 1, 2, or 3. In some embodiments is a compound of Formula (III), (IIIa), (IIIb), or (IIIc), or a pharmaceutically acceptable salt or solvate thereof, wherein p is 1. In some embodiments is a compound of Formula (III), (IIIa), (IIIb), or (IIIc), or a pharmaceutically acceptable salt or solvate thereof, wherein p is 2. In some embodiments is a compound of Formula (III), (IIIa), (IIIb), or (IIIc), or a pharmaceutically acceptable salt or solvate thereof, wherein p is 3. In some embodiments is a compound of Formula (III), (IIIa), (IIIb), or (IIIc), or a pharmaceutically acceptable salt or solvate thereof, wherein p is 4.

In some embodiments is a compound of Formula (III), (IIIa), (IIIb), or (IIIc), or a pharmaceutically acceptable salt or solvate thereof, wherein p is 0.

In some embodiments is a compound of Formula (III), (IIIa), (IIIb), or (IIIc), or a pharmaceutically acceptable salt or solvate thereof, wherein each $R^1$ is independently selected from halogen, —CN, —$OR^{10}$, $C_{1-6}$alkyl, and $C_{1-6}$haloalkyl, wherein $C_{1-6}$alkyl and $C_{1-6}$haloalkyl are optionally substituted with 1-5 $R^{5a}$ groups. In some embodiments is a compound of Formula (III), (IIIa), (IIIb), or (IIIc), or a pharmaceutically acceptable salt or solvate thereof, wherein each $R^1$ is independently selected from halogen, —CN, —$OR^{10}$, unsubstituted $C_{1-6}$alkyl, and unsubstituted $C_{1-6}$haloalkyl. In some embodiments is a compound of Formula (III), (IIIa), (IIIb), or (IIIc), or a pharmaceutically acceptable salt or solvate thereof, wherein each $R^1$ is independently selected from halogen and unsubstituted $C_{1-6}$alkyl. In some embodiments is a compound of Formula (III), (IIIa), (IIIb), or (IIIc), or a pharmaceutically acceptable salt or solvate thereof, wherein each $R^1$ is independently selected from halogen, —CN, —OH, —$OCH_3$, —$CH_3$, and —$CF_3$. In some embodiments is a compound of Formula (III), (IIIa), (IIIb), or (IIIc), or a pharmaceutically acceptable salt or solvate thereof, wherein each $R^1$ is independently selected from halogen and —$CH_3$. In some embodiments is a compound of Formula (III), (IIIa), (IIIb), or (IIIc), or a pharmaceutically acceptable salt or solvate thereof, wherein each $R^1$ is independently selected from halogen. In some embodiments is a compound of Formula (III), (IIIa), (IIIb), or (IIIc), or a pharmaceutically acceptable salt or solvate thereof, wherein each $R^1$ is independently selected from $C_{1-6}$alkyl. In some embodiments is a compound of Formula (III), (IIIa), (IIIb), or (IIIc), or a pharmaceutically acceptable salt or solvate thereof, wherein each $R^1$ is —$CH_3$.

In some embodiments is a compound of Formula (III), (IIIa), (IIIb), or (IIIc), or a pharmaceutically acceptable salt or solvate thereof, wherein n is 1, 2, or 3. In some embodiments is a compound of Formula (III), (IIIa), (IIIb), or (IIIc), or a pharmaceutically acceptable salt or solvate thereof, wherein n is 1. In some embodiments is a compound of Formula (III), (IIIa), (IIIb), or (IIIc), or a pharmaceutically acceptable salt or solvate thereof, wherein n is 2. In some embodiments is a compound of Formula (III), (IIIa), (IIIb), or (IIIc), or a pharmaceutically acceptable salt or solvate thereof, wherein n is 3. In some embodiments is a compound of Formula (III), (IIIa), (IIIb), or (IIIc), or a pharmaceutically acceptable salt or solvate thereof, wherein n is 4.

In some embodiments is a compound of Formula (III), (IIIa), (IIIb), or (IIIc), or a pharmaceutically acceptable salt or solvate thereof, wherein n is 0.

In some embodiments, described herein is a compound of Formula (IVa), or a pharmaceutically acceptable salt or solvate thereof:

Formula (IVa)

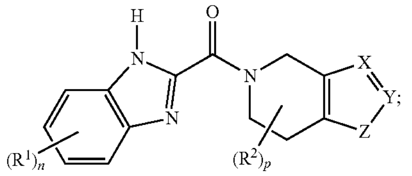

wherein:

X is $C(R^{3a})$;

Y is selected from $C(R^3)$ and N;

Z is selected from O, S, and $N(R^4)$;

$R^1$ is selected from halogen, —CN, —$OR^{10}$, —$SR^{10}$, —$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{6-10}$aryl, and $C_{1-9}$heteroaryl are optionally substituted with 1-5 $R^{5a}$ groups;

each $R^2$ is independently selected from halogen, —CN, —$OR^{10}$, —$SR^{10}$, —$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5b}$ groups;

$R^3$ is selected from hydrogen, halogen, —CN, $C_{1-6}$alkyl, $C_{1-6}$haloalkyl, $C_{3-6}$cycloalkyl, $C_{2-9}$heterocycloalkyl, —$OR^{10}$, —$SR^{10}$, —$N(R^{10})(R^{11})$, —$C(O)OR^{10}$, —$C(O)R^{13}$, —$C(O)N(R^{10})(R^{11})$, —$N(R^{12})C(O)R^{13}$, —$S(O)_2R^{13}$, and —$S(O)_2N(R^{10})(R^{11})$—, wherein $C_{1-6}$alkyl, $C_{3-6}$cycloalkyl, and $C_{2-9}$heterocycloalkyl are optionally substituted with 1-5 $R^{5c}$ groups;

$R^{3a}$ is selected from hydrogen, halogen, —CN, $C_{1-6}$alkyl, $C_{1-6}$haloalkyl, $C_{3-6}$cycloalkyl, $C_{2-9}$heterocycloalkyl, —$OR^{10}$, —$SR^{10}$, —$N(R^{10})(R^{11})$, —$C(O)OR^{10}$, —$C(O)R^{13}$, —$C(O)N(R^{10})(R^{11})$, —$N(R^{12})C(O)R^{13}$, —$S(O)_2R^{13}$, and —$S(O)_2N(R^{10})(R^{11})$—, wherein $C_{1-6}$alkyl, $C_{3-6}$cycloalkyl, and $C_{2-9}$heterocycloalkyl are optionally substituted with 1-5 $R^{5c}$ groups;

$R^4$ is selected from hydrogen, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, and —$C(O)R^{13}$, wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with 1-5 $R^{5d}$ groups;

each $R^{5a}$, $R^{5b}$, $R^{5c}$, and $R^{5d}$ is each independently selected from halogen, oxo, —CN, $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$ heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$S(=O)(=NH)N(R^{10})(R^{11})$, —$C(=NOR^{11})R^{13}$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl are optionally substituted with one, two, or three groups selected from halogen, —CN, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, —$OR^{10}$, and —$N(R^{10})(R^{11})$;

each $R^{10}$ is independently selected from hydrogen, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and n is 0, 1, 2, 3, or 4; and p is 0, 1, 2, 3, or 4.

In some embodiments, described herein is a compound of Formula (IVb), or a pharmaceutically acceptable salt or solvate thereof:

Formula (IVb)

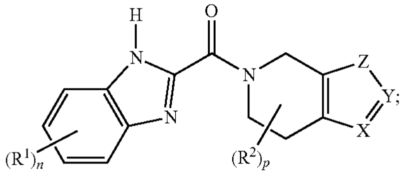

wherein:

X is $C(R^{3a})$;

Y is selected from $C(R^3)$ and N;

Z is selected from O, S, and $N(R^4)$;

$R^1$ is selected from halogen, —CN, —$OR^{10}$, —$SR^{10}$, —$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{6-10}$aryl, and $C_{1-9}$heteroaryl are optionally substituted with 1-5 $R^{5a}$ groups;

each $R^2$ is independently selected from halogen, —CN, —$OR^{10}$, —$SR^{10}$, —$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5b}$ groups;

$R^3$ is selected from hydrogen, halogen, —CN, $C_{1-6}$alkyl, $C_{1-6}$haloalkyl, $C_{3-6}$cycloalkyl, $C_{2-9}$heterocycloalkyl, —$OR^{10}$, —$SR^{10}$, —$N(R^{10})(R^{11})$, —$C(O)OR^{10}$, —$C(O)R^{13}$, —$C(O)N(R^{10})(R^{11})$, —$N(R^{12})C(O)R^{13}$, —$S(O)_2R^{13}$, and —$S(O)_2N(R^{10})(R^{11})$—, wherein $C_{1-6}$alkyl, $C_{3-6}$cycloalkyl, and $C_{2-9}$heterocycloalkyl are optionally substituted with 1-5 $R^{5c}$ groups;

$R^{3a}$ is selected from hydrogen, halogen, —CN, $C_{1-6}$alkyl, $C_{1-6}$haloalkyl, $C_{3-6}$cycloalkyl, $C_{2-9}$heterocycloalkyl, —$OR^{10}$, —$SR^{10}$, —$N(R^{10})(R^{11})$, —$C(O)OR^{10}$, —$C(O)R^{13}$, —$C(O)N(R^{10})(R^{11})$, —$N(R^{12})C(O)R^{13}$, —$S(O)_2R^{13}$, and —$S(O)_2N(R^{10})(R^{11})$—, wherein $C_{1-6}$alkyl, $C_{3-6}$cycloalkyl, and $C_{2-9}$heterocycloalkyl are optionally substituted with 1-5 $R^{5c}$ groups;

$R^4$ is selected from hydrogen, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, and —$C(O)R^{13}$, wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with 1-5 $R^{5d}$ groups;

each $R^{5a}$, $R^{5b}$, $R^{5c}$, and $R^{5d}$ is each independently selected from halogen, oxo, —CN, $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$ heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$S(=O)(=NH)N(R^{10})(R^{11})$, —$C(=NOR^{11})R^{13}$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl are optionally substituted with one, two, or three groups selected from halogen, —CN, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, —$OR^{10}$, and —$N(R^{10})(R^{11})$;

each $R^{10}$ is independently selected from hydrogen, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and n is 0, 1, 2, 3, or 4; and p is 0, 1, 2, 3, or 4.

In some embodiments is a compound of Formula (IVa) or (IVb), or a pharmaceutically acceptable salt or solvate thereof, wherein X is N. In some embodiments is a compound of Formula (IVa) or (IVb), or a pharmaceutically acceptable salt or solvate thereof, wherein X is $C(R^{3a})$ and $R^{3a}$ is selected from hydrogen, $C_{1-6}$alkyl $C_{1-6}$haloalkyl, —$SR^{10}$, —$N(R^{12})C(O)R^{13}$, and —$S(O)_2R^{13}$, wherein $C_{1-6}$alkyl and $C_{1-6}$haloalkyl are optionally substituted with 1-5 $R^5$, groups. In some embodiments is a compound of Formula (IVa) or (IVb), or a pharmaceutically acceptable salt or solvate thereof, wherein $R^{3a}$ is selected from hydrogen, unsubstituted $C_{1-6}$alkyl, unsubstituted $C_{1-6}$haloalkyl, —$SR^{10}$, —$N(H)C(O)R^{13}$, and —$S(O)_2R^{13}$, wherein $R^{13}$ is unsubstituted $C_{1-6}$alkyl. In some embodiments is a compound of Formula (IVa) or (IVb), or a pharmaceutically acceptable salt or solvate thereof, wherein $R^{3a}$ is selected from hydrogen, unsubstituted $C_{1-6}$alkyl, unsubstituted $C_{1-6}$haloalkyl, and —$N(R^{12})C(O)R^{13}$. In some embodiments is a compound of Formula (IVa) or (IVb), or a pharmaceutically acceptable salt or solvate thereof, wherein $R^{3a}$ is selected from hydrogen, unsubstituted $C_{1-6}$alkyl, unsubstituted $C_{1-6}$haloalkyl, and —$N(H)C(O)R^{13}$, wherein $R^{13}$ is unsubstituted $C_{1-6}$alkyl. In some embodiments is a compound of Formula (IVa) or (IVb), or a pharmaceutically acceptable salt or solvate thereof, wherein $R^{3a}$ is selected from hydrogen, unsubstituted $C_{1-6}$alkyl, and unsubstituted $C_{1-6}$haloalkyl. In some embodiments is a compound of Formula (IVa) or (IVb), or a pharmaceutically acceptable salt or solvate thereof, wherein $R^{3a}$ is selected from hydrogen and unsubstituted $C_{1-6}$alkyl. In some embodiments is a compound of Formula (IVa) or (IVb), or a pharmaceutically acceptable salt or solvate thereof, wherein $R^{3a}$ is hydrogen. In some embodiments is a compound of Formula (IVa) or (IVb), or a pharmaceutically acceptable salt or solvate thereof, wherein $R^{3a}$ is unsubstituted $C_{1-6}$alkyl. In some embodiments is a compound of Formula (IVa) or (IVb), or a pharmaceutically acceptable salt or solvate thereof, wherein $R^{3a}$ is —$CH_3$. In some embodiments is a compound of Formula (IVa) or (IVb), or a pharmaceutically acceptable salt or solvate thereof, wherein $R^{3a}$ is unsubstituted $C_{1-6}$haloalkyl. In some embodiments is a compound of Formula (IVa) or (IVb), or a pharmaceutically acceptable salt or solvate thereof, wherein $R^{3a}$ is —$CF_3$. In some embodiments is a compound of Formula (IVa) or (IVb), or a pharmaceutically acceptable salt or solvate thereof, wherein $R^{3a}$ is —$SR^{10}$. In some embodiments is a compound of Formula (IVa) or (IVb), or a pharmaceutically acceptable salt or solvate thereof, wherein $R^{3a}$ is —$SCH_3$. In some embodiments is a compound of Formula (IVa) or (IVb), or a pharmaceutically acceptable salt or solvate thereof, wherein $R^{3a}$ is —$S(O)_2R^{13}$. In some embodiments is a compound of Formula (IVa) or (IVb), or a pharmaceutically acceptable salt or solvate thereof, wherein $R^{3a}$ is —$S(O)_2CH_3$. In some embodiments is a compound of Formula (IVa) or (IVb), or a pharmaceutically acceptable salt or solvate thereof, wherein $R^{3a}$ is —$N(R^{12})C(O)R^{13}$. In some embodiments is a compound of Formula (IVa) or (IVb), or a pharmaceutically acceptable salt or solvate thereof, wherein $R^{3a}$ is —$N(H)C(O)CH_3$.

In some embodiments is a compound of Formula (IVa) or (IVb), or a pharmaceutically acceptable salt or solvate thereof, wherein Y is N. In some embodiments is a compound of Formula (IVa) or (IVb), or a pharmaceutically acceptable salt or solvate thereof, wherein Y is $C(R^3)$.

In some embodiments is a compound of Formula (IVa) or (IVb), or a pharmaceutically acceptable salt or solvate thereof, wherein Y is $C(R^3)$ and $R^3$ is selected from hydrogen, $C_{1-6}$alkyl $C_{1-6}$ haloalkyl, —$SR^{10}$, —$N(R^{12})C(O)R^{13}$, and —$S(O)_2R^{13}$, wherein $C_{1-6}$alkyl and $C_{1-6}$haloalkyl are optionally substituted with 1-5 $R^{5c}$ groups. In some embodiments is a compound of Formula (IVa) or (IVb), or a pharmaceutically acceptable salt or solvate thereof, wherein $R^3$ is selected from hydrogen, unsubstituted $C_{1-6}$alkyl, unsubstituted $C_{1-6}$haloalkyl, —$SR^{10}$, —$N(H)C(O)R^{13}$, and —$S(O)_2R^{13}$, wherein $R^{13}$ is unsubstituted $C_{1-6}$alkyl. In some embodiments is a compound of Formula (IVa) or (IVb), or a pharmaceutically acceptable salt or solvate thereof, wherein $R^3$ is selected from hydrogen, unsubstituted $C_{1-6}$alkyl, unsubstituted $C_{1-6}$haloalkyl, and —$N(R^{12})C(O)R^{13}$. In some embodiments is a compound of Formula (IVa) or (IVb), or a pharmaceutically acceptable salt or solvate thereof, wherein $R^3$ is selected from hydrogen, unsubstituted $C_{1-6}$alkyl, unsubstituted $C_{1-6}$haloalkyl, and —$N(H)C(O)R^{13}$, wherein $R^{13}$ is unsubstituted $C_{1-6}$alkyl. In some embodiments is a compound of Formula (IVa) or (IVb), or a pharmaceutically acceptable salt or solvate thereof, wherein $R^3$ is selected from hydrogen, unsubstituted $C_{1-6}$alkyl, and unsubstituted $C_{1-6}$haloalkyl. In some embodiments is a compound of Formula (IVa) or (IVb), or a pharmaceutically acceptable salt or solvate thereof, wherein $R^3$ is selected from hydrogen and unsubstituted $C_{1-6}$alkyl. In some embodiments is a compound of Formula (IVa) or (IVb), or a pharmaceutically acceptable salt or solvate thereof, wherein $R^3$ is hydrogen. In some embodiments is a compound of Formula (IVa) or (IVb), or a pharmaceutically acceptable salt or solvate thereof, wherein $R^3$ is unsubstituted $C_{1-6}$alkyl. In some embodiments is a compound of Formula (IVa) or (IVb), or a pharmaceutically acceptable salt or solvate thereof, wherein $R^3$ is —$CH_3$. In some embodiments is a compound of Formula (IVa) or (IVb), or a pharmaceutically acceptable salt or solvate thereof, wherein $R^3$ is unsubstituted $C_{1-6}$haloalkyl. In some embodiments is a compound of Formula (IVa) or (IVb), or a pharmaceutically acceptable salt or solvate thereof, wherein $R^3$ is —$CF_3$. In some embodiments is a compound of Formula (IVa) or (IVb), or a pharmaceutically acceptable salt or solvate thereof, wherein $R^3$ is —$SR^{10}$. In some embodiments is a compound of Formula (IVa) or (IVb), or a pharmaceutically acceptable salt or solvate thereof, wherein $R^3$ is —$SCH_3$. In some embodiments is a compound of Formula (IVa) or (IVb), or a pharmaceutically acceptable salt or solvate thereof, wherein $R^3$ is —$S(O)_2R^{13}$. In some embodiments is a compound of Formula (IVa) or (IVb), or a pharmaceutically acceptable salt or solvate thereof, wherein $R^3$ is —$S(O)_2CH_3$. In some embodiments is a compound of Formula (IVa) or (IVb), or a pharmaceutically acceptable salt or solvate thereof, wherein $R^3$ is —$N(R^{12})C(O)R^{13}$. In some embodiments is a compound of Formula (IVa) or (IVb), or a pharmaceutically acceptable salt or solvate thereof, wherein $R^3$ is —$N(H)C(O)CH_3$.

In some embodiments is a compound of Formula (IVa) or (IVb), or a pharmaceutically acceptable salt or solvate thereof, wherein Z is S. In some embodiments is a compound of Formula (IVa) or (IVb), or a pharmaceutically acceptable salt or solvate thereof, wherein Z is O. In some embodiments is a compound of Formula (IVa) or (IVb), or a pharmaceutically acceptable salt or solvate thereof, wherein Z is $N(R^4)$. In some embodiments is a compound of Formula (IVa) or (IVb), or a pharmaceutically acceptable salt or solvate thereof, wherein $R^4$ is selected from hydrogen, $C_{1-6}$alkyl $C_{1-6}$haloalkyl, and —$C(O)R^{13}$, wherein $C_{1-6}$alkyl and $C_{1-6}$haloalkyl are optionally substituted with 1-5 $R^{5d}$ groups. In some embodiments is a compound of Formula (IVa) or (IVb), or a pharmaceutically acceptable salt or solvate thereof, wherein $R^4$ is selected from hydrogen, unsubstituted $C_{1-6}$alkyl, and unsubstituted $C_{1-6}$haloalkyl. In some embodiments is a compound of Formula (IVa) or (IVb), or a pharmaceutically acceptable salt or solvate thereof, wherein $R^4$ is selected from hydrogen and unsubstituted $C_{1-6}$alkyl. In some embodiments is a compound of Formula (IVa) or (IVb), or a pharmaceutically acceptable salt or solvate thereof, wherein $R^4$ is hydrogen. In some embodiments is a compound of Formula (IVa) or (IVb), or a pharmaceutically acceptable salt or solvate thereof, wherein $R^4$ is unsubstituted $C_{1-6}$alkyl. In some embodiments is a compound of Formula (IVa) or (IVb), or a pharmaceutically acceptable salt or solvate thereof, wherein $R^4$ is —$CH_3$. In some embodiments is a compound of Formula (IVa) or (IVb), or a pharmaceutically acceptable salt or solvate thereof, wherein $R^4$ is unsubstituted $C_{1-6}$haloalkyl. In some embodiments is a compound of Formula (IVa) or (IVb), or a pharmaceutically acceptable salt or solvate thereof, wherein $R^4$ is —$CF_3$. In some embodiments is a compound of Formula (IVa) or (IVb), or a pharmaceutically acceptable salt or solvate thereof, wherein $R^4$ is —$CF_2H$.

In some embodiments, described herein is a compound of Formula (IVc), or a pharmaceutically acceptable salt or solvate thereof:

Formula (IVc)

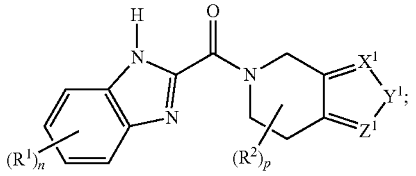

wherein:

$X^1$ is selected from $C(R^3)$ and N;

$Y^1$ is selected from O, S, and $N(R^4)$;

$Z^1$ is selected from $C(R^3)$ and N;

$R^1$ is selected from halogen, —CN, —$OR^{10}$, —$SR^{10}$, —$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{6-10}$aryl, and $C_{1-9}$heteroaryl are optionally substituted with 1-5 $R^{5a}$ groups;

each $R^2$ is independently selected from halogen, —CN, —$OR^{10}$, —$SR^{10}$, —$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5b}$ groups;

each $R^3$ is independently selected from hydrogen, halogen, —CN, $C_{1-6}$alkyl, $C_{1-6}$haloalkyl, $C_{3-6}$cycloalkyl, $C_{2-9}$heterocycloalkyl, —$OR^{10}$, —$SR^{10}$, —$N(R^{10})(R^{11})$, —$C(O)OR^{10}$, —$C(O)R^{13}$, —$C(O)N(R^{10})(R^{11})$, —$N(R^{12})C(O)R^{13}$, —$S(O)_2R^{13}$, and —$S(O)_2N(R^{10})(R^{11})$—, wherein $C_{1-6}$alkyl, $C_{3-6}$cycloalkyl, and $C_{2-9}$heterocycloalkyl are optionally substituted with 1-5 $R^{5c}$ groups;

$R^4$ is selected from hydrogen, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, and —C(O)$R^{13}$, wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with 1-5 $R^{5d}$ groups;

each $R^{5a}$, $R^{5b}$, $R^{5c}$, and $R^{5d}$ is each independently selected from halogen, oxo, —CN, $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$ heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —N($R^{10}$)($R^{11}$), —C(O)O$R^{10}$, —OC(O)N($R^{10}$)($R^{11}$), —N($R^{12}$)C(O)N($R^{10}$)($R^{11}$), —N($R^{12}$)C(O)O$R^{13}$, —N($R^{12}$)S$(O)_2R^{13}$, —C(O)$R^{13}$, —S(O)$R^{13}$, —OC(O)$R^{13}$, —C(O)N($R^{10}$)($R^{11}$), —C(O)C(O)N($R^{10}$)($R^{11}$), —N($R^{12}$)C(O)$R^{13}$, —S$(O)_2R^{13}$, —S$(O)_2$N($R^{10}$)($R^{11}$)—, —S(=O)(=NH)N($R^{10}$)($R^{11}$), —C(=NO$R^{11}$)$R^{13}$, —$CH_2$C(O)N($R^{10}$)($R^{11}$), —$CH_2$N($R^{12}$)C(O)$R^{13}$, —$CH_2$S$(O)_2R^{13}$, and —$CH_2$S$(O)_2$N($R^{10}$)($R^{11}$), wherein $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl are optionally substituted with one, two, or three groups selected from halogen, —CN, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, —$OR^{10}$, and —N($R^{10}$)($R^{11}$);

each $R^{10}$ is independently selected from hydrogen, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl; each $R^{12}$ is independently selected from hydrogen, $C_{1-6}$alkyl, and $C_{1-6}$haloalkyl; each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and n is 0, 1, 2, 3, or 4; and p is 0, 1, 2, 3, or 4.

In some embodiments is a compound of Formula (IVc), or a pharmaceutically acceptable salt or solvate thereof, wherein $X^1$ is N. In some embodiments is a compound of Formula (IVc), or a pharmaceutically acceptable salt or solvate thereof, wherein $X^1$ is C($R^3$).

In some embodiments is a compound of Formula (IVc), or a pharmaceutically acceptable salt or solvate thereof, wherein $Y^1$ is N. In some embodiments is a compound of Formula (IVc), or a pharmaceutically acceptable salt or solvate thereof, wherein $X^1$ is C($R^3$).

In some embodiments is a compound of Formula (IVc), or a pharmaceutically acceptable salt or solvate thereof, wherein $R^3$ is selected from hydrogen, $C_{1-6}$alkyl $C_{1-6}$haloalkyl, —$SR^{10}$, —N($R^{12}$)C(O)$R^{13}$, and —S$(O)_2R^{13}$, wherein $C_{1-6}$alkyl and $C_{1-6}$haloalkyl are optionally substituted with 1-5 $R^{5c}$ groups. In some embodiments is a compound of Formula (IVc), or a pharmaceutically acceptable salt or solvate thereof, wherein $R^3$ is selected from hydrogen, unsubstituted $C_{1-6}$alkyl, unsubstituted $C_{1-6}$haloalkyl, —$SR^{10}$, —N(H)C(O)$R^{13}$, and —S$(O)_2R^{13}$, wherein $R^{13}$ is unsubstituted $C_{1-6}$ alkyl. In some embodiments is a compound of Formula (IVc), or a pharmaceutically acceptable salt or solvate thereof, wherein $R^3$ is selected from hydrogen, unsubstituted $C_{1-6}$alkyl, unsubstituted $C_{1-6}$ haloalkyl, and —N($R^{12}$)C(O)$R^{13}$. In some embodiments is a compound of Formula (IVc), or a pharmaceutically acceptable salt or solvate thereof, wherein $R^3$ is selected from hydrogen, unsubstituted $C_{1-6}$alkyl, unsubstituted $C_{1-6}$haloalkyl, and —N(H)C(O)$R^{13}$, wherein $R^{13}$ is unsubstituted $C_{1-6}$alkyl. In some embodiments is a compound of Formula (IVc), or a pharmaceutically acceptable salt or solvate thereof, wherein $R^3$ is selected from hydrogen, unsubstituted $C_{1-6}$alkyl, and unsubstituted $C_{1-6}$haloalkyl. In some embodiments is a compound of Formula (IVc), or a pharmaceutically acceptable salt or solvate thereof, wherein $R^3$ is selected from hydrogen and unsubstituted $C_{1-6}$alkyl. In some embodiments is a compound of Formula (IVc), or a pharmaceutically acceptable salt or solvate thereof, wherein $R^3$ is hydrogen. In some embodiments is a compound of Formula (IVc), or a pharmaceutically acceptable salt or solvate thereof, wherein $R^3$ is unsubstituted $C_{1-6}$alkyl. In some embodiments is a compound of Formula (IVc), or a pharmaceutically acceptable salt or solvate thereof, wherein $R^3$ is —$CH_3$. In some embodiments is a compound of Formula (IVc), or a pharmaceutically acceptable salt or solvate thereof, wherein $R^3$ is unsubstituted $C_{1-6}$haloalkyl. In some embodiments is a compound of Formula (IVc), or a pharmaceutically acceptable salt or solvate thereof, wherein $R^3$ is —$CF_3$. In some embodiments is a compound of Formula (IVc), or a pharmaceutically acceptable salt or solvate thereof, wherein $R^3$ is —$SR^{10}$. In some embodiments is a compound of Formula (IVc), or a pharmaceutically acceptable salt or solvate thereof, wherein $R^3$ is —$SCH_3$. In some embodiments is a compound of Formula (IVc), or a pharmaceutically acceptable salt or solvate thereof, wherein $R^3$ is —S$(O)_2R^{13}$. In some embodiments is a compound of Formula (IVc), or a pharmaceutically acceptable salt or solvate thereof, wherein $R^3$ is —S$(O)_2CH_3$. In some embodiments is a compound of Formula (IVc), or a pharmaceutically acceptable salt or solvate thereof, wherein $R^3$ is —N($R^{12}$)C(O)$R^{13}$. In some embodiments is a compound of Formula (IVc), or a pharmaceutically acceptable salt or solvate thereof, wherein $R^3$ is —N(H)C(O)$CH_3$.

In some embodiments is a compound of Formula (IVc), or a pharmaceutically acceptable salt or solvate thereof, wherein $Z^1$ is S. In some embodiments is a compound of Formula (IVc), or a pharmaceutically acceptable salt or solvate thereof, wherein $Z^1$ is O. In some embodiments is a compound of Formula (IVc), or a pharmaceutically acceptable salt or solvate thereof, wherein $Z^1$ is N($R^4$). In some embodiments is a compound of Formula (IVc), or a pharmaceutically acceptable salt or solvate thereof, wherein $R^4$ is selected from hydrogen, $C_{1-6}$alkyl $C_{1-6}$haloalkyl, and —C(O)$R^{13}$ wherein $C_{1-6}$alkyl and $C_{1-6}$haloalkyl are optionally substituted with 1-5 $R^{5d}$ groups. In some embodiments is a compound of Formula (IVc), or a pharmaceutically acceptable salt or solvate thereof, wherein $R^4$ is selected from hydrogen, unsubstituted $C_{1-6}$alkyl, and unsubstituted $C_{1-6}$ haloalkyl. In some embodiments is a compound of Formula (IVc), or a pharmaceutically acceptable salt or solvate thereof, wherein $R^4$ is selected from hydrogen and unsubstituted $C_{1-6}$alkyl. In some embodiments is a compound of Formula (IVc), or a pharmaceutically acceptable salt or solvate thereof, wherein $R^4$ is hydrogen. In some embodiments is a compound of Formula (IVc), or a pharmaceutically acceptable salt or solvate thereof, wherein $R^4$ is unsubstituted $C_{1-6}$alkyl. In some embodiments is a compound of Formula (IVc), or a pharmaceutically acceptable salt or solvate thereof, wherein $R^4$ is —$CH_3$. In some embodiments is a compound of Formula (IVc), or a pharmaceutically acceptable salt or solvate thereof, wherein $R^4$ is unsubstituted $C_{1-6}$haloalkyl. In some embodiments is a compound of Formula (IVc), or a pharmaceutically acceptable salt or solvate thereof, wherein $R^4$ is —$CF_3$. In some embodiments is a compound of Formula (IVc), or a pharmaceutically acceptable salt or solvate thereof, wherein $R^4$ is —$CF_2H$.

In some embodiments is a compound of Formula (IVa), (IVb), or (IVc), or a pharmaceutically acceptable salt or solvate thereof, wherein each $R^2$ is independently selected from $C_{1-6}$alkyl, $C_{1-6}$haloalkyl, and $C_{3-6}$cycloalkyl, wherein $C_{1-6}$alkyl, $C_{1-6}$haloalkyl, and $C_{3-6}$cycloalkyl are optionally substituted with 1-5 $R^{5b}$ groups. In some embodiments is a compound of Formula (IVa), (IVb), or (IVc), or a pharmaceutically acceptable salt or solvate thereof, wherein each $R^2$ is $C_{1-6}$alkyl optionally substituted with 1-5 $R^{5b}$ groups. In some embodiments is a compound of Formula (IVa), (IVb), or (IVc), or a pharmaceutically acceptable salt or solvate thereof, wherein each $R^2$ is independently selected from unsubstituted $C_{1-6}$alkyl and unsubstituted $C_{1-6}$haloalkyl. In some embodiments is a compound of Formula (IVa), (IVb), or (IVc), or a pharmaceutically acceptable salt or solvate thereof, wherein each $R^2$ is independently selected from unsubstituted $C_{1-6}$alkyl. In some embodiments is a compound of Formula (IVa), (IVb), or (IVc), or a pharmaceutically acceptable salt or solvate thereof, wherein each $R^2$ is independently selected from —$CH_3$. In some embodiments is a compound of Formula (IVa), (IVb), or (IVc), or a pharmaceutically acceptable salt or solvate thereof, wherein each $R^2$ is independently selected from unsubstituted $C_{1-6}$haloalkyl. In some embodiments is a compound of Formula (IVa), (IVb), or (IVc), or a pharmaceutically acceptable salt or solvate thereof, wherein each $R^2$ is —$CF_2H$. In some embodiments is a compound of Formula (IVa), (IVb), or (IVc), or a pharmaceutically acceptable salt or solvate thereof, wherein each $R^2$ is —$CH_2F$. In some embodiments is a compound of Formula (IVa), (IVb), or (IVc), or a pharmaceutically acceptable salt or solvate thereof, wherein each $R^2$ is —$CF_3$.

In some embodiments is a compound of Formula (IVa), (IVb), or (IVc), or a pharmaceutically acceptable salt or solvate thereof, wherein p is 1, 2, or 3. In some embodiments is a compound of Formula (IVa), (IVb), or (IVc), or a pharmaceutically acceptable salt or solvate thereof, wherein p is 1. In some embodiments is a compound of Formula (IVa), (IVb), or (IVc), or a pharmaceutically acceptable salt or solvate thereof, wherein p is 2. In some embodiments is a compound of Formula (IVa), (IVb), or (IVc), or a pharmaceutically acceptable salt or solvate thereof, wherein p is 3. In some embodiments is a compound of Formula (IVa), (IVb), or (IVc), or a pharmaceutically acceptable salt or solvate thereof, wherein p is 4.

In some embodiments is a compound of Formula (IVa), (IVb), or (IVc), or a pharmaceutically acceptable salt or solvate thereof, wherein p is 0.

In some embodiments is a compound of Formula (IVa), (IVb), or (IVc), or a pharmaceutically acceptable salt or solvate thereof, wherein each $R^1$ is independently selected from halogen, —CN, —$OR^{10}$, $C_{1-6}$alkyl, and $C_{1-6}$haloalkyl, wherein $C_{1-6}$alkyl and $C_{1-6}$haloalkyl are optionally substituted with 1-5 $R^{5a}$ groups. In some embodiments is a compound of Formula (IVa), (IVb), or (IVc), or a pharmaceutically acceptable salt or solvate thereof, wherein each $R^1$ is independently selected from halogen, —CN, —$OR^{10}$, unsubstituted $C_{1-6}$alkyl, and unsubstituted $C_{1-6}$haloalkyl. In some embodiments is a compound of Formula (IVa), (IVb), or (IVc), or a pharmaceutically acceptable salt or solvate thereof, wherein each $R^1$ is independently selected from halogen and unsubstituted $C_{1-6}$ alkyl. In some embodiments is a compound of Formula (IVa), (IVb), or (IVc), or a pharmaceutically acceptable salt or solvate thereof, wherein each $R^1$ is independently selected from halogen, —CN, —OH, —$OCH_3$, —$CH_3$, and —$CF_3$. In some embodiments is a compound of Formula (IVa), (IVb), or (IVc), or a pharmaceutically acceptable salt or solvate thereof, wherein each $R^1$ is independently selected from halogen and —$CH_3$. In some embodiments is a compound of Formula (IVa), (IVb), or (IVc), or a pharmaceutically acceptable salt or solvate thereof, wherein each $R^1$ is independently selected from halogen. In some embodiments is a compound of Formula (IVa), (IVb), or (IVc), or a pharmaceutically acceptable salt or solvate thereof, wherein each $R^1$ is independently selected from $C_{1-6}$alkyl. In some embodiments is a compound of Formula (IVa), (IVb), or (IVc), or a pharmaceutically acceptable salt or solvate thereof, wherein each $R^1$ is —$CH_3$.

In some embodiments is a compound of Formula (IVa), (IVb), or (IVc), or a pharmaceutically acceptable salt or solvate thereof, wherein n is 1, 2, or 3. In some embodiments is a compound of Formula (IVa), (IVb), or (IVc), or a pharmaceutically acceptable salt or solvate thereof, wherein n is 1. In some embodiments is a compound of Formula (IVa), (IVb), or (IVc), or a pharmaceutically acceptable salt or solvate thereof, wherein n is 2. In some embodiments is a compound of Formula (IVa), (IVb), or (IVc), or a pharmaceutically acceptable salt or solvate thereof, wherein n is 3. In some embodiments is a compound of Formula (IVa), (IVb), or (IVc), or a pharmaceutically acceptable salt or solvate thereof, wherein n is 4.

In some embodiments is a compound of Formula (IVa), (IVb), or (IVc), or a pharmaceutically acceptable salt or solvate thereof, wherein n is 0.

In some embodiments, described herein is a compound of Formula (V), or a pharmaceutically acceptable salt or solvate thereof:

Formula (V)

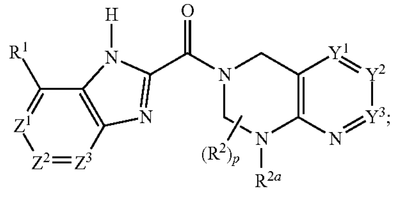

wherein:

$Y^1$, $Y^2$, and $Y^3$ are each independently $C(R^3)$ or N, wherein at least one of $Y^2$ and $Y^3$ is $C(R^3)$;

$Z^1$, $Z^2$, and $Z^3$ are each independently $C(R^4)$ or N, wherein at least one of $Z^1$, $Z^2$, and $Z^3$ is $C(R^4)$;

$R^1$ is selected from hydrogen, halogen, —CN, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —OC(O)$R^{13}$, —C(O)N($R^{10}$)($R^{11}$), —N($R^{12}$)C(O)$R^{13}$, —S(O)$_2R^{13}$, —S(O)$_2$N($R^{10}$)($R^{11}$)—, —S(=O)(=NH)N($R^{10}$)($R^{11}$), $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5a}$ groups;

each $R^2$ is independently selected from halogen, —CN, —OR$^{10}$, —SR$^{10}$, —N($R^{10}$)($R^{11}$), $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5b}$ groups;

$R^{2a}$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —C(O)OR$^{10}$, —C(O)$R^{13}$, —S(O)$R^{13}$, —C(O)N($R^{10}$)($R^{11}$), and —S(O)$_2R^{13}$, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5b}$ groups;

each $R^3$ is independently selected from hydrogen, halogen, —CN, —SR$^{10}$, —N($R^{10}$)($R^{11}$), $C_{1-6}$alkyl, $C_{1-6}$haloalkyl, $C_{1-6}$alkoxy, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{1-6}$alkoxy, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5c}$ groups;

each $R^4$ is independently selected from hydrogen, halogen, —CN, —OR$^{10}$, —SR$^{10}$, —N($R^{10}$)($R^{11}$), $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5d}$ groups;

each $R^{5a}$, $R^{5b}$, $R^{5c}$, and $R^{5d}$ is each independently selected from halogen, oxo, —CN, $C_{1-6}$alkyl, $C_{1-6}$haloalkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —CH$_2$—$C_{1-9}$heteroaryl, —OR$^{10}$, —SR$^{10}$, —N($R^{10}$)($R^{11}$), —C(O)OR$^{10}$, —OC(O)N($R^{10}$)($R^{11}$), —N($R^{12}$)C(O)N($R^{10}$)($R^{11}$), —N($R^{12}$)C(O)OR$^{13}$, —N($R^{12}$)S(O)$_2R^{13}$, —C(O)$R^{13}$, —S(O)$R^{13}$, —OC(O)$R^{13}$, —C(O)N($R^{10}$)($R^{11}$), —C(O)C(O)N($R^{10}$)($R^{11}$), —N($R^{12}$)C(O)$R^{13}$, —S(O)$_2R^{13}$, —S(O)$_2$N($R^{10}$)($R^{11}$)—, —S(=O)(=NH)N($R^{10}$)($R^{11}$), —C(=NOR$^{11}$)$R^{13}$, —CH$_2$C(O)N($R^{10}$)($R^{11}$), —CH$_2$N($R^{12}$)C(O)$R^{13}$, —CH$_2$S(O)$_2R^{13}$, and —CH$_2$S(O)$_2$N($R^{10}$)($R^{11}$), wherein $C_{1-6}$alkyl, $C_{1-6}$haloalkyl, $C_{2-6}$alkenyl, $C_{2-6}$alkynyl, $C_{3-6}$cycloalkyl, —CH$_2$—$C_{3-6}$ cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —CH$_2$—$C_{1-9}$heteroaryl are optionally substituted with one, two, or three groups selected from halogen, —CN, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, —OR$^{10}$, and —N($R^{10}$)($R^{11}$);

each $R^{10}$ is independently selected from hydrogen, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and p is 0, 1, 2, 3, or 4.

In some embodiments is a compound of Formula (V), or a pharmaceutically acceptable salt or solvate thereof, wherein $Y^1$, $Y^2$, and $Y^3$ are each C($R^3$). In some embodiments is a compound of Formula (V), or a pharmaceutically acceptable salt or solvate thereof, wherein $Y^1$, $Y^2$, and $Y^3$ are each independently C($R^3$) or N, wherein at least one of $Y^2$ and $Y^3$ is C($R^3$). In some embodiments is a compound of Formula (V), or a pharmaceutically acceptable salt or solvate thereof, wherein $Y^1$ is N, and $Y^2$ and $Y^3$ are C($R^3$). In some embodiments is a compound of Formula (V), or a pharmaceutically acceptable salt or solvate thereof, wherein $Y^2$ is N, and $Y^1$ and $Y^3$ are C($R^3$). In some embodiments is a compound of Formula (V), or a pharmaceutically acceptable salt or solvate thereof, wherein $Y^3$ is N, and $Y^1$ and $Y^2$ are C($R^3$).

In some embodiments is a compound of Formula (V), or a pharmaceutically acceptable salt or solvate thereof, having the structure of Formula (Va):

Formula (Va)

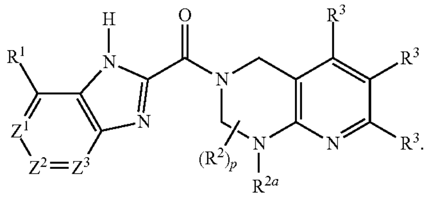

In some embodiments is a compound of Formula (V) or (Va), or a pharmaceutically acceptable salt or solvate thereof, wherein $R^{2a}$ is selected from hydrogen, $C_{1-6}$alkyl, and —S(O)$_2R^{13}$ wherein $C_{1-6}$alkyl is optionally substituted with 1-5 $R^{5b}$ groups. In some embodiments is a compound of Formula (V) or (Va), or a pharmaceutically acceptable salt or solvate thereof, wherein $R^{2a}$ is selected from hydrogen, unsubstituted $C_{1-6}$alkyl, and —S(O)$_2R^{13}$, wherein $R^{13}$ is unsubstituted $C_{1-6}$alkyl. In some embodiments is a compound of Formula (V) or (Va), or a pharmaceutically acceptable salt or solvate thereof, wherein $R^{2a}$ is selected from hydrogen. In some embodiments is a compound of Formula (V) or (Va), or a pharmaceutically acceptable salt or solvate thereof, wherein $R^{2a}$ is unsubstituted $C_{1-6}$alkyl. In some embodiments is a compound of Formula (V) or (Va), or a pharmaceutically acceptable salt or solvate thereof, wherein $R^{2a}$ is —CH$_3$. In some embodiments is a compound of Formula (V) or (Va), or a pharmaceutically acceptable salt or solvate thereof, wherein $R^{2a}$ is —$S(O)_2R^{13}$, wherein $R^{13}$ is unsubstituted $C_{1-6}$alkyl. In some embodiments is a compound of Formula (V) or (Va), or a pharmaceutically acceptable salt or solvate thereof, wherein $R^{2a}$ is —$S(O)_2CH_3$.

In some embodiments is a compound of Formula (V) or (Va), or a pharmaceutically acceptable salt or solvate thereof, wherein each $R^3$ is independently selected from hydrogen, halogen, $C_{1-6}$alkyl, and $C_{1-6}$haloalkyl, wherein $C_{1-6}$alkyl and $C_{1-6}$haloalkyl are optionally substituted with 1-5 $R^{5c}$ groups. In some embodiments is a compound of Formula (V) or (Va), or a pharmaceutically acceptable salt or solvate thereof, wherein each $R^3$ is independently selected from hydrogen, halogen, unsubstituted $C_{1-6}$alkyl, and unsubstituted $C_{1-6}$haloalkyl. In some embodiments is a compound of Formula (V) or (Va), or a pharmaceutically acceptable salt or solvate thereof, wherein each $R^3$ is independently selected from hydrogen, halogen, and unsubstituted $C_{1-6}$alkyl. In some embodiments is a compound of Formula (V) or (Va), or a pharmaceutically acceptable salt or solvate thereof, wherein each $R^3$ is independently selected from hydrogen and halogen. In some embodiments is a compound of Formula (V) or (Va), or a pharmaceutically acceptable salt or solvate thereof, wherein each $R^3$ is independently selected from hydrogen and unsubstituted $C_{1-6}$alkyl. In some embodiments is a compound of Formula (V) or (Va), or a pharmaceutically acceptable salt or solvate thereof, wherein each $R^3$ is hydrogen.

In some embodiments is a compound of Formula (V) or (Va), or a pharmaceutically acceptable salt or solvate thereof, wherein $R^1$ is selected from halogen, —CN, —$OR^{10}$, $C_{1-6}$alkyl, and $C_{1-6}$haloalkyl, wherein $C_{1-6}$alkyl and $C_{1-6}$haloalkyl are optionally substituted with 1-5 $R^{5a}$ groups. In some embodiments is a compound of Formula (V) or (Va), or a pharmaceutically acceptable salt or solvate thereof, wherein $R^1$ is selected from halogen, —CN, —$OR^{10}$, unsubstituted $C_{1-6}$alkyl, and unsubstituted $C_{1-6}$haloalkyl. In some embodiments is a compound of Formula (V) or (Va), or a pharmaceutically acceptable salt or solvate thereof, wherein $R^1$ is selected from halogen, —CN, —OH, —$OCH_3$, —$CH_3$, and —$CF_3$. In some embodiments is a compound of Formula (V) or (Va), or a pharmaceutically acceptable salt or solvate thereof, wherein $R^1$ is halogen. In some embodiments is a compound of Formula (V) or (Va), or a pharmaceutically acceptable salt or solvate thereof, wherein $R^1$ is —CN. In some embodiments is a compound of Formula (V) or (Va), or a pharmaceutically acceptable salt or solvate thereof, wherein $R^1$ is —OH. In some embodiments is a compound of Formula (V) or (Va), or a pharmaceutically acceptable salt or solvate thereof, wherein $R^1$ is —$OCH_3$. In some embodiments is a compound of Formula (V) or (Va), or a pharmaceutically acceptable salt or solvate thereof, wherein $R^1$ is —$CH_3$. In some embodiments is a compound of Formula (V) or (Va), or a pharmaceutically acceptable salt or solvate thereof, wherein $R^1$ is $CF_3$.

In some embodiments is a compound of Formula (V) or (Va), or a pharmaceutically acceptable salt or solvate thereof, wherein $Z^1$, $Z^2$, and $Z^3$ are each $C(R^4)$. In some embodiments is a compound of Formula (V) or (Va), or a pharmaceutically acceptable salt or solvate thereof, wherein $Z^1$ is N, and $Z^2$ and $Z^3$ are $C(R^4)$. In some embodiments is a compound of Formula (V) or (Va), or a pharmaceutically acceptable salt or solvate thereof, wherein $Z^2$ is N, and $Z^1$ and $Z^3$ are $C(R^4)$. In some embodiments is a compound of Formula (V) or (Va), or a pharmaceutically acceptable salt or solvate thereof, wherein $Z^3$ is N, and $Z^1$ and $Z^2$ are $C(R^4)$. In some embodiments is a compound of Formula (V) or (Va), or a pharmaceutically acceptable salt or solvate thereof, wherein $Z^2$ is $C(R^4)$, and $Z^1$ and $Z^3$ are N. In some embodiments is a compound of Formula (V) or (Va), or a pharmaceutically acceptable salt or solvate thereof, wherein $Z^3$ is $C(R^4)$, and $Z^1$ and $Z^2$ are N. In some embodiments is a compound of Formula (V) or (Va), or a pharmaceutically acceptable salt or solvate thereof, wherein $Z^1$ is $C(R^4)$, and $Z^2$ and $Z^3$ are N.

In some embodiments is a compound of Formula (V) or (Va), or a pharmaceutically acceptable salt or solvate thereof, wherein each $R^4$ is independently selected from hydrogen, halogen, —CN, —$OR^{10}$, $C_{1-6}$alkyl, $C_{1-6}$haloalkyl, and $C_{3-6}$cycloalkyl, wherein $C_{1-6}$alkyl, $C_{1-6}$haloalkyl, and $C_{3-6}$cycloalkyl are optionally substituted with 1-5 $R^{5d}$ groups. In some embodiments is a compound of Formula (V) or (Va), or a pharmaceutically acceptable salt or solvate thereof, wherein each $R^4$ is independently selected from hydrogen, halogen, —CN, —$OR^{10}$, unsubstituted $C_{1-6}$alkyl, and unsubstituted $C_{1-6}$haloalkyl. In some embodiments is a compound of Formula (V) or (Va), or a pharmaceutically acceptable salt or solvate thereof, wherein each $R^4$ is independently selected from hydrogen, halogen, unsubstituted $C_{1-6}$alkyl, and unsubstituted $C_{1-6}$haloalkyl. In some embodiments is a compound of Formula (V) or (Va), or a pharmaceutically acceptable salt or solvate thereof, wherein each $R^4$ is independently selected from hydrogen, halogen, and unsubstituted $C_{1-6}$alkyl. In some embodiments is a compound of Formula (V) or (Va), or a pharmaceutically acceptable salt or solvate thereof, wherein each $R^4$ is independently selected from hydrogen and halogen. In some embodiments is a compound of Formula (V) or (Va), or a pharmaceutically acceptable salt or solvate thereof, wherein each $R^4$ is hydrogen.

In some embodiments is a compound of Formula (V) or (Va), or a pharmaceutically acceptable salt or solvate thereof, wherein each $R^2$ is independently selected from $C_{1-6}$alkyl, $C_{1-6}$haloalkyl, and $C_{3-6}$cycloalkyl, wherein $C_{1-6}$alkyl, $C_{1-6}$haloalkyl, and $C_{3-6}$cycloalkyl are optionally substituted with 1-5 $R^{5b}$ groups. In some embodiments is a compound of Formula (V) or (Va), or a pharmaceutically acceptable salt or solvate thereof, wherein each $R^2$ is $C_{1-6}$alkyl optionally substituted with 1-5 $R^{5b}$ groups. In some embodiments is a compound of Formula (V) or (Va), or a pharmaceutically acceptable salt or solvate thereof, wherein each $R^2$ is independently selected from unsubstituted $C_{1-6}$alkyl and unsubstituted $C_{1-6}$haloalkyl. In some embodiments is a compound of Formula (V) or (Va), or a pharmaceutically acceptable salt or solvate thereof, wherein each $R^2$ is independently selected from unsubstituted $C_{1-6}$alkyl. In some embodiments is a compound of Formula (V) or (Va), or a pharmaceutically acceptable salt or solvate thereof, wherein each $R^2$ is independently selected from —$CH_3$. In some embodiments is a compound of Formula (V) or (Va), or a pharmaceutically acceptable salt or solvate thereof, wherein each $R^2$ is independently selected from unsubstituted $C_{1-6}$haloalkyl. In some embodiments is a compound of Formula (V) or (Va), or a pharmaceutically acceptable salt or solvate thereof, wherein each $R^2$ is —$CF_2H$. In some embodiments is a compound of Formula (V) or (Va), or a pharmaceutically acceptable salt or solvate thereof, wherein each $R^2$ is —$CH_2F$. In some embodiments is a compound of Formula (V) or (Va), or a pharmaceutically acceptable salt or solvate thereof, wherein each $R^2$ is —$CF_3$.

In some embodiments is a compound of Formula (V) or (Va), or a pharmaceutically acceptable salt or solvate thereof, wherein p is 1, 2, or 3. In some embodiments is a compound of Formula (V) or (Va), or a pharmaceutically acceptable salt or solvate thereof, wherein p is 1. In some embodiments is a compound of Formula (V) or (Va), or a pharmaceutically acceptable salt or solvate thereof, wherein p is 2. In some embodiments is a compound of Formula (V) or (Va), or a pharmaceutically acceptable salt or solvate thereof, wherein p is 3. In some embodiments is a compound of Formula (V) or (Va), or a pharmaceutically acceptable salt or solvate thereof, wherein p is 4.

In some embodiments is a compound of Formula (V) or (Va), or a pharmaceutically acceptable salt or solvate thereof, wherein p is 0.

In some embodiments, described herein is a compound of Formula (VI), or a pharmaceutically acceptable salt or solvate thereof:

Formula (VI)

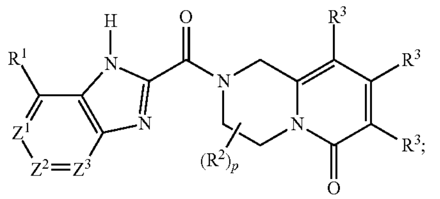

wherein:

- $Z^1$, $Z^2$, and $Z^3$ are each independently $C(R^4)$ or N, wherein at least one of $Z^1$, $Z^2$, and $Z^3$ is $C(R^4)$;
- $R^1$ is selected from hydrogen, halogen, —CN, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$N(R^{12})C(O)R^{13}$, —$S(O)_2R^{13}$, —$S(O)_2N(R^{10})(R^{11})$—, —S(=O)(=NH)$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5a}$ groups;
- each $R^2$ is independently selected from halogen, —CN, —$OR^{10}$, —$SR^{10}$, —$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5b}$ groups;
- each $R^3$ is independently selected from hydrogen, halogen, —CN, —$SR^{10}$, —$N(R^{10})(R^{11})$, $C_{1-6}$alkyl, $C_{1-6}$haloalkyl, $C_{1-6}$alkoxy, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{1-6}$alkoxy, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5c}$ groups;
- each $R^4$ is independently selected from hydrogen, halogen, —CN, —$OR^{10}$, —$SR^{10}$, —$N(R^{10})(R^{11})$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with 1-5 $R^{5d}$ groups;
- each $R^{5a}$, $R^{5b}$, $R^{5c}$, and $R^{5d}$ is each independently selected from halogen, oxo, —CN, $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$ heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —S(=O)(=NH)$N(R^{10})(R^{11})$, —C(=$NOR^{11}$)$R^{13}$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{1-6}$haloalkyl, $C_{2-6}$alkenyl, $C_{2-6}$alkynyl, $C_{3-6}$cycloalkyl, —$CH_2$—$C_{3-6}$ cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl are optionally substituted with one, two, or three groups selected from halogen, —CN, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, —$OR^{10}$, and —$N(R^{10})(R^{11})$;
- each $R^{10}$ is independently selected from hydrogen, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;
- each $R^{11}$ is independently selected from hydrogen, $C_{1-6}$alkyl, and $C_{1-6}$haloalkyl;
- each $R^{12}$ is independently selected from hydrogen, $C_{1-6}$alkyl, and $C_{1-6}$haloalkyl;
- each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and
- p is 0, 1, 2, 3, or 4.

In some embodiments is a compound of Formula (VI), or a pharmaceutically acceptable salt or solvate thereof, wherein each $R^3$ is independently selected from hydrogen, halogen, $C_{1-6}$alkyl, and $C_{1-6}$haloalkyl, wherein $C_{1-6}$alkyl and $C_{1-6}$haloalkyl are optionally substituted with 1-5 $R^{5c}$ groups. In some embodiments is a compound of Formula (VI), or a pharmaceutically acceptable salt or solvate thereof, wherein each $R^3$ is independently selected from hydrogen, halogen, unsubstituted $C_{1-6}$alkyl, and unsubstituted $C_{1-6}$haloalkyl. In some embodiments is a compound of Formula (VI), or a pharmaceutically acceptable salt or solvate thereof, wherein each $R^3$ is independently selected from hydrogen, halogen, and unsubstituted $C_{1-6}$alkyl. In some embodiments is a compound of Formula (VI), or a pharmaceutically acceptable salt or solvate thereof, wherein each $R^3$ is independently selected from hydrogen and halogen. In some embodiments is a compound of Formula (VI), or a pharmaceutically acceptable salt or solvate thereof, wherein each $R^3$ is independently selected from hydrogen and unsubstituted $C_{1-6}$alkyl. In some embodiments is a compound of Formula (VI), or a pharmaceutically acceptable salt or solvate thereof, wherein each $R^3$ is hydrogen.

In some embodiments is a compound of Formula (VI), or a pharmaceutically acceptable salt or solvate thereof, wherein $R^1$ is selected from halogen, —CN, —$OR^{10}$, $C_{1-6}$alkyl, and $C_{1-6}$ haloalkyl, wherein $C_{1-6}$alkyl and $C_{1-6}$haloalkyl are optionally substituted with 1-5 $R^{5a}$ groups. In some embodiments is a compound of Formula (VI), or a pharmaceutically acceptable salt or solvate thereof, wherein $R^1$ is selected from halogen, —CN, —$OR^{10}$, unsubstituted $C_{1-6}$alkyl, and unsubstituted $C_{1-6}$haloalkyl. In some embodiments is a compound of Formula (VI), or a pharmaceutically acceptable salt or solvate thereof, wherein $R^1$ is selected from halogen, —CN, —OH, —$OCH_3$, —$CH_3$, and —$CF_3$. In some embodiments is a compound of Formula (VI), or a pharmaceutically acceptable salt or solvate thereof, wherein $R^1$ is halogen. In some embodiments is a compound of Formula (VI), or a pharmaceutically acceptable salt or solvate thereof, wherein $R^1$ is —CN. In some embodiments is a compound of Formula (VI), or a pharmaceutically acceptable salt or solvate thereof, wherein $R^1$ is —OH. In some embodiments is a compound of Formula (VI), or a pharmaceutically acceptable salt or solvate thereof, wherein $R^1$ is —$OCH_3$. In some embodiments is a compound of Formula (VI), or a pharmaceutically acceptable salt or solvate thereof, wherein $R^1$ is —$CH_3$. In some embodiments is a compound of Formula (VI), or a pharmaceutically acceptable salt or solvate thereof, wherein $R^1$ is $CF_3$.

In some embodiments is a compound of Formula (VI), or a pharmaceutically acceptable salt or solvate thereof, wherein $Z^1$, $Z^2$, and $Z^3$ are each $C(R^4)$. In some embodiments is a compound of Formula (VI), or a pharmaceutically acceptable salt or solvate thereof, wherein $Z^1$ is N, and $Z^2$ and $Z^3$ are $C(R^4)$. In some embodiments is a compound of Formula (VI), or a pharmaceutically acceptable salt or solvate thereof, wherein $Z^2$ is N, and $Z^1$ and $Z^3$ are $C(R^4)$. In some embodiments is a compound of Formula (VI), or a pharmaceutically acceptable salt or solvate thereof, wherein $Z^3$ is N, and $Z^1$ and $Z^2$ are $C(R^4)$. In some embodiments is a compound of Formula (VI), or a pharmaceutically acceptable salt or solvate thereof, wherein $Z^2$ is $C(R^4)$, and $Z^1$ and $Z^3$ are N. In some embodiments is a compound of Formula (VI), or a pharmaceutically acceptable salt or solvate thereof, wherein $Z^3$ is $C(R^4)$, and $Z^1$ and $Z^2$ are N. In some embodiments is a compound of Formula (VI), or a pharmaceutically acceptable salt or solvate thereof, wherein $Z^1$ is $C(R^4)$, and $Z^2$ and $Z^3$ are N.

In some embodiments is a compound of Formula (VI), or a pharmaceutically acceptable salt or solvate thereof, wherein each $R^4$ is independently selected from hydrogen, halogen, —CN, —$OR^{10}$, $C_{1-6}$alkyl, $C_{1-6}$haloalkyl, and $C_{3-6}$cycloalkyl, wherein $C_{1-6}$alkyl, $C_{1-6}$haloalkyl, and $C_{3-6}$cycloalkyl are optionally substituted with 1-5 $R^{5d}$ groups. In some embodiments is a compound of Formula (VI), or a pharmaceutically acceptable salt or solvate thereof, wherein each $R^4$ is independently selected from hydrogen, halogen, —CN, —$OR^{10}$, unsubstituted $C_{1-6}$alkyl, and unsubstituted $C_{1-6}$haloalkyl. In some embodiments is a compound of Formula (VI), or a pharmaceutically acceptable salt or solvate thereof, wherein each $R^4$ is independently selected from hydrogen, halogen, unsubstituted $C_{1-6}$alkyl, and unsubstituted $C_{1-6}$haloalkyl. In some embodiments is a compound of Formula (VI), or a pharmaceutically acceptable salt or solvate thereof, wherein each $R^4$ is independently selected from hydrogen, halogen, and unsubstituted $C_{1-6}$alkyl. In some embodiments is a compound of Formula (VI), or a pharmaceutically acceptable salt or solvate thereof, wherein each $R^4$ is independently selected from hydrogen and halogen. In some embodiments is a compound of Formula (VI), or a pharmaceutically acceptable salt or solvate thereof, wherein each $R^4$ is hydrogen.

In some embodiments is a compound of Formula (VI), or a pharmaceutically acceptable salt or solvate thereof, wherein each $R^2$ is independently selected from $C_{1-6}$alkyl, $C_{1-6}$haloalkyl, and $C_{3-6}$cycloalkyl, wherein $C_{1-6}$alkyl, $C_{1-6}$haloalkyl, and $C_{3-6}$cycloalkyl are optionally substituted with 1-5 $R^{5b}$ groups. In some embodiments is a compound of Formula (VI), or a pharmaceutically acceptable salt or solvate thereof, wherein each $R^2$ is $C_{1-6}$alkyl optionally substituted with 1-5 $R^{51}$ groups. In some embodiments is a compound of Formula (VI), or a pharmaceutically acceptable salt or solvate thereof, wherein each $R^2$ is independently selected from unsubstituted $C_{1-6}$alkyl and unsubstituted $C_{1-6}$haloalkyl. In some embodiments is a compound of Formula (VI), or a pharmaceutically acceptable salt or solvate thereof, wherein each $R^2$ is independently selected from unsubstituted $C_{1-6}$alkyl. In some embodiments is a compound of Formula (VI), or a pharmaceutically acceptable salt or solvate thereof, wherein each $R^2$ is independently selected from —$CH_3$. In some embodiments is a compound of Formula (VI), or a pharmaceutically acceptable salt or solvate thereof, wherein each $R^2$ is independently selected from unsubstituted $C_{1-6}$haloalkyl. In some embodiments is a compound of Formula (VI), or a pharmaceutically acceptable salt or solvate thereof, wherein each $R^2$ is —$CF_2H$. In some embodiments is a compound of Formula (VI), or a pharmaceutically acceptable salt or solvate thereof, wherein each $R^2$ is —$CH_2F$. In some embodiments is a compound of Formula (VI), or a pharmaceutically acceptable salt or solvate thereof, wherein each $R^2$ is —$CF_3$.

In some embodiments is a compound of Formula (VI), or a pharmaceutically acceptable salt or solvate thereof, wherein p is 1, 2, or 3. In some embodiments is a compound of Formula (VI), or a pharmaceutically acceptable salt or solvate thereof, wherein p is 1. In some embodiments is a compound of Formula (VI), or a pharmaceutically acceptable salt or solvate thereof, wherein p is 2. In some embodiments is a compound of Formula (VI), or a pharmaceutically acceptable salt or solvate thereof, wherein p is 3. In some embodiments is a compound of Formula (VI), or a pharmaceutically acceptable salt or solvate thereof, wherein p is 4.

In some embodiments is a compound of Formula (VI), or a pharmaceutically acceptable salt or solvate thereof, wherein p is 0.

Any combination of the groups described above for the various variables is contemplated herein. Throughout the specification, groups and substituents thereof are chosen by one skilled in the field to provide stable moieties and compounds.

In some embodiments is a compound, or a pharmaceutically acceptable salt or solvate thereof, selected from:

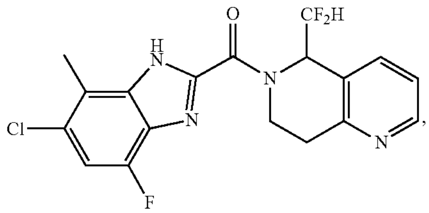
,

-continued
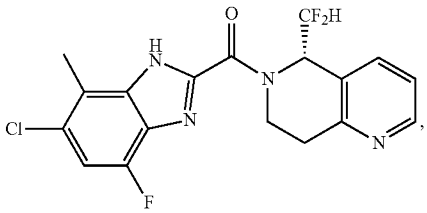,
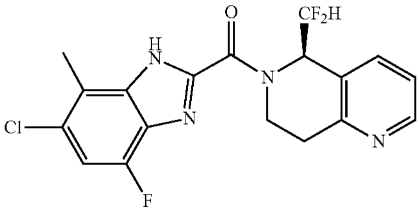,
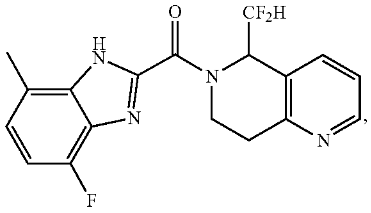,
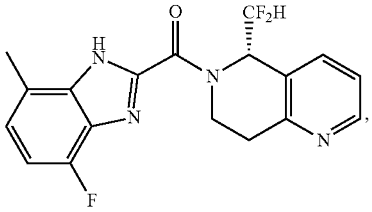,
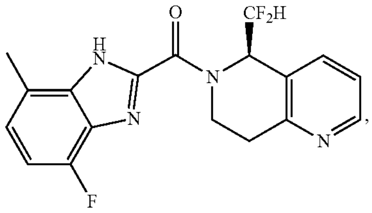,
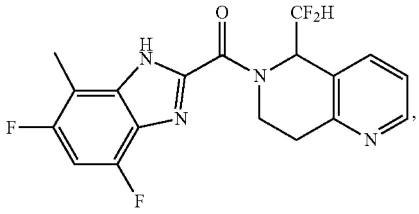,
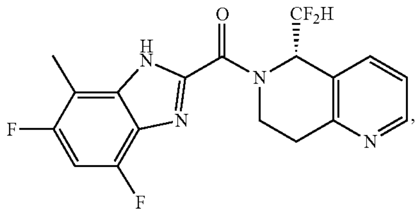,
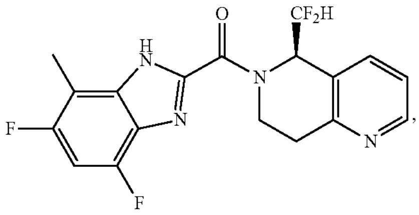,
-continued
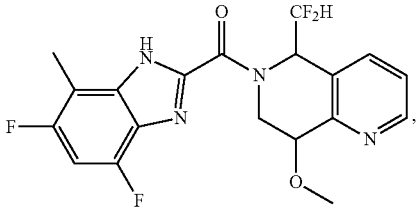,
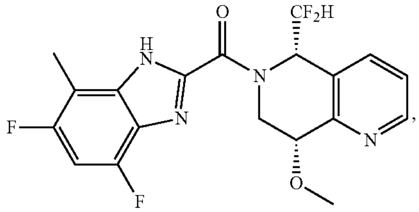,
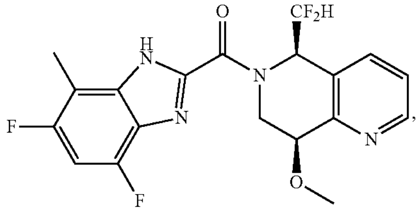,
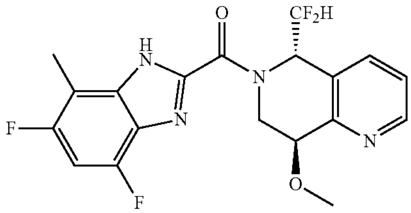,
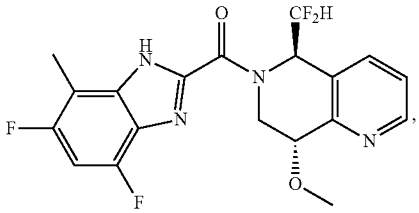,
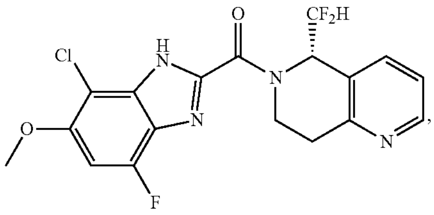,
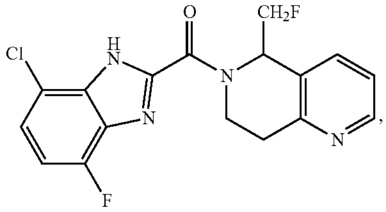,
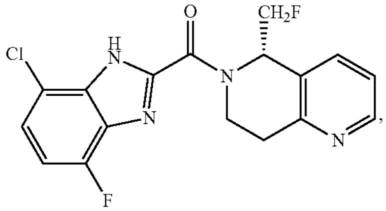, -continued
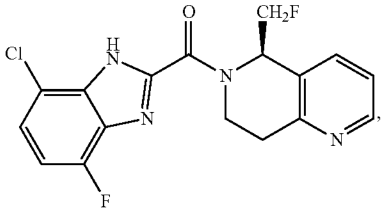
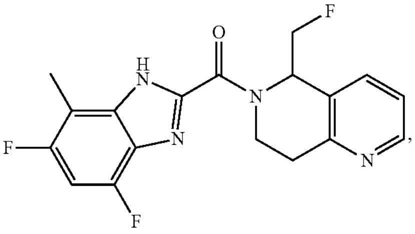
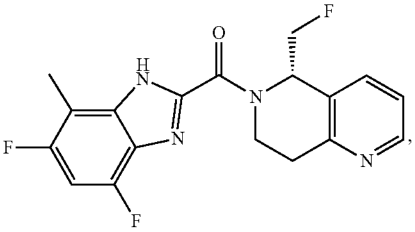
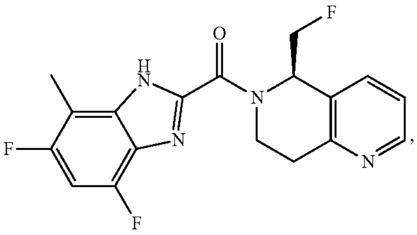
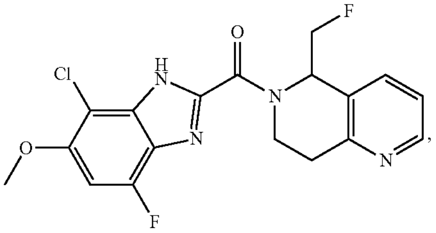
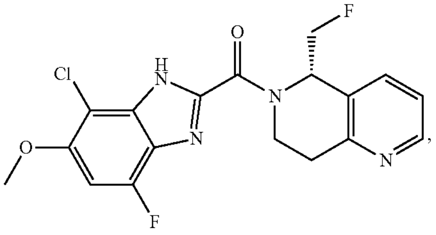
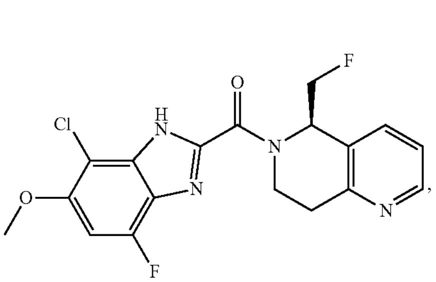
-continued
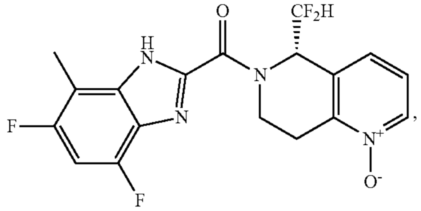
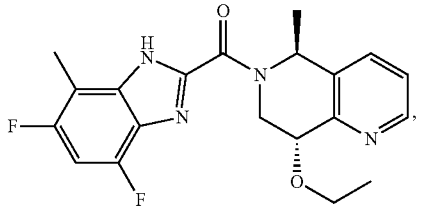
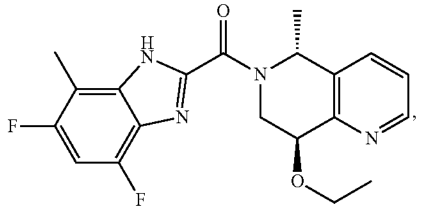
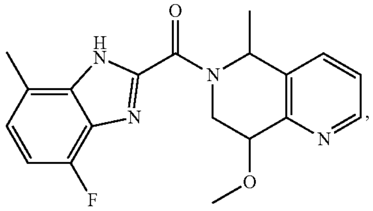
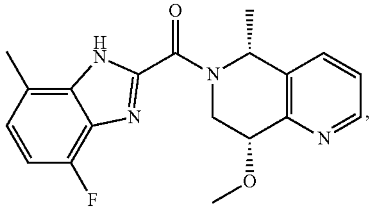
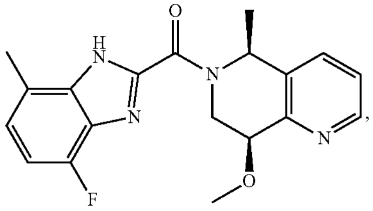
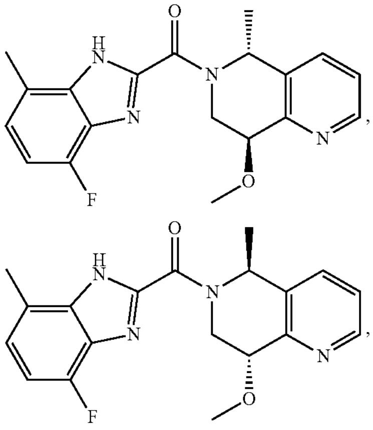

-continued
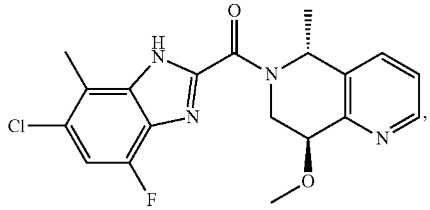
,
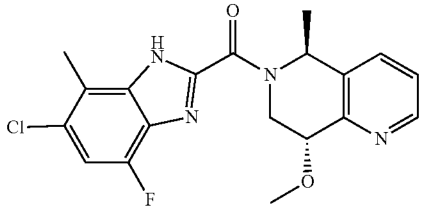
,
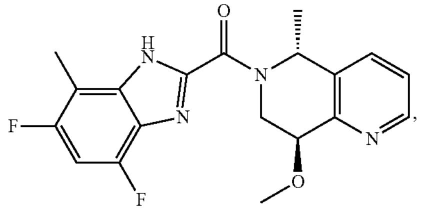
,
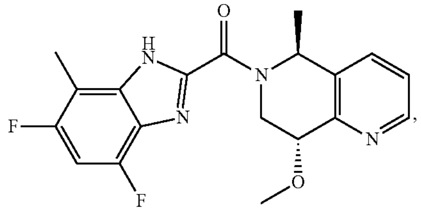
,
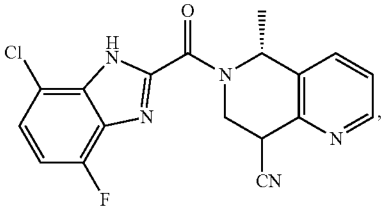
,
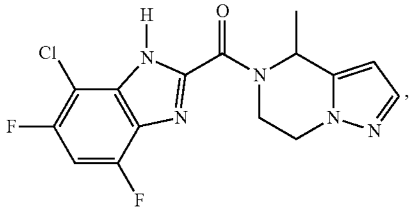
,
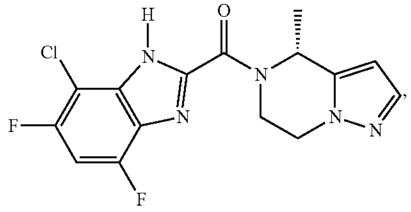
,
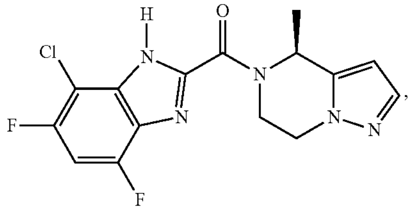
,
-continued
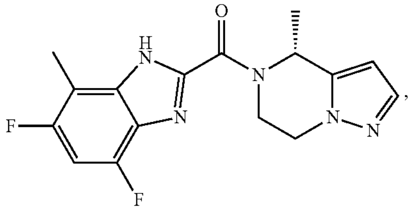
,
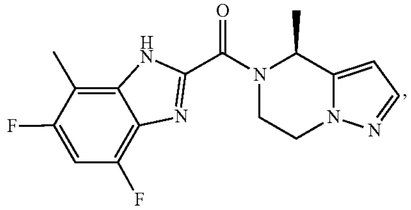
,
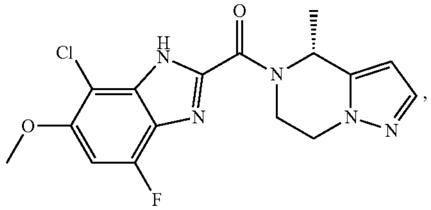
,
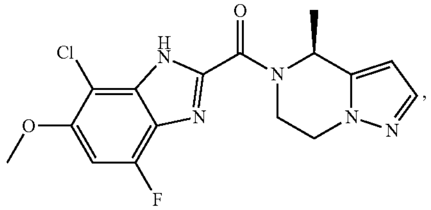
,
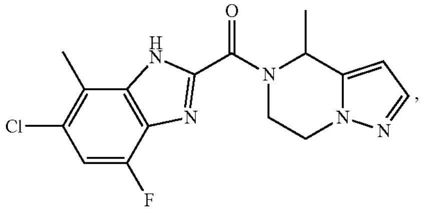
,
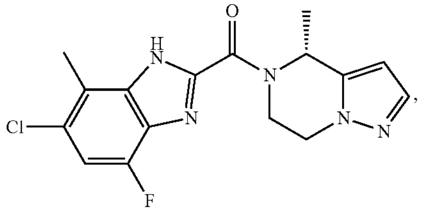
,
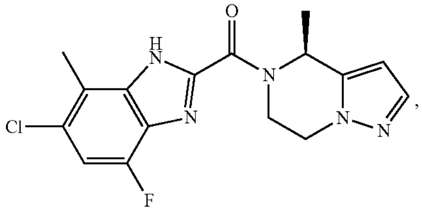
,
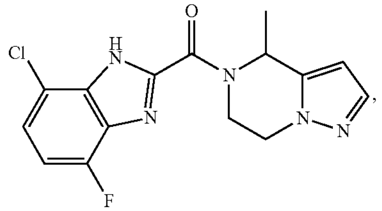
, -continued
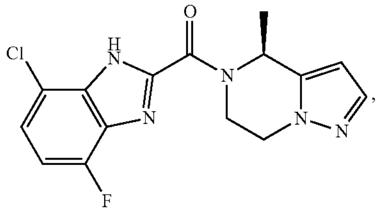
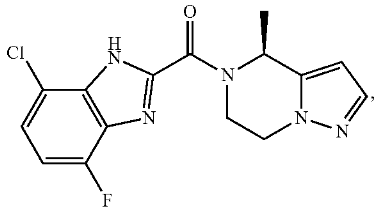
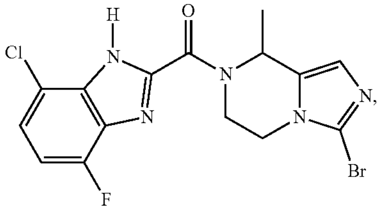
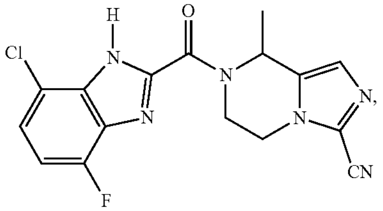
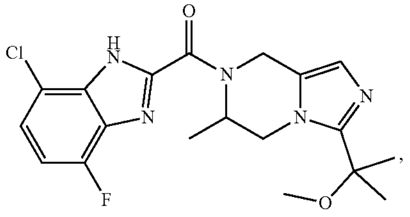
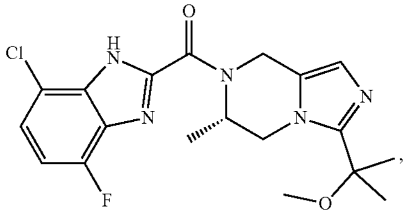
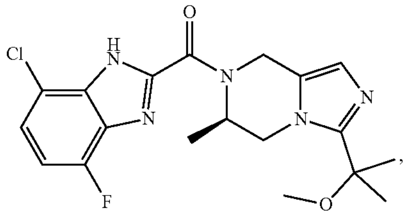
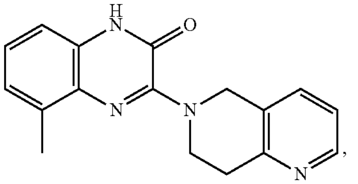
-continued
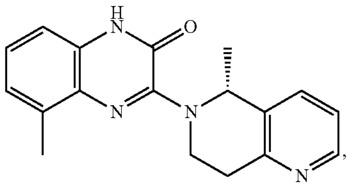
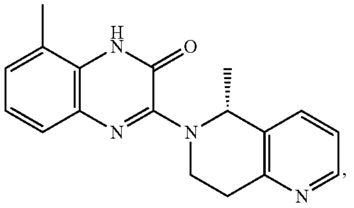
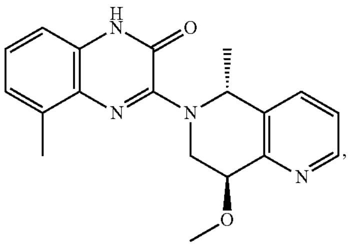
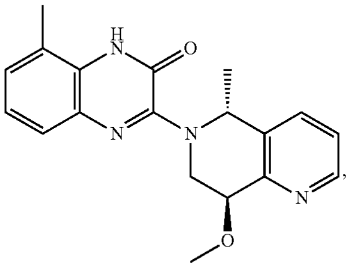
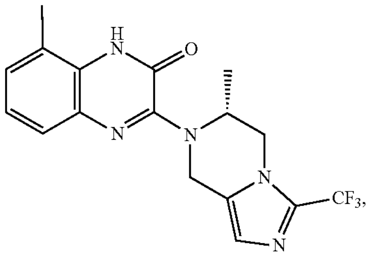
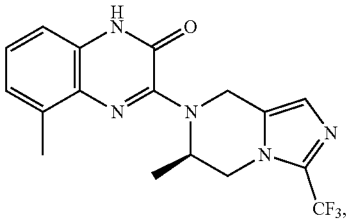
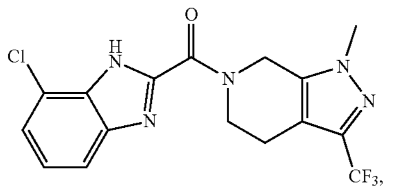

-continued
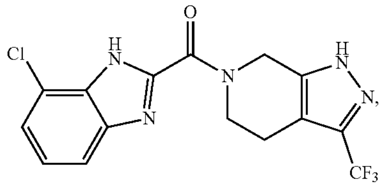
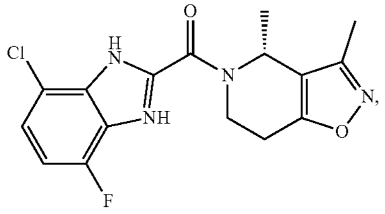
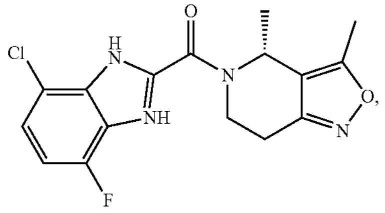
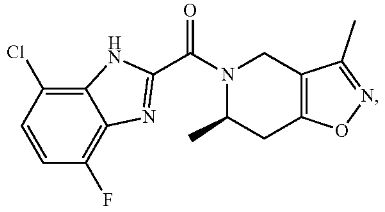
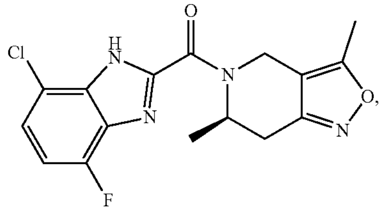
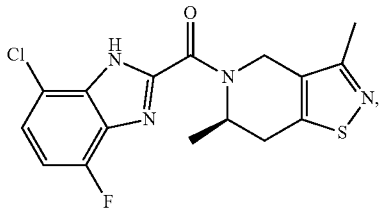
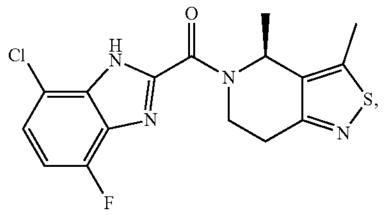
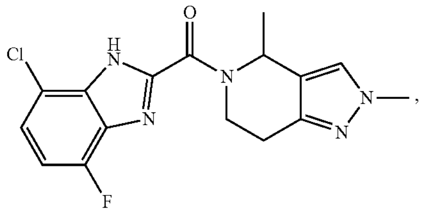
-continued
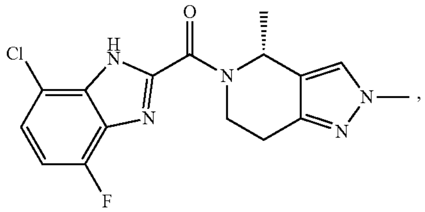
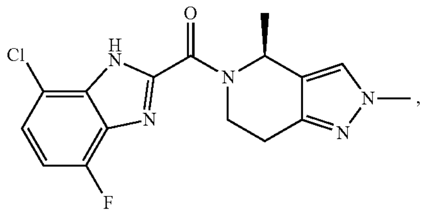
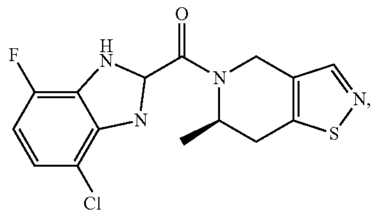
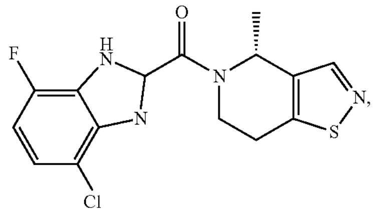
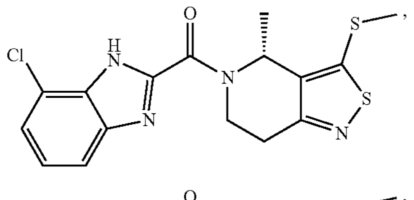
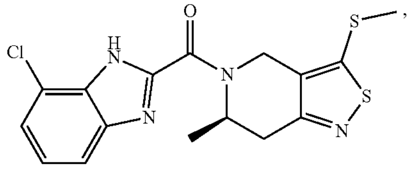
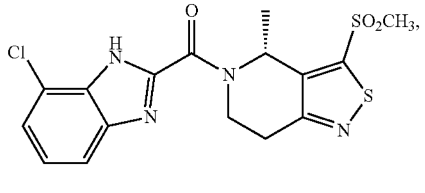
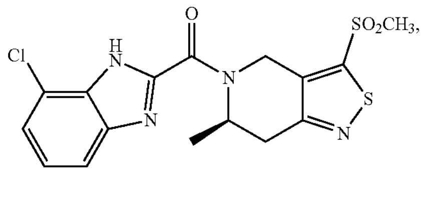

-continued
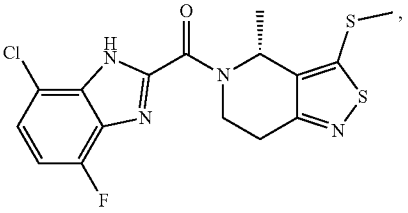
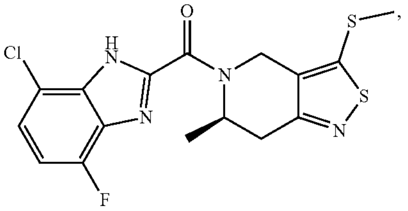
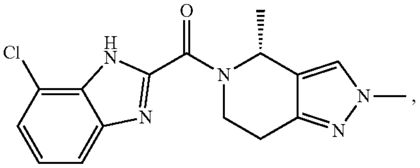
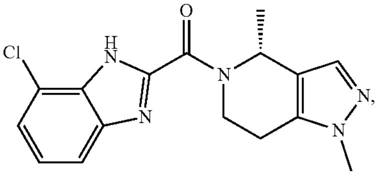
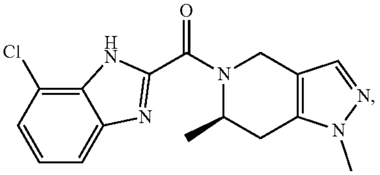
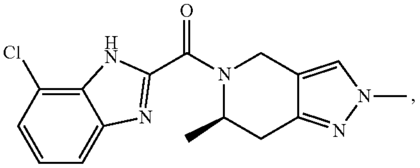
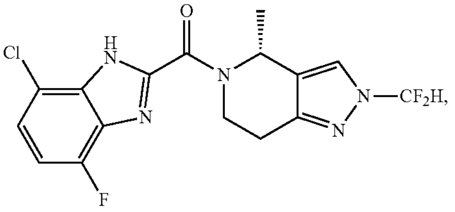
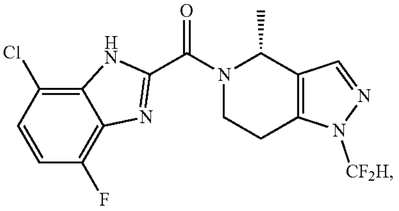
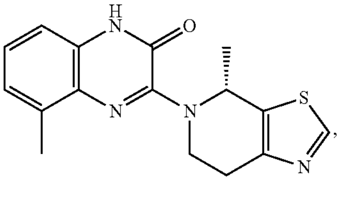
-continued
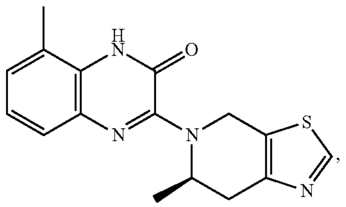
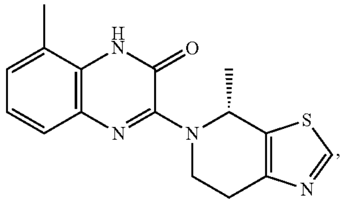
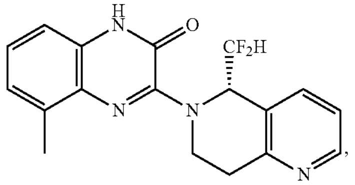
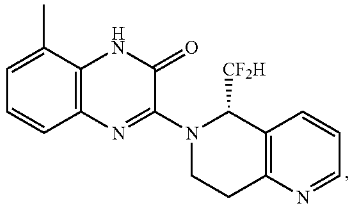
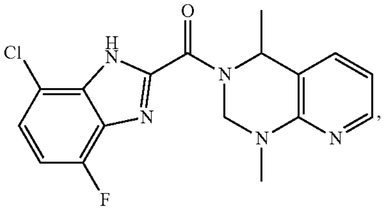
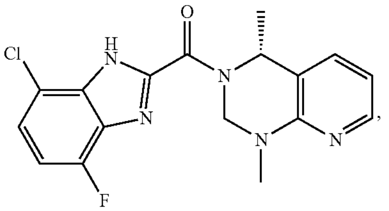
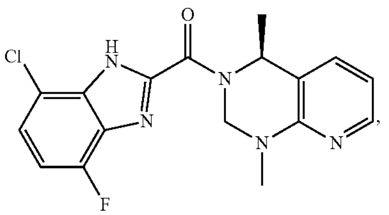
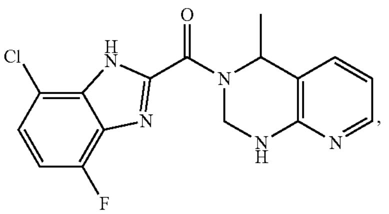

-continued

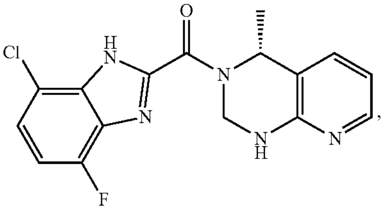

,

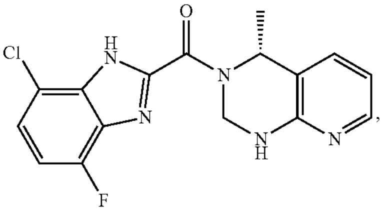

,

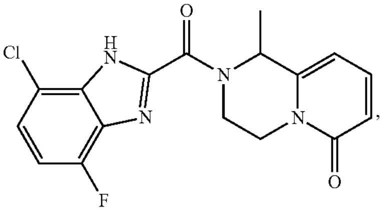

,

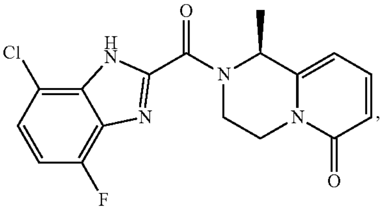

,

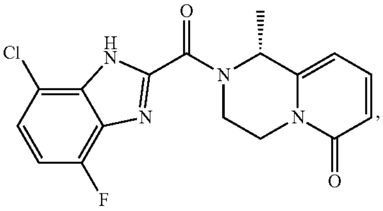

,

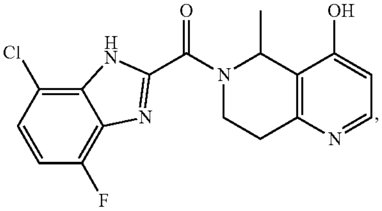

,

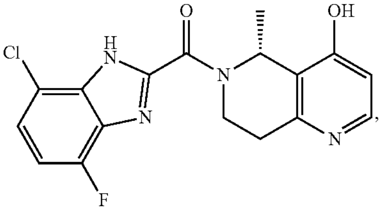

,

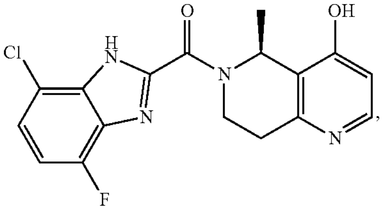

, and

-continued

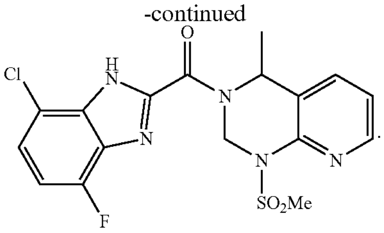

.

In some embodiments, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible, and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound described herein with an acid to provide a "pharmaceutically acceptable acid addition salt." In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid;

formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt.

In some embodiments, pharmaceutically acceptable salts are obtained by reacting a compound described herein with a base to provide a "pharmaceutically acceptable base addition salt."

In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of isolating or purifying the compound with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms of the compounds described herein is replaced with deuterium.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley and Sons, Inc., 1981. In some embodiments, stereoisomers are obtained by stereoselective synthesis.

A tautomer refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. The compounds presented herein include all tautomeric forms as well as the appropriate mixtures thereof.

Synthesis of Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, $6^{th}$ Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In some embodiments, compounds are prepared as described in the Examples.

Methods of Treatment

In some embodiments, described herein is a method of treating retinal degeneration in a subject in need thereof comprising administering to the patient a compound of Formula (I), (Ia), (II), (IIa), (II), (IIIa), (IV), or (IVa), or a pharmaceutically acceptable salt or solvate thereof. In some embodiments is a method of treating autosomal dominant retinitis pigmentosa (adRP) in a subject in need thereof comprising administering to the patient a compound of Formula (I), (Ia), (II), (IIa), (II), (IIIa), (IV), or (IVa), or a pharmaceutically acceptable salt or solvate thereof.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Administration of the compounds and compositions described herein can be affected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the installation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

In some embodiments, a compound disclosed herein is formulated in such a manner that delivery of the compound to a particular region of the gastrointestinal tract is achieved. For example, a compound disclosed herein is formulated for oral delivery with bioadhesive polymers, pH-sensitive coatings, time dependent, biodegradable polymers, microflora activated systems, and the like, in order to effect delivering of the compound to a particular region of the gastrointestinal tract.

In some embodiments, a compound disclosed herein is formulated to provide a controlled release of the compound. Controlled release refers to the release of the compound described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

Approaches to deliver the intact therapeutic compound to the particular regions of the gastrointestinal tract (e.g. such as the colon), include:

(i) Coating with polymers: The intact molecule can be delivered to the colon without absorbing at the upper part of the intestine by coating of the drug molecule with the suitable polymers, which degrade only in the colon.

(ii) Coating with pH-sensitive polymers: The majority of enteric and colon targeted delivery systems are based on the coating of tablets or pellets, which are filled into conventional hard gelatin capsules. Most commonly used pH-dependent coating polymers are methacrylic acid copolymers, commonly known as Eudragit® S, more specifically Eudragit® L and Eudragit® S. Eudragit® L100 and S 100 are copolymers of methacrylic acid and methyl methacrylate.

(iii) Coating with biodegradable polymers;

(iv) Embedding in matrices;

(v) Embedding in biodegradable matrices and hydrogels;
(vi) Embedding in pH-sensitive matrices;
(vii) Timed release systems;
(viii) Redox-sensitive polymers;
(ix) Bioadhesive systems;
(x) Coating with microparticles;
(xi) Osmotic controlled drug delivery;

Another approach towards colon-targeted drug delivery or controlled-release systems includes embedding the drug in polymer matrices to trap it and release it in the colon. These matrices can be pH-sensitive or biodegradable. Matrix-Based Systems, such as multi-matrix (MMX)-based delayed-release tablets, ensure the drug release in the colon.

Additional pharmaceutical approaches to targeted delivery of therapeutics to particular regions of the gastrointestinal tract are known. Chourasia M K, Jain S K, Pharmaceutical approaches to colon targeted drug delivery systems, J Pharm Sci. 2003 January-April; 6(1):33-66. Patel M, Shah T, Amin A. Therapeutic opportunities in colon-specific drug-delivery systems Crit Rev Ther Drug Carrier Syst. 2007; 24(2):147-202. Kumar P, Mishra B. Colon targeted drug delivery systems—an overview. Curr Drug Deliv. 2008 July; 5(3):186-98. Van den Mooter G. Colon drug delivery. Expert Opin Drug Deliv. 2006 January; 3(1):111-25. Seth Amidon, Jack E. Brown, and Vivek S. Dave, Colon-Targeted Oral Drug Delivery Systems: Design Trends and Approaches, AAPS PharmSciTech. 2015 August; 16(4): 731-741.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from administration of a small molecule corrector of rhodopsin. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments, wherein the patient's condition does not improve, upon the doctor's discretion, the compounds are administered chronically, that is, for an extended period of time, including throughout the duration of the patient's life in order to ameliorate or otherwise control or limit the symptoms of the patient's disease or condition.

In certain embodiments, wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

Examples

The following examples are provided for illustrative purposes only and not to limit the scope of the claims provided herein.

As used above, and throughout the description of the invention, the following abbreviations, unless otherwise indicated, shall be understood to have the following meanings:

| | |
|---|---|
| ACN, MeCN | Acetonitrile |
| AcOH | Acetic acid |
| AmB | Ammonium bicarbonate |
| AmF | Ammonium formate |
| aq. | aqueous |
| anh. | anhydrous |
| Boc | tert-butoxy carbonyl |
| BOP-Cl | Bis(2-oxo-3-oxazolidinyl)phosphinic chloride |
| CPME | Cyclopropylmethyl ether |
| CV | Column Volume |
| DCE | 1,2-dichloroethane |
| DCM | Dichloromethane |
| DMAc | Dimethylacetamide |
| DIPEA, iPrNEt$_2$ | N,N-Diisopropyl ethylamine |
| DME | 1,2-Dimethoxyethane |
| DMF | Dimethylformamide |
| DMSO | Dimethylsulfoxide |
| eq(s). | equivalent(s) |
| EtOAc | Ethyl acetate |
| Et$_3$N | Triethylamine |
| FA | Formic Acid |
| g | gram(s) |
| h | hour(s) |
| HATU | Hexafluorophosphate Azabenzotriazole Tetramethyl Uronium |
| HBTU | Hexafluorophosphate Benzotriazole Tetramethyl Uronium |
| $K_2CO_3$ | Potassium carbonate |
| LCMS | liquid chromatography mass spectrometry |
| MeOH | Methanol |
| mg | milligram(s) |
| min | Minute(s) |
| mL | milliliter(s) |
| NaOH | Sodium hydroxide |
| $Na_2SO_4$ | Sodium sulfate |
| n-BuLi | n-Butyllithium |
| NMP | N-Methyl-2-pyrrolidone |
| NMR | Nuclear magnetic resonance |
| Pd$_2$(dba)$_3$ | Tris(dibenzylideneacetone)dipalladium(0) |
| Pd(dppf)Cl$_2$ | 1,1'-Bis(diphenylphosphino)ferrocene dichloropalladium (II) |
| Ph | phenyl |
| PPA | Polyphosphoric acid |
| PTSA | p-Toluenesulfonic acid |
| r.t. or RT | Room temperature |
| tBuXPhos | 2-Di-tert-butylphosphino-2',4',6'-triisopropylbiphenyl |
| TFA | Trifluoroacetic acid |
| THF | Tetrahydrofuran |
| THP | 3,4-Dihydro-2H-pyran |
| Ts | Toluenesulfonyl |
| UPLC-MS | Ultra-performance liquid chromatography-mass spectrometry |

6-Chloro-4-fluoro-7-methyl-1H-benzo[d]imidazole-2-carboxylic acid

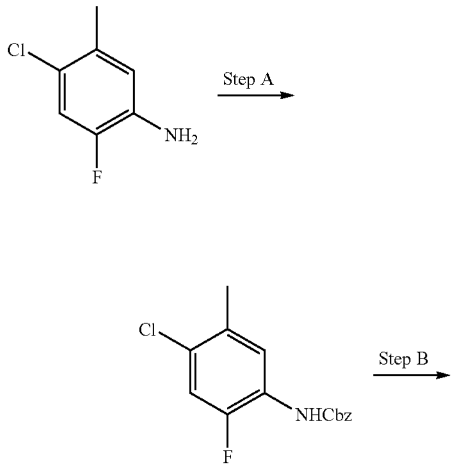

-continued

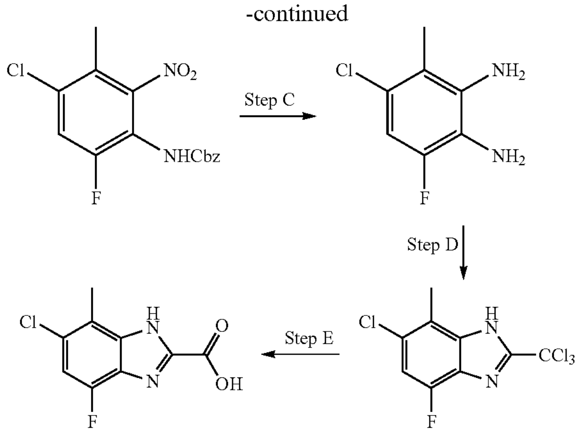

Step A: 4-Chloro-2-fluoro-5-methyl aniline (2.01 g, 12.3 mmol) was dissolved in TIFF (40.0 mL) at room temperature under nitrogen. $K_2CO_3$ (3.04 g, 22.0 mmol) and then benzyl chloroformate (2.99 mL, 20.1 mmol) were added. The flask was equipped with a condenser and the mixture was heated at 70° C. for 3 h and allowed to cool down to room temperature. The mixture was adsorbed on silica gel to be purified by flash chromatography on silica gel using a solution of DCM in heptanes (0 to 10000 gradient) to give benzyl (4-chloro-2-fluoro-5-methylphenyl)carbamate. $^1H$ NMR (400 MHz, $CDCl_3$) δ 8.01 (d, J=7.8 Hz, 1H), 7.44-7.32 (m, 5H), 7.08 (d, J=10.6 Hz, 1H), 6.80 (br s, 1H), 5.21 (s, 2H), 2.33 (s, 3H).

Step B: Benzyl (4-chloro-2-fluoro-5-methylphenyl)carbamate (3.58 g, 12.2 mmol) and ammonium cerium(IV) nitrate (9.77 g, 17.6 mmol) were combined, and benzyl (4-chloro-2-fluoro-5-methylphenyl)carbamate (3.58 g, 12.2 mmol) was added as a solution in MeCN (25.0 mL) and DCE (25.0 mL) at r.t. The flask was equipped with a condenser and the mixture was heated at 90° C. overnight. The mixture was filtered on celite using EtOAc. The filtrate was adsorbed on silica to be purified by flash chromatography on silica gel using a solution of EtOAc in heptanes (0 to 100% gradient) to give benzyl (4-chloro-6-fluoro-3-methyl-2-nitrophenyl)carbamate. $^1H$ NMR (400 MHz, $CDCl_3$) δ 7.44-7.27 (m, 6H), 6.42 (br s, 1H), 5.18 (s, 2H), 2.34 (d, J=1.2 Hz, 3H).

Step C: Benzyl (4-chloro-6-fluoro-3-methyl-2-nitrophenyl)carbamate (2.12 g, 6.26 mmol) was dissolved in MeOH (40.0 mL). The vessel purged with nitrogen/vacuum cycle 3×, and palladium on carbon (10%, contains 67% water, 333 mg, 0.313 mmol) was added. Hydrogen was introduced via vacuum cycle, and the solution was stirred for two hours. The hydrogen atmosphere was removed, the solution filtered over celite, and concentrated onto silica. The solids were purified by silica chromatography (0 to 100% EtOAc in heptanes gradient over 12 CV, with 3% IPA throughout, 40 g column) and the relevant fractions concentrated to afford 4-chloro-6-fluoro-3-methylbenzene-1,2-diamine (865 mg, 79%).

Step D: 4-Chloro-6-fluoro-3-methylbenzene-1,2-diamine (500 mg, 2.86 mmol) was dissolved in AcOH (25.0 mL), and methyl 2,2,2-trichloroacetamide (541 mg, 3.01 mmol) was added. The solution was stirred for 2 hours, after which the crude reaction was concentrated and then diluted with EtOAc and water. The organic layer was concentrated onto silica, and purified by normal phase chromatography (0 to 100% EtOAc in heptanes over 10 CV, 40 g column). The relevant fractions were concentrated to afford 6-chloro-4-fluoro-7-methyl-2-(trichloromethyl)-1H-benzo[d]imidazole (712 mg, 82%) that was carried forward without further purification. LC-MS: 302.5 $[M+H]^+$.

Step E: 6-Chloro-4-fluoro-7-methyl-2-(trichloromethyl)-1H-benzo[d]imidazole (356 mg, 1.18 mmol) was sonicated in sodium hydroxide (1M, 5.89 mL, 5.89 mmol) for 10 minutes, and the pH adjusted to ~3 with citric acid solution. The solids were removed by filtration, and the filtrate was extracted with EtOAc. The aqueous layer was loaded directly onto a C18 column for purification (0 to 15% ACN in 10 mM AmF solution over 10 CV, 40 g column) and the relevant fractions were lyophilized to afford 6-chloro-4-fluoro-7-methyl-2-(trichloromethyl)-1H-benzo[d]imidazole (42.0 mg, 16%). LC-MS: 228.6 $[M+H]^+$.

4-Fluoro-7-methyl-1H-benzo[d]imidazole-2-carboxylic acid

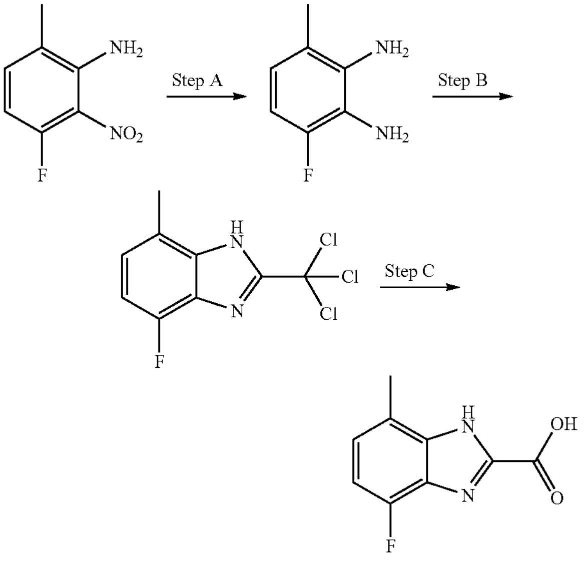

Step A: A solution of 3-fluoro-6-methyl-2-nitroaniline (500 mg, 6.25 mmol) and 10% palladium on carbon (500 mg) in EtOAc (100 mL) was degassed and purged with hydrogen for three times. The mixture was stirred at 20° C. for 1 h under hydrogen (15 psi). The suspension was filtered through a pad of Celite, and the cake was washed with EtOAc (20.0 mL×3). The combined filtrates were concentrated under vacuum to give 3-fluoro-6-methylbenzene-1,2-diamine. LC-MS: 141.3 $[M+H]^+$.

Step B: A solution of 3-fluoro-6-methylbenzene-1,2-diamine (200 mg, 1.43 mmol, 1.0 eq) and methyl 2,2,2-trichloroacetimidate (252 mg, 1.43 mol, 1.0 eq) in AcOH (2.0 mL) was stirred at 20° C. for 1 h. LCMS indicated that the starting material was completely consumed, and the desired mass was detected. The mixture was poured into saturated $NaHCO_3$ aqueous (20 mL) and extracted with EtOAc (30 mL×3). The combined organic layers were dried over $Na_2SO_4$, filtered, and concentrated under vacuum to give the crude product 7-fluoro-4-methyl-2-(trichloromethyl)-1H-benzo[d]imidazole (210 mg, crude). LCMS: [M+H]=267.1.

Step C: A solution of 7-fluoro-4-methyl-2-(trichloromethyl)-1H-benzo[d]imidazole (100 mg, 384 mol, 1.0 eq) and NaOH (2M aqueous, 2.5 mL) was stirred at 20° C. for 1 h.

LCMS indicated that the starting material was completely consumed, and the desired mass was detected. The mixture is lyophilized to give 7-fluoro-4-methyl-1H-benzo[d]imidazole-2-carboxylic acid (150 mg, Na salt). LCMS: 193.1 [M-H]—. $^1$H NMR (400 MHz, DMSO-$d_6$) δ 7.14-6.89 (m, 2H), 2.49-2.49 (m, 3H).

4,6-Difluoro-7-methyl-1H-benzo[d]imidazole-2-carboxylic acid

Step D: To a solution of N-(4,6-difluoro-3-methyl-2-nitrophenyl)acetamide (350 mg, 1.52 mmol) in MeOH (4.00 mL) was added HCl aqueous (2M, 3.80 mL). The mixture was stirred at 70° C. for 12 h. The reaction mixture was poured into $H_2O$ (10.0 mL) and extracted with EtOAc (30.0 mL×3). The combined organic layers were dried over $Na_2SO_4$, filtered, and concentrated under vacuum to give a residue which was purified by flash silica gel chromatography using a gradient of petroleum/EtOAc ether from 30/1 to 19/1 to give 4,6-difluoro-3-methyl-2-nitroaniline. LC-MS:

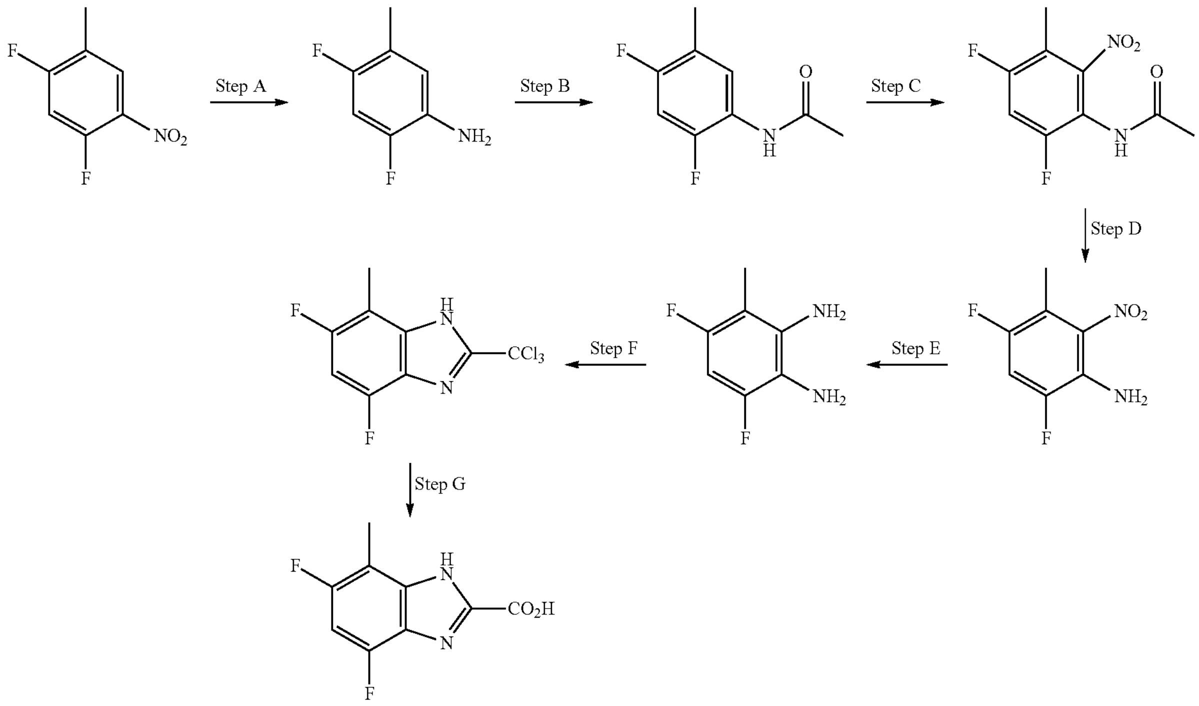

Step A: To a solution of 1,5-difluoro-2-methyl-4-nitrobenzene (800 mg, 4.62 mmol) in EtOH (24.0 mL) and $H_2O$ (8.00 mL) was added iron powder (2.06 g, 37.0 mmol) and ammonium chloride (1.98 g, 37.0 mmol). The mixture was stirred at 80° C. for 12 h. The reaction mixture was filtered and the filtrate was concentrated under vacuum to give 2,4-difluoro-5-methylaniline. $^1$H NMR (400 MHz, DMSO-$d_6$) δ 6.92 (dd, J=9.8, 11.3 Hz, 1H), 6.61 (dd, J=8.4, 9.7 Hz, 1H), 4.88 (br s, 2H), 2.10-2.05 (m, 3H).

Step B: To a solution of 2,4-difluoro-5-methylaniline (500 mg, 3.49 mmol) in DCM (20.0 mL) was added acetic anhydride (428 mg, 4.19 mmol) and TEA (1.06 g, 10.5 mmol). The mixture was stirred at 25° C. for 12 h. The reaction mixture was poured into $H_2O$ (20 mL) and extracted with DCM (20.0 mL×3). The combined organic layers were dried over $Na_2SO_4$, filtered, and concentrated under vacuum to give a residue which was purified by flash silica gel chromatography using a gradient of petroleum/EtOAc ether from 30/1 to 19/1 to give N-(2,4-difluoro-5-methylphenyl)acetamide. LC-MS: 186.5 $[M+H]^+$.

Step C: To a solution of N-(2,4-difluoro-5-methylphenyl)acetamide (350 mg, 1.89 mmol) in $H_2SO_4$ (6.00 mL) was added $HNO_3$ (595 mg, 9.45 mmol). The mixture was stirred at 0° C. for 1 h. The reaction mixture was poured into water. The precipitate was collected by filtration and dried in vacuo to give N-(4,6-difluoro-3-methyl-2-nitrophenyl)acetamide. LC-MS: 231.4 $[M+H]^+$.

187.5 $[M-H]^-$. $^1$H NMR (400 MHz, DMSO-$d_6$) δ 7.47 (dd, J=9.6, 11.2 Hz, 1H), 6.72-5.41 (m, 2H), 2.15 (dd, J=1.2, 2.3 Hz, 3H).

Step E: To a solution of 4,6-difluoro-3-methyl-2-nitroaniline (130 mg, 0.691 mmol) in EtOH (6.00 mL) and $H_2O$ (2.00 mL) was added iron powder (309 mg, 5.53 mmol) and ammonium chloride (296 mg, 5.53 mmol). The mixture was stirred at 80° C. for 12 h. The reaction mixture was filtered and concentrated under reduced pressure to give 4,6-difluoro-3-methylbenzene-1,2-diamine. LC-MS: 157.1 $[M-H]^-$.

Step F: To a solution of 4,6-difluoro-3-methylbenzene-1,2-diamine (100 mg, 0.632 mmol) in HOAc (2.00 mL) was added methyl 2,2,2-trichloroethanimidate (112 mg, 0.632 mmol). The mixture was stirred at 25° C. for 1 h. The reaction mixture was filtered. The filter cake was washed with $H_2O$ (2.00 mL), and dried under reduced pressure to give 4,6-difluoro-7-methyl-2-(trichloromethyl)-1H-benzo[d]imidazole. LC-MS: 285.1 $[M+H]^+$.

Step G: A solution of 4,6-difluoro-7-methyl-2-(trichloromethyl)-1H-benzo[d]imidazole (70 mg, 0.245 mmol) and NaOH (2M aqueous, 7.00 mL) was stirred at 25° C. for 1 h. The mixture was adjusted to pH 5-6 with HCl (6M aqueous). The resulting precipitate was filtered and the filter cake was dried under vacuum to give 4,6-difluoro-7-methyl-1H-benzo[d]imidazole-2-carboxylic acid. LC-MS: 213.2 $[M+H]^+$.

7-Chloro-4-fluoro-1H-benzo[d]imidazole-2-carboxylic acid and 7-Chloro-4,6-difluoro-1H-benzo[d]imidazole-2-carboxylic acid

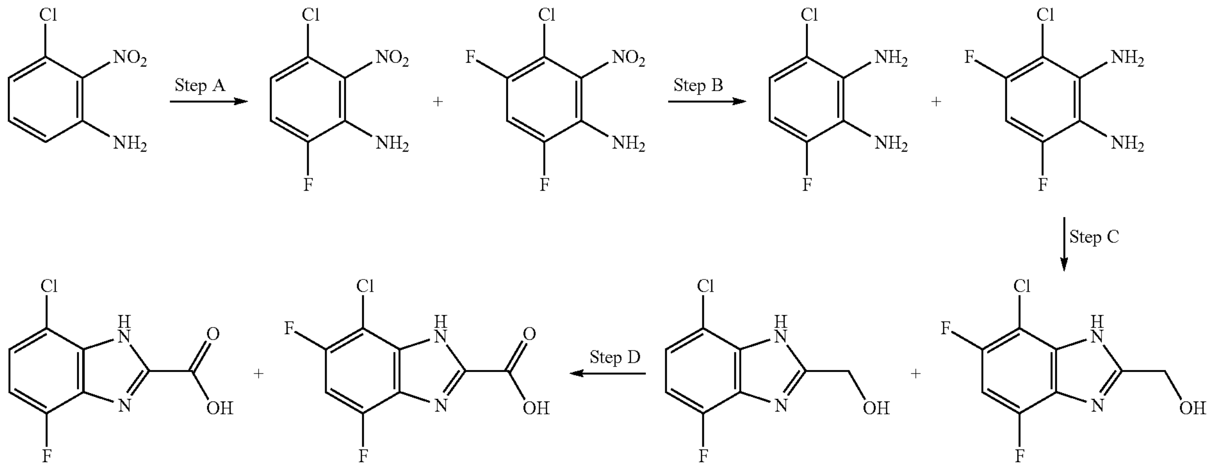

Step A: 3-Chloro-2-nitroaniline (10.0 g, 57.9 mmol) was dissolved in ACN (400 mL) under nitrogen, and SelectFluor (21.4 g, 57.9 mmol) was added. The reaction was heated at 85° C. for 16 h, after which an additional 0.25 equivalents of SelectFluor were added, and the mixture stirred for an additional hour. The solvent was removed and the residue diluted with EtOAc and water. The organic layer was removed, concentrated, and carried forward to the next step without further purification as a mixture of mono-fluorinated and di-fluorinated products.

Step B: 3-Chloro-6-fluoro-2-nitroaniline (crude, 11.0 g, 57.7 mmol) was dissolved in MeOH (200 mL) under nitrogen atmosphere, and palladium on (10% on carbon, 6.14 g, 5.77 mmol) was added. A hydrogen atmosphere was introduced, and the reaction stirred for 16 h. The suspension was filtered over celite and concentrated to afford a mixture of 3-chloro-6-fluorobenzene-1,2-diamine and 3-chloro-4,6-difluorobenzene-1,2-diamine which was used without further purification.

Step C: 3-Chloro-6-fluorobenzene-1,2-diamine and 3-chloro-4,6-difluorobenzene-1,2-diamine (crude, 5.80 g, 36.1 mmol) and glycolic acid (11.2 mL, 181 mmol) were dissolved in NMP (20.0 mL) and heated at 140° C. for 16 h. An additional 10 equivalents of glycolic acid were added, and the solution was stirred for an additional 24 hours. The reaction was concentrated and the mixture of (4-chloro-7-fluoro-1H-benzo[d]imidazol-2-yl)methanol and (7-chloro-4,6-difluoro-1H-benzo[d]imidazol-2-yl)methanol, which was used without further purification.

Step D: (4-Chloro-7-fluoro-1H-benzo[d]imidazol-2-yl) methanol and (7-chloro-4,6-difluoro-1H-benzo[d]imidazol-2-yl)methanol (crude, 7.25 g, 36.1 mmol) were suspended in water (200 mL). Sodium carbonate (5.47 g, 50.6 mmol) and potassium permanganate (8.08 mL, 50.6 mmol) were added. The suspension was heated at 100° C. for 20 minutes, after which the crude reaction was filtered hot through celite. The aqueous layer was concentrated and purified by flash chromatography on C18 gel using 10 mM HCl (aqueous) and MeCN (0 to 30% gradient) to give 7-chloro-4-fluoro-1H-benzo[d]imidazole-2-carboxylic acid (406 mg, 5.2%) after lyophilization. LCMS: 215.1 $[M+H]^+$. 7-chloro-4,6-difluoro-1H-benzo[d]imidazole-2-carboxylic acid (215 mg, 2.6%), eluted second and was isolated. LCMS: 233.1 $[M+H]^+$.

(R)-5-Methyl-5,6,7,8-tetrahydro-1,6-naphthyridine

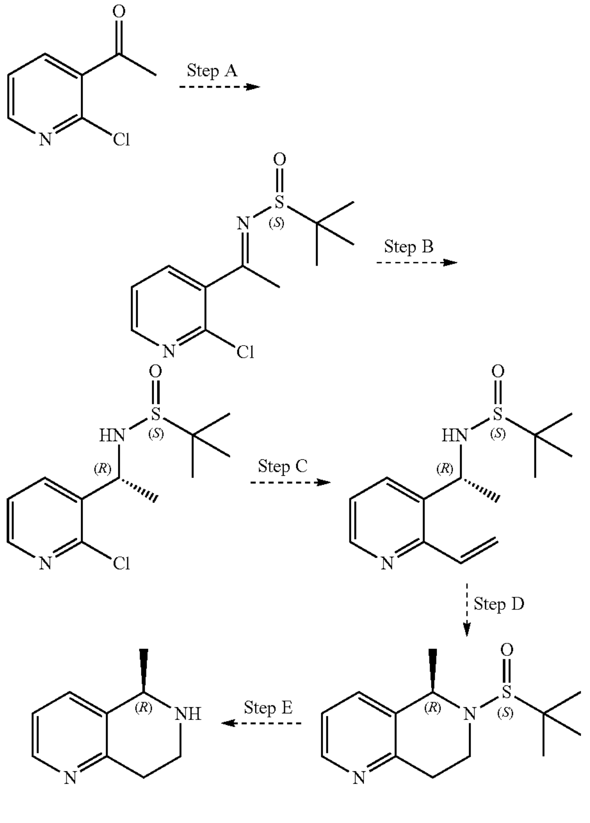

Step A: In a 100 mL pressure flask, 3-acetyl-2-chloropyridine (520 mg, 3.24 mmol) was dissolved in THF (6.0 mL) at room temperature and (S)-(−)-t-butylsulfinamide (612 mg, 4.90 mmol) was added. Then, titanium(IV) ethoxide (3.20 g, 12.8 mmol) was added as a solution in THF (4.0 ml) to the stirring solution. The flask was sealed and the mixture was heated at 80° C. overnight. The mixture was allowed to cool down to room temperature and water was added. A solid precipitated and was filtered. The solid was rinsed with water and the filtrate was extracted with EtOAc (3x25 mL). The combined organic layers were washed with brine (2x25 mL), dried over anhydrous $Na_2SO_4$, filtered and concentrated to give a yellow oil. The crude material was purified by flash chromatography on silica gel using a solution of EtOAc in heptanes (0 to 100% gradient) to give (S,E)-N-(1-(2-chloropyridin-3-yl)ethylidene)-2-methylpropane-2-sulfinamide (706 mg, 84%). LCMS: 259.1 $[M+H]^+$.

Step B: To a flame-dried flask containing a solution of (S,E)-N-(1-(2-chloropyridin-3-yl)ethylidene)-2-methylpropane-2-sulfinamide (506 mg, 1.96 mmol) in THF (19.5 mL) at −78° C. under $N_2$ was slowly added L-Selectride, 1M THF (4.40 mL, 4.40 mmol) down the walls of the flask over 10 minutes and stirred at −78° C. for 1 h. Quenched by the addition of aq. sat. $NH_4Cl$ and warmed to 25° C. Concentrated under reduced pressure and re-partitioned between EtOAc and water and adjusted to pH 8 with aq. sat. $NaHCO_3$. Rinsed the organics with brine (2×) and dried ($Na_2SO_4$). Filtered and concentrated under reduced pressure with $SiO_2$ and purified by flash column chromatography on $SiO_2$ (40 g, 0-100% EtOAc/DCM). Concentrated pure fractions under reduced pressure to give (S)—N—((R)-1-(2-chloropyridin-3-yl)ethyl)-2-methylpropane-2-sulfinamide (478 mg, 94%). LCMS: 261.2 $[M+H]^+$.

Step C: To a solution of (S)—N—((R)-1-(2-chloropyridin-3-yl)ethyl)-2-methylpropane-2-sulfinamide (473 mg, 1.81 mmol) in dioxane (17.8 mL) was added potassium vinyltrifluoroborate (372 mg, 2.72 mmol), [1,1'-Bis(diphenylphosphino)ferrocene]dichloropalladium(II), complex with dichloromethane (74.1 mg, 0.0907 mmol) and Cesium carbonate (1.79 g, 5.44 mmol) and sparged with $N_2$ for 5 minutes, then heated via microwave irradiation for 2 h at 120° C. Added another portion of both [1,1'-Bis(diphenylphosphino)ferrocene]dichloropalladium(II), complex with dichloromethane (148 mg, 0.181 mmol) and [1,1'-Bis(diphenylphosphino)ferrocene]dichloropalladium(II), complex with dichloromethane (148 mg, 0.181 mmol) and sparged with $N_2$ for 5 minutes, then heated at 130° C. for 2 h via microwave irradiation. Cooled to 25° C. and diluted with EtOAc and filtered through a pad of celite. The filtrate was rinsed with aq. sat. $NaHCO_3$ (1×), brine (1×) and dried ($Na_2SO_4$). Filtered and concentrated under reduced pressure with $SiO_2$ and purified by flash column chromatography on $SiO_2$ (40 g, 0-100% iPrOH/DCM). Concentrated under reduced pressure to give (S)-2-methyl-N—((R)-1-(2-vinylpyridin-3-yl)ethyl)propane-2-sulfinamide (167 mg, 36%). LCMS: 253.0 $[M+H]^+$. $^1H$ NMR (500 MHz, DMSO-$d_6$): δ=8.45 (dd, J=4.5, 1.2 Hz, 1H), 7.82 (dd, J=7.9, 1.3 Hz, 1H), 7.29 (dd, J=7.9, 4.6 Hz, 1H), 7.17 (dd, J=16.7, 10.6 Hz, 1H), 6.31 (dd, J=16.7, 2.6 Hz, 1H), 5.50-5.43 (m, 2H), 4.77 (quint, J=6.6 Hz, 1H), 1.46 (d, J=6.7 Hz, 3H), 1.09 (s, 9H).

Step D: To a suspension of sodium hydride 60% in dispersion in mineral oil (23.8 mg, 0.594 mmol) in DMF (1.00 mL) was added (S)-2-methyl-N—((R)-1-(2-vinylpyridin-3-yl)ethyl)propane-2-sulfinamide (50.0 mg, 0.198 mmol) in DMF (1.00 mL) and stirred at 100° C. for 15 minutes. Cooled to 25° C. and diluted with 1:1 EtOAc:10% aq. LiCl. Extracted with EtOAc (1×) and rinsed the combined organic with aq. sat. NaCl (1×) and dried ($Na_2SO_4$). Filtered and concentrated under reduced pressure with $SiO_2$ and purified by flash column chromatography on $SiO_2$ (40 g, 0-100% iPrOH/DCM). Concentrated pure fractions under reduced pressure to give (R)-6-((S)-tert-butylsulfinyl)-5-methyl-5,6,7,8-tetrahydro-1,6-naphthyridine (15.3 mg, 31%). LCMS: 253.2 $[M+H]^+$ $^1H$ NMR (400 MHz, $CD_3OD$): δ=8.33 (dd, J=4.9, 1.5 Hz, 1H), 7.62 (dd, J=7.9, 1.4 Hz, 1H), 7.26 (dd, J=7.9, 4.8 Hz, 1H), 4.70 (q, J=7.0 Hz, 1H), 3.62-3.49 (m, 2H), 3.21-3.11 (m, 1H), 2.95-2.87 (m, 1H), 1.59 (d, J=7.0 Hz, 3H), 1.24 (s, 9H).

Step E: To a solution of (R)-6-((S)-tert-butylsulfinyl)-5-methyl-5,6,7,8-tetrahydro-1,6-naphthyridine (15.3 mg, 0.0606 mmol) in MeOH (600 uL) was added 4.0 M hydrochloric acid (60.6 uL, 0.242 mmol) in dioxane and stirred at 25° C. for 1 h. Concentrated under reduced pressure and lyophilized to give (R)-5-methyl-5,6,7,8-tetrahydro-1,6-naphthyridine (8.98 mg, 100%). $^1H$ NMR (400 MHz, $D_2O$): δ=8.76 (dd, J=5.8, 0.8 Hz, 1H), 8.57 (d, J=8.2 Hz, 1H), 8.02 (dd, J=8.2, 5.9 Hz, 1H), 4.99 (q, J=6.9 Hz, 1H), 3.86 (dt, J=13.2, 6.2 Hz, 1H), 3.70 (dt, J=13.2, 6.4 Hz, 1H), 3.56 (q, J=6.2 Hz, 2H), 1.82 (d, J=7.0 Hz, 3H).

Examples 1A and 1B: (R) or (S)-(6-Chloro-4-fluoro-7-methyl-1H-benzo[d]imidazol-2-yl)(5-(difluoromethyl)-7,8-dihydro-1,6-naphthyridin-6(5H)-yl)methanone and (R) or (S)-(6-Chloro-4-fluoro-7-methyl-1H-benzo[d]imidazol-2-yl)(5-(difluoromethyl)-7,8-dihydro-1,6-naphthyridin-6(5H)-yl)methanone

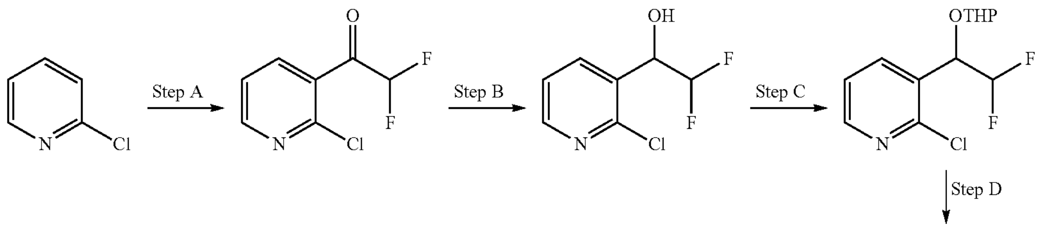

-continued

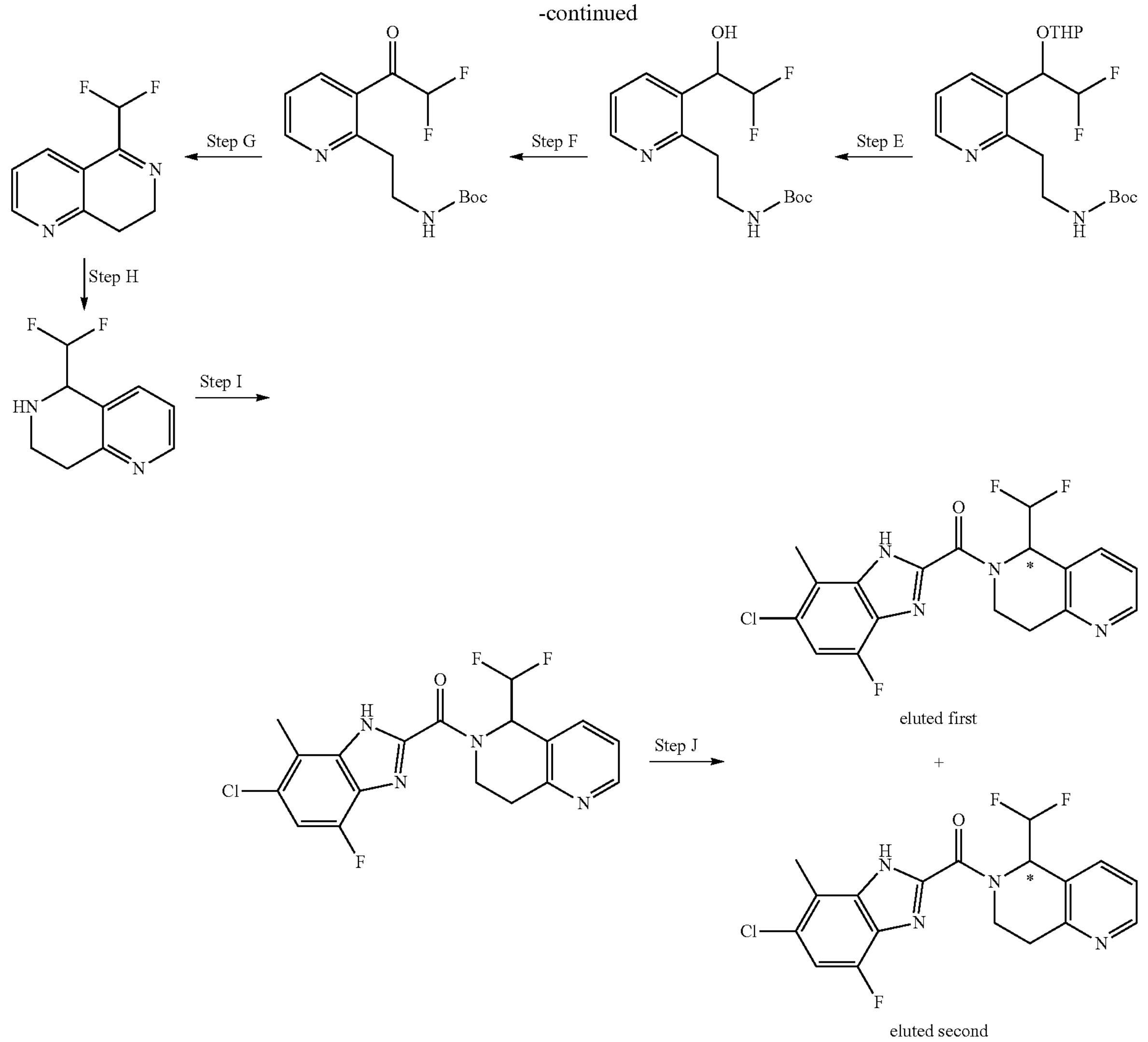

Step A: To a stirred solution of diisopropylamine (70.0 g, 444 mmol) in THF (480 mL) at −78° C. was added n-BuLi (2.5 M, 170 mL in hexane) dropwise under nitrogen. The reaction mixture was stirred at −78° C. for 0.5 h. 2-Chloropyridine (24.0 g, 211 mmol) was added dropwise. The resulting yellow solution was stirred at −78° C. for 3 h. Ethyl 2,2-difluoroacetate (32.0 g, 254 mmol) was then added dropwise. The mixture was stirred at −78° C. for 1 h. The reaction mixture was poured into saturated aq. $NH_4Cl$ (200 mL) and extracted with EtOAc (200 mL×3). The combined organic layers were dried over $MgSO_4$, filtered, and concentrated under vacuum to give 1-(2-chloropyridin-3-yl)-2,2-difluoroethan-1-one (36.0 g, crude).

Step B: A mixture 1-(2-chloro-3-pyridyl)-2,2-difluoroethanone (36.0 g, 186 mmol) and sodium borohydride (14.2 g, 375 mmol) in MeOH (1.44 L) was stirred at 0° C. for 1 h. The reaction mixture was poured into water (800 mL) and extracted with DCM (800 mL×5). The combined organic layers were dried over sodium sulfate, filtered, and concentrated under vacuum to give a residue which was purified by flash silica gel chromatography to give 1-(2-chloropyridin-3-yl)-2,2-difluoroethan-1-ol (5.6 g, 15%). LC-MS: 194.1 $[M+H]^+$.

Step C: A mixture of 1-(2-chloro-3-pyridyl)-2,2-difluoroethanol (5.60 g, 29 mmol), Dess-Martin periodinane (3.60 g, 43.4 mmol) and pyridinium p-toluenesulfonate (726 mg, 2.9 mmol) in DCM (260 mL) was stirred at 50° C. for 4 h. The reaction mixture was poured into $H_2O$ (50 mL) and extracted with DCM (50 mL×3). The combined organic layers were dried over sodium sulfate, filtered, and concentrated under vacuum to give a residue which was purified by flash silica gel chromatography to yield 2-chloro-3-(2,2-difluoro-1-((tetrahydro-2H-pyran-2-yl)oxy)ethyl)pyridine (5.50 g, 62%). LC-MS: 278.1 $[M+H]^+$.

Step D: To a mixture of 2-chloro-3-(2,2-difluoro-1-tetrahydropyran-2-yloxy-ethyl)pyridine (2.50 g, 9.00 mmol), potassium (2-((tert-butoxycarbonyl)amino)ethyl)trifluoroborate, cataCXium A Pd G3 (656 mg, 0.900 mmol) in cyclopenylmethyl ether (60 mL) was added cesium carbonate (5.87 g, 18 mmol) in $H_2O$ (15.0 mL). The mixture was degassed and purged with nitrogen for 3 times, and then the mixture was stirred at 80° C. for 12 h under $N_2$ atmosphere. The reaction mixture was poured into $H_2O$ (20 mL) and extracted with EtOAc (20 mL×3). The combined organic layers were dried over $Na_2SO_4$, filtered, and concentrated under vacuum to give a residue which was purified by flash silica gel chromatography to give t-butyl (2-(3-(2,2-difluoro-1-((tetrahydro-2H-pyran-2-yl)oxy)ethyl)pyridin-2-yl)ethyl)carbamate (1.65 g, 61%). LC-MS: 387.3 $[M+H]^+$.

Step E: A mixture of tert-Butyl (2-(3-(2,2-difluoro-1-((tetrahydro-2H-pyran-2-yl)oxy)ethyl)pyridin-2-yl)ethyl) carbamate (1.65 g, 4.27 mmol) and p-toluenesulfonic acid (700 mg, 4.07 mmol) in MeOH (50 mL) was stirred at 60° C. for 12 h. The reaction mixture was poured into $H_2O$ (10 mL) and extracted with DCM (10 mL×3). The combined organic layers were dried over $Na_2SO_4$, filtered, and concentrated under vacuum to give a residue which was purified by flash silica gel chromatography to give tert-butyl (2-(3-(2,2-difluoro-1-hydroxyethyl)pyridin-2-yl)ethyl)carbamate (600 mg, 43%). LC-MS: 303.2 $[M+H]^+$.

Step F: A mixture of tert-butyl (2-(3-(2,2-difluoro-1-hydroxyethyl)pyridin-2-yl)ethyl)carbamate (320 mg, 1.06 mmol) and Dess-Martin periodinane (673 mg, 1.59 mmol) in DCM (5 mL) was stirred at 20° C. for 1 h. The reaction mixture was poured into $H_2O$ (5 mL) and extracted with DCM (5 mL×3). The combined organic layers were dried over sodium sulfate $Na_2SO_4$, filtered, and concentrated under vacuum to give a residue which was purified by flash silica gel chromatography to give tert-butyl (2-(3-(2,2-difluoroacetyl)pyridin-2-yl)ethyl)carbamate (240 mg, 73%). LC-MS: 301.2 $[M+H]^+$.

Step G: To a solution of tert-butyl (2-(3-(2,2-difluoroacetyl)pyridin-2-yl)ethyl)carbamate (90 mg, 0.300 mmol) in EtOAc (1 mL) was added 4 M HCl in EtOAc (9 mL). The resulting mixture was stirred at 20° C. for 12 h. The mixture was concentrated under vacuum at 30° C. to give 5-(difluoromethyl)-7,8-dihydro-1,6-naphthyridine (200 mg, crude). LC-MS: 183.2 $[M+H]^+$.

Step H: To a solution of 5-(difluoromethyl)-7,8-dihydro-1,6-naphthyridine (100 mg, 0.549 mmol) in MeOH (4.00 mL) was added $NaBH_3CN$ (100 mg, 1.59 mmol). The mixture was stirred at 20° C. for 1 h. The reaction mixture was poured into $H_2O$ (5 mL) and extracted with DCM (5 mL×3). The combined organic layers were dried over sodium sulfate, filtered, and concentrated under vacuum to give 5-(difluoromethyl)-5,6,7,8-tetrahydro-1,6-naphthyridine (80 mg, crude). LC-MS: 185.2 $[M+H]^+$.

Step I: To a solution of 5-(difluoromethyl)-5,6,7,8-tetrahydro-1,6-naphthyridine (80.0 mg, 0.434 mmol) in DCM (1.00 mL) was added 6-chloro-4-fluoro-7-methyl-1H-benzo[d]imidazole-2-carboxylic acid (99.3 mg, 0.434 mmol), TEA (132 mg, 1.30 mmol) and Phosphoric acid bis(2-oxooxazolidide) chloride (221 mg, 0.869 mmol). The mixture was stirred at 25° C. for 2 h. The reaction mixture was poured into $H_2O$ (2 mL) and extracted with EtOAc (2 mL×3). The combined organic layers were washed with brine (1 mL×3), dried over $Na_2SO_4$, filtered, and concentrated under vacuum to give a residue which was purified by flash silica gel chromatography using a gradient of EtOAc in petroleum ether from 20 5o 25% to give (6-chloro-4-fluoro-7-methyl-1H-benzo[d]imidazol-2-yl)(5-(difluoromethyl)-7,8-dihydro-1,6-naphthyridin-6(5H)-yl)methanone (60.0 mg, 34%). LC-MS: 395.2 $[M+H]^+$.

Step J: (6-Chloro-4-fluoro-7-methyl-1H-benzo[d]imidazol-2-yl)(5-(difluoromethyl)-7,8-dihydro-1,6-naphthyridin-6(5H)-yl)methanone (60.0 mg) was separated by SFC separation (DAICEL CHIRALPAK IC (250×30 mm, 10 μm); flow rate: 30 mL/min; gradient: 25% B over 14 min; mobile phase A: heptane, mobile phase B: $CO_2$—IPA (0.1% $NH_3H_2O$) to afford a first eluted compound and a second eluted compound. First eluted compound (Example 1A): LC-MS: 395.1 $[M+H]^+$. $^1$H NMR (400 MHz, DMSO-$d_6$) δ 14.15-13.41 (m, 1H), 8.53 (d, J=4.4 Hz, 1H), 7.87 (br dd, J=7.7, 40.1 Hz, 1H), 7.42-7.24 (m, 2H), 7.13-6.01 (m, 2H), 5.53-4.75 (m, 1H), 4.13-3.40 (m, 1H), 3.26-3.13 (m, 1H), 3.07 (br dd, J=3.8, 7.9 Hz, 1H), 2.55 (d, J=3.1 Hz, 3H). Second eluted compound (Example 1B): LC-MS: 395.1 $[M+H]^+$. $^1$H NMR (400 MHz, DMSO-$d_6$) δ 14.17-13.58 (m, 1H), 8.53 (d, J=4.0 Hz, 1H), 7.87 (br dd, J=7.4, 41.0 Hz, 1H), 7.42-7.22 (m, 2H), 7.15-6.02 (m, 2H), 5.52-4.74 (m, 1H), 4.00-3.41 (m, 1H), 3.26-3.14 (m, 1H), 3.06 (br dd, J=4.3, 8.3 Hz, 1H), 2.55 (d, J=3.1 Hz, 3H). The absolute stereochemistry for the first and second eluted compounds was not determined.

Examples 2A and 2B: (R) or (S)-(5-(Difluoromethyl)-7,8-dihydro-1,6-naphthyridin-6(5H)-yl)(4-fluoro-7-methyl-1H-benzo[d]imidazol-2-yl)methanone and (R) or (S)-(5-(Difluoromethyl)-7,8-dihydro-1,6-naphthyridin-6(5H)-yl)(4-fluoro-7-methyl-11H-benzo[d]imidazol-2-yl)methanone

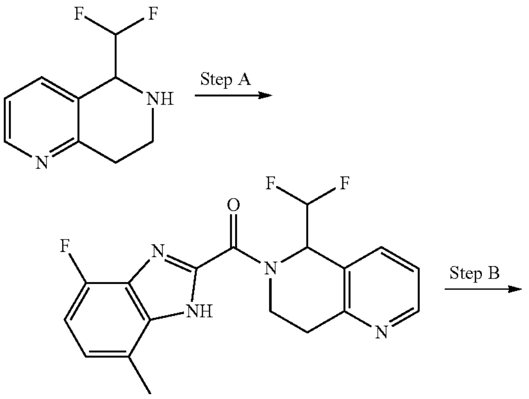

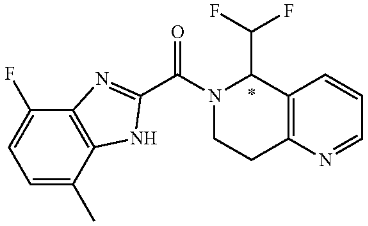

eluted first

+

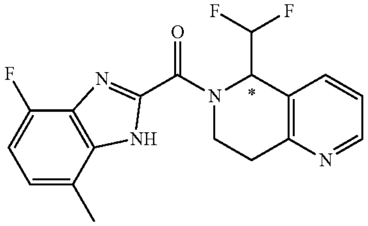

eluted second

Step A: A mixture of 5-(difluoromethyl)-5,6,7,8-tetrahydro-1,6-naphthyridine (80 mg, 0.434 mmol) (product of Example 1, Step H), 4-fluoro-7-methyl-1H-benzimidazole-2-carboxylic acid (169 mg, 0.869 mmol), DIEA (168 mg, 1.30 mmol) and HATU (165 mg, 0.434 mmol) in DMF (1.50 mL) was stirred at 20° C. for 1 h. The reaction mixture was poured into $H_2O$ (0.5 mL) and extracted with DCM (0.5 mL×4). The combined organic layers were dried over sodium sulfate, filtered, and concentrated under vacuum to give a residue which was purified by flash silica gel chromatography to give (5-(difluoromethyl)-7,8-dihydro-1,6-naphthyridin-6(5H)-yl)(4-fluoro-7-methyl-1H-benzo[d]imidazol-2-yl)methanone (100 mg, 64%). LC-MS: 361.4 $[M+H]^+$.

Step B: Two enantiomers of (5-(difluoromethyl)-7,8-dihydro-1,6-naphthyridin-6(5H)-yl)(4-fluoro-7-methyl-1H-benzo[d]imidazol-2-yl)methanone (100 mg) was separated by chiral SFC (DAICEL CHIRALPAK IC (250×30 mm, 10 μm); flow rate: 30 mL/min; gradient: 50% B over 14 min; mobile phase A: heptane, mobile phase B: $CO_2$-EtOH (0.1% $NH_3H_2O$) to afford a first eluted compound and a second eluted compound. First eluted compound (Example 2A): LC-MS: $[MH]^+$=361.1. $^1H$ NMR (400 MHz, DMSO-$d_6$) δ 8.53 (d, J=4.8 Hz, 1H), 7.95-7.75 (m, 1H), 7.45-7.30 (m, 1H), 7.26-6.85 (m, 3H), 6.79-6.37 (m, 1H), 6.21-5.42 (m, 1H), 4.98-3.84 (m, 1H), 3.60-3.42 (m, 1H), 3.21 (br d, J=17.3 Hz, 1H), 3.12-2.95 (m, 2H), 2.53 (br s, 1H). Second eluted compound (Example 2B): LC-MS: 361.1 $[M+H]^+$. $^1H$ NMR (400 MHz, DMSO-$d_6$) δ 8.54 (d, J=4.8 Hz, 1H), 7.88 (br dd, J=7.8, 34.9 Hz, 1H), 7.35 (td, J=4.8, 7.9 Hz, 1H), 7.28-6.82 (m, 3H), 6.77-6.37 (m, 1H), 6.22-5.43 (m, 1H), 4.91-3.76 (m, 1H), 3.55-3.42 (m, 1H), 3.26-3.12 (m, 1H), 3.10-2.95 (m, 2H), 2.53 (br s, 1H). The absolute stereochemistry for the first and second eluted compounds was not determined.

Example 3: (S)-(4,6-Difluoro-7-methyl-1H-benzo[d]imidazol-2-yl)(5-(difluoromethyl)-7,8-dihydro-1,6-naphthyridin-6(5H)-yl)methanone min and 2,2-difluoro-N-methoxy-N-methylacetamide (2.77 g, 19.9 mmol) was added. The mixture was stirred for 3 h allowing the temperature to rise slowly to 20° C. The reaction mixture was quenched with saturated aq. $NH_4Cl$ solution (50 mL) and extracted with ethyl acetate (50 mL×3). The combined organic phase was washed with brine (50 mL), dried over anhydrous sodium sulfate, filtered and concentrated under vacuum to give a residue. The residue was adsorbed on silica gel to be purified by flash silica gel chromatography to give tert-butyl (2-(3-(2,2-difluoroacetyl)pyridin-2-yl)ethyl)carbamate (2.00 g, 19%). $^1H$ NMR (400 MHz, DMSO-$d_6$) δ=8.46 (d, J=4.0 Hz, 1H), 7.97 (d, J=7.6 Hz, 1H), 7.21-7.18 (m, 1H), 6.28 (t, J=57.2 Hz, 1H), 4.06-4.01 (m, 1H), 3.27-3.23 (m, 1H), 3.07-3.04 (m, 1H), 2.92-2.88 (m, 1H), 1.46 (s, 9H).

Step B: tert-Butyl (2-(3-(2,2-difluoroacetyl)pyridin-2-yl)ethyl)carbamate (2.0 g, 6.66 mmol) was dissolved into 4 M HCl in EtOAc (25 mL) and the mixture was stirred at 20° C. for 30 min. The reaction mixture was concentrated to give 5-(difluoromethyl)-7,8-dihydro-1,6-naphthyridine hydrochloride (1.60 g), which was used in the next step directly. $^1H$ NMR (400 MHz, DMSO-$d_6$) δ 8.53-8.51 (m, 1H), 7.98-7.96 (m, 1H), 7.22-7.13 (m, 1H), 6.23 (t, J=54.4 Hz, 1H), 3.96-3.92 (m, 2H), 2.94-2.90 (m, 2H).

Step C: To a solution of 5-(difluoromethyl)-7,8-dihydro-1,6-naphthyridine hydrochloride (1.6 g) and $Boc_2O$ (2.4 g, 11 mmol) in MeOH (20 mL) was added sodium borohydride (1.94 g, 51.2 mmol) in portions at 0° C. The mixture was stirred at 0° C. for 1 h. The reaction mixture was quenched with saturated aq. $NH_4Cl$ solution (30 mL) and extracted with ethyl acetate (30 mL×3). The combined organic phase was washed with brine (15 mL), dried over anhydrous

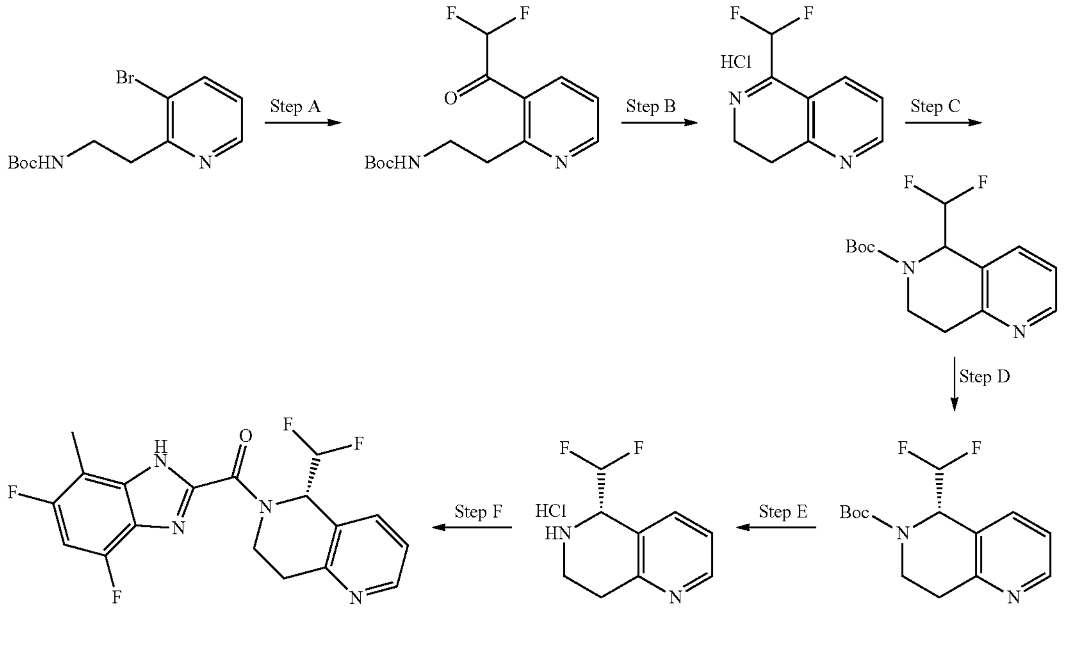

Step A: To a solution of tert-butyl (2-(3-bromopyridin-2-yl)ethyl)carbamate (3.00 g, 9.96 mmol) in toluene (30 mL) was added 60% sodium hydride in mineral oil (0.797 g, 1.39 mol) at 0° C. The reaction mixture was stirred at 0° C. for 30 min. Then the above mixture and n-BuLi (1.6 M in THF, 46.7 mL) were added into toluene (30 mL) at the same time at −78° C. The reaction mixture was stirred at −78° C. for 30

$Na_2SO_4$, filtered and concentrated to give a residue. The residue was purified by silica gel chromatography to give tert-butyl 5-(difluoromethyl)-7,8-dihydro-1,6-naphthyridine-6(5H)-carboxylate (1.10 g, 39%). LC-MS: 285.1 $[M+H]^+$.

Step D: tert-Butyl 5-(difluoromethyl)-7,8-dihydro-1,6-naphthyridine-6(5H)-carboxylate (800 mg was dissolved in isopropyl alcohol (20 mL), and the resulting solution was purified by chiral SFC (column: DAICEL CHIRALPAK AD (250 mm*30 mm, 10 μm); mobile phase: [$CO_2$-EtOH]; B %: 20%, isocratic elution mode). The relevant fractions were lyophilized to afford tert-butyl (S)-5-(difluoromethyl)-7,8-dihydro-1,6-naphthyridine-6(5H)-carboxylate as the first eluting enantiomer (0.400 g, 50%, elutes first). LC-MS: 302.1 $[M+H]^+$. $^1H$ NMR (400 MHz, $CDCl_3$) δ 8.53 (br d, J=4.4 Hz, 1H), 7.74-7.60 (m, 1H), 7.22 (dd, J=4.9, 7.8 Hz, 1H), 6.30-5.72 (m, 1H), 5.49-5.12 (m, 1H), 4.40-3.98 (m, 1H), 3.67-3.30 (m, 1H), 3.13-2.90 (m, 2H), 1.52 (s, 9H)

Step E: tert-Butyl (S)-5-(difluoromethyl)-7,8-dihydro-1,6-naphthyridine-6(5H)-carboxylate (360 mg, 12.7 mmol) was dissolved in 4 M HCl in EtOAc (2 mL). The mixture was stirred at 20° C. for 1 h. The reaction mixture was concentrated to give (S)-5-(difluoromethyl)-5,6,7,8-tetrahydro-1,6-naphthyridine hydrochloride (0.292 g, crude). LC-MS: 185.1 $[M+H]^+$.

Step F: To a solution of (S)-5-(difluoromethyl)-5,6,7,8-tetrahydro-1,6-naphthyridine hydrochloride (292 mg 1.32 mmol) and 4,6-difluoro-7-methyl-1H-benzimidazole-2-carboxylic acid (336 mg, 1.59 mmol) in THF (100 mL) were added phosphoric acid bis(2-oxooxazolidide) chloride (370 mg, 1.46 mmol) and DIEA (427 mg, 3.31 mmol). The mixture was stirred at 20° C. for 16 h. The reaction mixture was filtered and the filtrate was concentrated to give a residue which was purified by flash silica gel chromatography to give (S)-(4,6-difluoro-7-methyl-1H-benzo[d]imidazol-2-yl)(5-(difluoromethyl)-7,8-dihydro-1,6-naphthyridin-6(5H)-yl)methanone. (0.229 g, 45%). LC-MS: 379.1 $[M+H]^+$. $^1H$ NMR (400 MHz, DMSO-$d_6$) δ 14.09-13.70 (m, 1H), 8.54 (d, J=4.6 Hz, 1H), 7.96-7.79 (m, 1H), 7.36 (td, J=5.0, 7.8 Hz, 1H), 7.28-6.06 (m, 3H), 5.58-4.76 (m, 1H), 4.13-3.43 (m, 1H), 3.26-2.99 (m, 2H), 2.48-2.39 (m, 3H).

Examples 4A and 4B: (5S,8R) or (5R,8S)-(4,6-Difluoro-7-methyl-1H-benzo[d]imidazol-2-yl)(5-(difluoromethyl)-8-methoxy-7,8-dihydro-1,6-naphthyridin-6(5H)-yl)methanone and (5S,8R) or (5R,8S)-(4,6-Difluoro-7-methyl-1H-benzo[d]imidazol-2-yl)(5-(difluoromethyl)-8-methoxy-7,8-dihydro-1,6-naphthyridin-6(5H)-yl)methanone

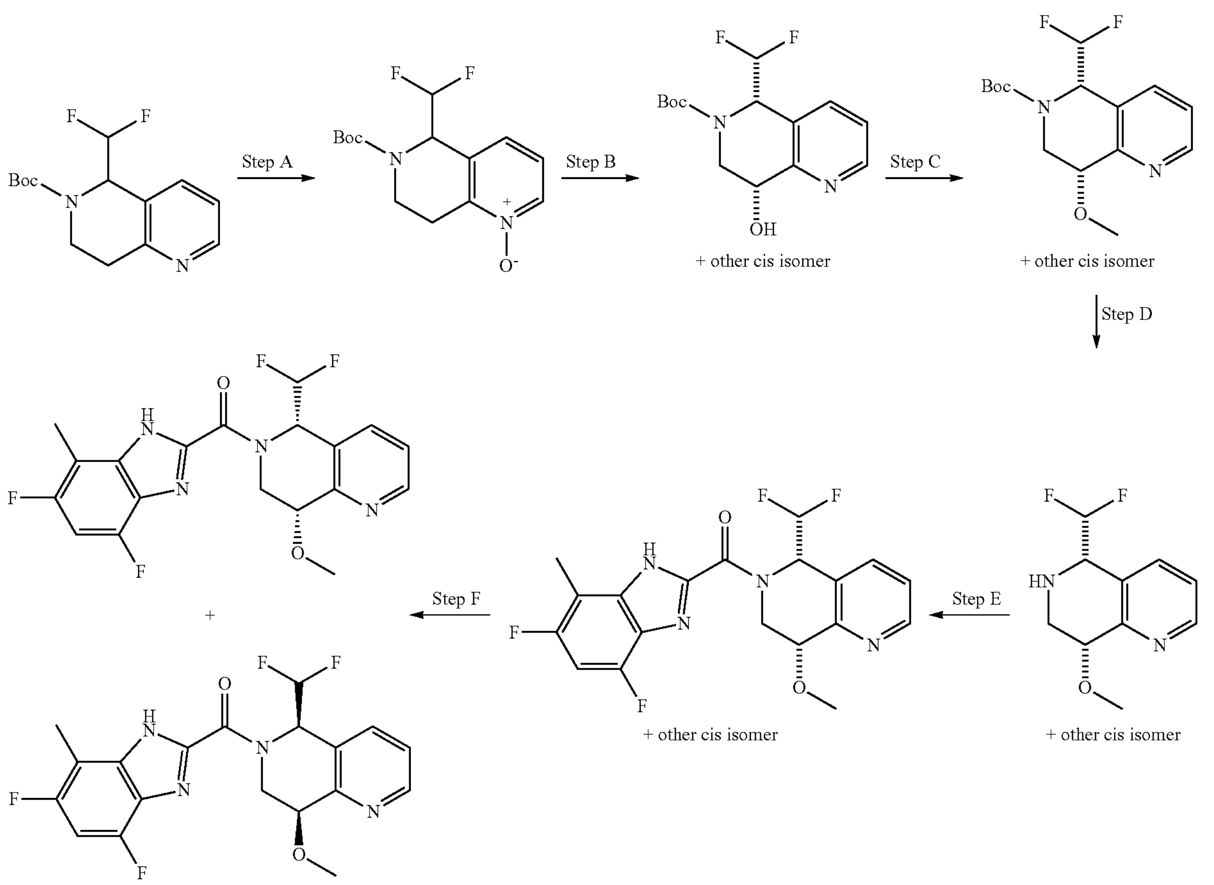

Step A: To a solution of tert-butyl 5-(difluoromethyl)-7,8-dihydro-1,6-naphthyridine-6(5H)-carboxylate (product of Example 3, Step C) (700 mg, 2.46 mmol) in DCM (20.0 mL) was added meta-chloroperoxybenzoic acid (1.00 g, 4.92 mmol, 85% purity) at 0° C. under nitrogen. The reaction mixture was stirred at 20° C. for 12 h, and then it was quenched by saturated aq. sodium sulfite solution (100 mL) and extracted with DCM (30 mLx3). The combined organic phase was washed with brine (50 mL), dried over anhydrous sodium sulfate, filtered and concentrated under vacuum to give a residue which was purified by flash silica gel chromatography to give 6-(tert-butoxycarbonyl)-5-(difluoromethyl)-5,6,7,8-tetrahydro-1,6-naphthyridine 1-oxide (600 mg, 68%). LC-MS: 301.2 $[M+H]^+$.

Step B: To a solution of 6-(tert-butoxycarbonyl)-5-(difluoromethyl)-5,6,7,8-tetrahydro-1,6-naphthyridine 1-oxide (500 mg, 1.66 mmol) in DMF (9.00 mL) was added trifluoroacetic anhydride (1.40 g, 6.66 mmol) at 0° C. The mixture was stirred at 60° C. for 1 h. The reaction mixture was filtered and the filtrate was concentrated to give a residue. The residue was dissolved in DMF (5 mL), and the resulting solution was purified by prep-HPLC (Phenomenex luna C18 (100×40 mm, 15 mm), Flow rate: 60.00 ml/min; gradient: 5%-35% B over 8 min; mobile phase A: water (0.04% HCl); mobile phase B: acetonitrile). The cis isomer eluted first, providing rac-tert-butyl (cis)-5-(difluoromethyl)-8-hydroxy-7,8-dihydro-1,6-naphthyridine-6(5H)-carboxylate.) LC-MS: 301.2 $[M+H]^+$.

The trans isomer eluted second, providing rac-tert-butyl (trans)-5-(difluoromethyl)-8-hydroxy-7,8-dihydro-1,6-naphthyridine-6(5H)-carboxylate (120 mg, 22%, eluted second) and used in Example 5. LC-MS: 301.1 $[M+H]^+$.

Step C: To a solution of rac-tert-butyl (cis)-5-(difluoromethyl)-8-hydroxy-7,8-dihydro-1,6-naphthyridine-6(5H)-carboxylate (150 mg, 0.445 mmol in ACN (5.00 mL) were added methyl iodide (632 mg, 4.45 mmol) and silver oxide (310 mg, 1.34 mmol). The mixture was stirred at 20° C. for 1 h. The reaction mixture was filtered and the filtrate was concentrated to give rac-tert-butyl (cis)-5-(difluoromethyl)-8-methoxy-7,8-dihydro-1,6-naphthyridine-6(5H)-carboxylate (150 mg, crude). LC-MS: 315.1 $[M+H]^+$.

Step D: Rac-tert-butyl (cis)-5-(difluoromethyl)-8-methoxy-7,8-dihydro-1,6-naphthyridine-6(5H)-carboxylate (150 mg, 0.477 mmol) was dissolved in 4 M HCl in ethyl acetate (5 mL) and the mixture was stirred at 20° C. for 1 h. The reaction mixture was filtered and the filter cake was dried to give rac-(cis)-5-(difluoromethyl)-8-methoxy-5,6,7,8-tetrahydro-1,6-naphthyridine hydrochloride (150 mg, crude, HCl). LC-MS: 215.1 $[M+H]^+$.

Step E: To a solution of rac-(cis)-5-(difluoromethyl)-8-methoxy-5,6,7,8-tetrahydro-1,6-naphthyridine hydrochloride (150 mg, 0.598 mmol) and 4,6-difluoro-7-methyl-1H-benzimidazole-2-carboxylic acid (127 mg, 0.598 mmol) in THF (2.00 mL) was added phosphoric acid bis(2-oxooxazolidide) chloride (305 mg, 1.20 mmol) and DIEA (155 mg, 1.20 mmol). The mixture was stirred at 20° C. for 1 h. The reaction mixture was filtered and the filtrate was concentrated in vacuo to give a residue. The residue was dissolved in ACN (1.00 mL), and the resulting solution was purified by prep-HPLC (Waters Xbridge Prep OBD C18 (150×40 mm, 10 μm), Flow rate: 60.00 ml/min; gradient: 31%-61% B over 8 min; mobile phase A: water (10 mM $NH_4HCO_3$); mobile phase B: acetonitrile) to give rac-(4,6-difluoro-7-methyl-1H-benzo[d]imidazol-2-yl)((5R,8S)-5-(difluoromethyl)-8-methoxy-7,8-dihydro-1,6-naphthyridin-6(5H)-yl)methanone (20 mg, 7.06%). LC-MS: 409.0 $[M+H]^+$.

Step F: rac-(4,6-Difluoro-7-methyl-1H-benzo[d]imidazol-2-yl)((5R,8S)-5-(difluoromethyl)-8-methoxy-7,8-dihydro-1,6-naphthyridin-6(5H)-yl)methanone (20 mg) was purified by chiral SFC (column: DAICEL CHIRALPAK IG (250 mm×30 mm, 10 μm); mobile phase: [$CO_2$-MeOH (0.1% $NH_3H_2O$)]; B %: 35%, isocratic elution mode) to afford a first eluted compound and a second eluted compound. First eluted compound (Example 4A): LC-MS: 409.1 $[M+H]^+$. $^1H$ NMR (400 MHz, DMSO-$d_6$) δ 14.04-13.64 (m, 1H), 8.70-8.58 (m, 1H), 8.05-7.80 (m, 1H), 7.46 (dd, J=4.8, 7.8 Hz, 1H), 7.49-7.09 (m, 1H), 6.87-6.35 (m, 1H), 6.14-5.40 (m, 1H), 4.84-3.97 (m, 2H), 3.59 (d, J=6.1 Hz, 3H), 3.56-3.39 (m, 1H), 2.43 (br s, 3H). Second eluted compound (Example 4B): LC-MS: 409.1 $[M+H]^+$. $^1H$ NMR (400 MHz, DMSO-$d_6$) δ 13.99-13.80 (m, 1H), 8.73-8.57 (m, 1H), 8.07-7.83 (m, 1H), 7.46 (dd, J=4.8, 7.8 Hz, 1H), 7.30-6.34 (m, 2H), 6.15-5.37 (m, 1H), 4.89-3.96 (m, 2H), 3.59 (d, J=5.9 Hz, 3H), 3.52 (br dd, J=8.3, 13.7 Hz, 1H), 2.43 (br s, 3H). The absolute stereochemistry for the first and second eluted compounds was not determined.

Example 5: rac-(4,6-Difluoro-7-methyl-1H-benzo[d]imidazol-2-yl)((trans)-5-(difluoromethyl)-8-methoxy-7,8-dihydro-1,6-naphthyridin-6(5H)-yl)methanone

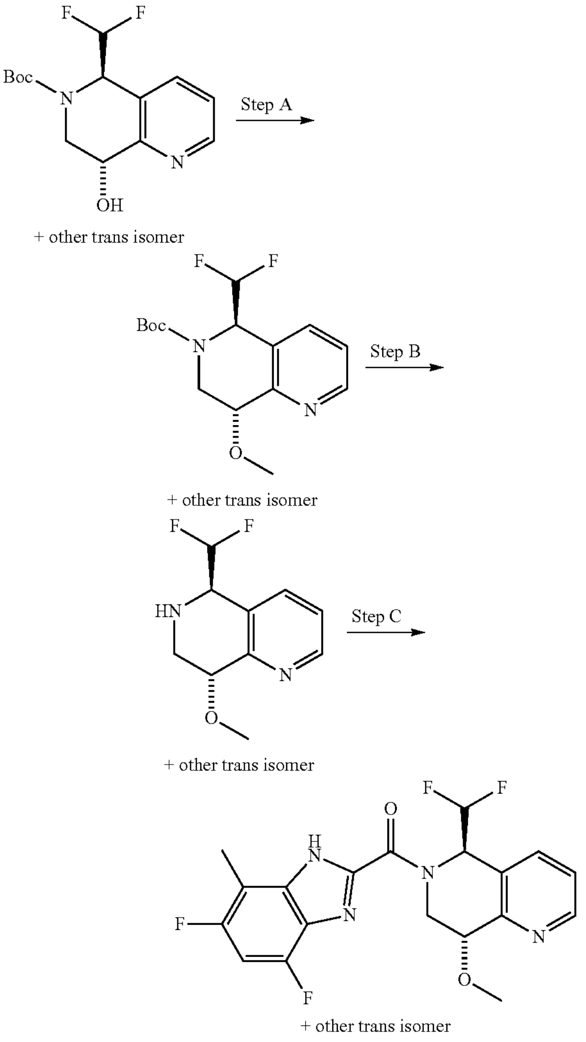

Step A: To a solution of rac-tert-butyl (trans)-5-(difluoromethyl)-8-hydroxy-7,8-dihydro-1,6-naphthyridine-6(5H)-carboxylate (trans isomers of Example 4A and 4B, Step B) (120 mg, 0.356 mmol) in ACN (2.00 mL) was added silver oxide (248 mg, 1.07 mmol) and methyl iodide (506 mg, 3.56 mmol). The mixture was stirred at 20° C. for 1 h. The reaction mixture was filtered and the filtrate was concentrated to give a residue which was purified by flash silica gel chromatography using a 0 to 100% EtOAc in petroleum ether to give rac-tert-butyl (trans)-5-(difluoromethyl)-8-methoxy-7,8-dihydro-1,6-naphthyridine-6(5H)-carboxylate (80 mg, 55%). LC-MS: 314.9 $[M+H]^+$.

Step B: Rac-tert-butyl (trans)-5-(difluoromethyl)-8-methoxy-7,8-dihydro-1,6-naphthyridine-6(5H)-carboxylate (80 mg, 0.254 mmol) was dissolved in 4M HCl in EtOAc (2.00 mL) and the mixture was stirred at 20° C. for 1 h. The reaction mixture was filtered and the filtered cake was dried to give rac-(trans)-5-(difluoromethyl)-8-methoxy-5,6,7,8-tetrahydro-1,6-naphthyridine hydrochloride (80 mg, crude). LC-MS: 214.9 $[M+H]^+$.

Step C: To a solution of rac-(trans)-5-(difluoromethyl)-8-methoxy-5,6,7,8-tetrahydro-1,6-naphthyridine hydrochloride (80.0 mg, 3.18 mmol) and 4,6-difluoro-7-methyl-1H-benzimidazole-2-carboxylic acid (67.7 mg, 3.18 mmol) in THF (2.00 mL) were added Phosphoric acid bis(2-oxooxazolidide) chloride (162.4 mg, 0.636 mmol) and DIEA (82.4 mg, 0.636 mmol). The mixture was stirred at 20° C. for 1 h. The reaction mixture was filtered and the filtrate was concentrated to give a residue. The residue was dissolved in ACN (1.00 mL), and the resulting solution was purified by prep-HPLC (Waters Xbridge Prep OBD C18 (150x40 mm, 10 μm), Flow rate: 60 ml/min; gradient: 27%-57% B over 8 min; mobile phase A: water (10 mM $NH_4HCO_3$), mobile phase B: acetonitrile) to afford rac-(4,6-difluoro-7-methyl-1H-benzo[d]imidazol-2-yl)((5R,8R)-5-(difluoromethyl)-8-methoxy-7,8-dihydro-1,6-naphthyridin-6(5H)-yl)methanone (20.64 mg, 14%, trans racemic). LC-MS: 409.1 $[M+H]^+$. $^1H$ NMR (400 MHz, $CDCl_3$) δ 10.65-10.29 (m, 1H), 8.72 (br d, J=4.6 Hz, 1H), 8.20-8.01 (m, 1H), 7.76-7.49 (m, 2H), 6.97-5.99 (m, 3H), 5.49-4.66 (m, 1H), 3.89 (br d, J=14.9 Hz, 1H), 3.67-3.51 (m, 3H), 2.58-2.37 (m, 3H).

Examples 5A and 5B: (5S,8S) or (5R,8R)-(4,6-Difluoro-7-methyl-1H-benzo[d]imidazol-2-yl)(5-(difluoromethyl)-8-methoxy-7,8-dihydro-1,6-naphthyridin-6(5H)-yl)methanone and (5S,8S) or (5R,8R)-(4,6-Difluoro-7-methyl-1H-benzo[d]imidazol-2-yl)(5-(difluoromethyl)-8-methoxy-7,8-dihydro-1,6-naphthyridin-6(5H)-yl)methanone

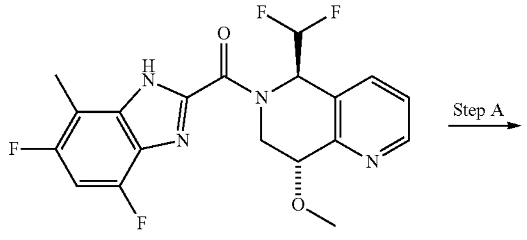

+ other trans isomer

-continued

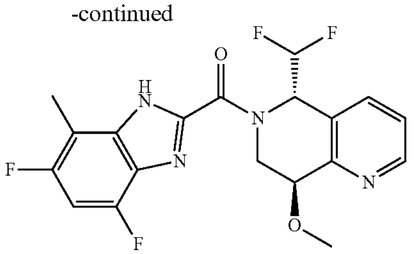

+

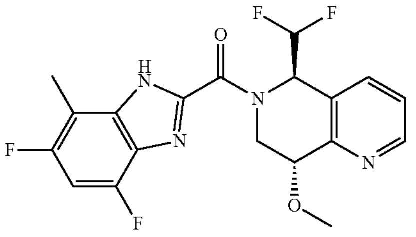

Step A: rac-(4,6-Difluoro-7-methyl-1H-benzo[d]imidazol-2-yl)((5R,8S)-5-(difluoromethyl)-8-methoxy-7,8-dihydro-1,6-naphthyridin-6(5H)-yl)methanone (20 mg) was purified by chiral SFC (column: DAICEL CHIRALPAK IG (250 mmx30 mm, 10 μm); mobile phase: [$CO_2$-MeOH (0.1% $NH_3H_2O$)]; B %: 35%, isocratic elution mode) to afford a first eluted compound and a second eluted compound. First eluted compound (Example 5A): LC-MS: 409.1 $[M+H]^+$. $^1H$ NMR (400 MHz, DMSO-$d_6$) δ 13.99-13.73 (m, 1H), 8.68-8.57 (m, 1H), 8.11-7.89 (m, 1H), 7.55-7.44 (m, 1H), 7.37-6.22 (m, 3H), 6.15 (br d, J=15.0 Hz, 1H), 5.28-3.84 (m, 2H), 3.43 (s, 1H), 3.09 (s, 2H), 2.43 (br d, J=3.6 Hz, 3H). Second eluted compound (Example 5B): LC-MS: 409.1 $[M+H]^+$. $^1H$ NMR (400 MHz, DMSO-$d_6$) δ 14.02-13.64 (m, 1H), 8.68-8.60 (m, 1H), 8.08-7.91 (m, 1H), 7.54-7.46 (m, 1H), 7.35-6.11 (m, 4H), 5.27-3.86 (m, 2H), 3.43 (s, 1H), 3.09 (s, 2H), 2.43 (br d, J=3.9 Hz, 3H). The absolute stereochemistry for the first and second eluted compounds was not determined.

Example 6: (S)-(7-Chloro-4-fluoro-6-methoxy-1H-benzo[d]imidazol-2-yl)(5-(difluoromethyl)-7,8-dihydro-1,6-naphthyridin-6(5H)-yl)methanone

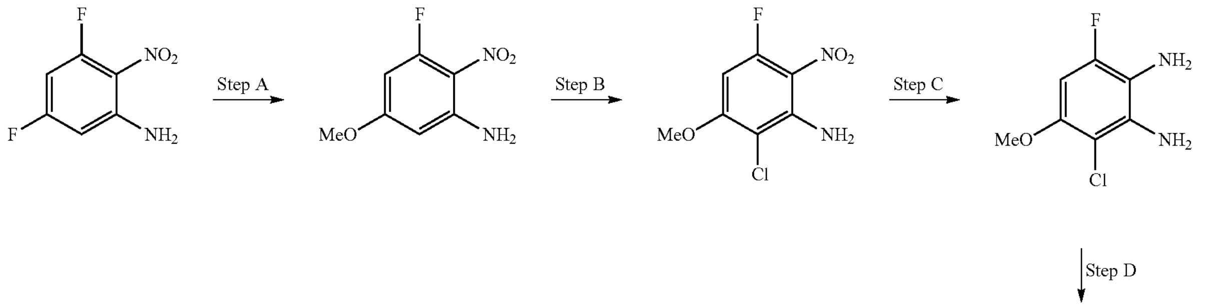

-continued

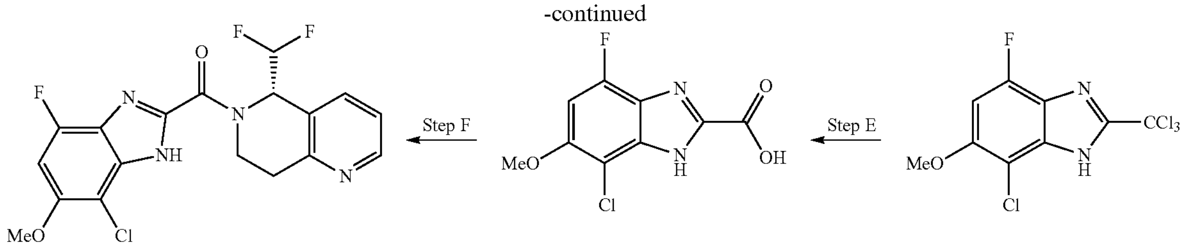

Step A: To a solution of 3,5-difluoro-2-nitro-aniline (2.50 g, 14.3 mmol) in THF (50.0 mL) was added a solution of sodium methoxide (930 mg, 17.2 mmol) in MeOH (10.0 mL) dropwise at −78° C. under a nitrogen atmosphere. The mixture was stirred at 20° C. for 12 h. The reaction mixture was poured into H2O (20.0 mL) and extracted with EtOAc (20.0 mL×3). The combined organic layers were dried over anhydrous sodium sulfate, filtered, and concentrated under vacuum to give a residue which was purified by flash silica gel chromatography to afford 3-fluoro-5-methoxy-2-nitroaniline (1.60 g, 30%). $^1$H NMR (400 MHz, DMSO-d6) δ 7.30 (br s, 2H), 6.33-6.12 (m, 2H), 3.76 (s, 3H).

Step B: To a solution of 3-fluoro-5-methoxy-2-nitro-aniline (1.60 g, 8.60 mmol) in acetonitrile (20.0 mL) was added N-chlorosuccinimide (1.15 g, 8.60 mmol). The mixture was stirred at 70° C. for 12 h. The reaction mixture was poured into $H_2O$ (30.0 mL) and extracted with EtOAc (30.0 mL×3). The combined organic layers were dried over $Na_2SO_4$, filtered, and concentrated under vacuum to give 2-chloro-5-fluoro-3-methoxy-6-nitro-aniline (1.1 g, 58%). LC-MS: 221.1 $[M+H]^+$.

Step C: To a solution of 2-chloro-5-fluoro-3-methoxy-6-nitro-aniline (500 mg, 2.27 mmol) in EtOH (6.00 mL) and $H_2O$ (2.00 mL) was added iron powder (1.01 g, 18.1 mmol) and ammonium chloride (969 mg, 18.1 mmol). The mixture was stirred at 70° C. for 1 h. The reaction mixture was filtered and the filtrate was concentrated under vacuum to give a residue. The residue was diluted with DCM (100 ml) and washed with brine (100 mL×3). The organic layer was dried over sodium sulfate, filtered and concentrated to give a crude product which was purified by flash silica gel chromatography to afford 3-chloro-6-fluoro-4-methoxybenzene-1,2-diamine (380 mg, 88%). LC-MS: 191.1 $[M+H]^+$.

Step D: To a solution of 3-chloro-6-fluoro-4-methoxybenzene-1,2-diamine (350 mg, 1.84 mmol) in acetic acid (4.00 mL) was added methyl 2,2,2-trichloroethanimidate (324 mg, 1.84 mmol). The mixture was stirred at 20° C. for 2 h. The reaction mixture was filtered, and the filter cake was washed with water (10 mL), dried under reduced pressure to give 7-chloro-4-fluoro-6-methoxy-2-(trichloromethyl)-1H-benzimidazole (500 mg, crude).

Step E: A mixture of 7-chloro-4-fluoro-6-methoxy-2-(trichloromethyl)-1H-benzimidazole (500 mg, 1.57 mmol) and NaOH (2 M aqueous, 4.31 mL) was stirred at 20° C. for 2 h. The reaction mixture was filtered, and the filter cake was washed with water (10 mL), and dried under reduced pressure to afford 7-chloro-4-fluoro-6-methoxy-1H-benzimidazole-2-carboxylic acid (320 mg, 83%). LC-MS: 245.0 $[M+H]^+$.

Step F: To a solution of 7-chloro-4-fluoro-6-methoxy-1H-benzimidazole-2-carboxylic acid (50 mg, 0.204 mmol) and (5S)-5-(difluoromethyl)-5,6,7,8-tetrahydro-1,6-naphthyridine (product of Example 3, Step E) (45.1 mg, 0.204 mmol, HCl) in THF (2.00 mL) was added phosphoric acid bis(2-oxooxazolidide) chloride (104 mg, 409 mmol) and DIEA (52.8 mg, 409 mmol). The mixture was stirred at 20° C. for 1 h. The reaction mixture was filtered and the filtrate was concentrated to give a residue. The residue was purified by prep-TLC to give (S)-(7-chloro-4-fluoro-6-methoxy-1H-benzo[d]imidazol-2-yl)(5-(difluoromethyl)-7,8-dihydro-1,6-naphthyridin-6(5H)-yl)methanone (20.3 mg, 24%). LC-MS: 411.0 $[M+H]^+$. $^1$H NMR (400 MHz, DMSO-$d_6$) δ 8.53 (dd, J=1.3, 4.7 Hz, 1H), 7.99-7.69 (m, 1H), 7.34 (dt, J=4.8, 8.1 Hz, 1H), 7.28-7.08 (m, 1H), 7.06-6.01 (m, 2H), 5.44-4.61 (m, 1H), 3.90 (d, J=3.9 Hz, 3H), 3.81-3.37 (m, 1H), 3.24-2.91 (m, 2H).

Examples 7A and 7B: (R) or (S)-(7-Chloro-4-fluoro-1H-benzo[d]imidazol-2-yl)(5-(fluoromethyl)-7,8-dihydro-1,6-naphthyridin-6(5H)-yl)methanone and (R) or (S)-(7-Chloro-4-fluoro-1H-benzo[d]imidazol-2-yl)(5-(fluoromethyl)-7,8-dihydro-1,6-naphthyridin-6(5H)-yl)methanone

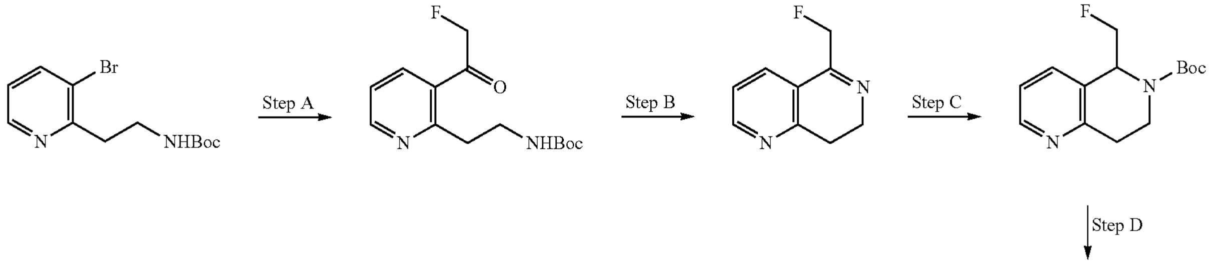

-continued

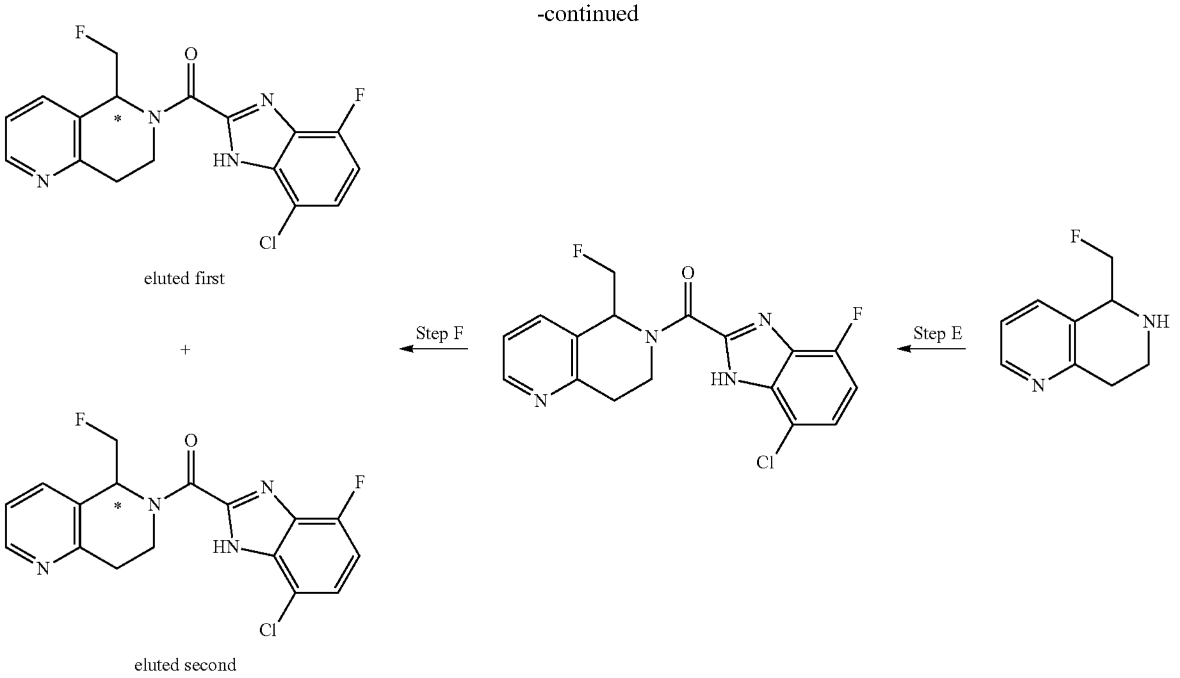

Step A: To a solution of tert-butyl (2-(3-bromopyridin-2-yl)ethyl)carbamate (2.00 g, 6.64 mmol) in toluene (20.0 mL) was added 60% sodium hydride in mineral oil (531 mg, 13.3 mmol) at 0° C. under $N_2$. The reaction mixture was stirred at 0° C. for 0.5 h. The above mixture and a 1.6 M n-butyllithium solution in hexanes (1.60 M, 16.1 mL) were added into toluene (20.0 mL) at the same time at −78° C. under nitrogen. The reaction mixture was stirred at −78° C. for 0.5 h. 2-Fluoro-N-methoxy-N-methyl-acetamide (1.61 g, 13.3 mmol, 4.00 mL) in toluene (5 mL) was then added drop wise. The mixture was stirred at same temperature for 1 h, then allowed to warm to 20° C. The mixture was poured into saturated ammonium chloride aqueous solution (20 mL) and extracted with EtOAc (15 mLx3). The combined organic layers were dried over $Na_2SO_4$, filtered, and concentrated to give a residue which was purified by flash silica gel chromatography to give tert-butyl (2-(3-(2-fluoroacetyl)pyridin-2-yl)ethyl)carbamate (400 mg, 1.19 mmol, 17%). LC-MS: 283.2 $[M+H]^+$.

Step B: A mixture of tert-butyl (2-(3-(2-fluoroacetyl) pyridin-2-yl)ethyl)carbamate (300 mg, 1.06 mmol) and 4M HCl in EtOAc (3.00 mL) was stirred at 20° C. for 1 h. The reaction mixture was concentrated to give 5-(fluoromethyl)-7,8-dihydro-1,6-naphthyridine hydrochloride (200 mg, crude). LC-MS: 164.9 $[M+H]^+$.

Step C: To a solution of 5-(fluoromethyl)-7,8-dihydro-1,6-naphthyridine hydrochloride (200 mg, 0.997 mmol) and $Boc_2O$ (326 mg, 1.50 mmol) in MeOH (5.00 mL) was added sodium borohydride (283 mg, 7.48 mmol) at 0° C. The mixture was stirred at 0° C. for 1 h, then was poured into saturated aqueous $NH_4Cl$ solution (10.0 mL) and extracted with EtOAc (10 mLx3). The combined organic layers were washed with brine (10.0 mL), dried over anhydrous sodium sulfate, filtered and concentrated under vacuum to give a residue, which was purified by flash silica gel chromatography to afford tert-butyl 5-(fluoromethyl)-7,8-dihydro-5H-1,6-naphthyridine-6-carboxylate (170 mg, 0.458 mmol, 45%). LC-MS: 267.2 $[M+H]^+$.

Step D: A solution of tert-butyl 5-(fluoromethyl)-7,8-dihydro-5H-1,6-naphthyridine-6-carboxylate (130 mg, 0.488 mmol) in 4M HCl in EtOAc (5.00 mL) was stirred at 20° C. for 1 h. The reaction mixture was concentrated under vacuum to give 5-(fluoromethyl)-5,6,7,8-tetrahydro-1,6-naphthyridine hydrochloride (98.9 mg, crude). LC-MS: 167.2 $[M+H]^+$. 1. Step E: To a solution of 7-chloro-4-fluoro-1H-benzimidazole-2-carboxylic acid (103 mg, 0.480 mmol) and 5-(fluoromethyl)-5,6,7,8-tetrahydro-1,6-naphthyridine hydrochloride (97.3 mg, 0.480 mmol) in DCM (5.00 mL) was added TEA (194 mg, 1.92 mmol, 267 μL) and Phosphoric acid bis(2-oxooxazolidide) chloride (244 mg, 0.960 mmol) at 20° C. The mixture was stirred at 20° C. for 1 h. The mixture was then filtered and the filtrate was purified by preparative HPLC (Waters Xbridge Prep OBD C18 column (150x40 mm, 10 μm); flow rate: 60 mL/min; gradient: 20%-50% B over 8 min; mobile phase A: water (10 mM $NH_4HCO_3$), mobile phase B: acetonitrile) to give 7-chloro-4-fluoro-1H-benzo[d]imidazol-2-yl)(5-(fluoromethyl)-7,8-dihydro-1,6-naphthyridin-6(5H)-yl)methanone (120 mg, 68%). LC-MS: 363.0 $[M+H]^+$.

Step F: (7-Chloro-4-fluoro-1H-benzimidazol-2-yl)-[5-(fluoromethyl)-7,8-dihydro-5H-1,6-naphthyridin-6-yl] methanone (80 mg) was dissolved in isopropanol (2.00 mL), and the resulting solution was purified by chiral SFC (column: ChiralPak IH, 250*30 mm, 10 um; mobile phase: 35% CO2 over IPA (0.1% $NH_3H_2O$ (isocratic elution mode) to afford a first eluted compound (10.9 mg) and a second eluted compound (10.5 mg). First eluted compound (Example 7A): LC-MS: 363.0 $[M+H]^+$; $^1H$ NMR (400 MHz, $CD_3CN$) δ 11.87-11.28 (m, 1H), 8.47 (d, J=4.50 Hz, 1H), 7.85-7.65 (m, 1H), 7.40-7.21 (m, 2H), 7.16-7.03 (m, 1H), 6.07-5.64 (m, 1H), 5.09-4.64 (m, 3H), 3.97-3.43 (m, 1H), 3.29-2.99 (m, 2H). Second eluted compound (Example 7B): LC-MS: 363.0 $[M+H]^+$; $^1H$ NMR (400 MHz, $CD_3CN$) δ 11.91-11.24 (m, 1H), 8.48 (d, J=4.38 Hz, 1H), 7.81-7.63 (m, 1H), 7.39-7.21 (m, 2H), 7.16-6.92 (m, 1H), 6.08-5.61 (m, 1H), 5.08-4.70 (m, 3H), 4.00-3.41 (m, 1H), 3.29-2.98 (m, 2H).

The absolute stereochemistry for the first and second eluted compounds was not determined.

Examples 8A and 8B: (R) or (S)-(4,6-Difluoro-7-methyl-1H-benzo[d]imidazol-2-yl)(5-(fluoromethyl)-7,8-dihydro-1,6-naphthyridin-6(5H)-yl)methanone and (R) or (S)-(4,6-Difluoro-7-methyl-1H-benzo[d]imidazol-2-yl)(5-(fluoromethyl)-7,8-dihydro-1,6-naphthyridin-6(5H)-yl)methanone

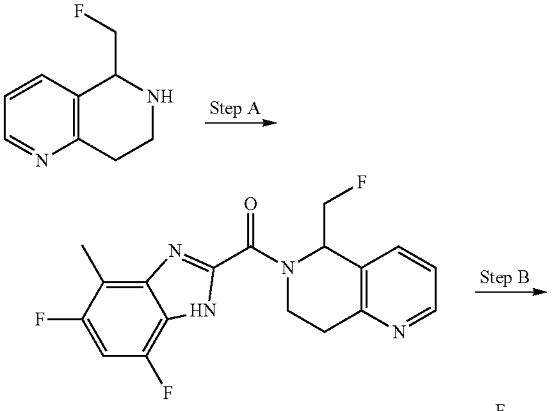

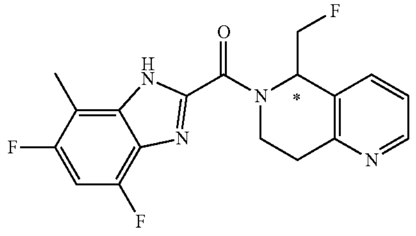

eluted first

+

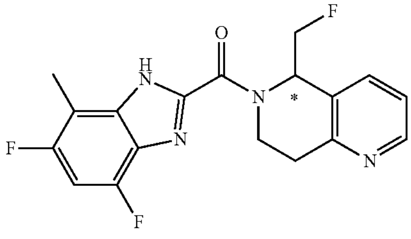

eluted second

Step A: To a solution of 5-(fluoromethyl)-5,6,7,8-tetrahydro-1,6-naphthyridine hydrochloride (product of Example 7A and 7B, Step D) (50.0 mg, 0.247 mmol) and 4,6-difluoro-7-methyl-1H-benzimidazole-2-carboxylic acid (52.3 mg, 0.247 mmol) in DCM (5.00 mL) was added TEA (49.9 mg, 0.493 mmol, 68.7 μL) and phosphoric acid bis(2-oxooxazolidide) chloride (94.2 mg, 0.370 mmol) at 20° C. and the mixture was stirred at 20° C. for 1 h. The reaction mixture was purified by flash silica gel chromatography to give (5,7-difluoro-4-methyl-1H-benzimidazol-2-yl)-[5-(fluoromethyl)-7,8-dihydro-5H-1,6-naphthyridin-6-yl]methanone (50.0 mg, 56%). LC-MS: 361.0 $[M+H]^+$.

Step B: (4,6-Difluoro-7-methyl-1H-benzo[d]imidazol-2-yl)(5-(fluoromethyl)-7,8-dihydro-1,6-naphthyridin-6(5H)-yl)methanone (50.0 mg, 138 mol) was purified by chiral SFC (column: ChiralPak IH, 250×30 mm, 10 um; mobile phase: 20% $[CO_2$—IPA](isocratic elution mode) to afford a first eluted compound and a second eluted compound. First eluted compound (Example 8A): LC-MS: 361.0 $[M+H]^+$; $^1H$ NMR (400 MHz, $CD_3CN$) δ 11.54-11.16 (m, 1H), 8.47 (d, J=4.6 Hz, 1H), 7.91-7.58 (m, 1H), 7.31-7.10 (m, 1H), 7.06-6.85 (m, 1H), 6.03-5.85 (m, 1H), 4.98-4.76 (m, 2H), 3.94-3.41 (m, 1H), 3.29-2.95 (m, 2H), 2.55-2.38 (m, 3H). Second eluted compound (Example 8B): LC-MS: 361.0 $[M+H]^+$; $^1H$ NMR (400 MHz, $CD_3CN$) δ 11.44 (br s, 1H), 8.47 (d, J=4.6 Hz, 1H), 7.89-7.60 (m, 1H), 7.29-7.12 (m, 1H), 7.03-6.80 (m, 1H), 6.10-5.76 (m, 1H), 4.98-4.75 (m, 2H), 3.94-3.41 (m, 1H), 3.28-2.99 (m, 2H), 2.53-2.36 (m, 3H). The absolute stereochemistry for the first and second eluted compounds was not determined.

Examples 9A and 9B: (R) or (S)-(7-Chloro-4-fluoro-6-methoxy-1H-benzo[d]imidazol-2-yl)(5-(fluoromethyl)-7,8-dihydro-1,6-naphthyridin-6(5H)-yl)methanone and (R) or (S)-(7-Chloro-4-fluoro-6-methoxy-1H-benzo[d]imidazol-2-yl)(5-(fluoromethyl)-7,8-dihydro-1,6-naphthyridin-6(5H)-yl)methanone

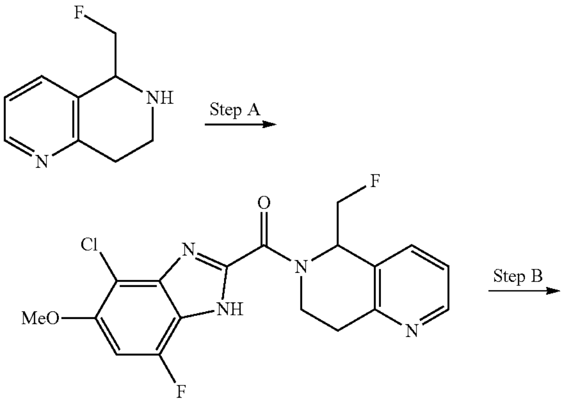

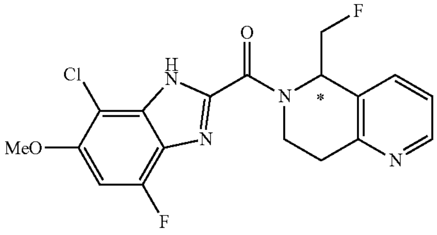

eluted first

+

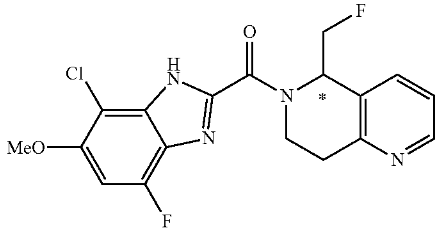

eluted second

Step A: A mixture of 5-(fluoromethyl)-5,6,7,8-tetrahydro-1,6-naphthyridine hydrochloride (product of Example 7A and 7B, Step D) (32.0 mg, 0.193 mmol), 7-chloro-4-fluoro-6-methoxy-1H-benzimidazole-2-carboxylic acid (product of Example 6, Step E) (47.1 mg, 0.193 mmol), HATU (73.2 mg, 0.193 mmol) and DIEA (74.7 mg, 0.578 mmol) in DMF (2.00 mL) was stirred at 25° C. for 2 h. The reaction mixture was poured into $H_2O$ (2.00 mL) and extracted with DCM (2.00 mL×4). The combined organic layers were dried over $Na_2SO_4$, filtered, and concentrated under vacuum to give a residue which was purified by preparative HPLC (Waters Xbridge Prep OBD C18 column 150×40 mm×10 um); flow rate: 25 mL/min; gradient: 25%-55% B over 8 min; mobile phase A: 10 mM aqueous $NH_4HCO_3$, mobile phase B: acetonitrile) to give (7-chloro-4-fluoro-6-methoxy-1H-benzo[d]imidazol-2-yl)(5-(fluoromethyl)-7,8-dihydro-1,6-naphthyridin-6(5H)-yl)methanone (55.0 mg, 71%). LC-MS: 393.1 $[M+H]^+$.

Step B: (7-Chloro-4-fluoro-6-methoxy-1H-benzo[d]imidazol-2-yl)(5-(fluoromethyl)-7,8-dihydro-1,6-naphthyridin-6(5H)-yl)methanone (55.0 mg) was further purified by chiral SFC DAICEL CHIRALPAK IG (250×30 mm, 10 μm); flow rate: 80 mL/min; gradient: 35% B over 66 min; mobile phase A: heptane, mobile phase B: $CO_2$-EtOH (0.1% $NH_3H_2O$) to afford a first eluted compound and a second eluted compound. First eluted compound (Example 9A): LC-MS: 393.1 $[M+H]^+$; $^1H$ NMR (400 MHz, DMSO-$d_6$) δ 14.30-13.56 (m, 1H), 8.65-8.35 (m, 1H), 8.04-7.75 (m, 1H), 7.45-7.06 (m, 2H), 6.91-5.87 (m, 1H), 5.47-4.97 (m, 1H), 4.97-4.76 (m, 2H), 3.91 (d, J=5.0 Hz, 3H), 3.83 (br s, 1H), 3.23-3.08 (m, 1H), 3.05-2.93 (m, 1H). Second eluted compound (Example 9B): LC-MS: 393.1 $[M+H]^+$; $^1H$ NMR (400 MHz, DMSO-$d_6$) δ 14.17-13.57 (m, 1H), 8.61-8.27 (m, 1H), 8.04-7.70 (m, 1H), 7.45-7.03 (m, 2H), 6.83-5.90 (m, 1H), 5.20-4.97 (m, 1H), 4.97-4.75 (m, 2H), 3.91 (d, J=5.1 Hz, 3H), 3.83 (br s, 1H), 3.27-3.08 (m, 1H), 3.04-2.94 (m, 1H). The absolute stereochemistry for the first and second eluted compounds was not determined.

Example 10: (S)-(4,6-Difluoro-7-methyl-1H-benzo[d]imidazol-2-yl)(5-(difluoromethyl)-7,8-dihydro-1,6-naphthyridin-6(5H)-yl)methanone

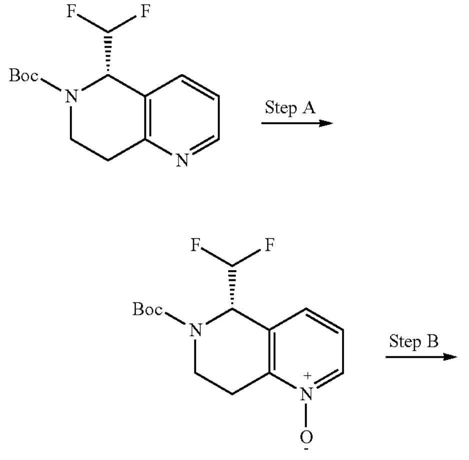

-continued

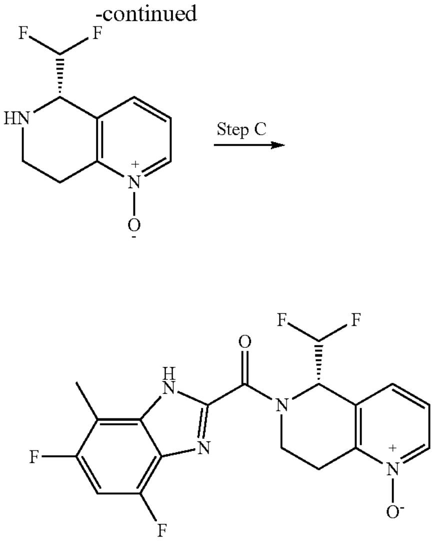

Step A: To a solution of (S)-tert-butyl 5-(difluoromethyl)-7,8-dihydro-1,6-naphthyridine-6(5H)-carboxylate (product of Example 3, Step D) (100 mg, 0.351 mmol) in DCM (5 mL) was added m-CPBA (143 mg, 0.703 mmol, 85% purity) at 0° C. under $N_2$, then the mixture was stirred at 20° C. for 16 h. The reaction mixture was quenched by saturated sodium sulfite aqueous solution (10 mL) and extracted with EtOAc (3.0 mL×3). The combined organic phases were washed with brine (5.0 mL), dried over anhydrous sodium sulfate, filtered and concentrated in vacuum to give a residue which was purified by flash silica gel chromatography to give (S)-6-(tert-butoxycarbonyl)-5-(difluoromethyl)-5,6,7,8-tetrahydro-1,6-naphthyridine 1-oxide (80 mg, 74.12%). LC-MS: 301.2 $[M+H]^+$.

Step B: To a solution of (S)-6-(tert-butoxycarbonyl)-5-(difluoromethyl)-5,6,7,8-tetrahydro-1,6-naphthyridine 1-oxide (80 mg, 0.266 mmol) in DCM (2 mL) was added trifluoroacetic acid (30.38 mg, 0.266 mmol). The mixture was stirred at 20° C. for 1 h. The reaction mixture was concentrated to give (S)-5-(difluoromethyl)-5,6,7,8-tetrahydro-1,6-naphthyridine 1-oxide trifluoroacetic acid salt (80 mg, crude). LC-MS: 200.8 $[M+H]^+$.

Step C: To a solution of (S)-5-(difluoromethyl)-5,6,7,8-tetrahydro-1,6-naphthyridine 1-oxide trifluoroacetic acid salt (80 mg, 0.254 mmol) and 4,6-difluoro-7-methyl-1H-benzimidazole-2-carboxylic acid (54.02 mg, 0.254 mmol) in THF (2.0 mL) were added phosphoric acid bis(2-oxooxazolidide) chloride (130 mg, 0.509 mmol) and DIEA (65.8 mg, 0.509 mmol). The mixture was stirred at 20° C. for 16 h. The reaction mixture was filtered and the filtrate was concentrated to give a residue which was purified by preparative HPLC (Column: WePure Biotech XP tC18 150*40*7 um, Flow rate: 50.00 ml/min, Gradient: B from 20.00% to 60.00% in 8.00 min, Mobile phase: A: $H_2O$ (10 mM $NH_4HCO_3$); B: ACN) to give (S)-6-(4,6-difluoro-7-methyl-1H-benzo[d]imidazole-2-carbonyl)-5-(difluoromethyl)-5,6,7,8-tetrahydro-1,6-naphthyridine 1-oxide (28.8 mg, 28%). LC-MS: 395.1 $[M+H]^+$; $^1H$ NMR (400 MHz, DMSO-$d_6$) δ 14.01-13.72 (m, 1H), 8.36 (d, J=6.0 Hz, 1H), 7.57-7.12 (m, 4H), 6.91-6.45 (m, 1H), 6.21-5.61 (m, 1H), 4.99-3.68 (m, 1H), 3.18 (dt, J=3.9, 18.9 Hz, 1H), 2.99-2.69 (m, 1H), 2.43 (br s, 3H).

Examples 11A and 11B: (5R,8S) or (5S,8R)-(4,6-Difluoro-7-methyl-1H-benzo[d]imidazol-2-yl)(8-ethoxy-5-methyl-7,8-dihydro-1,6-naphthyridin-6(5H)-yl)methanone and (5R,8S) or (5S,8R)-(4,6-Difluoro-7-methyl-1H-benzo[d]imidazol-2-yl)(8-ethoxy-5-methyl-7,8-dihydro-1,6-naphthyridin-6(5H)-yl)methanone (8.00 g, 40.0 mmol, 85% purity). The mixture was stirred at 25° C. for 2 h, then was poured into saturated sodium sulfite aqueous solution (200 mL) and extracted with DCM (200 mL×3). The combined organic layers were dried over anhydrous sodium sulfate, filtered, and concentrated to give 6-(tert-butoxycarbonyl)-5-methyl-5,6,7,8-tetrahydro-1,6-naphthyridine 1-oxide (5.00 g, 94%). LC-MS: 265.2 [M+H]+.

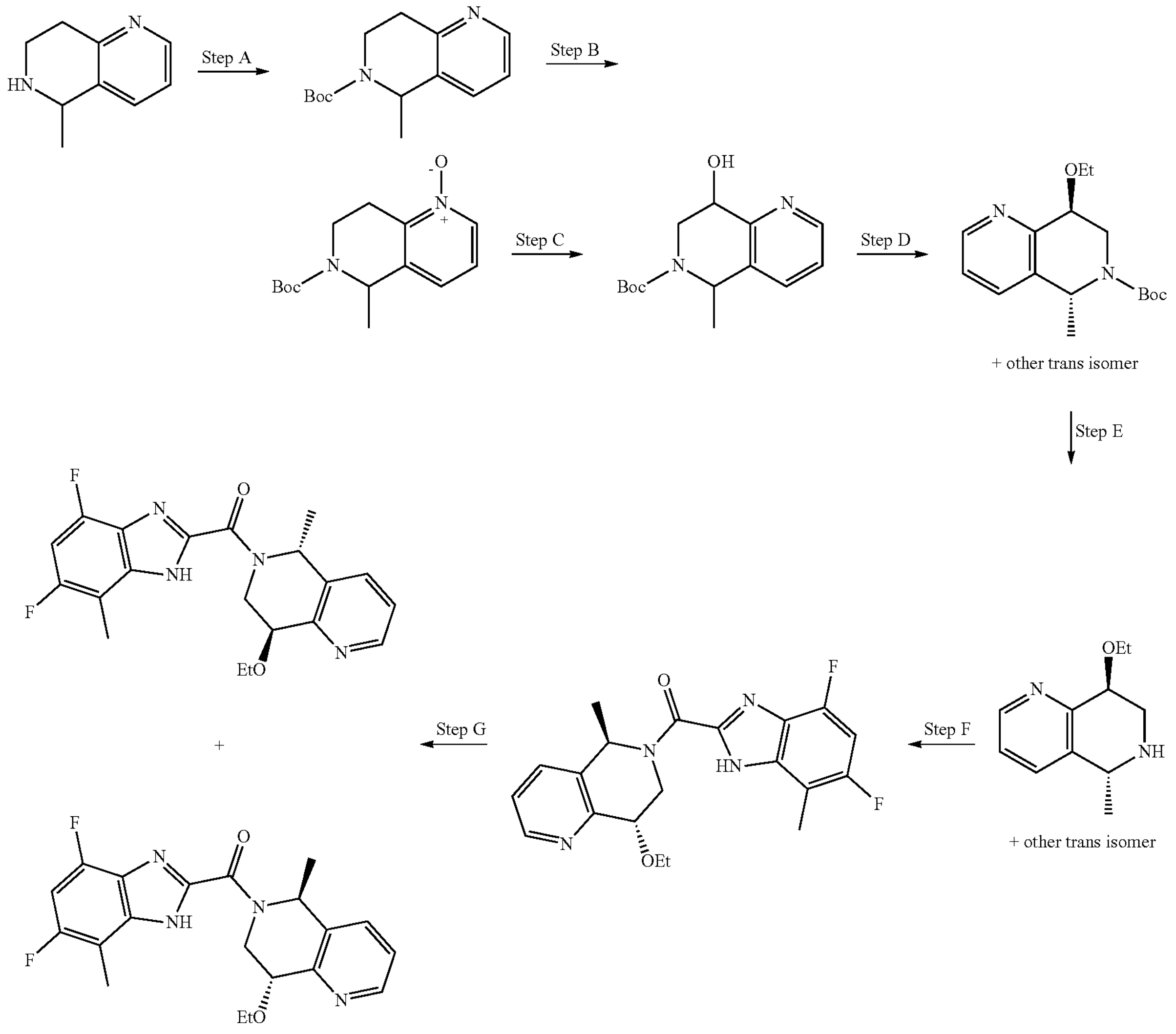

Step A: To a solution of 5-methyl-5,6,7,8-tetrahydro-1,6-naphthyridine hydrochloride (14.0 g, 75.8 mmol) in DCM (140 mL) was added di-tert-butyl dicarbonate (19.9 g, 91.0 mmol) and TEA (15.3 g, 152 mmol, 21.1 mL). The mixture was stirred at 20° C. for 1 h. The reaction mixture was poured into $H_2O$ (100 mL) and extracted with DCM (100 mL×3). The combined organic layers were dried over anhydrous sodium sulfate filtered, and concentrated under vacuum to give a residue which was purified by flash silica gel chromatography to give tert-butyl 5-methyl-7,8-dihydro-1,6-naphthyridine-6(5H)-carboxylate (16.0 g, 85%). LC-MS: 249.3 [M+H]+.

Step B: To a solution of tert-butyl 5-methyl-7,8-dihydro-1,6-naphthyridine-6(5H)-carboxylate (5.00 g, 20.0 mmol) in DCM (50.0 mL) was added m-chloroperoxybenzoic acid Step C: To a solution of 6-(tert-butoxycarbonyl)-5-methyl-5,6,7,8-tetrahydro-1,6-naphthyridine 1-oxide (4.00 g, 15.0 mmol) in DMF (40.0 mL) was added trifluoroacetic anhydride (13.0 g, 61.0 mmol, 8.00 mL) at 0° C. The mixture was then heated to 60° C. and stirred for 1 h. The reaction mixture was allowed to cool to RT, then was concentrated under vacuum. The residue was diluted with saturated sodium carbonate aqueous solution (60.0 mL) and extracted with EtOAc (80.0 mL×3). The combined organic layers were washed with saturated aqueous lithium chloride solution (80.0 mL×5), dried over anhydrous sodium sulfate, filtered and concentrated to give a residue which was purified by flash silica gel chromatography to give tert-butyl 8-hydroxy-5-methyl-7,8-dihydro-1,6-naphthyridine-6(5H)-carboxylate (4.00 g, 100%). LC-MS: 265.2 [M+H]+.

Step D: To a solution of tert-butyl 8-hydroxy-5-methyl-7,8-dihydro-1,6-naphthyridine-6(5H)-carboxylate (1.00 g, 3.78 mmol) in THF (100 mL) was added sodium tert-butoxide (1.09 g, 11.3 mmol) and iodoethane (9.44 g, 60.5 mmol, 4.84 mL). The mixture was stirred at 25° C. for 1 h under nitrogen atmosphere. The reaction mixture was diluted with $H_2O$ (50.0 mL) and extracted with EtOAc (100 mL×3). The combined organic layers were dried over anhydrous sodium sulfate, filtered and concentrated under reduced pressure to give a residue which was purified by prep-HPLC (column: Waters Xbridge Prep OBD C18 150×40 mm×10 μm; mobile phase: [$H_2O$ (10 mM $NH_4HCO_3$)-ACN]; gradient: 30%-60% 8.0 min.) to give tert-butyl 8-ethoxy-5-methyl-7,8-dihydro-1,6-naphthyridine-6(5H)-carboxylate (120 mg, 11%, trans racemate) and the cis isomer racemate. LC-MS: 293.1 $[M+H]^+$.

Step E: To a solution of tert-butyl 8-ethoxy-5-methyl-7,8-dihydro-1,6-naphthyridine-6(5H)-carboxylate (90.0 mg, 0.308 mmol, trans racemate) in EtOAc (1.00 mL) was added 4 M HCl in EtOAc (4.00 mL). The mixture was stirred at 20° C. for 2 h. The reaction mixture was concentrated under reduced pressure to give rac-trans-8-ethoxy-5-methyl-5,6,7,8-tetrahydro-1,6-naphthyridine hydrochloride. LC-MS: 193.1 $[M+H]^+$.

Step F: To a solution of rac-trans-8-ethoxy-5-methyl-5,6,7,8-tetrahydro-1,6-naphthyridine hydrochloride (70.0 mg, 0.306 mmol) in DMF (1.00 mL) were added DIEA (79.1 mg, 0.612 mmol, 0.106 mL), 4,6-difluoro-7-methyl-1H-benzo[d]imidazole-2-carboxylic acid (71.4 mg, 0.337 mmol) and hexafluorophosphate Azabenzotriazole Tetramethyl Uronium (174 mg, 0.459 mmol). The mixture was stirred at 20° C. for 0.5 h. The reaction mixture was purified by preparative HPLC (Phenomenex Luna C18 column (100×40 mm, 5 μm); flow rate: 60 mL/min; gradient: 10%-50% B over 8 min; mobile phase A: 0.04% aqueous HCl, mobile phase B: acetonitrile) to give rac-trans-(4,6-difluoro-7-methyl-1H-benzo[d]imidazol-2-yl)(8-ethoxy-5-methyl-7,8-dihydro-1,6-naphthyridin-6(5H)-yl)methanone (40.0 mg, 34%, trans racemate). LC-MS: 387.2 $[M+H]^+$.

Step G: The enantiomers of rac-trans-(4,6-difluoro-7-methyl-1H-benzo[d]imidazol-2-yl)(8-ethoxy-5-methyl-7,8-dihydro-1,6-naphthyridin-6(5H)-yl)methanone (40.0 mg, 0.103 mmol) were separated by chiral SFC(REGIS (s,s) WHELK-01 (250 mm×30 mm, 5 μm); mobile phase: 50% $CO_2$ over EtOH (0.1% $NH_3H_2O$) isocratic mode to afford a first eluted compound and a second eluted compound. First eluted compound (Example 11A): LC-MS: 387.1 $[M+H]^+$; $^1H$ NMR (400 MHz, DMSO-$d_6$) δ 13.87-13.48 (m, 1H), 8.49 (br d, J=2.9 Hz, 1H), 7.97-7.72 (m, 1H), 7.49-7.28 (m, 1H), 7.20-7.08 (m, 1H), 6.61-5.01 (m, 2H), 4.54-4.24 (m, 1H), 3.92-3.60 (m, 1H), 3.41 (br d, J=6.9 Hz, 2H), 2.42 (br s, 3H), 1.68-1.46 (m, 3H), 1.15-0.65 (m, 3H). Second eluted compound (Example 11B): LC-MS: 387.1 $[M+H]^+$. $^1H$ NMR (400 MHz, DMSO-$d_6$) δ 13.83-13.55 (m, 1H), 8.55-8.43 (m, 1H), 7.88 (d, J=7.3 Hz, 1H), 7.46-7.31 (m, 1H), 7.14 (br s, 1H), 6.67-4.95 (m, 2H), 4.54-4.23 (m, 1H), 3.89-3.61 (m, 1H), 3.51-3.34 (m, 2H), 2.42 (br s, 3H), 1.71-1.46 (m, 3H), 1.14-0.69 (m, 3H). The absolute stereochemistry for the first and second eluted compounds was not determined.

Examples 12A and 12B: (4-Fluoro-7-methyl-1H-benzo[d]imidazol-2-yl)((trans)-8-methoxy-5-methyl-7,8-dihydro-1,6-naphthyridin-6(5H)-yl)methanone (trans racemic) and cis-(4-Fluoro-7-methyl-1H-benzo[d]imidazol-2-yl)((cis)-8-methoxy-5-methyl-7,8-dihydro-1,6-naphthyridin-6(5H)-yl)methanone (Cis Racemic)

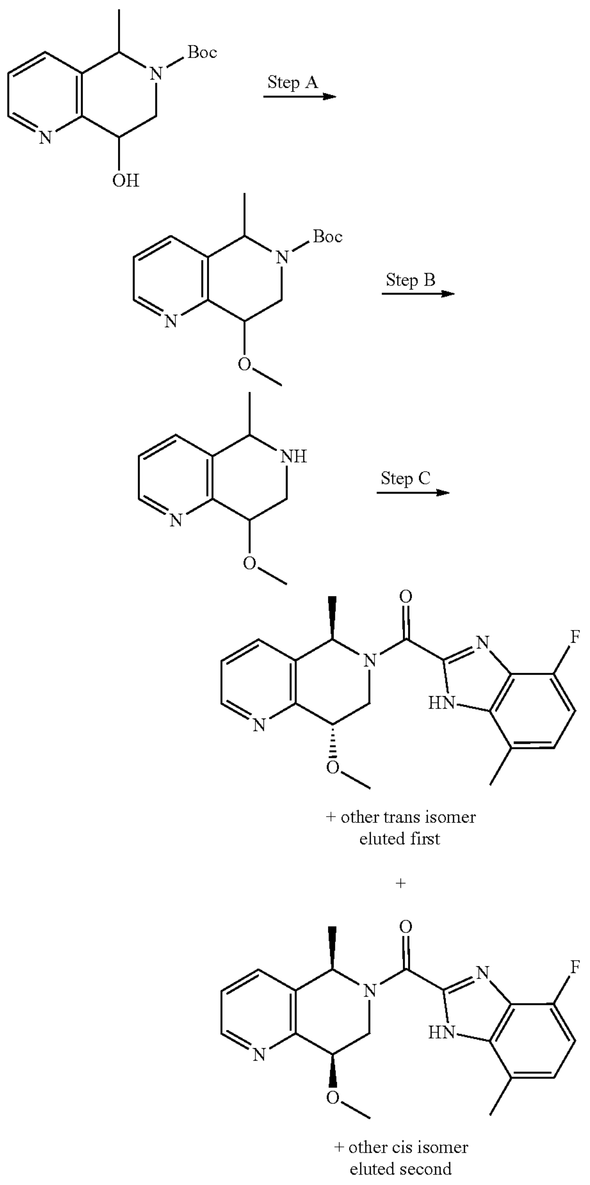

Step A: To a solution of tert-butyl 8-hydroxy-5-methyl-7,8-dihydro-1,6-naphthyridine-6(5H)-carboxylate (product of Examples 11A and 11B, Step C) (500 mg, 2.00 mmol) in THF (5.00 mL) were added sodium tert-butoxide (545 mg, 6.00 mmol) and methyl iodide (537 mg, 4.00 mmol). The mixture was stirred at 25° C. for 2 h under $N_2$ atmosphere. The reaction mixture was concentrated under reduced pressure, and then diluted with $H_2O$ (20.0 mL) and extracted with EtOAc (30.0 mL×3). The combined organic layers were washed with saturated aqueous lithium chloride solution (10.0 mL×5), dried over sodium sulfate, and filtered to give tert-butyl 8-methoxy-5-methyl-7,8-dihydro-1,6-naphthyridine-6(5H)-carboxylate (400 mg, crude) as a mixture of cis and trans diastereomers. LC-MS: 279.2 $[M+H]^+$.

Step B: A solution of tert-butyl 8-methoxy-5-methyl-7,8-dihydro-1,6-naphthyridine-6(5H)-carboxylate (200 mg, 0.719 mmol) in 4M HCl in EtOAc (5.00 mL) was stirred at 25° C. for 1 h. The reaction mixture was concentrated under reduced pressure to give 8-methoxy-5-methyl-5,6,7,8-tetrahydro-1,6-naphthyridine hydrochloride (150 mg, crude). LC-MS: 179.3 $[M+H]^+$.

Step C: To a solution of 8-methoxy-5-methyl-5,6,7,8-tetrahydro-1,6-naphthyridine (80.0 mg, 0.373 mmol), 4-fluoro-7-methyl-1H-benzimidazole-2-carboxylic acid (86.8 mg, 0.447 mmol) in DMF (1.00 mL) were added DIEA (144 mg, 1.12 mmol) and HATU (142 mg, 0.373 mmol). The mixture was stirred at 20° C. for 1 h. The reaction mixture was poured into $H_2O$ (2.00 mL) and extracted with EtOAc (3.00 mL×3). The combined organic layers were dried over anhydrous sodium sulfate, filtered and concentrated under reduced pressure to give a residue which was purified by prep-HPLC (column: Phenomenex luna C18 150×40 mm×10 um; mobile phase A: water (10 mM $NH_4HCO_3$), mobile phase B: acetonitrile) to give (4-fluoro-7-methyl-1H-benzo[d]imidazol-2-yl)((5S,8R)-8-methoxy-5-methyl-7,8-dihydro-1,6-naphthyridin-6(5H)-yl)methanone (6.81 mg, HPLC eluted first, trans racemic) (Example 12A). LC-MS: 355.1 $[M+H]^+$; H NMR (400 MHz, DMSO-$d_6$) δ 8.55-8.32 (m, 1H), 7.98-7.72 (m, 1H), 7.53-7.20 (m, 1H), 7.15-6.89 (m, 2H), 6.57-5.99 (m, 1H), 5.97-5.06 (m, 1H), 4.49-4.15 (m, 1H), 3.91-3.63 (m, 1H), 3.46 (s, 1H), 3.22-3.08 (m, 2H), 1.73-1.38 (m, 3H). (4-fluoro-7-methyl-1H-benzo[d]imidazol-2-yl)((5S,8S)-8-methoxy-5-methyl-7,8-dihydro-1,6-naphthyridin-6(5H)-yl)methanone (22.4 mg, HPLC eluted second, cis racemic) (Example 12B). LC-MS: 355.1 $[M+H]^+$; $^1H$ NMR (400 MHz, DMSO-$d_6$) δ 13.55 (br s, 1H), 8.62-8.34 (m, 1H), 7.92-7.57 (m, 1H), 7.45-7.22 (m, 1H), 7.15-6.91 (m, 2H), 6.38-5.53 (m, 1H), 5.44-5.03 (m, 1H), 4.80-4.55 (m, 1H), 4.54-3.81 (m, 1H), 3.73-3.51 (m, 3H), 1.78-1.44 (m, 3H).

Example 13: rac-trans-(6-Chloro-4-fluoro-7-methyl-1H-benzo[d]imidazol-2-yl)(8-methoxy-5-methyl-7,8-dihydro-1,6-naphthyridin-6(5H)-yl)methanone

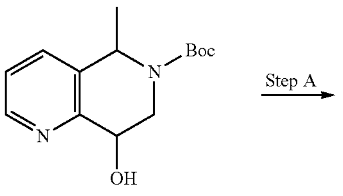

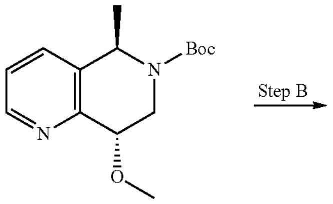

+ other trans isomer

-continued

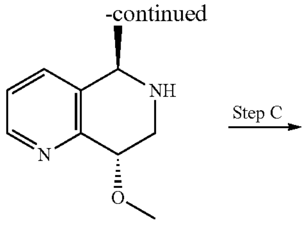

+ other trans isomer

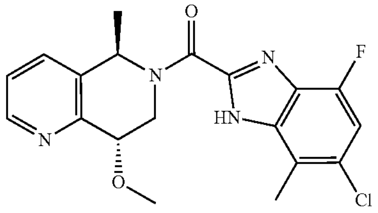

+ other trans isomer

Step A: To a solution of tert-butyl 8-hydroxy-5-methyl-7,8-dihydro-5H-1,6-naphthyridine-6-carboxylate (product of Examples 11A and 11B, Step C) (400 mg, 1.51 mmol) in THF (4.00 mL) was added sodium tert-butoxide (436 mg, 4.54 mmol) and methyl iodide (430 mg, 3.03 mmol). The mixture was stirred at 25° C. for 2 h under $N_2$ atmosphere. The residue was diluted with $H_2O$ (10.0 mL) and extracted with EtOAc (10.0 mL×3). The combined organic layers were dried over anhydrous sodium sulfate, filtered and concentrated under reduced pressure to give a residue which was purified by prep-HPLC (column: Phenomenex luna C18 150×40 mm×10 um; mobile phase A: water (10 mM $NH_4HCO_3$), mobile phase B: acetonitrile) to give tert-butyl 8-methoxy-5-methyl-7,8-dihydro-1,6-naphthyridine-6(5H)-carboxylate (20 mg, trans racemic, eluted first). LC-MS: 279.1 $[M+H]^+$.

Step B: To a solution of rac-trans-tert-butyl 8-methoxy-5-methyl-7,8-dihydro-1,6-naphthyridine-6(5H)-carboxylate (20.0 mg, 0.072 mmol) in EtOAc (1.00 mL) was added 2 M HCl in EtOAc (1.00 mL). The mixture was stirred at 20° C. for 1 h. The reaction mixture was concentrated under reduced pressure to give trans-8-methoxy-5-methyl-5,6,7,8-tetrahydro-1,6-naphthyridine (20 mg, crude, trans racemic). LC-MS: 179.3 $[M+H]^+$.

Step C: To a solution of rac-trans-8-methoxy-5-methyl-5,6,7,8-tetrahydro-1,6-naphthyridine (20.0 mg, 0.093 mmol), 6-chloro-4-fluoro-7-methyl-1H-benzimidazole-2-carboxylic acid (21.3 mg, 0.093 mmol) in DMF (1.50 mL) were added DIEA (12.0 mg, 0.093 mmol) and HATU (35.4 mg, 0.093 mmol). The mixture was stirred at 20° C. for 1 h. The reaction mixture was quenched by addition to $H_2O$ (2.00 mL) and extracted with EtOAc (3.00 mL×3). The combined organic layers were dried over anhydrous sodium sulfate, filtered and concentrated under reduced pressure to give a residue which was purified by preparative HPLC (Phenomenex Luna C18 column 100×40 mm×5 um); flow rate: 25 mL/min; gradient: 20%-50% B over 8 min; mobile phase A: 0.04% aqueous HCl, mobile phase B: acetonitrile) to give trans-(6-chloro-4-fluoro-7-methyl-1H-benzo[d]imidazol-2-yl)(8-methoxy-5-methyl-7,8-dihydro-1,6-naphthyridin-6(5H)-yl)methanone (13.6 mg, 45%, trans racemic). LC-MS: 389.1 $[M+H]^+$; $^1H$ NMR (400 MHz, DMSO-$d_6$) δ 8.64 (br d, J=3.9 Hz, 1H), 8.30-7.85 (m, 1H), 7.77-7.17 (m, 2H), 6.55-6.00 (m, 1H), 5.98-5.07 (m, 1H), 4.55-4.33 (m, 1H), 3.50 (s, 2H), 3.19 (s, 2H), 2.57-2.52 (m, 3H), 1.79-1.33 (m, 3H).

Examples 14A and 14B: (5R,8S) or (5S,8R)-(4,6-Difluoro-7-methyl-1H-benzo[d]imidazol-2-yl)(8-methoxy-5-methyl-7,8-dihydro-1,6-naphthyridin-6(5H)-yl)methanone and (5R,8S) or (5S,8R)-(4,6-Difluoro-7-methyl-1H-benzo[d]imidazol-2-yl)(8-methoxy-5-methyl-7,8-dihydro-1,6-naphthyridin-6(5H)-yl)methanone

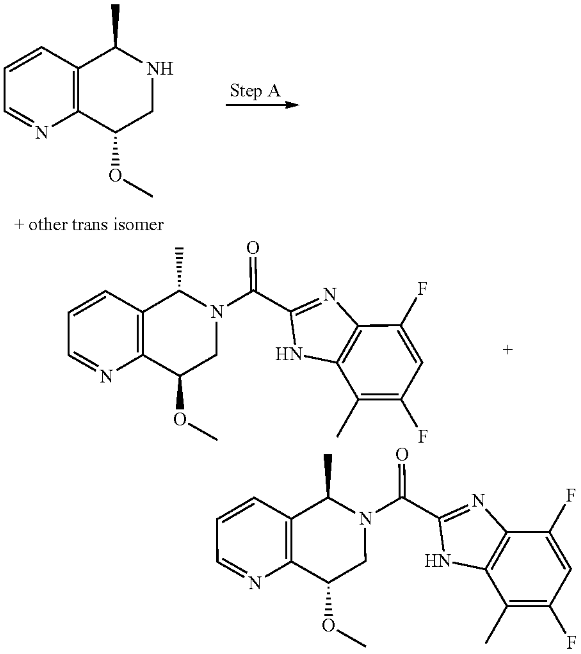

Step A: To a solution of rac-trans-8-methoxy-5-methyl-5,6,7,8-tetrahydro-1,6-naphthyridine (product of Example 13, Step B) (130 mg, 0.606 mmol) in DMF (2.00 mL) was added 4,6-difluoro-7-methyl-1H-benzimidazole-2-carboxylic acid (128 mg, 0.606 mmol), DIEA (235 mg, 1.82 mmol) and HATU (230 mg, 0.606 mmol). The mixture was stirred at 20° C. for 1 h. The residue was diluted with $H_2O$ (5.00 mL) and extracted with EtOAc (5.00 mL×3). The combined organic layers were dried over $Na_2SO_4$, filtered and concentrated under reduced pressure to give a residue which was purified by flash silica gel chromatography using 0 to 30% methanol in dichloromethane to give rac-trans-(4,6-difluoro-7-methyl-1H-benzo[d]imidazol-2-yl)(-8-methoxy-5-methyl-7,8-dihydro-1,6-naphthyridin-6(5H)-yl)methanone. The material was further purified by chiral SFC (REGIS (s,s) WHELK-01 (250 mm×30 mm, 5 um); flow rate: 30 mL/min; gradient: 30% B over 14 min; mobile phase A: heptane, mobile phase B: CO2-EtOH (0.1% NH3H2O)). First eluted compound (Example 14A): LC-MS: 373.1 $[M+H]^+$; $^1H$ NMR (400 MHz, DMSO-$d_6$) δ 13.90-13.59 (m, 1H), 8.74-8.43 (m, 1H), 8.10-7.77 (m, 1H), 7.52-7.28 (m, 1H), 7.25-6.85 (m, 1H), 6.54-5.97 (m, 1H), 5.94-5.02 (m, 1H), 4.50-4.10 (m, 1H), 3.80 (br d, J=13.9 Hz, 1H), 3.46 (br d, J=0.8 Hz, 2H), 3.16 (d, J=0.9 Hz, 2H), 2.43 (br s, 3H), 1.76-1.40 (m, 3H). Second eluted compound (Example 14B): LC-MS: 373.1 [M+H]; $^1H$ NMR (400 MHz, DMSO-$d_6$) δ 13.96-13.42 (m, 1H), 8.51 (d, J=3.8 Hz, 1H), 8.06-7.65 (m, 1H), 7.48-7.35 (m, 1H), 7.24-7.08 (m, 1H), 6.52-5.97 (m, 1H), 5.92-4.99 (m, 1H), 4.41-4.14 (m, 1H), 3.90-3.68 (m, 1H), 3.48-3.45 (m, 1H), 3.16 (s, 2H), 2.43 (br s, 3H), 1.72-1.47 (m, 3H). The absolute stereochemistry for the first and second eluted compounds was not determined.

Example 15: (5R)-6-(7-Chloro-4-fluoro-1H-benzo[d]imidazole-2-carbonyl)-5-methyl-5,6,7,8-tetrahydro-1,6-naphthyridine-8-carbonitrile

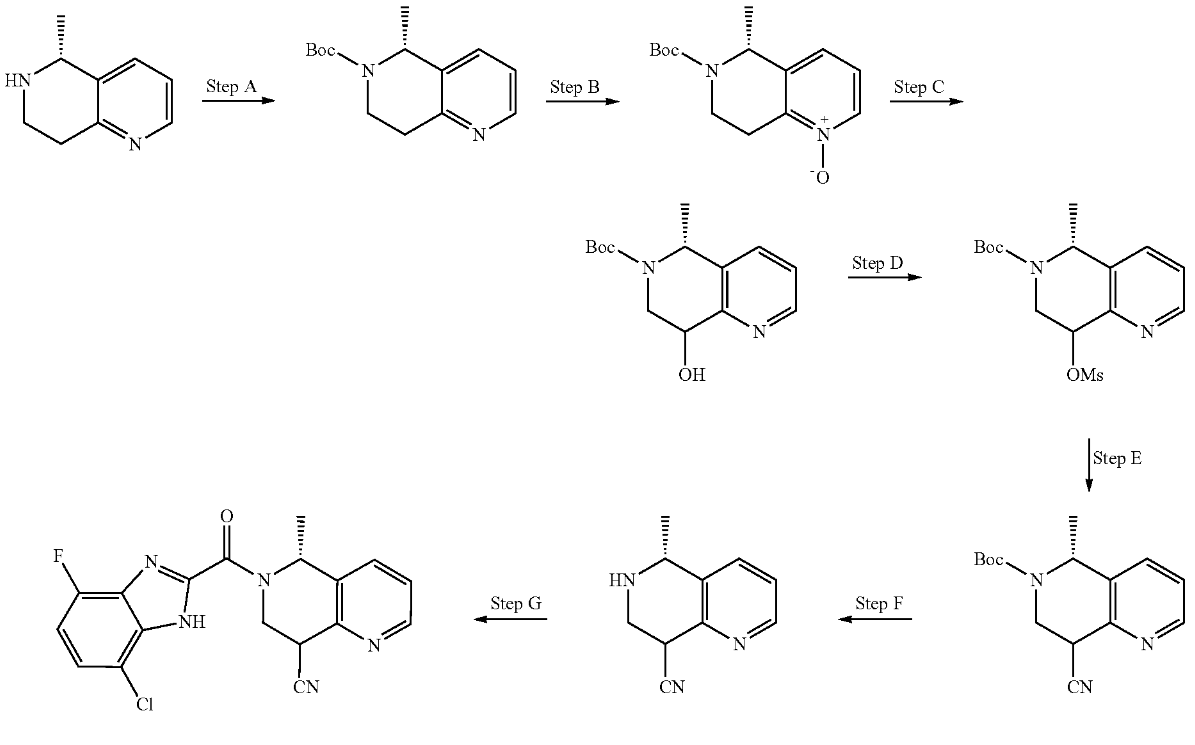

Step A: To a solution of (5R)-5-methyl-5,6,7,8-tetrahydro-1,6-naphthyridine (4.5 g, 24.4 mmol, HCl) in DCM (50.0 mL) was added TEA (4.93 g, 48.7 mmol) and di-tert-butyl dicarbonate (6.38 g, 29.2 mmol) at 20° C. and the mixture was stirred at 20° C. for 1 h. The reaction mixture was concentrated to give a residue, which was purified by flash silica gel chromatography to give tert-butyl (R)-5-methyl-7,8-dihydro-1,6-naphthyridine-6(5H)-carboxylate (5.25 g, 80%). LC-MS: 249.2 $[M+H]^+$.

Step B: To a solution of tert-butyl (R)-5-methyl-7,8-dihydro-1,6-naphthyridine-6(5H)-carboxylate (4.75 g, 19.1 mmol) in DCM (100 mL) was added meta-chloroperoxybenzoic acid (7.77 g, 38.2 mmol, 85% purity) at 0° C. and the mixture was stirred at 20° C. for 1 h. The reaction mixture was quenched by saturated sodium sulfite aqueous solution (200 mL) and extracted with DCM (200 mL×3). The combined organic phases were washed with brine (100 mL), dried over anhydrous sodium sulfate, filtered and concentrated under vacuum. The residue was purified by flash silica gel chromatography to give (R)-6-(tert-butoxycarbonyl)-5-methyl-5,6,7,8-tetrahydro-1,6-naphthyridine 1-oxide (5.25 g, 78%). LC-MS: 265.2 $[M+H]^+$.

Step C: To a solution of (R)-6-(tert-butoxycarbonyl)-5-methyl-5,6,7,8-tetrahydro-1,6-naphthyridine 1-oxide (5.25 g, 19.86 mmol) in DMF (50.0 mL) was added trifluoroacetic anhydride (16.7 g, 79.5 mmol) at 0° C. and the mixture was stirred at 60° C. for 3 h. The reaction mixture was diluted with $H_2O$ (300 mL) and extracted with EtOAc (100 mL×3). The combined organic phase was washed with brine (300 mL×1), dried over anhydrous sodium sulfate, filtered and concentrated give a residue which was purified by flash silica gel chromatography to give tert-butyl (5R)-8-hydroxy-5-methyl-7,8-dihydro-1,6-naphthyridine-6(5H)-carboxylate (5 g, 69%). LC-MS: 265.2 $[M+H]^+$.

Step D: To a solution of tert-butyl (5R)-8-hydroxy-5-methyl-7,8-dihydro-1,6-naphthyridine-6(5H)-carboxylate (2 g, 7.57 mmol) in DCM (20 mL) was added TEA (1.53 g, 15.13 mmol, 2.11 mL) and methanesulfonyl chloride (1.73 g, 15.13 mmol, 1.17 mL) at 0° C. and the mixture was stirred at 20° C. for 1 h. The reaction mixture was concentrated under vacuum. The residue was diluted with $H_2O$ (30 mL) and extracted with EtOAc (30 mL×3). The combined organic layers were dried over anhydrous sodium sulfate, filtered and concentrated under vacuum. The residue was purified by flash silica gel chromatography to give tert-butyl (5R)-5-methyl-8-((methylsulfonyl)oxy)-7,8-dihydro-1,6-naphthyridine-6(5H)-carboxylate (500 mg, 17%). LC-MS: 343.2 $[M+H]^+$.

Step E: To a solution of tert-butyl (5R)-5-methyl-8-((methylsulfonyl)oxy)-7,8-dihydro-1,6-naphthyridine-6(5H)-carboxylate (0.5 g, 1.46 mmol) in DMF (10.0 mL) was added sodium cyanide (501 mg, 10.2 mmol) at 20° C. and the mixture was stirred at 50° C. for 12 h. The reaction mixture was allowed to cool to RT, then was poured into water (10.0 mL) and extracted with EtOAc (10 mL×3). The combined organic layers were washed with brine (10 mL×1), dried over anhydrous sodium sulfate, filtered and concentrated under vacuum. The residue was dissolved in acetonitrile (1.00 mL), and the resulting solution was purified by prep-HPLC (Xbridge Prep OBD C18 (150×40 mm, 10 μm), Flow rate: 100 ml/min; gradient: 20%-50% B over 8 min; mobile phase A: water (10 mM $NH_4HCO_3$), mobile phase B: acetonitrile) to give tert-butyl (5R)-8-cyano-5-methyl-7,8-dihydro-1,6-naphthyridine-6(5H)-carboxylate (40 mg, 10%). LC-MS: 274.3 $[M+H]^+$.

Step F: tert-Butyl (5R)-8-cyano-5-methyl-7,8-dihydro-1,6-naphthyridine-6(5H)-carboxylate (40 mg, 146.34 mol) was treated with 4M HCl in EtOAc (2 mL) at 20° C. and the mixture was stirred at 20° C. for 1 h. The reaction mixture was concentrated to give (5R)-5-methyl-5,6,7,8-tetrahydro-1,6-naphthyridine-8-carbonitrile hydrochloride.

Step G: To a solution of (5R)-5-methyl-5,6,7,8-tetrahydro-1,6-naphthyridine-8-carbonitrile hydrochloride (30.7 mg, 0.146 mmol) and 7-chloro-4-fluoro-1H-benzimidazole-2-carboxylic acid (31.4 mg, 0.146 mmol) in DCM (2.00 mL) were added TEA (59.2 mg, 0.585 mmol) and phosphoric acid bis(2-oxooxazolidide) chloride (74.5 mg, 0.293 mmol) at 20° C. The mixture was stirred at 20° C. for 1 h. The reaction mixture was concentrated under vacuum to give a residue which was purified by prep-HPLC (Xbridge Prep OBD C18 (150×40 mm, 10 μm), Flow rate: 100 ml/min; gradient: 25%-55% B over 8 min; mobile phase A: water (10 mM $NH_4HCO_3$), mobile phase B: acetonitrile) to give (5R)-6-(7-chloro-4-fluoro-1H-benzo[d]imidazole-2-carbonyl)-5-methyl-5,6,7,8-tetrahydro-1,6-naphthyridine-8-carbonitrile (7.20 mg, 14). LC-MS: 370.0 $[M+H]^+$; $^1H$ NMR (400 MHz, $CD_3CN$) δ 8.59-8.47 (m, 1H), 7.91-7.57 (m, 1H), 7.54-7.21 (m, 2H), 7.16-6.98 (m, 1H), 6.87-6.11 (m, 1H), 6.00-5.09 (m, 1H), 4.78-4.22 (m, 1H), 4.01-3.58 (m, 1H), 1.78-1.57 (m, 3H).

Examples 16A and 16B: (R) or (S)-(7-Chloro-4,6-difluoro-1H-benzo[d]imidazol-2-yl)(4-methyl-6,7-dihydropyrazolo[1,5-a]pyrazin-5(4H)-yl)methanone and (R) or (S)-(7-Chloro-4,6-difluoro-1H-benzo[d]imidazol-2-yl)(4-methyl-6,7-dihydropyrazolo[1,5-a]pyrazin-5(4H)-yl)methanone

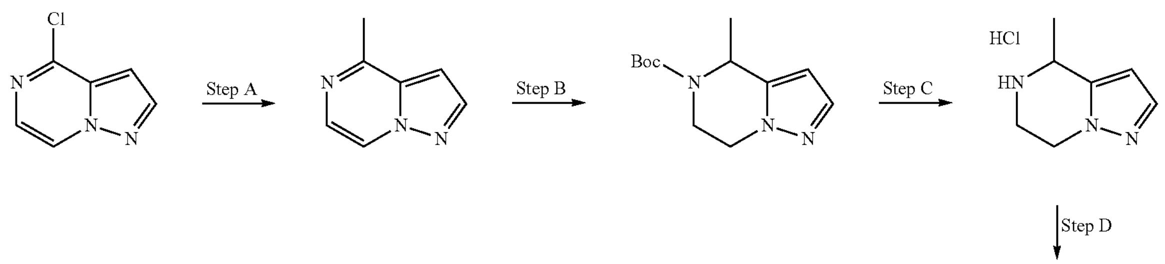

-continued

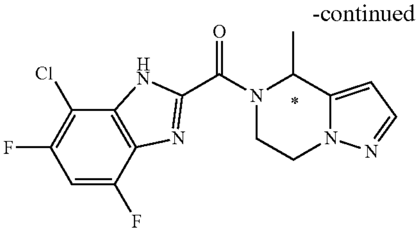

eluted first

+

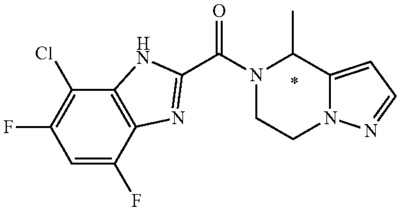

eluted second

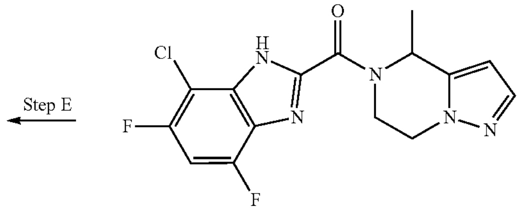

Step A: To a solution of 4-chloropyrazolo[1,5-a]pyrazine (5.0 g, 32.6 mmol) in dioxane (120 mL) and $H_2O$ (12 mL) was added 2,4,6-trimethyl-1,3,5,2,4,6-trioxatriborinane (3.5 M, 23.2 mL) and cesium carbonate (31.8 g, 97.6 mmol). The suspension was purged with $N_2$ for 2 minutes, then Pd(dppf)$Cl_2$ (4.76 g, 6.52 mmol) was added. The mixture was then stirred at 100° C. for 12 h. The reaction mixture was allowed to cool to RT, then was quenched by the addition of water (200 mL) at 25° C. and extracted with EtOAc (200 mL×3). The combined organic layers were dried over anhydrous sodium sulfate, filtered and concentrated under reduced pressure. The residue was purified by flash silica gel chromatography to give 4-methylpyrazolo[1,5-a]pyrazine (2.5 g, 53%). LC-MS: 134.2 $[M+H]^+$.

Step B: To a suspension of palladium on carbon (5.39 g, 10% purity) in THF (50 mL) were added 4-methylpyrazolo[1,5-a]pyrazine (2.5 g, 18.8 mmol) and $Boc_2O$ (4.10 g, 18.8 mmol). The mixture was stirred at 20° C. for 1 hour under a hydrogen atmosphere (15 psi). The mixture was filtered and the filtrate was concentrated under reduced pressure to give a crude material. The residue was purified by flash silica gel chromatography afford tert-butyl 4-methyl-6,7-dihydropyrazolo[1,5-a]pyrazine-5(4H)-carboxylate (3.5 g, 75%). LC-MS: 238.2 $[M+H]^+$.

Step C: A mixture of tert-butyl 4-methyl-6,7-dihydropyrazolo[1,5-a]pyrazine-5(4H)-carboxylate (31 g, 131 mmol) in 2 M HCl in EtOAc (358 mL) was stirred at 20° C. for 10 h. The mixture was concentrated under reduced pressure to give 4-methyl-4,5,6,7-tetrahydropyrazolo[1,5-a]pyrazine hydrochloride (25.0 g, crude). LC-MS: 138.3 $[M+H]^+$. 2. Step D: To a solution of 7-chloro-4,6-difluoro-1H-benzimidazole-2-carboxylic acid (70.0 mg, 0.301 mmol), 4-methyl-4,5,6,7-tetrahydropyrazolo[1,5-a]pyrazine hydrochloride (49.6 mg, 0.361 mmol) in DMF (1.5 mL) were added DIEA (117 mg, 0.903 mmol) and HBTU (114 mg, 0.301 mmol). The mixture was stirred at 20° C. for 1 h. The reaction mixture was quenched by addition to $H_2O$ (2.00 mL) and extracted with EtOAc (3.00 mL×3). The combined organic layers were dried over anhydrous sodium sulfate, filtered and concentrated under reduced pressure to give a residue which was purified by preparative HPLC (Phenomenex Luna C18 column (150×40 mm, 10 μm); flow rate: 25 mL/min; gradient: 25%-55% B over 8 min; mobile phase A: water (10 mM NH4HCO3), mobile phase B: acetonitrile) to give (7-chloro-4,6-difluoro-1H-benzo[d]imidazol-2-yl)(4-methyl-6,7-dihydropyrazolo[1,5-a]pyrazin-5(4H)-yl)methanone (45 mg, 40%). LC-MS: 352.1 $[M+H]^+$.

Step E: (7-Chloro-4,6-difluoro-1H-benzo[d]imidazol-2-yl)(4-methyl-6,7-dihydropyrazolo[1,5-a]pyrazin-5(4H)-yl) methanone (45 mg) was further purified by chiral SFC (DAICEL CHIRALPAK AD (250×30 mm, 10 μm; flow rate: 30 mL/min; gradient: 25% B over 14 min; mobile phase A: heptane, mobile phase B: CO2-IPA (0.1% NH3H2O) to give (7-chloro-4,6-difluoro-1H-benzo[d]imidazol-2-yl)(4-methyl-6,7-dihydropyrazolo[1,5-a]pyrazin-5(4H)-yl)methanone (9.20 mg, eluted first). LC-MS: 352.1 $[M+H]^+$; $^1H$ NMR (400 MHz, $CDCl_3$) δ 11.11-10.67 (m, 1H), 7.55 (s, 1H), 7.24-6.93 (m, 1H), 6.59 (br d, J=13.5 Hz, 1H), 6.25-6.10 (m, 1H), 6.05-5.07 (m, 1H), 4.58-4.18 (m, 2H), 3.92-3.52 (m, 1H), 1.79 (br d, J=6.6 Hz, 1H), 1.63 (d, J=6.9 Hz, 2H). (7-chloro-4,6-difluoro-1H-benzo[d]imidazol-2-yl)(4-methyl-6,7-dihydropyrazolo[1,5-a]pyrazin-5(4H)-yl)methanone (10.2 mg, eluted second). LC-MS: 352.0 $M+H]^+$; $^1H$ NMR (400 MHz, $CDCl_3$) δ 11.21-10.40 (m, 1H), 7.54 (br s, 1H), 7.21-6.82 (m, 1H), 6.74-6.38 (m, 1H), 6.25-6.11 (m, 1H), 6.07-4.96 (m, 1H), 4.54-4.10 (m, 2H), 3.95-3.31 (m, 1H), 1.79 (br d, J=6.5 Hz, 1H), 1.62 (d, J=6.8 Hz, 2H). The absolute stereochemistry for the first and second eluted compounds was not determined.

Example 17: (R) or (S)-(4,6-Difluoro-7-methyl-1H-benzo[d]imidazol-2-yl)(4-methyl-6,7-dihydropyrazolo[1,5-a]pyrazin-5(4H)-yl)methanone

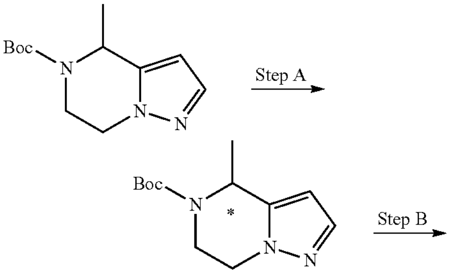

-continued

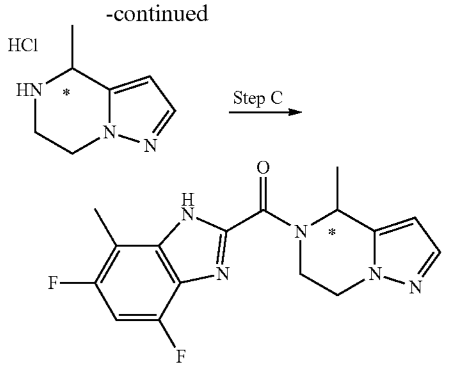

Step A: tert-Butyl 4-methyl-6,7-dihydropyrazolo[1,5-a]pyrazine-5(4H)-carboxylate (product of Examples 16A and 16B, Step B) (70.0 g, 295 mmol), was further separated by SFC separation DAICEL CHIRALPAK IG (250×50 mm, 10 μm); flow rate: 30 mL/min; gradient: 15% B over 14 min; mobile phase A: heptane, mobile phase B: $CO_2$-EtOH (0.1% $NH_3H_2O$) to afford (R) or (S)-tert-butyl 4-methyl-6,7-dihydropyrazolo[1,5-a]pyrazine-5(4H)-carboxylate (31.0 g, eluted first). LC-MS: [MH]=238.3. The absolute stereochemistry was not determined.

Step B: A mixture of (R) or (S)-tert-butyl 4-methyl-6,7-dihydropyrazolo[1,5-a]pyrazine-5(4H)-carboxylate (31 g, 131 mmol) in 2 M HCl in EtOAc (2 M, 357.69 mL) was stirred at 20° C. for 10 h. The mixture was concentrated under reduced pressure to give (R) or (S)-4-methyl-4,5,6,7-tetrahydropyrazolo[1,5-a]pyrazine hydrochloride (25.0 g, crude). LC-MS: 138.3 $[M+H]^+$. The absolute stereochemistry was not determined.

Step C: A mixture of (R) or (S)-4-methyl-4,5,6,7-tetrahydropyrazolo[1,5-a]pyrazine hydrochloride (60.0 mg, 0.346 mmol), 4,6-difluoro-7-methyl-1H-benzimidazole-2-carboxylic acid (73.3 mg, 0.346 mmol), DIEA (134 mg, 1.04 mmol) and HATU (131 mg, 0.346 mmol) in DMF (2.00 mL) was stirred at 25° C. for 2 h. The reaction mixture was poured into $H_2O$ (2.00 mL) and extracted with DCM (2.00 mL×4). The combined organic layers were dried over $Na_2SO_4$, filtered, and concentrated under vacuum to give a residue which was purified by preparative HPLC (Phenomenex Gemini C18 column (150×40 mm, 10 μm; flow rate: 25 mL/min; gradient: 30%-60% B over 8 min; mobile phase A: 10 mM $NH_4HCO_3$, mobile phase B: acetonitrile) to give (R) or (S)-(4,6-difluoro-7-methyl-1H-benzo[d]imidazol-2-yl)(4-methyl-6,7-dihydropyrazolo[1,5-a]pyrazin-5(4H)-yl)methanone (44.0 mg, 38%). LC-MS: 332.1 $[M+H]^+$; $^1H$ NMR (400 MHz, DMSO-$d_6$) δ 7.55-7.33 (m, 1H), 7.15 (br t, J=10.6 Hz, 1H), 6.63-6.15 (m, 1H), 5.93-5.65 (m, 1H), 4.93-4.27 (m, 1H), 4.25-3.98 (m, 1H), 3.92-3.54 (m, 1H), 3.47 (s, 1H), 2.41 (s, 3H), 1.73-1.47 (m, 3H). The absolute stereochemistry was not determined.

Example 18: (R) or (S)-(7-Chloro-4-fluoro-6-methoxy-1H-benzo[d]imidazol-2-yl)(4-methyl-6,7-dihydropyrazolo[1,5-a]pyrazin-5(4H)-yl)methanone

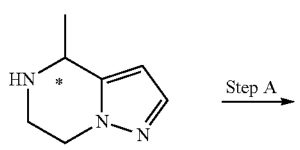

-continued

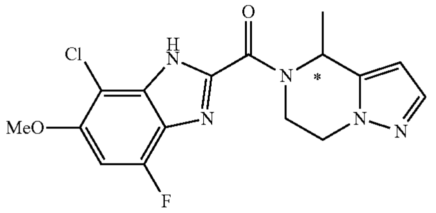

Step A: A mixture of (R) or (S)-4-methyl-4,5,6,7-tetrahydropyrazolo[1,5-a]pyrazine hydrochloride (56.0 mg, 0.323 mmol), 7-chloro-4-fluoro-6-methoxy-1H-benzimidazole-2-carboxylic acid (78.9 mg, 0.323 mmol), DIEA (125 mg, 0.968 mmol) and HATU (123 mg, 0.323 mmol) in DMF (1.00 mL) was stirred at 25° C. for 2 h. The reaction mixture was poured into $H_2O$ (2.00 mL) and extracted with DCM (2.00 mL×4). The combined organic layers were dried over $Na_2SO_4$, filtered, and concentrated under vacuum to give a residue. The mixture was purified by preparative HPLC (Phenomenex Gemini C18 column (150×40 mm, 10 μm); flow rate: 25 mL/min; gradient: 25%-55% B over 8 min; mobile phase A: 10 mM $NH_4HCO_3$, mobile phase B: acetonitrile) to give (R) or (S)-(7-chloro-4-fluoro-6-methoxy-1H-benzo[d]imidazol-2-yl)(4-methyl-6,7-dihydropyrazolo[1,5-a]pyrazin-5(4H)-yl)methanone (78.4 mg, 67% yield). LC-MS: 364.1 $[M+H]^+$; $^1H$ NMR (400 MHz, DMSO-$d_6$) δ 14.10-13.40 (m, 1H), 7.64-7.32 (m, 1H), 7.23 (br d, J=11.5 Hz, 1H), 6.48-6.08 (m, 1H), 5.94-5.31 (m, 1H), 4.92-4.26 (m, 1H), 4.25-3.99 (m, 1H), 3.76-3.76 (m, 1H), 3.99-3.52 (m, 3H), 2.49-2.45 (m, 1H), 1.82-1.35 (m, 3H).

Examples 19A and 19B: (R) or (S)-(6-Chloro-4-fluoro-7-methyl-1H-benzo[d]imidazol-2-yl)(4-methyl-6,7-dihydropyrazolo[1,5-a]pyrazine-5(4H)-yl)methanone and (R) or (S)-(6-Chloro-4-fluoro-7-methyl-1H-benzo[d]imidazol-2-yl)(4-methyl-6,7-dihydropyrazolo[1,5-a]pyrazin-5(4H)-yl)methanone

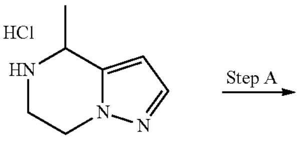

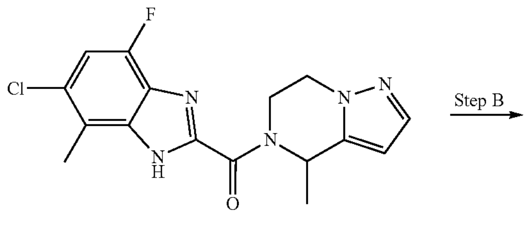

-continued

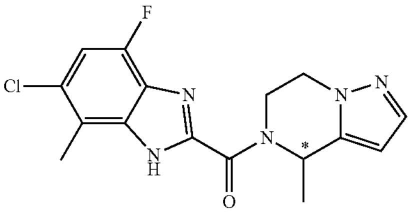

eluted first

+

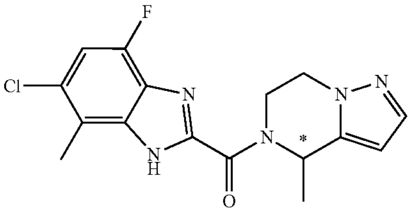

eluted second

Step A: To a solution of 6-chloro-4-fluoro-7-methyl-1H-benzimidazole-2-carboxylic acid (100 mg, 0.437 mmol) in DMF (2.00 mL) was added DIEA (113 mg, 0.875 mmol), 4-methyl-4,5,6,7-tetrahydropyrazolo[1,5-a]pyrazine hydrochloride (product of Examples 16A and 16B, Step C) (113 mg, 0.875 mmol) and HATU (83.2 mg, 0.219 mmol). The mixture was stirred at 25° C. for 1 h. The reaction mixture was poured into $H_2O$ (2.00 mL) and extracted with EtOAc (2.00 mL×3). The combined organic layers were washed with brine (2.00 mL×3), dried over $Na_2SO_4$, filtered, and concentrated under vacuum to give a residue which was purified by preparative TLC to give (6-chloro-4-fluoro-7-methyl-1H-benzo[d]imidazol-2-yl)(4-methyl-6,7-dihydropyrazolo[1,5-a]pyrazin-5(4H)-yl)methanone (100 mg, 64.8%). LC-MS: 348.2 $[M+H]^+$.

Step B: (6-Chloro-4-fluoro-7-methyl-1H-benzo[d]imidazol-2-yl)(4-methyl-6,7-dihydropyrazolo[1,5-a]pyrazin-5(4H)-yl)methanone (90.0 mg, 0.259 mmol) was further separated by chiral SFC (DAICEL CHIRALCEL OD (250×30 mm, 10 μm); flow rate: 30 mL/min; gradient: 30% B over 14 min; mobile phase A: heptane, mobile phase B: $CO_2$-EtOH (0.1% $NH_3H_2O$) to afford a first eluted compound (18.8 mg) and a second eluted compound (18.9 mg). First eluted compound (Example 19A): LC-MS: 348.1 $[M+H]^+$; $^1H$ NMR (400 MHz, $CDCl_3$) δ 10.95-10.30 (m, 1H), 7.53 (br d, J=2.1 Hz, 1H), 7.20-7.05 (m, 1H), 6.98-6.59 (m, 1H), 6.22-6.12 (m, 1H), 6.06-4.12 (m, 3H), 3.96-3.44 (m, 1H), 2.78-2.41 (m, 3H), 1.81-1.61 (m, 3H). Second eluted compound (Example 19B): LC-MS: 348.1 $[M+H]^+$; $^1H$ NMR (400 MHz, $CDCl_3$) δ 10.90-10.29 (m, 1H), 7.53 (s, 1H), 7.20-7.07 (m, 1H), 6.86-6.55 (m, 1H), 6.15 (s, 1H), 6.02-5.03 (m, 1H), 4.57-3.44 (m, 3H), 2.74-2.46 (m, 3H), 1.79-1.62 (m, 3H). The absolute stereochemistry for the first and second eluted compounds was not determined.

Examples 20A and 20B: (R) or (S)-(7-Chloro-4-fluoro-1H-benzo[d]imidazol-2-yl)(4-methyl-6,7-dihydropyrazolo[1,5-a]pyrazin-5(4H)-yl)methanone (R) or (S)-(7-Chloro-4-fluoro-1H-benzo[d]imidazol-2-yl)(4-methyl-6,7-dihydropyrazolo[1,5-a]pyrazin-5(4H)-yl)methanone

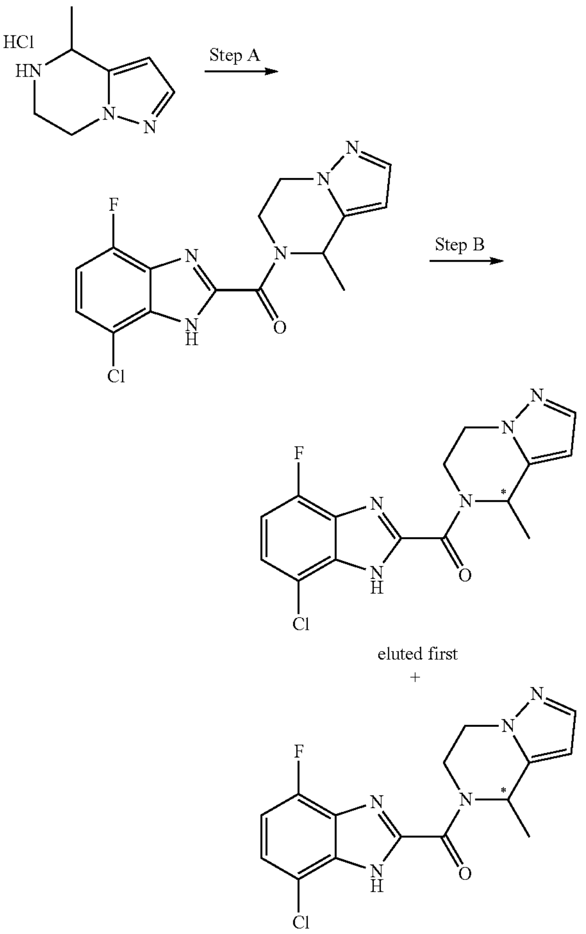

eluted second

Step A: To a solution of 7-chloro-4-fluoro-1H-benzimidazole-2-carboxylic acid (80.0 mg, 0.373 mmol) in DMF (1.00 mL) were added 4-methyl-4,5,6,7-tetrahydropyrazolo[1,5-a]pyrazine hydrochloride (product of Examples 16A and 16B, Step C) (51.2 mg, 0.373 mmol), DIEA (96.4 mg, 0.746 mmol) and HATU (70.9 mg, 0.186 mmol), and the resulting mixture was stirred at 25° C. for 1 h. The reaction mixture was quenched by addition $H_2O$ (4.00 mL), and then was diluted with EtOAc (2.00 mL×3). The combined organic layers were dried over $Na_2SO_4$, filtered and concentrated under reduced pressure to give a residue which was purified by preparative HPLC (Waters Xbridge BEH C18 column (100×30 mm, 10 m); flow rate: 25 mL/min; gradient: 35%-65% B over 8 min; mobile phase A: 10 mM aqueous $NH_4HCO_3$, mobile phase B: acetonitrile) to give (7-Chloro-4-fluoro-1H-benzo[d]imidazol-2-yl)(4-methyl-6,7-dihydropyrazolo[1,5-a]pyrazin-5(4H)-yl)methanone (28.0 mg, 24% yield). LC-MS: 334.1 $[M+H]^+$.

Step B: (7-Chloro-4-fluoro-1H-benzo[d]imidazol-2-yl)(4-methyl-6,7-dihydropyrazolo[1,5-a]pyrazin-5(4H)-yl)

methanone (28.0 mg, 0.084 mmol) was further purified by chiral SFC (DAICEL CHIRALPAK IC (250×30 mm, 10 μm); flow rate: 30 mL/min; gradient: 45% B over 14 min; mobile phase A: heptane, mobile phase B: $CO_2$-EtOH (0.1% $NH_3H_2O$) to afford a first eluted compound (5.98 mg) and a second eluted compound (6.35 mg). First eluted compound (Example 20A): LC-MS: 334.0 $[M+H]^+$; $^1H$ NMR (400 MHz, $CDCl_3$) δ 10.64-10.25 (m, 1H), 7.57 (s, 1H), 7.32 (br dd, J=3.5, 8.6 Hz, 2H), 7.09-6.96 (m, 1H), 6.75-5.07 (m, 2H), 4.61-4.46 (m, 1H), 4.44-3.44 (m, 2H), 1.80 (br d, J=6.5 Hz, 1H), 1.63 (d, J=6.9 Hz, 2H). Second eluted compound (Example 20B): LC-MS: 334.0 $[M+H]^+$; $^1H$ NMR (400 MHz, $CDCl_3$) δ 10.70-10.27 (m, 1H), 7.57 (br s, 1H), 7.32 (dd, J=3.9, 8.2 Hz, 1H), 7.30-7.28 (m, 1H), 7.10-6.97 (m, 1H), 6.74-4.97 (m, 2H), 4.62-4.48 (m, 1H), 4.44-3.41 (m, 2H), 1.80 (br d, J=6.5 Hz, 1H), 1.63 (d, J=6.9 Hz, 2H). The absolute stereochemistry for the first and second eluted compounds was not determined.

Example 21: (3-Bromo-8-methyl-5,6-dihydroimidazo[1,5-a]pyrazin-7(8H)-yl)(7-chloro-4-fluoro-1H-benzo[d]imidazol-2-yl)methanone

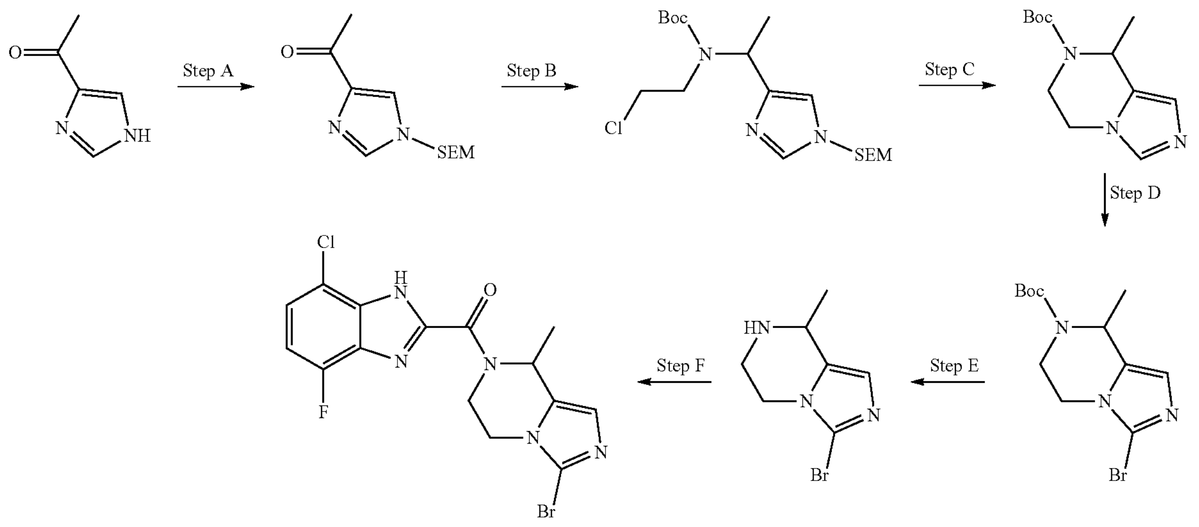

Step A: To a solution of 1-(1H-imidazol-4-yl)ethan-1-amine (2.00 g, 18.1 mmol) in THF (20.0 mL) was added sodium hydride in mineral oil (1.45 g, 36.3 mmol, 60% purity) at 0° C. The reaction mixture was stirred at the same temperature for 1 h, followed by the dropwise addition of a solution of (2-chloromethoxyethyl)trimethylsilane (4.54 g, 27.2 mmol) in THF (5.00 mL) at 0° C. The mixture was stirred at 20° C. for another 2 h. The reaction mixture was diluted with ice-water (20.0 mL) and extracted with EtOAc (20.0 mL×5). The combined organic layers were dried over $Na_2SO_4$, filtered and concentrated to give a residue which was purified by flash silica gel chromatography to give 1-(1-((2-(trimethylsilyl)ethoxy)methyl)-1H-imidazol-4-yl)ethan-1-one (2.10 g, 48%). LC-MS: 241.2 $[M+H]^+$.

Step B: To a solution of 1-(1-((2-(trimethylsilyl)ethoxy)methyl)-1H-imidazol-4-yl)ethan-1-amine (1.80 g, 7.49 mmol) in THF (30.0 mL) was added 2-chloroethanamine (1.30 g, 11.2 mmol), followed by dropwise addition of titanium isopropoxide (6.38 g, 22.4 mmol). The mixture was stirred at 20° C. for 12 h. Sodium borohydride (567 mg, 15.0 mmol) was added at 0° C. under nitrogen, and the resulting mixture was stirred at 20° C. for 1 h under nitrogen. The reaction mixture was poured into $H_2O$ (30.0 mL) The reaction mixture was adjusted to pH 9 by addition of NaOH (2M aqueous). Di-tert-butyl dicarbonate (2.45 g, 11.2 mmol) was then added and the mixture was stirred at 20° C. for 12 h. The reaction mixture was diluted with $H_2O$ (10.0 mL), filtered and extracted with EtOAc (5×40.0 mL). The combined organic layers were dried over anhydrous $Na_2SO_4$, filtered, and concentrated under vacuum to give a residue that was purified by flash silica gel chromatography to give tert-butyl (2-chloroethyl)(1-(1-((2-(trimethylsilyl)ethoxy)methyl)-1H-imidazol-4-yl)ethyl)carbamate (800 mg). LC-MS: 404.3 $[M+H]^+$.

Step C: To a solution of tert-butyl (2-chloroethyl)(1-(1-((2-(trimethylsilyl)ethoxy)methyl)-1H-imidazol-4-yl)ethyl)carbamate (500 mg, 1.24 mmol) in THF (5.00 mL) was added 1.0 M tetra-n-butylammonium fluoride in THF (6.19 mL). The reaction mixture was stirred at 50° C. for 12 h, then was allowed to cool to RT and was concentrated. The residue was diluted with $H_2O$ (15.0 mL) and extracted with EtOAc (15.0 mL×3). The combined organic layers were dried over $Na_2SO_4$, filtered and the filtrate was concentrated to give a residue which was purified by preparative HPLC (Phenomenex Gemini C18 column (180×70 mm, 10 μm); flow rate: 130 mL/min; gradient: 20%-50% B over 17.0 min; mobile phase A: water 10 mM $NH_4HCO_3$, mobile phase B: acetonitrile) to give tert-butyl 8-methyl-5,6-dihydroimidazo[1,5-a]pyrazine-7(8H)-carboxylate (220 mg, 68%). LC-MS: 238.1 $[M+H]^+$.

Step D: To a solution of tert-butyl 8-methyl-5,6-dihydroimidazo[1,5-a]pyrazine-7(8H)-carboxylate (160 mg, 0.674 mmol) in THF (4.50 mL) was added a solution of n-BuLi in hexane (2.5 M, 0.269 mL) at −78° C. under $N_2$. The reaction mixture was stirred at −78° C. for 0.5 h. 1,2-Dibromo-1,1,2,2-tetrachloro-ethane (219 mg, 0.674 mmol) was added at −78° C. The reaction mixture was stirred at −78° C. for 0.5 h under nitrogen. The reaction mixture was poured into saturated ammonium chloride aqueous solution (15.0 mL) and extracted with ethyl acetate (5.00 mL×3). The combined organic phase was dried over anhydrous $Na_2SO_4$, filtered and concentrated to give a residue. The residue was purified by prep-TLC to give tert-butyl 3-bromo-8-methyl-5,6-dihydroimidazo[1,5-a]pyrazine-7(8H)-carboxylate (60 mg, 25%). LC-MS: 316.1 $[M+H]^+$.

Step E: To a solution of tert-butyl 3-bromo-8-methyl-5,6-dihydroimidazo[1,5-a]pyrazine-7(8H)-carboxylate (15.0 mg, 0.047 mmol) in DCM (0.5 mL) was added trifluoroacetic acid (153 mg, 1.35 mmol). The reaction mixture was stirred at 20° C. for 0.5 h. The reaction mixture was concentrated to give 3-bromo-8-methyl-5,6,7,8-tetrahydroimidazo[1,5-a]pyrazine trifluoroacetic acid salt (15.0 mg, crude), which was used in next step directly. LC-MS: 216.3 $[M+H]^+$.

Step F: To a solution of 3-bromo-8-methyl-5,6,7,8-tetrahydroimidazo[1,5-a]pyrazine trifluoroacetic acid salt (33.0 mg, 0.152 mmol) in DMF (1.00 mL) were added HATU (63.8 mg, 0.167 mmol), 4-chloro-7-fluoro-1H-benzimidazole-2-carboxylic acid (32.7 mg, 0.152 mmol) and DIEA (78.9 mg, 0.610 mmol). The reaction mixture was stirred at 20° C. for 1 h. The reaction was purified by preparative HPLC (Phenomenex Gemini C18 column (75×30 mm, 3 μm); flow rate: 25 mL/min; gradient: 30%-68% B over 8.0 min; mobile phase A: water 0.04% HCl, mobile phase B: acetonitrile) to give (3-bromo-8-methyl-5,6-dihydroimidazo[1,5-a]pyrazin-7(8H)-yl)(7-chloro-4-fluoro-1H-benzo[d]imidazol-2-yl)methanone hydrochloride (6.28 mg, 9%). LC-MS: 412.0 [M+H]f; $^1$H NMR (400 MHz, MeOD) 7.71-7.61 (m, 1H), 7.35 (dd, J=8.57, 3.94 Hz, 1H), 7.13-7.03 (m, 1H), 6.12-5.97 (m, 1H), 4.53-4.28 (m, 2H), 4.19-4.19 (m, 2H), δ 1.61-1.92 (m, 3H).

Example 22: 7-(7-Chloro-4-fluoro-1H-benzo[d]imidazole-2-carbonyl)-8-methyl-5,6,7,8-tetrahydroimidazo[1,5-a]pyrazine-3-carbonitrile

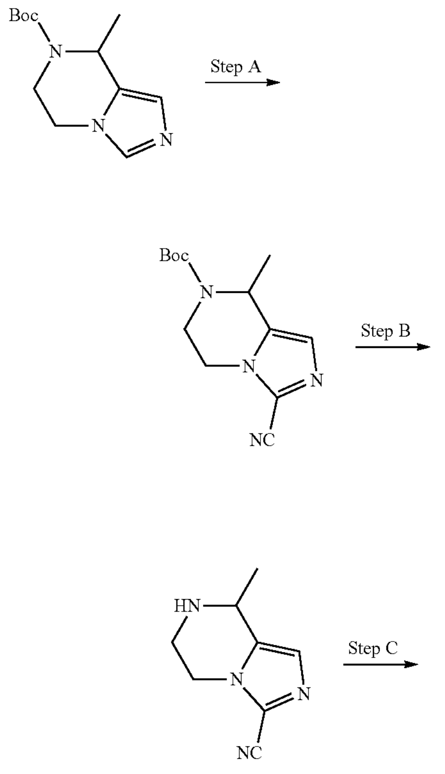

-continued

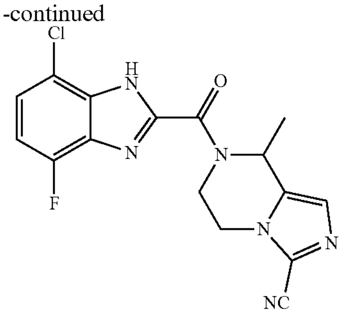

Step A: A mixture of 4-dimethylaminopyridine (128 mg, 1.05 mmol) and cyanogen bromide (111 mg, 1.05 mmol) in DMF (5.00 mL) under nitrogen was stirred at 20° C. to generate a yellow precipitate of the cyanoaminopyridinium salt and then tert-butyl 8-methyl-5,6-dihydroimidazo[1,5-a]pyrazine-7(8H)-carboxylate (product of Example 21, Step C) (100 mg, 0.421 mmol) was added under nitrogen. The reaction mixture was stirred at 40° C. for 16 h under nitrogen, then was quenched by addition of saturated sodium bicarbonate aqueous solution (20.0 mL) and extracted with EtOAc (20.0 mL×3). The combined organic layers were washed with brine (50.0 mL×1), dried over anhydrous $Na_2SO_4$, filtered and concentrated in vacuum to give a residue. The residue was purified by preparative HPLC (Phenomenex C18 75×30 mm×3 um; flow rate: 25.0 mL/min; gradient: 35%-60% B over 8.00 min; mobile phase A: $H_2O$ (0.1% TFA), mobile phase B: acetonitrile) to give tert-Butyl 3-cyano-8-methyl-5,6-dihydroimidazo[1,5-a]pyrazine-7(8H)-carboxylate (20.0 mg, 18%). LC-MS: 263.1 $[M+H]^+$.

Step B: To a solution of tert-butyl 3-cyano-8-methyl-5,6-dihydroimidazo[1,5-a]pyrazine-7(8H)-carboxylate (5.00 mg, 0.190 mmol) in DCM (0.500 mL) was added trifluoroacetic acid (153 mg, 1.35 mmol) at 20° C. The reaction mixture was stirred at 20° C. for 1 h. The reaction mixture was concentrated under vacuum to give 8-methyl-5,6,7,8-tetrahydroimidazo[1,5-a]pyrazine-3-carbonitrile trifluoroacetic acid salt (5.00 mg, crude. LC-MS: 163.3 $[M+H]^+$.

Step C: To a solution of 8-methyl-5,6,7,8-tetrahydroimidazo[1,5-a]pyrazine-3-carbonitrile trifluoroacetic acid salt (5.00 mg, 0.308 mmol) in DMF (0.500 mL) were added 7-chloro-4-fluoro-1H-benzimidazole-2-carboxylic acid (6.62 mg, 0.308 mmol), HATU (12.8 mg, 0.339 mmol) and DIEA (15.9 mg, 0.123 mmol). The reaction mixture was stirred at 20° C. for 1 h under nitrogen. The reaction was purified by preparative HPLC (3_Phenomenex Luna C18 75×30 mm×3 um; flow rate: 25 mL/min; gradient: 30%-60% B over 8.0 min; mobile phase A: $H_2O$ (0.04% HCl), mobile phase B: acetonitrile) and then further purified by preparative HPLC (Waters Xbridge BEH C18 100×30 mm×10 um; flow rate: 25 mL/min; gradient: 25%-70% B over 8.0 min; mobile phase A: $H_2O$ (10 mM $NH_4HCO_3$), mobile phase B: acetonitrile) to give 7-(7-chloro-4-fluoro-1H-benzo[d]imidazole-2-carbonyl)-8-methyl-5,6,7,8-tetrahydroimidazo[1,5-a]pyrazine-3-carbonitrile hydrochloride (3.60 mg, 32%). LC-MS: 359.0 $[M+H]^+$; $^1$H NMR (400 MHz, MeOD) δ 7.36-7.30 (m, 1H), 7.22-7.02 (m, 2H), 6.05-5.80 (m, 1H), 4.50 (br d, J=11.6 Hz, 1H), 4.42-4.12 (m, 1H), 3.93-3.51 (m, 2H), 1.83-1.59 (m, 3H).

Examples 23A and 23B: (R) or (S)-(7-Chloro-4-fluoro-1H-benzo[d]imidazol-2-yl)(3-(2-methoxypropan-2-yl)-6-methyl-5,6-dihydroimidazo[1,5-a]pyrazin-7(8H)-yl)methanone and (R) or (S)-(7-Chloro-4-fluoro-1H-benzo[d]imidazol-2-yl)(3-(2-methoxypropan-2-yl)-6-methyl-5,6-dihydroimidazo[1,5-a]pyrazin-7(8H)-yl)methanone

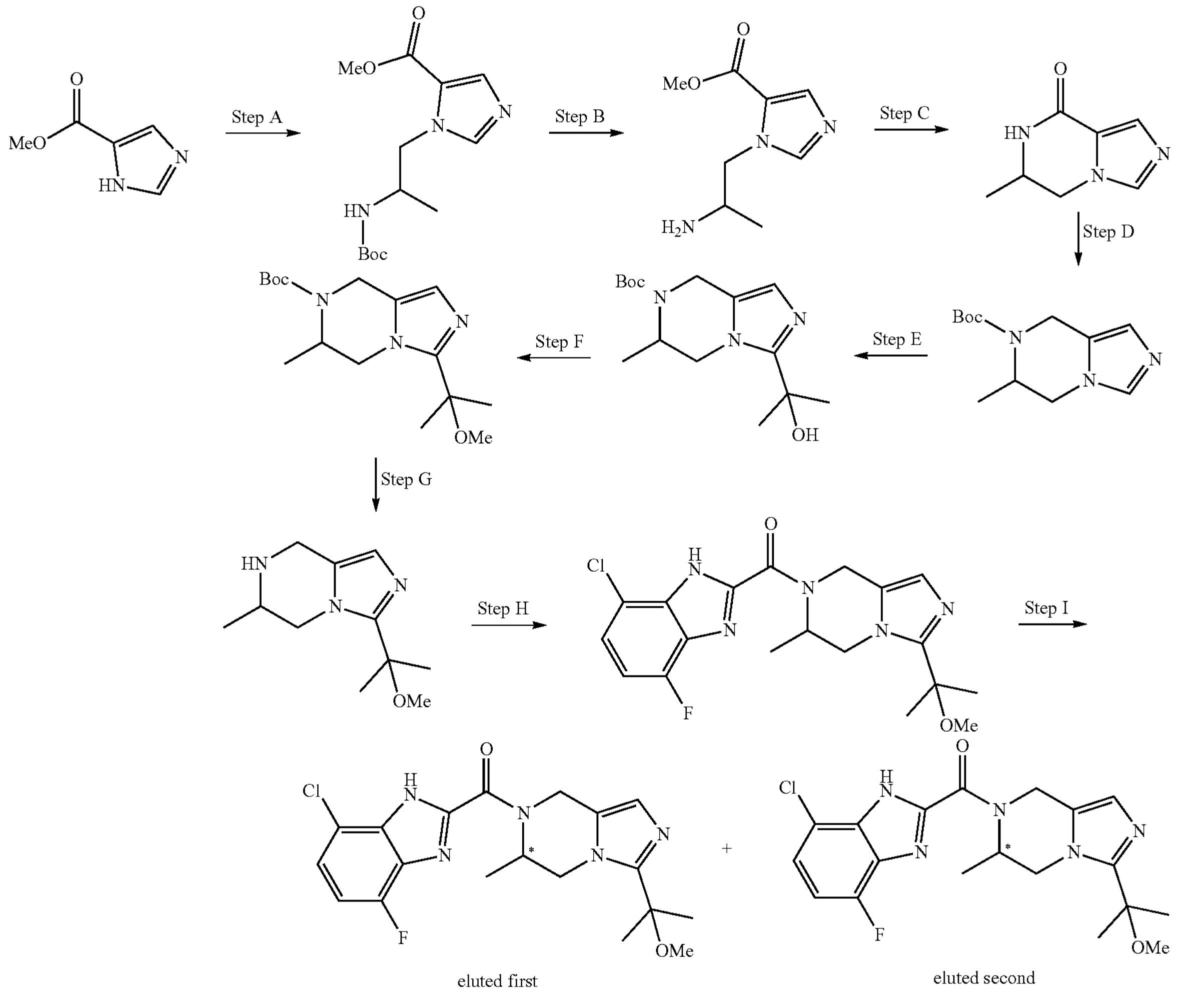

Step A: To a solution of methyl 1H-imidazole-5-carboxylate (5.00 g, 39.6 mmol) and tert-butyl N-(2-hydroxy-1-methyl-ethyl)carbamate (5.56 g, 31.7 mmol) in THF (300 mL) was added triphenylphosphine (14.9 g, 57.1 mmol) at 0° C. Diisopropyl azodicarboxylate (11.5 g, 57.1 mmol) was added dropwise at same temperature under $N_2$. The mixture was stirred at 20° C. for 12 h under $N_2$ atmosphere. The reaction mixture was poured into $H_2O$ (300 mL) and extracted with EtOAc (300 mL×3). The combined organic layers were dried over $Na_2SO_4$, filtered, and concentrated under vacuum to give a residue which was purified by flash silica gel chromatography. The combined fractions were further purified by trituration with a solvent mixture of petroleum ether (20.0 mL) and MTBE (20.0 mL) at 20° C. for 1 h. The mixture was filtered and the cake was dried under vacuum to give methyl 1-(2-((tert-butoxycarbonyl)amino)propyl)-1H-imidazole-5-carboxylate (9 g, crude). LC-MS: 284.2 $[M+H]^+$.

Step B: To a solution of methyl 1-(2-((tert-butoxycarbonyl)amino)propyl)-1H-imidazole-5-carboxylate (7.50 g, 26.4 mmol) in MeOH (50.0 mL) was added a 4 M solution of HCl in dioxane (50.0 mL). The mixture was stirred at 20° C. for 1 h. The reaction mixture was concentrated under vacuum to give methyl 1-(2-aminopropyl)-1H-imidazole-5-carboxylate hydrochloride (8.00 g, crude). LC-MS: 184.2 $[M+H]^+$.

Step C: To a solution of methyl 1-(2-aminopropyl)-1H-imidazole-5-carboxylate hydrochloride (8.00 g, 43.7 mmol) in MeOH (140 mL) was added TEA (18.2 g, 179 mmol). The mixture was stirred at 50° C. for 12 h. The reaction mixture was allowed to cool to RT, then was poured into $H_2O$ (50.0 mL) and washed with EtOAc (50.0 mL×3). The desired product was isolated from the aqueous phase by lyophilization to give 6-methyl-6,7-dihydroimidazo[1,5-a]pyrazin-8(5H)-one (10.5 g, crude). LC-MS: 152.5 $[M+H]^+$.

Step D: To a solution of 6-methyl-6,7-dihydro-5H-imidazo[1,5-a]pyrazin-8-one (7.00 g, 46.3 mmol) in THF (132 mL) was added a 2.5 M solution of lithium aluminum hydride in THF (37.0 mL) at 0° C. The mixture was heated to 80° C. and stirred for 12 h. The reaction mixture was then cooled to 0° C. and was quenched with $H_2O$ (1.66 g). After that aqueous sodium hydroxide solution (1.66 g, 10 w/w %) and $H_2O$ (5.00 g) were added at 0° C. The mixture was stirred at 20° C. for 1 h, and then di-tert-butyl dicarbonate (17.7 g, 81.2 mmol) was added to the mixture. The mixture was stirred at 20° C. for 12 h. The reaction mixture was poured into water (30 mL) and extracted with DCM (20 mL×3). The combined organic layers were dried and concentrated under vacuum to give a residue, which was purified by silica gel chromatography to give tert-butyl 6-methyl-5,6-dihydroimidazo[1,5-a]pyrazine-7(8H)-carboxylate (1.60 g, 12%). LC-MS: 238.5 $[M+H]^+$.

Step E: To a solution of tert-butyl 6-methyl-5,6-dihydroimidazo[1,5-a]pyrazine-7(8H)-carboxylate (500 mg, 2.11 mmol) in THF (10.0 mL) was added a 2.5 M n-BuLi in THF solution (1.52 mL) at −78° C. under $N_2$. The reaction mixture was stirred at −78° C. for 0.5 h. Acetone (183 mg, 3.16 mmol) in THF (1.00 mL) was added at −78° C. The reaction mixture was stirred at −78° C. for 2 h under $N_2$ atmosphere. The reaction mixture was then diluted with $H_2O$ (10.0 mL) and extracted with DCM (10.0 mL×3). The combined organic layers were dried over $Na_2SO_4$, filtered and concentrated under vacuum to give a residue. The residue was purified by flash silica gel chromatography using 0 to 50% EtOAc in petroleum ether to give tert-butyl 3-(2-hydroxypropan-2-yl)-6-methyl-5,6-dihydroimidazo[1,5-a]pyrazine-7(8H)-carboxylate (250 mg, 36%). LC-MS: 296.4 $[M+H]^+$.

Step F: To a solution of tert-butyl 6-methyl-5,6-dihydroimidazo[1,5-a]pyrazine-7(8H)-carboxylate (160 mg, 0.541 mmol) in THF (2.00 mL) were added sodium hydride in mineral oil (54.1 mg, 1.35 mmol, 60% purity) and methyl iodide (192 mg, 1.35 mmol) at 0° C. under $N_2$ atmosphere. The mixture was stirred at 25° C. for 2 h under $N_2$ atmosphere. The reaction mixture was poured into saturated aqueous ammonium chloride (5.00 mL) and extracted with DCM (5.00 mL×3). The combined organic layers were dried over $Na_2SO_4$, filtered, and concentrated under vacuum to give a residue which were purified by preparative TLC to give tert-butyl 3-(2-methoxypropan-2-yl)-6-methyl-5,6-dihydroimidazo[1,5-a]pyrazine-7(8H)-carboxylate (74.0 mg, 44%). LC-MS: 310.5 $[M+H]^+$.

Step G: To a solution of methyl 1-(2-((tert-butoxycarbonyl)amino)propyl)-1H-imidazole-5-carboxylate (74.0 mg, 0.239 mmol) in EtOAc (1.00 mL) was added a 2 M solution of HCl in EtOAc (0.925 mL). The mixture was stirred at 20° C. for 1 h. The reaction mixture was concentrated under vacuum to give 3-(2-methoxypropan-2-yl)-6-methyl-5,6,7,8-tetrahydroimidazo[1,5-a]pyrazine hydrochloride (50 mg, crude, HCl). LC-MS: 210.2 $[M+H]^+$.

Step H: To a solution of 3-(2-methoxypropan-2-yl)-6-methyl-5,6,7,8-tetrahydroimidazo[1,5-a]pyrazine hydrochloride (50.0 mg, 0.203 mmol) and 7-chloro-4-fluoro-1H-benzimidazole-2-carboxylic acid (43.6 mg, 0.203 mmol) in DMF (1.50 mL) were added DIEA (78.9 mg, 0.610 mmol) and HATU (38.7 mg, 0.101 mmol). The mixture was stirred at 25° C. for 1 h. The reaction mixture was filtered to remove precipitates and the filtrate was purified by preparative HPLC (column: WePure Biotech XP tC18 (150×40 mm, 7 m); flow rate: [$H_2O$ (10 mM $NH_4HCO_3$)-ACN]; gradient: 20%-50% B over 8 min to give 7-chloro-4-fluoro-1H-benzo[d]imidazol-2-yl)(3-(2-methoxypropan-2-yl)-6-methyl-5,6-dihydroimidazo[1,5-a]pyrazin-7(8H)-yl)methanone (25 mg). LC-MS: 406.2 $[M+H]^+$.

Step I: (7-Chloro-4-fluoro-1H-benzo[d]imidazol-2-yl)(3-(2-methoxypropan-2-yl)-6-methyl-5,6-dihydroimidazo[1,5-a]pyrazin-7(8H)-yl)methanone (25 mg) was further purified by chiral SFC column: DAICEL CHIRALPAK IG (250 mm×30 mm, 10 um); mobile phase: 50% $CO_2$-MeOH (0.1% $NH_3H_2O$)]; isocratic elution mode to afford a first eluted compound (7.0 mg) and a second eluted compound (6.5 mg). First eluted compound (Example 23A): LC-MS: 406.1 $[M+H]^+$; $^1H$ NMR (400 MHz, DMSO-$d_6$) δ 7.43-7.34 (m, 1H), 7.25-7.10 (m, 1H), 6.83-6.65 (m, 1H), 5.80-5.38 (m, 1H), 5.16-5.03 (m, 1H), 5.03-4.60 (m, 1H), 4.58-4.41 (m, 1H), 4.30-4.11 (m, 1H), 2.98 (d, J=7.8 Hz, 3H), 1.52 (s, 3H), 1.50 (br d, J=5.5 Hz, 3H), 1.19 (br dd, J=6.8, 10.1 Hz, 3H). Second eluted compound (Example 23A): LC-MS: 406.1 $[M+H]^+$; $^1H$ NMR (400 MHz, DMSO-$d_6$) δ 7.37 (br dd, J=3.3, 8.1 Hz, 1H), 7.18 (br t, J=9.1 Hz, 1H), 6.90-6.67 (m, 1H), 5.87-5.50 (m, 1H), 5.15-4.99 (m, 1H), 4.64 (br d, J=17.1 Hz, 1H), 4.53-4.43 (m, 1H), 4.30-4.14 (m, 1H), 2.98 (br d, J=7.9 Hz, 3H), 1.54-1.47 (m, 6H), 1.19 (br dd, J=6.9, 9.7 Hz, 3H). The absolute stereochemistry for the first and second eluted compounds was not determined.

Example 24: 3-(7,8-Dihydro-1,6-naphthyridin-6(5H)-yl)-5-methylquinoxalin-2(1H)-one

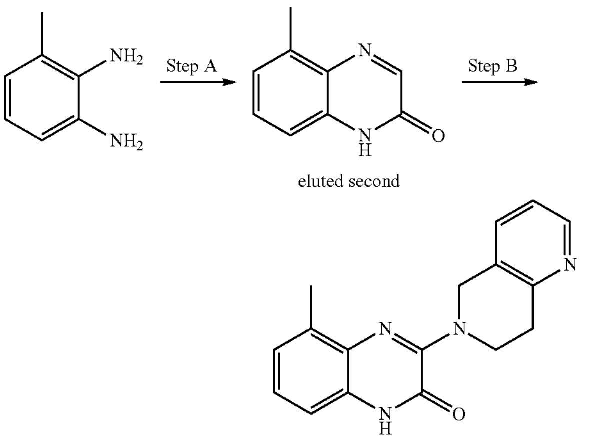

Step A: To a solution of 3-methylbenzene-1,2-diamine (2.00 g, 16.4 mmol) in EtOH (90.0 mL) was added ethyl 2-oxoacetate (4.01 g, 19.7 mmol). The reaction system was stirred at 85° C. for 1 h. The reaction mixture was allowed to cool to RT, then was filtered. The filter cake was washed with EtOH (20 mL) and dried under vacuum to give a residue which was purified by preparative HPLC (Phenomenex Luna C18 column (150×40 mm, 10 μm); flow rate: 25 mL/min; gradient: 1%-30% B over 8 min; mobile phase A: water (10 mM $NH_4HCO_3$), mobile phase B: acetonitrile) to give 8-methylquinoxalin-2(1H)-one, (230 mg, eluted first) and 5-methylquinoxalin-2(1H)-one (320 mg, eluted second). First eluted compound: LC-MS: 161.2 $[M+H]^+$; $^1H$ NMR (400 MHz, DMSO-$d_6$) δ 11.76 (br s, 1H), 8.17 (s, 1H), 7.62 (d, J=8.0 Hz, 1H), 7.40 (d, J=7.4 Hz, 1H), 7.25-7.14 (m, 1H), 2.42 (s, 3H). Second eluted compound: LC-MS: 161.2 $[M+H]^+$; $^1H$ NMR (400 MHz, DMSO-$d_6$) δ 12.06-11.27 (m, 1H), 8.16 (s, 1H), 7.42 (t, J=7.8 Hz, 1H), 7.15 (t, J=7.6 Hz, 2H), 2.56 (s, 3H).

Step B: To a solution of 5-methyl-1H-quinoxalin-2-one (40.0 mg, 0.250 mmol), 5,6,7,8-tetrahydro-1,6-naphthyridine (77.1 mg, 0.574 mmol) in DMSO (1.00 mL) was added copper (II) acetate (4.54 mg, 0.025 mmol). The resulting mixture was stirred at 60° C. for 12 h under an oxygen atmosphere. The reaction mixture was poured into water (10.0 mL) and extracted with DCM (10.0 mL×3). The combined organic layers were dried over $Na_2SO_4$, filtered and concentrated under vacuum to give a residue which was purified by preparative HPLC (Waters Xbridge C18 column (150×40 mm, 10 m); flow rate: 25 mL/min; gradient: 20%-50% B over 8 min; mobile phase A: 10 mM aqueous $NH_4HCO_3$, mobile phase B: acetonitrile) to give 3-(7,8-dihydro-1,6-naphthyridin-6(5H)-yl)-5-methylquinoxalin-2(1H)-one (13.76 mg, 19%). LC-MS: 293.1 $[M+H]^+$; $^1H$ NMR (400 MHz, DMSO-$d_6$) δ 12.11 (br s, 1H), 8.48-8.29 (m, 1H), 7.65 (d, J=7.1 Hz, 1H), 7.22 (dd, J=4.8, 7.7 Hz, 1H), 7.14-6.96 (m, 3H), 4.27 (t, J=5.9 Hz, 2H), 3.06 (t, J=5.8 Hz, 2H), 2.48 (s, 3H).

Example 25: (R)-5-Methyl-3-(5-methyl-7,8-dihydro-1,6-naphthyridin-6(5H)-yl)quinoxalin-2(1H)-one

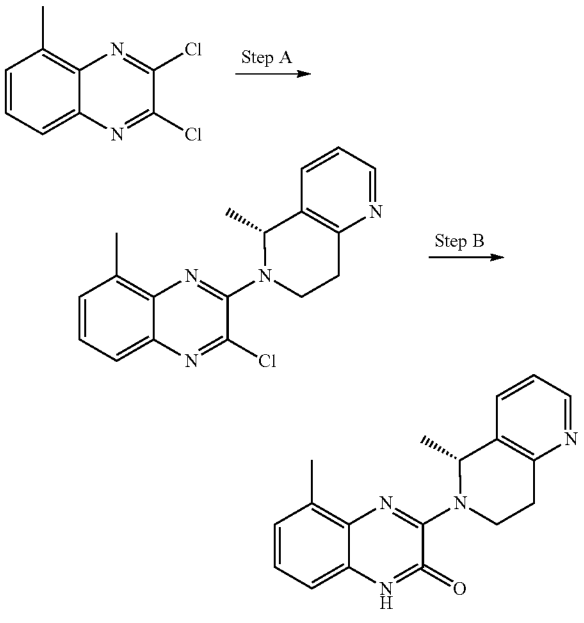

Step A: A mixture of 2,3-dichloro-5-methylquinoxaline (400 mg, 1.88 mmol) and (R)-5-methyl-5,6,7,8-tetrahydro-1,6-naphthyridine (362 mg, 2.44 mmol) in ACN (12.0 mL) was stirred at 80° C. for 12 h. The mixture was concentrated under vacuum at 30° C. to give a residue which was purified by preparative HPLC (Waters Xbridge Prep OBD C18 column (150×40 mm, 10 μm); flow rate: 25 mL/min; gradient: 45%-75% B over 8 min; mobile phase A: water (10 mM $NH_4HCO_3$), mobile phase B: acetonitrile) to give two regioisomers. The first eluting isomer was (R)-2-chloro-5-methyl-3-(5-methyl-7,8-dihydro-1,6-naphthyridin-6(5H)-yl)quinoxaline. LC-MS: 325.0 $[M+H]^+$. The second eluting isomer was (R)-3-chloro-5-methyl-2-(5-methyl-7,8-dihydro-1,6-naphthyridin-6(5H)-yl)quinoxaline. LC-MS: 325.0 $[M+H]^+$.

Step B: To a mixture of (R)-2-chloro-5-methyl-3-(5-methyl-7,8-dihydro-1,6-naphthyridin-6(5H)-yl)quinoxaline (100 mg, 0.308 mmol) in dioxane (2.00 mL) were added potassium hydroxide (173 mg, 3.08 mmol) and $Pd_2(dba)_3$ (28.2 mg, 0.0308 mmol). The mixture was degassed and purged with $N_2$ three times, then was stirred at 80° C. for 12 h under a $N_2$ atmosphere. The mixture was concentrated under vacuum at 30° C. to give a residue which was purified by preparative HPLC (Waters Xbridge Prep OBD C18 column (150×40 mm, 10 μm); flow rate: 25 mL/min; gradient: 30%-60% B over 8 min; mobile phase A: water (10 mM $NH_4HCO_3$), mobile phase B: acetonitrile) to give (R)-5-methyl-3-(5-methyl-7,8-dihydro-1,6-naphthyridin-6(5H)-yl)quinoxalin-2(1H)-one (22.8 mg, 21%). LC-MS: 307.0 $[M+H]^+$; $^1H$ NMR (400 MHz, DMSO-d6) δ 12.04-11.55 (m, 1H), 8.37 (br d, J=3.9 Hz, 1H), 7.69 (d, J=6.9 Hz, 1H), 7.27-7.15 (m, 1H), 7.08-7.00 (m, 3H), 6.18-5.98 (m, 1H), 5.18-4.98 (m, 1H), 3.47 (dt, J=3.7, 12.8 Hz, 1H), 3.25-3.13 (m, 1H), 2.90 (dd, J=1.8, 17.0 Hz, 1H), 2.48 (s, 3H), 1.59 (d, J=6.8 Hz, 3H).

Example 26: (R)-8-methyl-3-(5-methyl-7,8-dihydro-1,6-naphthyridin-6(5H)-yl)quinoxalin-2(1H)-one

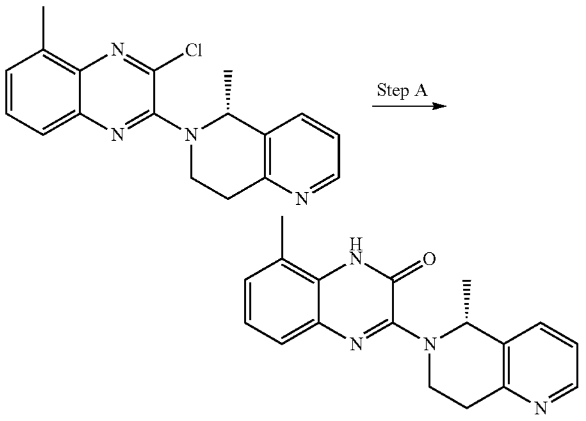

Step A: To a mixture of (R)-3-chloro-5-methyl-2-(5-methyl-7,8-dihydro-1,6-naphthyridin-6(5H)-yl)quinoxaline (product of Example 25, Step A second eluting isomer) (63.0 mg, 0.194 mmol) in dioxane (2.0 mL) were added potassium hydroxide (109 mg, 1.94 mmol) and $Pd_2(dba)_3$ (17.8 mg, 0.0194 mmol, 0.1 eq). The mixture was degassed and purged with $N_2$ three times, then was stirred at 80° C. for 12 h under $N_2$ atmosphere. The mixture was concentrated under vacuum at 30° C. to give a residue which was purified by preparative HPLC (Waters Xbridge Prep OBD C18 column (150×40 mm, 10 mm); flow rate: 25 mL/min; gradient: 30%-60% B over 8 min; mobile phase A: water (10 mM $NH_4HCO_3$), mobile phase B: acetonitrile) to give (R)-8-methyl-3-(5-methyl-7,8-dihydro-1,6-naphthyridin-6(5H)-yl)quinoxalin-2(1H)-one (9.95 mg, 17%). LC-MS: 307.0 $[M+H]^+$; $^1H$ NMR (400 MHz, DMSO-$d_6$) δ 11.29-11.05 (m, 1H), 8.37 (br d, J=4.0 Hz, 1H), 7.70 (d, J=7.0 Hz, 1H), 7.30-7.18 (m, 2H), 7.10-6.96 (m, 2H), 6.09 (br d, J=5.8 Hz, 1H), 5.19-4.99 (m, 1H), 3.46 (dt, J=3.6, 12.8 Hz, 1H), 3.22-3.08 (m, 1H), 2.95-2.85 (m, 1H), 2.38 (s, 3H), 1.56 (d, J=6.8 Hz, 3H).

Examples 27A and 27B: 3-((5R,8S)-8-Methoxy-5-methyl-7,8-dihydro-1,6-naphthyridin-6(5H)-yl)-8-methylquinoxalin-2(1H)-one and 3-((5R,8S)-8-Methoxy-5-methyl-7,8-dihydro-1,6-naphthyridin-6(5H)-yl)-5-methylquinoxalin-2(1H)-one

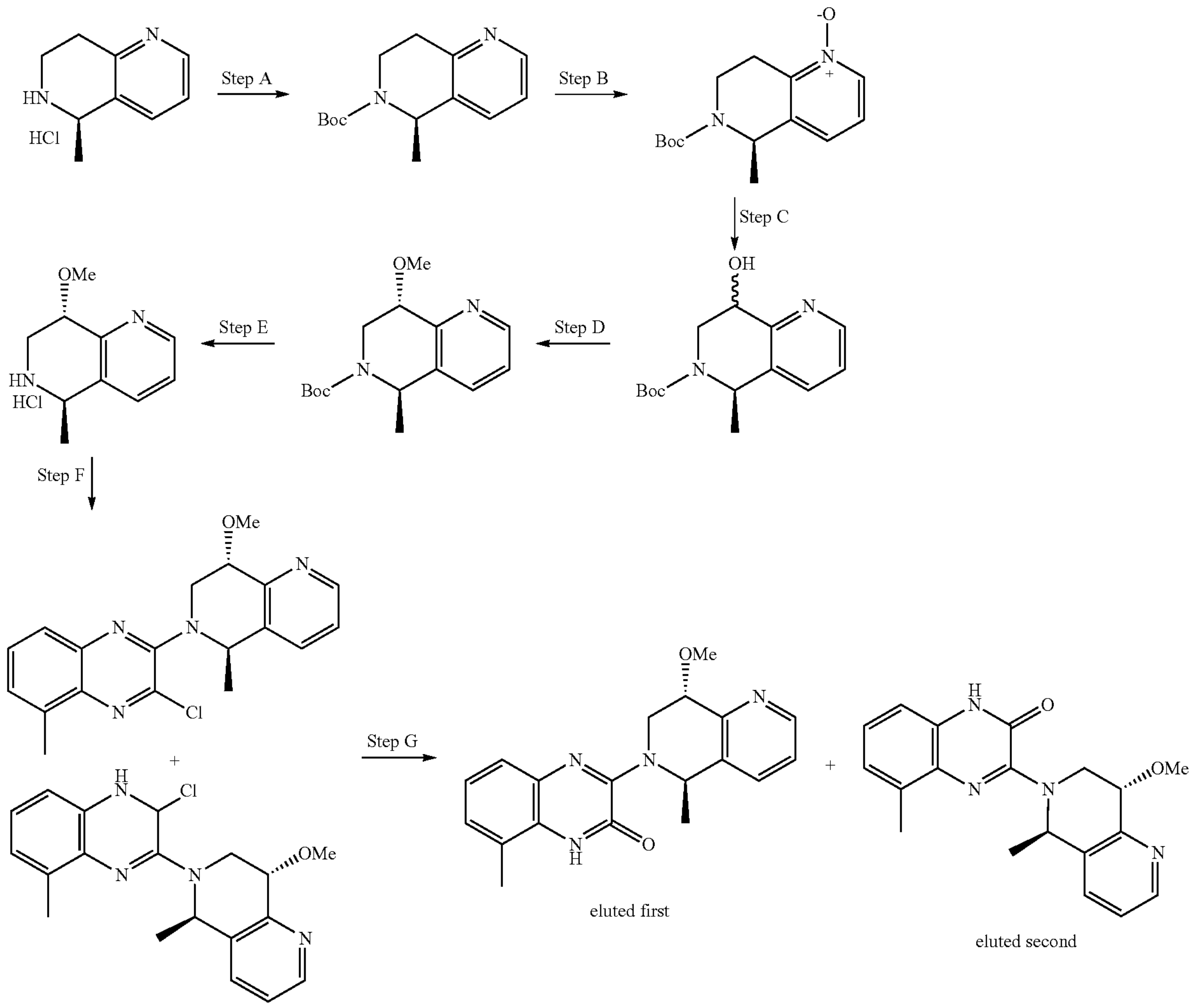

Step A: To a solution of (R)-5-methyl-5,6,7,8-tetrahydro-1,6-naphthyridine (30.0 g, 162 mmol, HCl salt) in DCM (300 mL) was added di-tert-butyl dicarbonate (42.5 g, 195 mmol) and TEA (32.9 g, 325 mmol, 45.2 mL). The mixture was stirred at 20° C. for 2 h. The reaction mixture was poured into $H_2O$ (200 mL) and extracted with DCM (200 mL×3). The combined organic layers were dried over $Na_2SO_4$, filtered, and concentrated under vacuum to give a residue, which was purified by flash silica gel chromatography to give tert-butyl (R)-5-methyl-7,8-dihydro-1,6-naphthyridine-6(5H)-carboxylate (32.0 g, 79%). LC-MS: 249.3 $[M+H]^+$.

Step B: To a solution of tert-butyl (R)-5-methyl-7,8-dihydro-1,6-naphthyridine-6(5H)-carboxylate (32.0 g, 129 mmol) in DCM (320 mL) was added meta-chloroperoxybenzoic acid (52.3 g, 258 mmol, 85% purity) at 0° C. The mixture was stirred at 25° C. for 3 h. The mixture was treated with saturated aqueous sodium sulfite solution (600 mL) and extracted with DCM (600 mL×5). The combined organic layers were dried over $Na_2SO_4$, filtered and concentrated under reduced pressure to give a residue, which was purified by flash silica gel chromatography to give (R)-6-(tert-butoxycarbonyl)-5-methyl-5,6,7,8-tetrahydro-1,6-naphthyridine 1-oxide (30.0 g, 88%). LC-MS: 265.1 $[M+H]^+$.

Step C: To a solution of (R)-6-(tert-butoxycarbonyl)-5-methyl-5,6,7,8-tetrahydro-1,6-naphthyridine 1-oxide (30.0 g, 114 mmol) in DMF (300 mL) was added trifluoroacetic anhydride (95.4 g, 454 mmol) at 0° C. The mixture was stirred at 60° C. for 3 h. The reaction mixture was added to saturated aqueous sodium carbonate solution (600 mL) and extracted with EtOAc (400 mL×3). The combined organic layers were dried over $Na_2SO_4$, filtered and concentrated under reduced pressure to give a residue which was purified by flash silica gel chromatography to give tert-butyl (5R)-8-hydroxy-5-methyl-7,8-dihydro-1,6-naphthyridine-6(5H)-carboxylate (30 g, 100%, mixture of diastereoisomers). LC-MS: 264.9 $[M+H]^+$.

Step D: To a solution of tert-butyl (5R)-8-hydroxy-5-methyl-7,8-dihydro-1,6-naphthyridine-6(5H)-carboxylate (30.0 g, 114 mmol, mixture of diastereoisomers) in THF (300 mL) were added sodium tert-butoxide (32.7 g, 341 mmol) and methyl iodide (32.2 g, 227 mmol) at 0° C. under a nitrogen atmosphere. The mixture was stirred at 25° C. for 3 h under $N_2$ atmosphere. The mixture was diluted with $H_2O$ (600 mL) and extracted with DCM (400 mL×5). The combined organic layers were dried over $Na_2SO_4$, filtered and concentrated under reduced pressure to give a residue which was purified by preparative HPLC (Phenomenex Gemini C18 column (250×100 mm, 10 μm); flow rate: 280 mL/min; gradient: 25%-55% B over 8 min; mobile phase A: $H_2O$ (10 mM $NH_4HCO_3$), mobile phase B: acetonitrile to give tert-butyl (5R,8S)-8-methoxy-5-methyl-7,8-dihydro-5H-1,6-naphthyridine-6-carboxylate (5.8 g, 18%). $^1$H NMR (400 MHz, DMSO-$d_6$) δ 8.46 (br d, J=3.1 Hz, 1H), 7.75 (br d, J=7.6 Hz, 1H), 7.36 (dd, J=4.7, 7.8 Hz, 1H), 5.34-5.03 (m, 1H), 4.51-4.33 (m, 1H), 4.28-4.02 (m, 1H), 3.45-3.34 (m, 3H), 3.28-3.08 (m, 1H), 1.49-1.24 (m, 12H).

Step E: To a solution of tert-butyl (5R,8S)-8-methoxy-5-methyl-7,8-dihydro-1,6-naphthyridine-6(5H)-carboxylate (3.00 g, 10.8 mmol) in EtOAc (60.0 mL) was added a 4 M solution of HCl in EtOAc (300 mL). The mixture was stirred at 25° C. for 12 h. The mixture was concentrated under reduced pressure to give (5R,8S)-8-methoxy-5-methyl-5,6,7,8-tetrahydro-1,6-naphthyridine hydrochloride (3 g, crude). LC-MS: 179.2 [M+H]$^+$.

Step F: A mixture of (5R,8S)-8-methoxy-5-methyl-5,6,7,8-tetrahydro-1,6-naphthyridine (101 mg, 0.567 mmol), 2,3-dichloro-5-methyl-quinoxaline (121 mg, 0.567 mmol) and DIEA (146 mg, 1.13 mmol) in DMSO (3.00 mL) was stirred at 90° C. for 12 h. The reaction mixture was poured into $H_2O$ (2.00 mL) and extracted with DCM (2.00 mL×4). The combined organic layers were dried over $Na_2SO_4$, filtered, and concentrated under vacuum to give a residue which was purified by prep-TLC to give a mixture of 3-chloro-2-((5R,8S)-8-methoxy-5-methyl-7,8-dihydro-1,6-naphthyridin-6(5H)-yl)-5-methylquinoxaline and 2-chloro-3-((5R,8S)-8-methoxy-5-methyl-7,8-dihydro-1,6-naphthyridin-6(5H)-yl)-5-methyl-1,2-dihydroquinoxaline (92.0 mg, 46%). LC-MS: 355.1 [M+H]$^+$.

Step G: To a solution of 3-chloro-2-((5R,8S)-8-methoxy-5-methyl-7,8-dihydro-1,6-naphthyridin-6(5H)-yl)-5-methylquinoxaline and 2-chloro-3-((5R,8S)-8-methoxy-5-methyl-7,8-dihydro-1,6-naphthyridin-6(5H)-yl)-5-methyl-1,2-dihydroquinoxaline (92.0 mg, 0.259 mmol) in dioxane (3.00 mL) and $H_2O$ (0.600 mL) was added potassium hydroxide (45.0 mg, 0.801 mmol) and Bis(dibenzylideneacetone)palladium(0) (2.39 mg, 0.004 mmol), tBuXPhos (2.75 mg, 0.006 mmol). The mixture was stirred at 100° C. for 2 h. The reaction mixture was poured into $H_2O$ (2.00 mL) and extracted with DCM (2.00 mL×4). The combined organic layers were dried over $Na_2SO_4$, filtered, and concentrated under vacuum to give a residue which was purified by preparative HPLC (Waters Xbridge Prep OBD C18 column 150×40 mm×10 um); flow rate: 25 mL/min; gradient: 20%-50% B over 8 min; mobile phase A: 10 mM aqueous $NH_4HCO_3$, mobile phase B: acetonitrile) to give 3-((5R,8S)-8-methoxy-5-methyl-7,8-dihydro-1,6-naphthyridin-6(5H)-yl)-8-methylquinoxalin-2(1H)-one (14.6 mg, first eluting regioisomer by HPLC). LC-MS: 337.1 [M+H]$^+$; $^1$H NMR (400 MHz, DMSO-$d_6$) δ 11.42 (br s, 1H), 8.47 (dd, J=1.1, 4.6 Hz, 1H), 7.84 (d, J=7.5 Hz, 1H), 7.38 (dd, J=4.6, 7.9 Hz, 1H), 7.21 (br d, J=7.4 Hz, 1H), 7.10-6.89 (m, 2H), 6.58-5.73 (m, 2H), 4.23 (s, 1H), 3.65-3.49 (m, 1H), 3.38 (s, 3H), 2.38 (s, 3H), 1.47 (d, J=6.9 Hz, 3H). 3-((5R,8S)-8-methoxy-5-methyl-7,8-dihydro-1,6-naphthyridin-6(5H)-yl)-5-methylquinoxalin-2(1H)-one (21.5 mg, second eluting regioisomer by HPLC). LC-MS: 337.1 [M+H]$^+$; $^1$H NMR (400 MHz, DMSO-$d_6$) δ 12.16-11.91 (m, 1H), 8.47 (dd, J=1.3, 4.6 Hz, 1H), 7.83 (d, J=7.5 Hz, 1H), 7.38 (dd, J=4.6, 7.9 Hz, 1H), 7.10-6.85 (m, 3H), 6.65-5.65 (m, 2H), 4.23 (br s, 1H), 3.54 (br d, J=13.3 Hz, 1H), 3.39 (s, 3H), 2.45-2.30 (m, 3H), 1.49 (d, J=6.9 Hz, 3H).

Example 28: (S)- or (R)-5-Methyl-3-(6-methyl-3-(trifluoromethyl)-5,6-dihydroimidazo[1,5-a]pyrazin-7(8H)-yl)quinoxalin-2(1H)-one

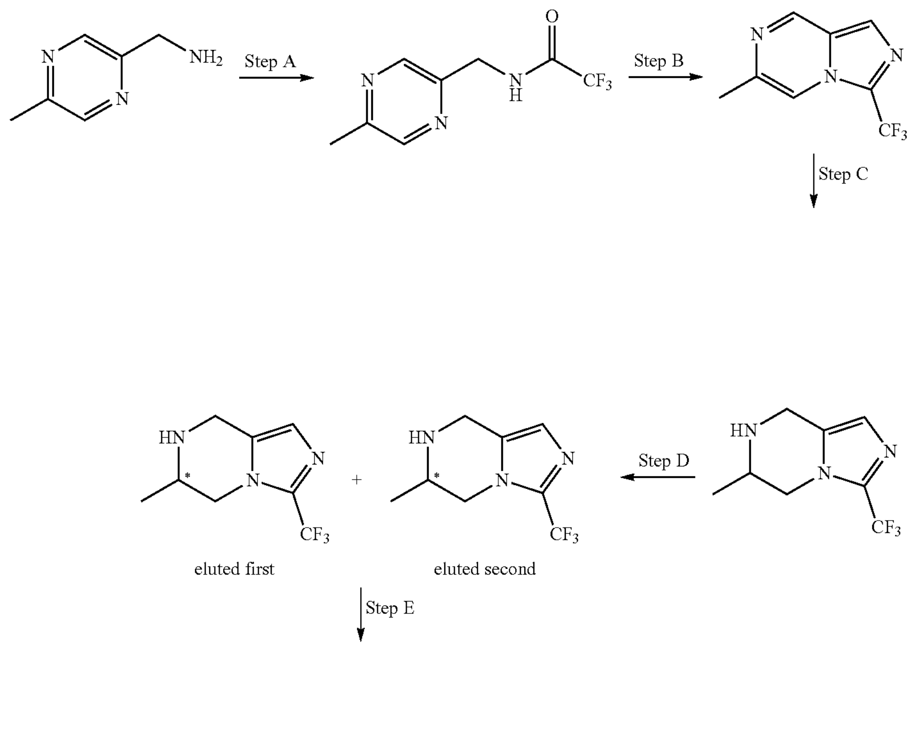

-continued

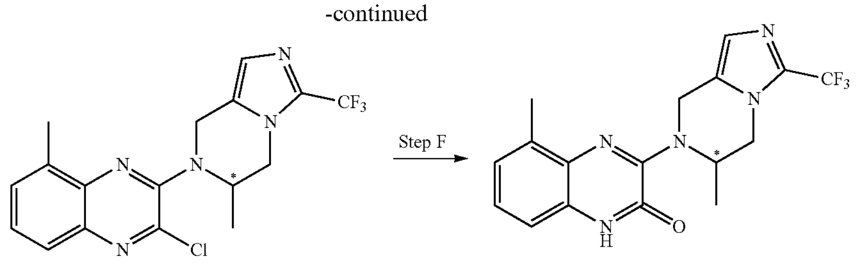

Step A: To a solution of (5-methylpyrazin-2-yl)methanamine (50.0 g, 406 mmol) in DCM (500 mL) was added trifluoroacetic anhydride (102 g, 487 mmol) under −10° C., then the mixture was stirred at 20° C. overnight. The mixture was poured into $H_2O$ (500 mL) and extracted with DCM (300 mL×5). The combined organic layers were dried over $Na_2SO_4$, filtered, and concentrated under vacuum to give a residue which was triturated with EtOAc/Petroleum ether (v/v)=10:1 (50 ml) at 20° C. for 30 min. The mixture was filtered and the cake was dried under vacuum to give 2,2,2-trifluoro-N-((5-methylpyrazin-2-yl)methyl)acetamide (80 g, 89.9% yield). LC-MS: 220.0 $[M+H]^+$.

Step B: To a solution of 2,2,2-trifluoro-N-((5-methylpyrazin-2-yl)methyl)acetamide (80.0 g, 365 mmol) in phosphoryl chloride (380 mL) was added phosphorus pentoxide (51.8 g, 365 mmol). The mixture was heated at 120° C. overnight. The reaction mixture was allowed to cool to room temperature, concentrated under vacuum to remove most of the phosphoryl chloride. The residue was diluted with EtOAc (400 mL), then poured into saturated aqueous sodium carbonate (400 ml) at 0° C. The solution was further diluted with $H_2O$ (200 mL) and extracted with DCM (500 mL×3). The combined organic layers were dried and concentrated under vacuum. The residue was purified by flash chromatography on silica gel to give 6-methyl-3-(trifluoromethyl)imidazo[1,5-a]pyrazine (65 g, 89% yield). LC-MS: 202.0 $[M+H]^+$.

Step C: To a mixture of 6-methyl-3-(trifluoromethyl) imidazo[1,5-a]pyrazine (50.0 g, 248 mmol) in THF (150 mL) was added Pd/C (47.5 g, 44.7 mmol, 10% purity). The mixture was degassed and purged with $H_2$ three times, then stirred at 20° C. for 12 h under a $H_2$ atmosphere. The mixture was filtered and the filtrate was concentrated under vacuum to give 6-methyl-3-(trifluoromethyl)-5,6,7,8-tetrahydroimidazo[1,5-a]pyrazine (43 g, 210 mmol, 84% yield). LC-MS: 206.0 $[M+H]^+$.

Step D: 6-Methyl-3-(trifluoromethyl)-5,6,7,8-tetrahydroimidazo[1,5-a]pyrazine (43 g, 210 mmol) was further purified by chiral SFC ((DAICEL CHIRALPAK IC (250×50 mm, 10 μm); flow rate: 64 mL/min; gradient: 25% B over 4 min; mobile phase A: $CO_2$, mobile phase B: isopropanol (0.1% $NH_3H_2O$)) to give a first eluting isomer, (R)- or (S)-6-methyl-3-(trifluoromethyl)-5,6,7,8-tetrahydroimidazo [1,5-a]pyrazine (18.0 g, eluted first). LC-MS: 206.0 $[M+H]^+$; $^1H$ NMR (400 MHz, DMSO-$d_6$) δ 6.84 (s, 1H), 4.19-4.01 (m, 2H), 3.83 (br d, J=16.0 Hz, 1H), 3.48 (t, J=11.3 Hz, 1H), 3.09-2.94 (m, 1H), 2.73-2.55 (m, 1H), 1.14 (d, J=6.4 Hz, 3H). The second eluting isomer was (S)- or (R)-6-methyl-3-(trifluoromethyl)-5,6,7,8-tetrahydroimidazo [1,5-a]pyrazine (16.8 g, eluted second). LC-MS: 206.0 $[M+H]^+$; $^1H$ NMR (400 MHz, DMSO-) δ 6.84 (s, 1H), 4.19-4.01 (m, 2H), 3.83 (br d, J=16.0 Hz, 1H), 3.48 (t, J=11.3 Hz, 1H), 3.09-2.94 (m, 1H), 2.73-2.55 (m, 1H), 1.14 (d, J=6.4 Hz, 3H). The absolute stereochemistry for the first and second eluted compounds was not determined.

Step E: To a solution of (S) or (R)-6-methyl-3-(trifluoromethyl)-5,6,7,8-tetrahydroimidazo[1,5-a]pyrazine (300 mg, 1.46 mmol, the second eluting isomer from Example 28, Step D) in DMSO (5.00 mL) were added DIEA (378 mg, 2.92 mmol, 509 μL) and 2,3-dichloro-5-methyl-quinoxaline (312 mg, 1.46 mmol) at 20° C. and the mixture was stirred at 90° C. for 12 h. The reaction mixture was concentrated to give a residue which was purified by semi-prep-HPLC (Phenomenex Luna C18 column (100×30 mm, 5 μm); flow rate: 25 mL/min; gradient: 50%-75% B over 8 min; mobile phase A: water (10 mM TFA), mobile phase B: acetonitrile) to give (S) or (R)-2-chloro-5-methyl-3-(6-methyl-3-(trifluoromethyl)-5,6-dihydroimidazo[1,5-a]pyrazin-7(8H)-yl)quinoxaline (30.0 mg, 5%). LC-MS: 382.1 $[M+H]^+$; Other fractions were lyophilized to afford (S) or (R)-3-chloro-5-methyl-2-(6-methyl-3-(trifluoromethyl)-5,6-dihydroimidazo[1,5-a]pyrazin-7(8H)-yl)quinoxaline (90.0 mg, 16%) (used in Example 29).

Step F: To a solution of (S)- or (R)-2-chloro-5-methyl-3-(6-methyl-3-(trifluoromethyl)-5,6-dihydroimidazo[1,5-a] pyrazin-7(8H)-yl)quinoxaline (30.0 mg, 0.079 mmol) in dioxane (2.00 mL) and $H_2O$ (0.500 mL) were added potassium hydroxide (13.6 mg, 0.242 mmol), $Pd(dba)_2$ (7.23 mg, 0.013 mmol) and tBuXPhos (8.34 mg, 0.020 mmol) at 20° C. The resulting mixture was stirred at 100° C. for 2 h. The reaction mixture was allowed to cool to RT, then was concentrated to give a residue which was purified by semi-prep-HPLC (Waters Xbridge Prep OBD C18 column (150×40 mm, 10 μm); flow rate: 60 mL/min; gradient: 40%-70% B over 8 min; mobile phase A: water (10 mM $NH_4HCO_3$), mobile phase B: acetonitrile) to give (S)- or (R)-5-methyl-3-(6-methyl-3-(trifluoromethyl)-5,6-dihydroimidazo[1,5-a] pyrazin-7(8H)-yl)quinoxalin-2(1H)-one (6.83 mg, 23%). LC-MS: 364.0 $[M+H]^+$; $^1H$ NMR (400 MHz, $CDCl_3$) δ 9.26 (br s, 1H), 7.22-7.13 (m, 2H), 7.05 (s, 1H), 6.93 (dd, J=1.1, 7.5 Hz, 1H), 5.93 (br d, J=4.5 Hz, 1H), 5.54 (br d, J=17.6 Hz, 1H), 4.72 (d, J=17.5 Hz, 1H), 4.46 (dd, J=4.3, 12.8 Hz, 1H), 4.22 (br d, J=12.8 Hz, 1H), 2.59 (s, 3H), 1.33 (d, J=6.9 Hz, 3H).

Example 29: (R)- or (S)-8-Methyl-3-(6-methyl-3-(trifluoromethyl)-5,6-dihydroimidazo[1,5-a]pyrazin-7(8H)-yl)quinoxalin-2(1H)-one

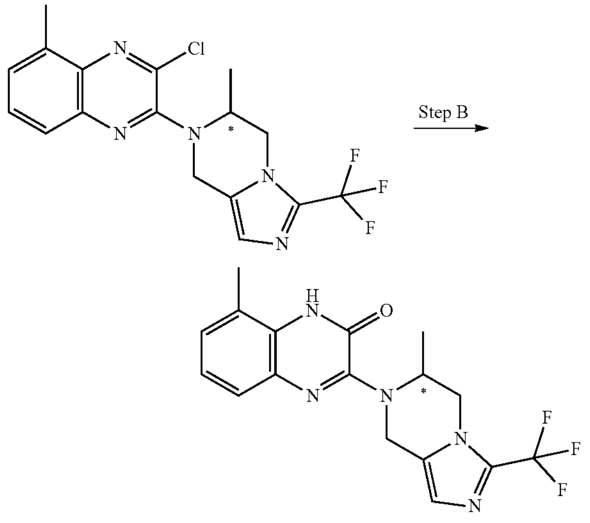

Step A: To a solution of (R)- or (S)-3-chloro-5-methyl-2-(6-methyl-3-(trifluoromethyl)-5,6-dihydroimidazo[1,5-a]pyrazin-7(8H)-yl)quinoxaline (the second eluting isomer from Example 28, Step E) (30.0 mg, 0.079 mmol) in dioxane (2.00 mL) and $H_2O$ (0.500 mL) were added potassium hydroxide (13.6 mg, 0.243 mmol), $Pd(dba)_2$ (7.23 mg, 0.013 mmol) and tBuXPhos (8.34 mg, 0.020 mmol) at 20° C. and the mixture was stirred at 100° C. for 2 h. The reaction mixture was concentrated to give a residue. The crude reaction was purified by prep-HPLC (Waters Xbridge Prep OBD C18 column (150×40 mm, 10 μm); flow rate: 60 mL/min; gradient: 35%-65% B over 8 min; mobile phase A: water (10 mM $NH_4HCO_3$), mobile phase B: acetonitrile) to afford (R)- or (S)-8-methyl-3-(6-methyl-3-(trifluoromethyl)-5,6-dihydroimidazo[1,5-a]pyrazin-7(8H)-yl)quinoxalin-2(1H)-one (6.58 mg, 23%). LC-MS: 364.0 $[M+H]^+$; $^1H$ NMR (400 MHz, DMSO-$d_6$) δ 11.42-10.88 (m, 1H), 7.31 (t, J=4.8 Hz, 1H), 7.11 (s, 1H), 7.07 (d, J=4.6 Hz, 2H), 5.80 (br d, J=1.9 Hz, 1H), 5.44 (br d, J=17.8 Hz, 1H), 4.64 (br d, J=17.5 Hz, 1H), 4.42-4.32 (m, 1H), 4.30-4.23 (m, 1H), 2.39 (s, 3H), 1.17 (d, J=6.9 Hz, 3H).

Example 30: (7-Chloro-1H-benzo[d]imidazol-2-yl)(1-methyl-3-(trifluoromethyl)-1,4,5,7-tetrahydro-6H-pyrazolo[3,4-c]pyridin-6-yl)methanone

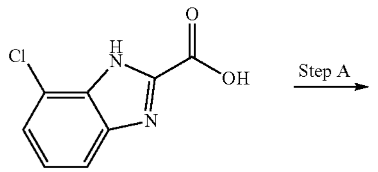

-continued

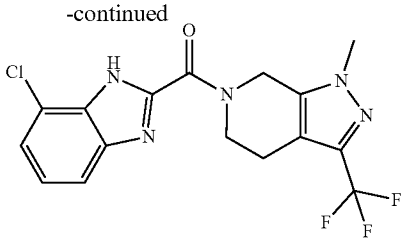

Step A: To a solution of 7-chloro-1H-benzimidazole-2-carboxylic acid (100 mg, 0.508 mmol) and 1-methyl-3-(trifluoromethyl)-4,5,6,7-tetrahydropyrazolo[3,4-c]pyridine (104 mg, 0.508 mmol) in DCM (5.00 mL) was added phosphoric acid bis(2-oxooxazolidide) chloride (259 mg, 1.02 mmol) and TEA (103 mg, 1.02 mmol). The mixture was stirred at 20° C. for 1 h. The crude reaction was filtered and the filtrate was purified by prep HPLC (Waters Xbridge Prep OBD C18 column (150×40 mm, 10 mm); flow rate: 60 mL/min; gradient: 35%-65% B over 8 min; mobile phase A: water (10 mM $NH_4HCO_3$), mobile phase B: acetonitrile) to give 7-chloro-1H-benzo[d]imidazol-2-yl)(1-methyl-3-(trifluoromethyl)-1,4,5,7-tetrahydro-6H-pyrazolo[3,4-c]pyridin-6-yl)methanone (141 mg, 71%). LC-MS: 384.0 $[M+H]^+$; $^1H$ NMR (400 MHz, DMSO-$d_6$) δ 13.38-13.68 (m, 1H), 7.48-7.63 (m, 1H), 7.28-7.43 (m, 2H), 5.52-5.78 (m, 1H), 4.93 (s, 1H), 4.50 (br s, 1H), 3.96 (br t, J=5.69 Hz, 1H), 3.79 (s, 1H), 3.88 (s, 2H), 2.68-2.92 (m, 2H).

Example 31: (7-Chloro-1H-benzo[d]imidazol-2-yl)(3-(trifluoromethyl)-1,4,5,7-tetrahydro-6H-pyrazolo[3,4-c]pyridin-6-yl)methanone

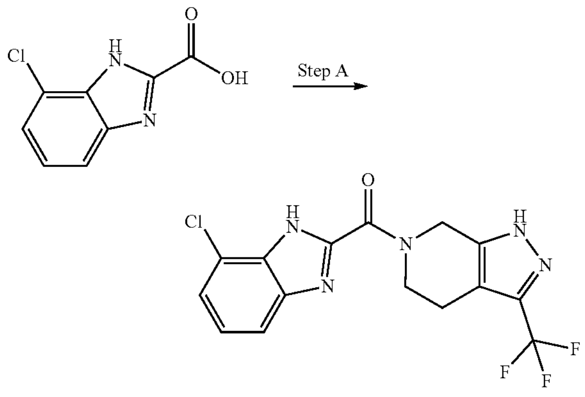

Step A: To a solution of 3-(trifluoromethyl)-4,5,6,7-tetrahydro-1H-pyrazolo[3,4-c]pyridine hydrochloride (70.0 mg, 0.308 mmol) in THF (2.00 mL) were added DIEA (99.4 mg, 0.769 mmol), 7-chloro-1H-benzimidazole-2-carboxylic acid (72.6 mg, 0.369 mmol) and Phosphoric acid bis(2-oxooxazolidide) chloride (86.1 mg, 0.338 mmol). The mixture was stirred at 20° C. for 12 h. The crude reaction was filtered and the filtrate was purified by preparative HPLC (Phenomenex Gemini C18 column (100×40 mm, 5 mm); flow rate: 60 mL/min; gradient: 25%-55% B over 8.0 min; mobile phase A: 0.04% HCl, mobile phase B: acetonitrile) to afford 7-chloro-1H-benzo[d]imidazol-2-yl)(3-(trifluoromethyl)-1,4,5,7-tetrahydro-6H-pyrazolo[3,4-c]pyridin-6-yl)methanone (61.7 mg, 58%). LC-MS: 370.0 $[M+H]^+$; $^1H$ NMR (400 MHz, DMSO-$d_6$) δ 13.69-13.21 (m, 1H), 7.55 (br t, J=6.7 Hz, 1H), 7.40-7.37 (m, 1H), 7.35-7.30 (m, 1H), 5.62 (s, 1H), 4.91 (s, 1H), 4.53 (br s, 1H), 3.98 (t, J=5.7 Hz, 1H), 2.86-2.80 (m, 1H), 2.74 (br t, J=5.4 Hz, 1H).

Examples 32A, 32B, 32C, and 32D: (R)-(7-Chloro-4-fluoro-1H-benzo[d]imidazol-2-yl)(3,4-dimethyl-6,7-dihydroisoxazolo[4,3-c]pyridin-5(4H)-yl)methanone, (R)-(7-Chloro-4-fluoro-1H-benzo[d]imidazol-2-yl)(3,4-dimethyl-6,7-dihydroisoxazolo[4,5-c]pyridin-5(4H)-yl)methanone, (R)-(7-Chloro-4-fluoro-1H-benzo[d]imidazol-2-yl)(3,6-dimethyl-6,7-dihydroisoxazolo[4,3-c]pyridin-5(4H)-yl)methanone, and (R)-(7-Chloro-4-fluoro-1H-benzo[d]imidazol-2-yl)(3,6-dimethyl-6,7-dihydroisoxazolo[4,5-c]pyridin-5(4H)-yl)methanone

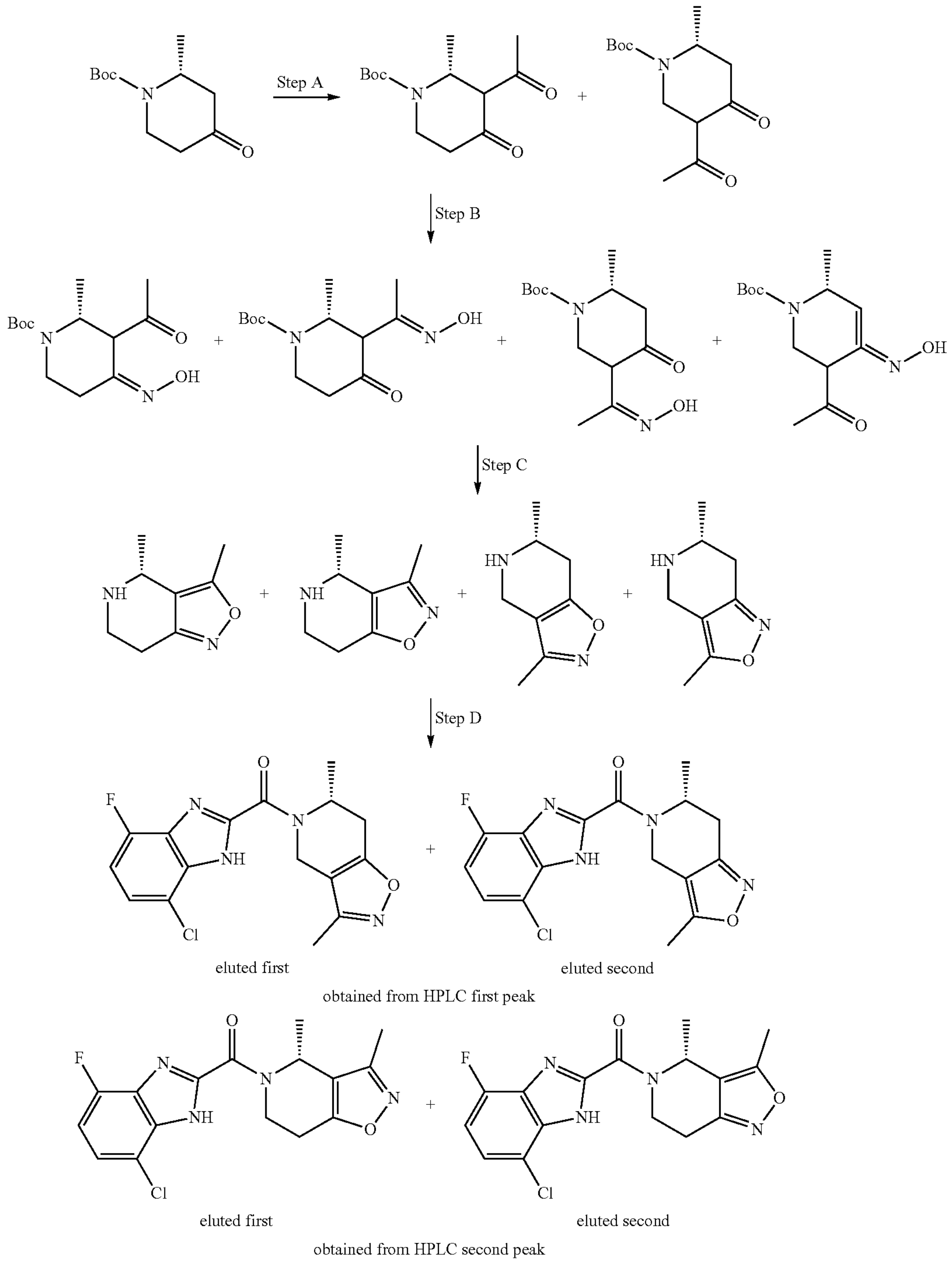

Step A: A mixture of tert-butyl (2R)-2-methyl-4-oxo-piperidine-1-carboxylate (5.50 g, 25.8 mmol) in THF (55.0 mL) was degassed and purged with nitrogen 3 times, then a solution of 1 M lithium bis(trimethylsilyl)amide in THF (28.4 mL) was added dropwise at −20° C. The resulting mixture was stirred at this temperature for 10 min under nitrogen atmosphere. Acetyl chloride (2.43 g, 31.0 mmol, 2.20 mL) was then added dropwise at −20° C. and the mixture was stirred at this temperature for 10 min under nitrogen atmosphere. The reaction mixture was quenched by addition of saturated aqueous ammonium chloride (80.0 mL) and extracted with EtOAc (50.0 mL×3). The combined organic layers were washed with brine (80.0 mL×1), dried over $Na_2SO_4$, filtered and concentrated under reduced pressure to give a residue which was purified by flash silica gel chromatography using 0 to 50% EtOAc in petroleum ether to give an inseparable mixture of tert-butyl (2R)-3-acetyl-2-methyl-4-oxopiperidine-1-carboxylate and tert-butyl (2R)-5-acetyl-2-methyl-4-oxopiperidine-1-carboxylate (4.70 g, 71%). LC-MS: 200.2 $[M-56+H]^+$.

Step B: To a solution of the mixture of tert-butyl (2R)-3-acetyl-2-methyl-4-oxopiperidine-1-carboxylate and tert-butyl (2R)-5-acetyl-2-methyl-4-oxopiperidine-1-carboxylate (4.70 g, 18.4 mmol) in EtOH (50.0 mL) were added sodium acetate (4.53 g, 55.2 mmol), $H_2O$ (995 mg, 55.2 mmol) and hydroxylamine hydrochloride (1.28 g, 18.4 mmol). The mixture was stirred at 80° C. for 4 h. The reaction mixture was concentrated under reduced pressure and the residue was diluted with $H_2O$ (80.0 mL) and extracted with EtOAc (50.0 mL×3). The combined organic layers were dried over $Na_2SO_4$, filtered and concentrated under reduced pressure to give a mixture of tert-butyl (2R,Z)-3-acetyl-4-(hydroxyimino)-2-methylpiperidine-1-carboxylate, tert-butyl (2R)-3-((E)-1-(hydroxyimino)ethyl)-2-methyl-4-oxopiperidine-1-carboxylate, tert-butyl (2R)-5-((Z)-1-(hydroxyimino)ethyl)-2-methyl-4-oxopiperidine-1-carboxylate, and tert-butyl (2R,E)-5-acetyl-4-(hydroxyimino)-2-methylpiperidine-1-carboxylate (4.9 g, 98%). LC-MS: 271.2 $[M+H]^+$.

Step C: To a solution of tert-butyl (2R,Z)-3-acetyl-4-(hydroxyimino)-2-methylpiperidine-1-carboxylate tert-butyl (2R)-3-((E)-1-(hydroxyimino)ethyl)-2-methyl-4-oxopiperidine-1-carboxylate, tert-butyl (2R)-5-((Z)-1-(hydroxyimino)ethyl)-2-methyl-4-oxopiperidine-1-carboxylate, and tert-butyl (2R,E)-5-acetyl-4-(hydroxyimino)-2-methylpiperidine-1-carboxylate (1.00 g, 3.70 mmol) in acetic acid (9.00 mL) was added concentrated HCl (3.00 mL). The mixture was stirred at 80° C. for 0.5 h. The reaction mixture was concentrated under reduced pressure to give a mixture of (R)-3,4-dimethyl-4,5,6,7-tetrahydroisoxazolo[4,3-c]pyridine, (R)-3,4-dimethyl-4,5,6,7-tetrahydroisoxazolo[4,5-c]pyridine, (R)-3,6-dimethyl-4,5,6,7-tetrahydroisoxazolo[4,5-c]pyridine, and (R)-3,6-dimethyl-4,5,6,7-tetrahydroisoxazolo[4,3-c]pyridine (700 mg, crude, HCl). LC-MS: 153.3 $[M+H]^+$.

Step D: To a solution of (R)-3,4-dimethyl-4,5,6,7-tetrahydroisoxazolo[4,3-c]pyridine (R)-3,4-dimethyl-4,5,6,7-tetrahydroisoxazolo[4,5-c]pyridine, (R)-3,6-dimethyl-4,5,6,7-tetrahydroisoxazolo[4,5-c]pyridine, and (R)-3,6-dimethyl-4,5,6,7-tetrahydroisoxazolo[4,3-c]pyridine hydrochloride (700 mg, 3.71 mmol) in THF (10.0 mL) were added DIEA (1.20 g, 9.28 mmol), 7-chloro-4-fluoro-1H-benzimidazole-2-carboxylic acid (955 mg, 4.45 mmol) and Phosphoric acid bis(2-oxooxazolidide) chloride (1.04 g, 4.08 mmol). The mixture was stirred at 20° C. for 12 h. The reaction mixture was filtered and concentrated under reduced pressure to give a residue, which was purified by preparative HPLC (Phenomenex Gemini C18 column (100×30 mm, 7 mm); flow rate: 40 mL/min; gradient: 20%-50% B over 20 min; mobile phase A: $H_2O$ (10 mM $NH_4HCO_3$), mobile phase B: acetonitrile) to give two major peaks. (75 mg, mixture, HPLC elutes first) and (70 mg, 6%, mixture, HPLC elutes second). The first eluting peak was further purified by chiral SFC (DAICEL CHIRALPAK IG (250×30 mm, 10 μm); flow rate: 80 mL/min; gradient: 40% B over 67 min; mobile phase A: heptane, mobile phase B: $CO_2$-EtOH (0.1% $NH_3H_2O$) to give (R)-(7-chloro-4-fluoro-1H-benzo[d]imidazol-2-yl)(3,6-dimethyl-6,7-dihydroisoxazolo[4,5-c]pyridin-5(4H)-yl)methanone (30.7 mg, 82%, first eluting peak) and (R)-(7-chloro-4-fluoro-1H-benzo[d]imidazol-2-yl)(3,6-dimethyl-6,7-dihydroisoxazolo[4,3-c]pyridin-5(4H)-yl)methanone (7.3 mg, 19%, second eluting peak). (R)-(7-chloro-4-fluoro-1H-benzo[d]imidazol-2-yl)(3,6-dimethyl-6,7-dihydroisoxazolo[4,5-c]pyridin-5(4H)-yl)methanone: LC-MS: 349.1 $[M+H]^+$; $^1H$ NMR (400 MHz, DMSO-$d_6$) δ 10.71 (br s, 1H), 7.29 (br d, J=3.6 Hz, 1H), 7.10-6.99 (m, 1H), 6.97-6.52 (m, 1H), 5.73-5.29 (m, 1H), 4.57-4.00 (m, 1H), 3.44-3.06 (m, 1H), 2.91-2.71 (m, 1H), 2.41-2.29 (m, 3H), 1.45-1.31 (m, 3H). (R)-(7-chloro-4-fluoro-1H-benzo[d]imidazol-2-yl)(3,6-dimethyl-6,7-dihydroisoxazolo[4,3-c]pyridin-5(4H)-yl)methanone: LC-MS: 349.1 $[M+H]^+$; $^1H$ NMR (400 MHz, DMSO-$d_6$) δ 11.24-10.39 (m, 1H), 7.29 (s, 1H), 7.10-6.98 (m, 1H), 6.95-6.58 (m, 1H), 5.69-5.27 (m, 1H), 4.69-4.00 (m, 1H), 3.33-2.79 (m, 2H), 2.45 (s, 3H), 1.39-1.30 (m, 3H). The second eluting peak was further purified by chiral SFC (DAICEL CHIRALPAK IG (250×30 mm, 10 μm); flow rate: 80 mL/min; gradient: 40% B over 66 min; mobile phase A: heptane, mobile phase B: $CO_2$-EtOH (0.1% $NH_3H_2O$) to give (R)-(7-chloro-4-fluoro-1H-benzo[d]imidazol-2-yl)(3,4-dimethyl-6,7-dihydroisoxazolo[4,5-c]pyridin-5(4H)-yl)methanone (21.2 mg, 61%, first eluting peak on SFC). LC-MS: 349.0 $[M+H]^+$; $^1H$ NMR (400 MHz, DMSO-$d_6$) δ 10.62 (br s, 1H), 7.33-7.28 (m, 1H), 7.12-6.83 (m, 1H), 6.43 (br dd, J=5.5, 13.8 Hz, 1H), 5.72-5.03 (m, 1H), 3.66-3.43 (m, 1H), 3.35-3.05 (m, 1H), 3.02-2.88 (m, 1H), 2.34 (s, 3H), 1.71-1.65 (m, 1H), 1.51 (d, J=6.6 Hz, 2H). The second eluting peak was (R)-(7-chloro-4-fluoro-1H-benzo[d]imidazol-2-yl)(3,4-dimethyl-6,7-dihydroisoxazolo[4,3-c]pyridin-5(4H)-yl)methanone (16.2 mg, 46%, SFC elutes second). LC-MS: $[MH]^+$=349.1. $^1H$ NMR (400 MHz, DMSO-$d_6$) δ 10.61 (br s, 1H), 7.33-7.28 (m, 1H), 7.10-6.92 (m, 1H), 6.50-5.91 (m, 1H), 5.85 (br d, J=6.6 Hz, 1H), 3.62-3.18 (m, 1H), 3.16-2.82 (m, 2H), 2.44 (s, 3H), 1.72-1.64 (m, 1H), 1.51 (d, J=6.6 Hz, 2H). The structures of the regioisomers were tentatively assigned.

Example 33A and 33B: (R)-(7-Chloro-4-fluoro-1H-benzo[d]imidazol-2-yl)(3,4-dimethyl-6,7-dihydroisothiazolo[4,3-c]pyridin-5(4H)-yl)methanone and (R)-(7-Chloro-4-fluoro-1H-benzo[d]imidazol-2-yl)(3,6-dimethyl-6,7-dihydroisothiazolo[4,5-c]pyridin-5(4H)-yl)methanone

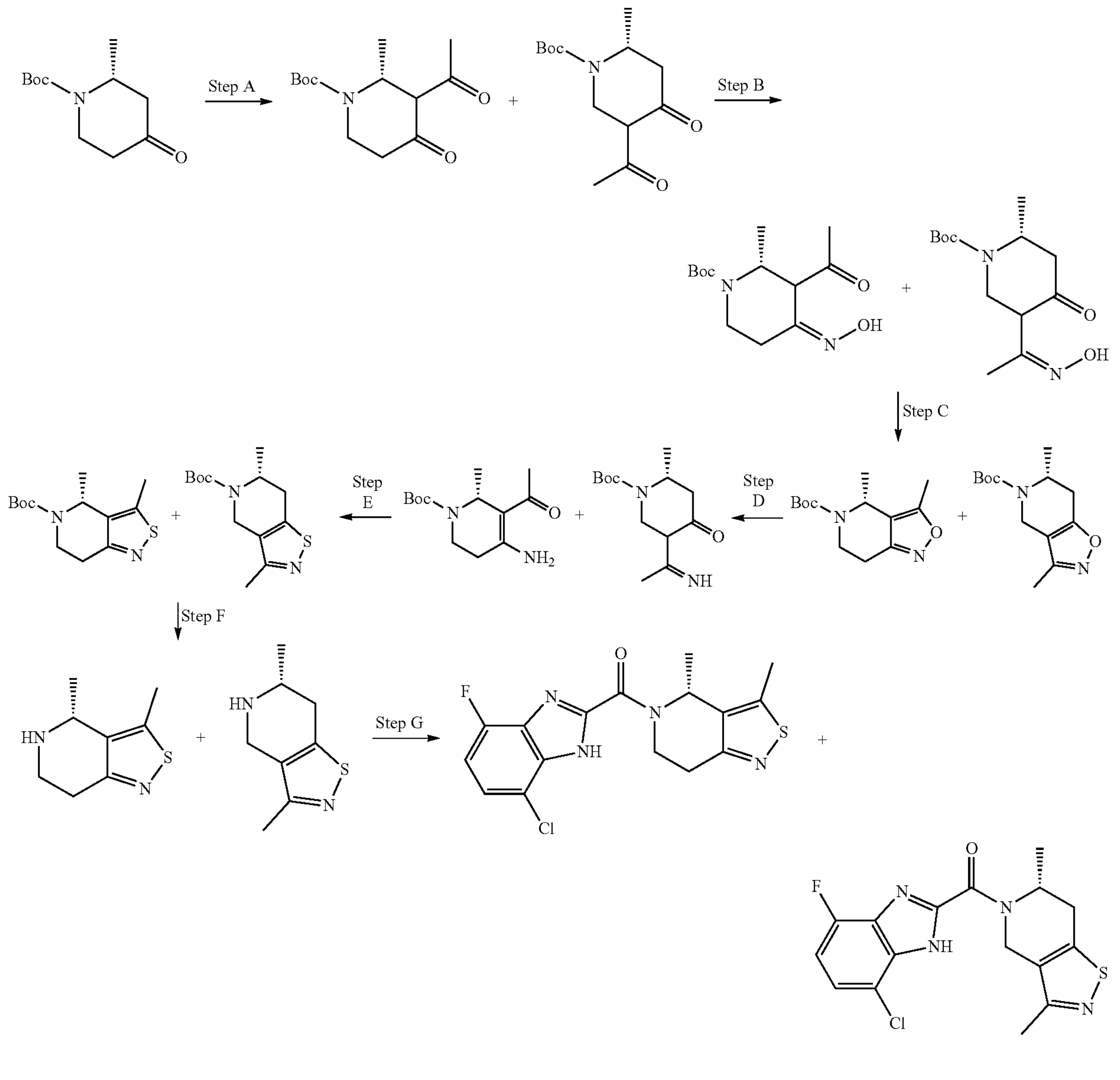

Step A: A mixture of tert-butyl (2R)-2-methyl-4-oxo-piperidine-1-carboxylate (5.50 g, 25.8 mmol) in THF (55.0 mL) was degassed and purged with nitrogen 3 times, then LiHMDS in THF (1 M, 28.4 mL) was added dropwise at −20° C. The resulting mixture was stirred at this temperature for 10 min under nitrogen atmosphere, then acetyl chloride (2.43 g, 31.0 mmol, 2.20 mL) was added dropwise at −20° C. and the mixture was stirred at this temperature for 10 min under nitrogen atmosphere. The reaction mixture was poured into saturated aqueous ammonium chloride (80.0 mL) and extracted with EtOAc (50.0 mL×3). The combined organic layers were washed with brine (80.0 mL), dried over $Na_2SO_4$, filtered and concentrated under reduced pressure to give a residue which was purified by flash silica gel chromatography using a 0 to 50% EtOAc in petroleum ether to give tert-butyl (2R)-3-acetyl-2-methyl-4-oxopiperidine-1-carboxylate (4.70 g, 71%). LC-MS: 200.2 $[M-56+H]^+$.

Step B: To a solution of tert-butyl (2R)-3-acetyl-2-methyl-4-oxopiperidine-1-carboxylate (4.70 g, 18.4 mmol) in ethanol (50.0 mL) were added sodium acetate (4.53 g, 55.2 mmol), $H_2O$ (995 mg, 55.2 mmol) and hydroxylamine hydrochloride (1.28 g, 18.4 mmol). The mixture was stirred at 80° C. for 4 h. The reaction mixture was concentrated under vacuum to remove solvent. The residue was diluted with $H_2O$ (80.0 mL) and extracted with EtOAc (50.0 mL×3). The combined organic layers were dried over $Na_2SO_4$, filtered and concentrated under vacuum to give tert-butyl (2R,Z)-3-acetyl-4-(hydroxyimino)-2-methylpiperidine-1-carboxylate (4.9 g) as a mixture of regioisomers. LC-MS: 271.2 $[M+H]^+$.

Step C: To a solution of tert-butyl (2R,Z)-3-acetyl-4-(hydroxyimino)-2-methylpiperidine-1-carboxylate (6.00 g, 11.1 mmol) in DCM (120 mL) were added TEA (6.88 g, 33.96 mmol) and mesyl chloride (7.48 g, 32.5 mmol). The mixture was stirred at 0° C. for 2 h. The reaction mixture was poured into $H_2O$ (100 mL) and extracted with DCM (200 mL×3). The combined organic layers were dried over $Na_2SO_4$, filtered and concentrated under vacuum to give a residue which was purified by flash silica gel chromatography using 0 to 50% EtOAc in petroleum ether to give tert-butyl (R)-3,4-dimethyl-6,7-dihydroisoxazolo[4,3-c]pyridine-5(4H)-carboxylate (4.5 g, 80%). LC-MS: 253.2 $[M+H]^+$.

Step D: A mixture of tert-butyl (4R)-3,4-dimethyl-6,7-dihydro-4H-isoxazolo[4,3-c]pyridine-5-carboxylate (2.70 g) in MeOH (81.0 mL) was stirred at 20° C. until becoming a clear solution. The solution was pumped by Pump 1 {S1, P1, 1.00 mL/min} to fixed bed {FLR1, SS, fixed bed, 6.350 (¼") mm, 5 mL, 50° C.}, which was packed with granular catalyst 1% Pt/C (1.00 eq). The $H_2$ back pressure regulator was adjusted to 2.5 MPa. The flow rate of $H_2$ was 30 mL/min. The reaction mixture was collected after running 20 min. The mixture was concentrated under vacuum to give tert-butyl (R)-5-acetyl-4-amino-6-methyl-3,6-dihydropyridine-1(2H)-carboxylate (2.5 g). LC-MS: 255.2 $[M+H]^+$.

Step E: To a solution of tert-butyl (R)-5-acetyl-4-amino-6-methyl-3,6-dihydropyridine-1(2H)-carboxylate (800 mg, 3.15 mmol) in THF (20.0 mL) was added phosphorus(V) sulfide (350 mg, 1.57 mmol) and $NaHCO_3$ (198 mg, 2.36 mmol) under $N_2$. The mixture was stirred at 70° C. for 12 h, then 2,3,5,6-tetrachloro-1,4-benzoquinone (526 mg, 2.14 mmol) was added. The mixture was stirred at 70° C. for 12 h, then was filtered and concentrated under vacuum to give a residue which was purified by flash silica gel chromatography using 0 to 50% EtOAc in petroleum ether to give tert-butyl (R)-3,4-dimethyl-6,7-dihydroisothiazolo[4,3-c]pyridine-5(4H)-carboxylate (260 mg, 15%). LC-MS: 269.2 $[M+H]^+$.

Step F: A solution of tert-butyl (R)-3,4-dimethyl-6,7-dihydroisothiazolo[4,3-c]pyridine-5(4H)-carboxylate (260 mg, 0.969 mmol) in 2 M HCl in EtOAc (5.20 mL) was stirred at 25° C. for 3 h. The mixture was concentrated under vacuum to give (R)-3,4-dimethyl-4,5,6,7-tetrahydroisothiazolo[4,3-c]pyridine hydrochloride (262 mg). LC-MS: 169.1 $[M+H]^+$.

Step G: To a solution of (R)-3,4-dimethyl-4,5,6,7-tetrahydroisothiazolo[4,3-c]pyridine (130 mg, 0.635 mmol) in DMF (4.00 mL) were added HATU (241 mg, 0.635 mmol), 7-chloro-4-fluoro-1H-benzimidazole-2-carboxylic acid (136 mg, 0.635 mmol) and DIEA (246 mg, 1.91 mmol). The mixture was stirred at 20° C. for 3 h. The reaction mixture was poured into $H_2O$ (1.00 mL) and extracted with DCM (1.00 mL×4). The combined organic layers were dried over $Na_2SO_4$, filtered, and concentrated under vacuum to give a residue which was purified by preparative HPLC (Phenomenex Luna C18 column (100×40 mm, 5 μm); flow rate: 60 mL/min; gradient: 30%-70% B over 8 min; mobile phase A: 0.04% aqueous HCl, mobile phase B: acetonitrile) to give (R)-(7-chloro-4-fluoro-1H-benzo[d]imidazol-2-yl)(3,4-dimethyl-6,7-dihydroisothiazolo[4,3-c]pyridin-5(4H)-yl)methanone (50.2 mg, first eluting regioisomer) and (R)-(7-chloro-4-fluoro-1H-benzo[d]imidazol-2-yl)(3,6-dimethyl-6,7-dihydroisothiazolo[4,5-c]pyridin-5(4H)-yl)methanone (28.5 mg, second eluting regioisomer). First eluted compound: LC-MS: 365.0 $[M+H]^+$; $^1H$ NMR (400 MHz, DMSO-$d_6$) δ 14.55-13.63 (m, 1H), 7.40-7.36 (m, 1H), 7.22-7.16 (m, 1H), 5.27 (br d, J=17.7 Hz, 1H), 4.39-4.08 (m, 1H), 3.24 (br dd, J=5.3, 17.4 Hz, 1H), 3.12-3.00 (m, 2H), 2.42 (s, 3H), 1.21 (d, J=6.8 Hz, 3H). Second eluted compound: LC-MS: 365.0 $[M+H]^+$; $^1H$ NMR (400 MHz, DMSO-$d_6$) δ 14.20-13.97 (m, 1H), 7.37 (dt, J=4.0, 8.8 Hz, 1H), 7.21 (br s, 1H), 5.68 (br d, J=4.8 Hz, 1H), 5.28-4.71 (m, 1H), 3.75-3.45 (m, 1H), 3.18-3.09 (m, 1H), 3.01-2.87 (m, 1H), 2.46-2.37 (m, 3H), 1.55-1.43 (m, 3H).

Examples 34A and 34B: (R) or (S)-(7-Chloro-4-fluoro-1H-benzo[d]imidazol-2-yl)(2,4-dimethyl-6,7-dihydro-2H-pyrazolo[4,3-c]pyridin-5(4H)-yl)methanone and (R) or (S)-(7-Chloro-4-fluoro-1H-benzo[d]imidazol-2-yl)(2,4-dimethyl-6,7-dihydro-2H-pyrazolo[4,3-c]pyridin-5(4H)-yl)methanone

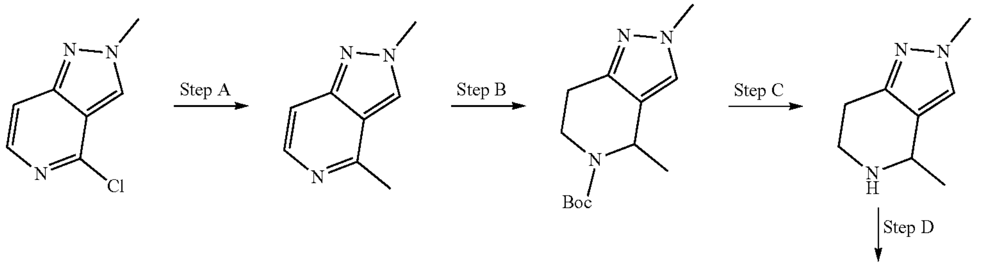

-continued

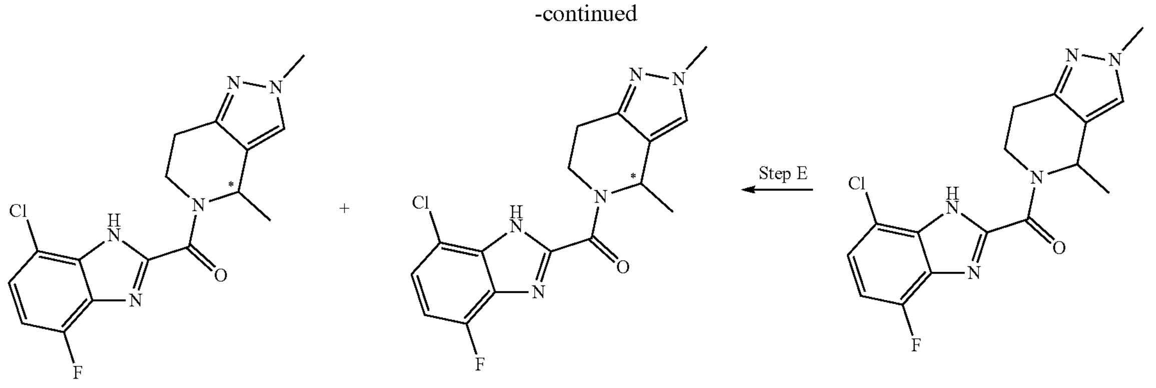

eluted first eluted second

Step A: A mixture of 4-chloro-2-methyl-pyrazolo[4,3-c] pyridine (450 mg, 2.69 mmol), 2,4,6-trimethyl-1,3,5,2,4,6-trioxatriborinane (1.01 g, 8.06 mmol, 1.13 mL), Palladium acetate (30.1 mg, 0.134 mmol), tricyclohexylphosphine (75.3 mg, 0.269 mmol) and tripotassium phosphate $K_3PO_4$ (1.71 g, 8.06 mmol) in toluene (5.00 mL) and $H_2O$ (0.500 mL) was degassed and purged with nitrogen for 3 times, and then the mixture was stirred at 90° C. for 12 h under nitrogen atmosphere. The reaction mixture was filtered, and the filtrate was diluted with $H_2O$ (10.0 mL) and extracted with EtOAc (8.00 mL×3). The combined organic layers were washed with brine (15.0 mL×1), dried over $Na_2SO_4$, filtered and concentrated under reduced pressure to give a residue, which was purified by prep-HPLC (Phenomenex Gemini C18 column (100×40 mm, 3 μm); flow rate: 25 mL/min; gradient: 5%-35% B over 18 min; mobile phase A: 0.04% HCl, mobile phase B: acetonitrile) to give 2,4-dimethyl-2H-pyrazolo[4,3-c]pyridine (230 mg, 57%). LC-MS: 148.1 $[M+H]^+$.

Step B: To a solution of platinum(IV) oxide (46.3 mg, 0.204 mmol) in 2,2,2-trifluoroethanol (3.00 mL) was added 2,4-dimethyl-2H-pyrazolo[4,3-c]pyridine (300 mg, 2.04 mmol) and di-tert-butyl dicarbonate (445 mg, 2.04 mmol) under nitrogen atmosphere. The suspension was degassed and purged with hydrogen for 3 times. The mixture was stirred under hydrogen (15 Psi) at 30° C. for 12 h. The reaction mixture was filtered and the filtrate was concentrated under reduced pressure to give tert-butyl 2,4-dimethyl-2,4,6,7-tetrahydro-5H-pyrazolo[4,3-c]pyridine-5-carboxylate (200 mg, 39%). LC-MS: 252.3 $[M+H]^+$.

Step C: A solution of tert-butyl 2,4-dimethyl-2,4,6,7-tetrahydro-5H-pyrazolo[4,3-c]pyridine-5-carboxylate (200 mg, 0.796 mmol) in 4M HCl/EtOAc (2.00 mL) was stirred at 20° C. for 0.5 h. The reaction mixture was filtered and the filtrate was concentrated under reduced pressure to give 2,4-dimethyl-4,5,6,7-tetrahydro-2H-pyrazolo[4,3-c]pyridine (120 mg, crude, HCl). LC-MS: 152.2 $[M+H]^+$.

Step D: To a solution of 2,4-dimethyl-4,5,6,7-tetrahydro-2H-pyrazolo[4,3-c]pyridine (100 mg, 0.533 mmol, HCl) in THF (2.00 mL) was added 7-chloro-4-fluoro-1H-benzimidazole-2-carboxylic acid (126 mg, 0.586 mmol) phosphoric acid bis(2-oxooxazolidide) chloride (1491 mg, 0.586 mmol) and DIEA (172 mg, 1.33 mmol). The mixture was stirred at 25° C. for 1 h. The reaction mixture was concentrated under reduced pressure to remove solvent. The residue was diluted with $H_2O$ (5.00 mL) and extracted with EtOAc (5.00 mL×3). The combined organic layers were washed with brine (10.0 mL×1), dried over $Na_2SO_4$, filtered and concentrated under reduced pressure to give a residue, which was purified by preparative HPLC (Phenomenex Gemini C18 column (150×40 mm, 10 μm); flow rate: 60 mL/min; gradient: 20%-50% B over 8 min; mobile phase A: $H_2O$ (10 mM $NH_4HCO_3$), mobile phase B: acetonitrile). (7-chloro-4-fluoro-1H-benzo[d]imidazol-2-yl)(2,4-dimethyl-2,4,6,7-tetrahydro-5H-pyrazolo[4,3-c]pyridin-5-yl)methanone (86.0 mg, 46%). LC-MS: 248.0 $[M+H]^+$.

Step E: (7-Chloro-4-fluoro-1H-benzo[d]imidazol-2-yl)(2,4-dimethyl-2,4,6,7-tetrahydro-5H-pyrazolo[4,3-c]pyridin-5-yl)methanone (86.0 mg, 0.247 mmol) was further separated by chiral SFC separation ChiralPak IH (250×30 mm, 10 μm); flow rate: 30 mL/min; gradient: 40% B over 14 min; mobile phase A: heptane, mobile phase B: $CO_2$-EtOH (0.1% $NH_3H_2O$) to afford a first eluted compound (27.9 mg) and a second eluted compound (30.2 mg). First eluted compound (Example 34A): LC-MS: 348.0 $[M+H]^+$. $^1H$ NMR (400 MHz, $CDCl_3$) δ 10.98-10.33 (m, 1H), 7.29 (br d, J=3.8 Hz, 1H), 7.24-7.19 (m, 1H), 7.08-6.94 (m, 1H), 6.51-6.21 (m, 1H), 5.92-4.85 (m, 1H), 3.99-3.77 (m, 3H), 3.61-3.16 (m, 1H), 3.11-2.76 (m, 2H), 1.73-1.64 (m, 1H), 1.51 (d, J=6.8 Hz, 2H). Second eluted compound (Example 34B): LC-MS: 348.0 $[M+H]^+$. $^1H$ NMR (400 MHz, $CDCl_3$) δ 10.53 (br d, J=3.3 Hz, 1H), 7.30 (br s, 1H), 7.23-7.19 (m, 1H), 7.10-6.93 (m, 1H), 6.31 (br dd, J=3.9, 13.4 Hz, 1H), 5.97-4.84 (m, 1H), 3.96-3.82 (m, 3H), 3.63-2.78 (m, 3H), 1.71-1.64 (m, 1H), 1.51 (d, J=6.8 Hz, 2H). The absolute stereochemistry for the first and second eluted compounds was not determined.

Examples 38A and 38B: (R)-(7-Chloro-4-fluoro-1H-benzo[d]imidazol-2-yl)(6-methyl-6,7-dihydroisothiazolo[4,5-c]pyridin-5(4H)-yl)methanone and (R)-(7-Chloro-4-fluoro-1H-benzo[d]imidazol-2-yl)(4-methyl-6,7-dihydroisothiazolo[4,5-c]pyridin-5(4H)-yl)methanone

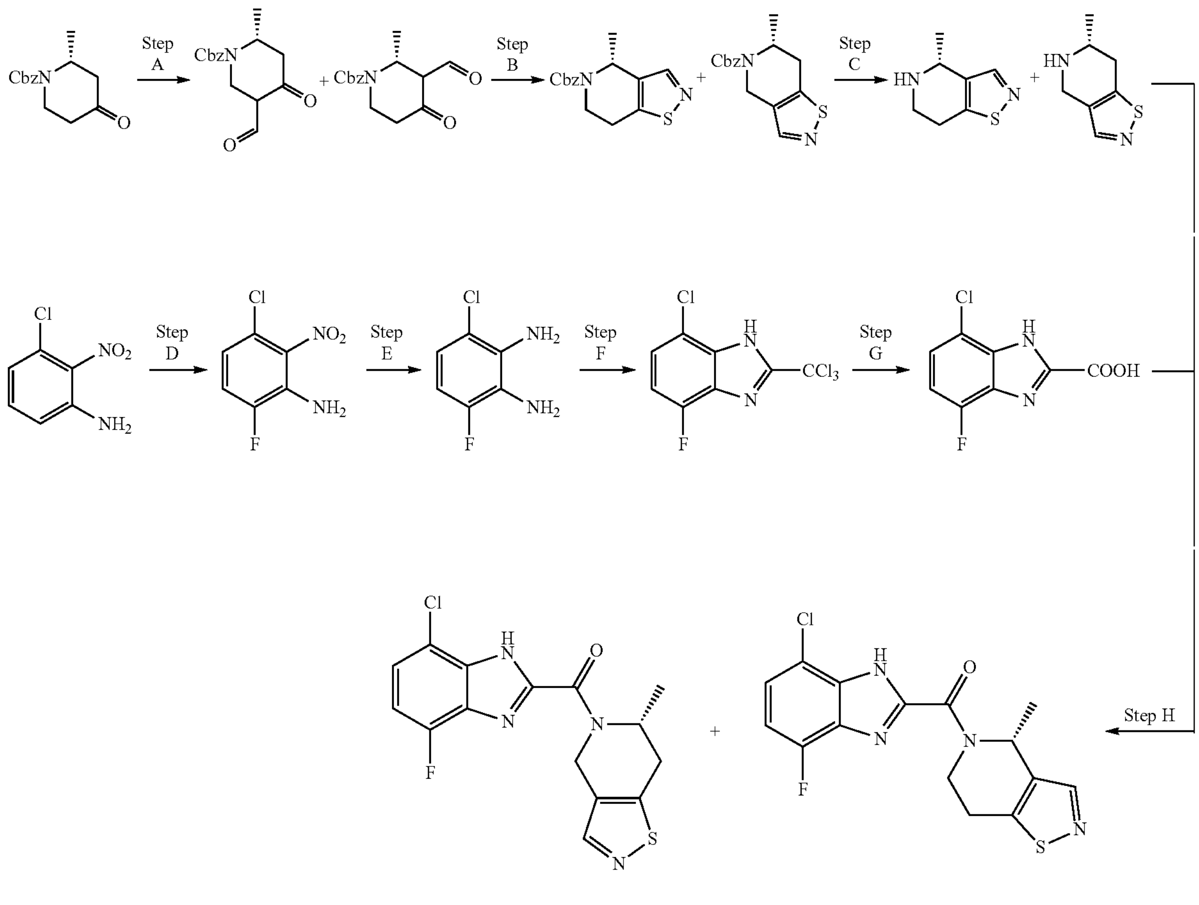

Step A: A solution of anhydrous dimethylformamide (282 uL, 3.64 mmol) in anhydrous DCM (2.50 mL) was cooled to 0° C. Phosphorus oxychloride (571 uL, 6.07 mmol) was added dropwise. Upon complete addition, the solution was stirred at 0° C. for 15 min and benzyl (R)-2-methyl-4-oxopiperidine-1-carboxylate (300 mg, 1.21 mmol) was added and the stirring was continued at room temperature for 3 h. The reaction mixture was quenched with water and extracted with dichloromethane. The organic layer was separated, dried over anhydrous $Na_2SO_4$ and concentrated under reduced pressure to afford a mixture of benzyl (2R)-5-formyl-2-methyl-4-oxopiperidine-1-carboxylate and benzyl (2R)-3-formyl-2-methyl-4-oxopiperidine-1-carboxylate (356 mg, 100%).

Step B: To a solution of benzyl (R)-4-chloro-5-formyl-6-methyl-3,6-dihydropyridine-1(2H)-carboxylate and (R)-4-chloro-3-formyl-6-methyl-3,6-dihydropyridine-1(2H)-carboxylate (356 mg, 1.21 mmol) in MeCN (12.1 mL) was added ammonium thiocyanate (473 mg, 6.06 mmol) at room temperature. The resulting mixture was heated at 55° C. for 1 h. The reaction was quenched with saturated aqueous $NaHCO_3$ solution and extracted with EtOAc twice. The organic layers were washed with water and brine, dried over $Na_2SO_4$, and concentrated under reduced pressure. The residue was purified by column chromatography to yield a mixture of (R)-4-methyl-4,5,6,7-tetrahydroisothazolo[4,5-c]pyridine and (R)-6-methyl-4,5,6,7-tetrahydroisothiazolo[4,5-5]pyridine (200 mg, 57%). LC-MS: 289.4 $[M+H]^+$.

Step C: A mixture of benzyl (R)-4-methyl-6,7-dihydroisothiazolo[4,5-c]pyridine-5(4H)-carboxylate and benzyl (R)-6-methyl-6,7-dihydroisothiazolo[4,5-c]pyridine-5(4H)-carboxylate (150 mg, 0.520 mmol) was dissolved in TFA (2.60 mL) and treated with thioanisole (617 uL, 5.20 mmol). The reaction mixture was stirred at room temperature for 64 h. Upon completion, the reaction was concentrated and co-evaporated with DCM (2×). The crude mixture was used as-is in the next step without further purification. LC-MS: 155.1 $[M+H]^+$.

Step D: 3-Chloro-2-nitroaniline (1.00 g, 5.79 mmol) was dissolved in MeCN (40.0 mL) under nitrogen, and Select-Fluor (2.14 g, 5.79 mmol) was added. The reaction was heated at 85° C. for 30 min, after which the solvent was removed, and the residue diluted with EtOAc and water. The organic layer was removed, concentrated onto silica, and the solids purified by column chromatography to give 3-chloro-6-fluoro-2-nitroaniline (1.10 g, 100%).

Step E: 3-Chloro-6-fluoro-2-nitroaniline (1.10 g, 5.79 mmol) was dissolved in MeOH (40.0 mL) under nitrogen, and palladium on carbon (10% loading, 308 mg, 0.290 mmol) was added. Hydrogen atmosphere was introduced via purge cycle, and the reaction stirred at room temperature for 16 h. The mixture filtered over celite, and the filtrate concentrated to afford 3-chloro-6-fluorobenzene-1,2-diamine (931 mg). The resulting crude material was used without further purification (considered 100% yield).

Step F: 3-Chloro-6-fluoro-benzene-1,2-diamine (931 mg, 5.86 mmol) was dissolved in acetic acid (25.0 mL), and methyl 2,2,2-trichloroacetamide (1.05 g, 5.86 mmol) was added. The solution was stirred for 2 h, after which the crude reaction was concentrated and then diluted with EtOAc and water. The organic layer was concentrated onto silica and purified by column chromatography to afford 4-chloro-7-fluoro-2-(trichloromethyl)-1H-benzo[d]imidazole (230 mg, 14%). LC-MS: 288.9 $[M+H]^+$.

Step G: 4-Chloro-7-fluoro-2-(trichloromethyl)-1H-benzo[d]imidazole (230 mg, 0.799 mmol) was sonicated in aqueous sodium hydroxide (1 M, 6 mL, 6 mmol) for 10 min, and the pH adjusted to 3 with citric acid solution. The solids were removed by filtration, and the filtrate was extracted with EtOAc. The aqueous layer was purified by reverse phase chromatography on a C-18 column using a solution of MeCN in 10 mM of ammonium formate in water (pH=3.8, 0 to 15% gradient). The relevant fractions were lyophilized to afford 7-chloro-4-fluoro-1H-benzo[d]imidazole-2-carboxylic acid (25.0 mg, 15%). LC-MS: 215.0 $[M+H]^+$.

Step H: To a solution of 7-chloro-4-fluoro-1H-benzo[d]imidazole-2-carboxylic acid (48.0 mg, 0.224 mmol), and HATU (102 mg, 0.268 mmol) in DMF (2.24 mL) was added the mixture of (R)-4-methyl-4,5,6,7-tetrahydroisothiazolo[4,5-c]pyridine 2,2,2-trifluoroacetate and (R)-6-methyl-4,5,6,7-tetrahydroisothiazolo[4,5-c]pyridine 2,2,2-trifluoroacetate (60.0 mg, 0.224 mmol) and N,N-diisopropylethylamine (157 uL, 0.895 mmol). The reaction was stirred at room temperature for 1 h. The reaction was treated with 2 M NaOH to cleave the guanidinyl adduct. The mixture was then purified by prep-HPLC (25-45% MeCN/10 mM ammonium formate buffer). Pure fractions were combined and lyophilized to afford (R)-(7-chloro-4-fluoro-1H-benzo[d]imidazol-2-yl)(6-methyl-6,7-dihydroisothiazolo[4,5-c]pyridin-5(4H)-yl)methanone (8.90 mg, 11%, first eluent) and (R)-(7-chloro-4-fluoro-1H-benzo[d]imidazol-2-yl)(4-methyl-6,7-dihydroisothiazolo[4,5-c]pyridin-5(4H)-yl)methanone (4.94 mg, 6.1%, second eluent). First eluted: LC-MS: 351.2 $[M+H]^+$. $^1H$ NMR (500 MHz, DMSO-$d_6$) δ 8.55-8.39 (m, 1H), 7.29-7.22 (m, 1H), 7.10-7.01 (m, 1H), 5.71-5 5.29 (m, 1H), 5.50-5.44 (m, 1H), 4.66-4.28 (m, 1H), 3.29-3.24 (m, 1H), 3.12-3.04 (m, 1H), 1.24-1.17 (m, 3H). Second eluted: LC-MS: 351.5 $[M+H]^+$. $^1H$ NMR (500 MHz, DMSO-$d_6$) δ 8.57-8.44 (m, 1H), 7.33-7.28 (m, 1H), 7.14-7.05 (m, 1H), 5.95-5.77 (m, 1H), 5.13-4.73 (m, 1H), 3.50-3.43 (m, 1H), 3.20-3.15 (m, 1H), 3.11-3.02 (m, 1H), 1.66-1.52 (m, 3H). The structures of the first and second eluted regioisomers were tentatively assigned.

Examples 39A and 39B: (R)-(7-Chloro-1H-benzo[d]imidazol-2-yl)(6-methyl-3-(methylthio)-6,7-dihydroisothiazolo[4,3-c]pyridin-5(4H)-yl)methanone and (R)-(7-Chloro-1H-benzo[d]imidazol-2-yl)(4-methyl-3-(methylthio)-6,7-dihydroisothiazolo[4,3-c]pyridin-5(4H)-yl)methanone

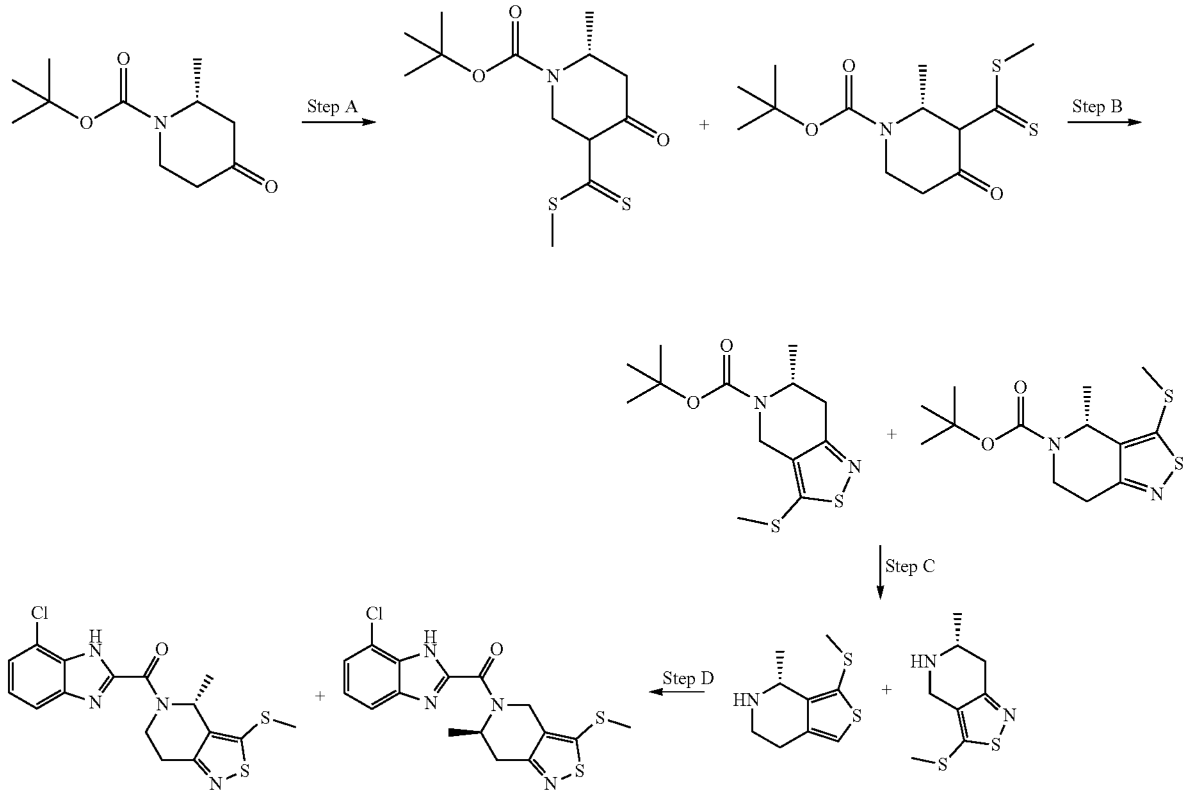

Step A: To a suspension of sodium hydride (6000 in dispersion in mineral oil, 703 mg, 17.6 mmol) in benzene (29.3 mL) and DMSO (1.85 mL) at room temperature under $N_2$ was added (R)-tert-butyl 2-methyl-4-oxopiperidine-1-carboxylate (750 mg, 3.52 mmol) in DMSO (4.00 mL). The mixture was stirred for 10 minutes, then 1-(methyl dithiocarbonyl)imidazole (592 mg, 3.52 mol) was added. The mixture was stirred for 1 h at room temperature and then quenched by the addition of ammonium chloride. The mixture was concentrated under reduced pressure and re-partitioned between EtOAc and water. The organic solution was washed with brine, dried ($Na_2SO_4$), filtered and concentrated under reduced pressure to give a mixture of (2R)-tert-butyl 2-methyl-5-((methylthio)carbonothioyl)-4-oxopiperidine-1-carboxylate and (2R)-tert-butyl 2-methyl-3-((methylthio)carbonothioyl)-4-oxopiperidine-1-carboxylate (1.07 g, 100%). LC-MS: 302.2 $[M+H]^+$.

Step B: To a solution of (2R)-tert-butyl 2-methyl-3-((methylthio)carbonothioyl)-4-oxopiperidine-1-carboxylate and (2R)-tert-butyl 2-methyl-5-((methylthio)carbonothioyl)-4-oxopiperidine-1-carboxylate (713 mg, 2.35 mmol) in acetic acid (9.33 mL) was added ammonium acetate (1.49 g, 18.8 mmol). The reaction mixture was heated at 80° C. for 16 h. The mixture was cooled to room temperature, concentrated under reduced pressure and re-partitioned between EtOAc and water. The organic solution was washed with brine, dried over $Na_2SO_4$, filtered and concentrated under reduced pressure. The residue was purified by flash column chromatography to give a mixture of (R)-tert-butyl 6-methyl-3-(methylthio)-6,7-dihydroisothiazolo[4,3-c]pyridine-5(4H)-carboxylate (174 mg, 25%) and (R)-tert-butyl 4-methyl-3-(methylthio)-6,7-dihydroisothiazolo[4,3-c]pyridine-5(4H)-carboxylate (348 mg, 50%). LC-MS: 301.3 $[M+H]^+$.

Step C: Prepared as in Examples 36A and 36B, Step D using (R)-tert-butyl 6-methyl-3-(methylthio)-6,7-dihydroisothiazolo[4,3-c]pyridine-5(4H)-carboxylate and (R)-tert-butyl 4-methyl-3-(methylthio)-6,7-dihydroisothiazolo[4,3-c]pyridine-5(4H)-carboxylate (150 mg, 0.499 mmol) to afford 1:1 mixture of (R)-6-methyl-3-(methylthio)-4,5,6,7-tetrahydroisothiazolo[4,3-c]pyridine and (R)-4-methyl-3-(methylthio)-4,5,6,7-tetrahydroisothiazolo[4,3-c]pyridine (100 mg, 100%). LC-MS: 201.2 $[M+H]^+$.

Step D: Prepared as in Examples 36A and 36B, Step E using 1:1 (R)-4-methyl-3-(methylthio)-4,5,6,7-tetrahydroisothiazolo[4,3-c]pyridine and (R)-6-methyl-3-(methylthio)-4,5,6,7-tetrahydroisothiazolo[4,3-c]pyridine (25.0 mg, 0.125 mmol) and 7-chloro-1H-benzo[d]imidazole-2-carboxylic acid (49 mg, 0.25 mmol) to afford (R)-(7-chloro-1H-benzo[d]imidazol-2-yl)(4-methyl-3-(methylthio)-6,7-dihydroisothiazolo[4,3-c]pyridin-5(4H)-yl)methanone (4.21 mg, 8.9%) and (R)-(7-chloro-1H-benzo[d]imidazol-2-yl)(6-methyl-3-(methylthio)-6,7-dihydroisothiazolo[4,3-c]pyridin-5(4H)-yl)methanone (3.40 mg, 7.2%). (R)-(7-chloro-1H-benzo[d]imidazol-2-yl)(4-methyl-3-(methylthio)-6,7-dihydroisothiazolo[4,3-c]pyridin-5(4H)-yl)methanone: LC-MS: 379.4 $[M+H]^+$. $^1H$ NMR (400 MHz, DMSO-$d_6$) δ 7.51 (t, J=8.1 Hz, 1H), 7.33 (d, J=7.2 Hz, 1H), 7.27 (t, J=7.8 Hz, 1H), 6.49-6.38 (m, 0.5H), 6.08-5.99 (m, 0.5H), 5.35-5.27 (m, 0.5H), 5.22 (d, J=17.5 Hz, 0.5H), 4.52 (d, J=17.1 Hz, 0.5H), 4.16 (d, J=17.4 Hz, 0.5H), 3.17-3.12 (m, 1H), 3.03-2.96 (m, 1H), 2.89-2.82 (m, 1H), 2.65 (d, J=17.3 Hz, 3H), 1.18 (d, J=6.7 Hz, 3H). (R)-(7-chloro-1H-benzo[d]imidazol-2-yl)(6-methyl-3-(methylthio)-6,7-dihydroisothiazolo[4,3-c]pyridin-5(4H)-yl)methanone: LC-MS: 379.4 $[M+H]^+$. $^1H$ NMR (400 MHz, DMSO-$d_6$) δ 7.54 (d, J=11.7 Hz, 1H), 7.36 (d, J=7.6 Hz, 1H), 7.32-7.26 (m, 1H), 6.80-6.74 (m, 0.5H), 5.70 (q, J=6.7 Hz, 0.5H), 5.61-5.55 (m, 0.5H), 4.78-4.73 (m, 0.5H), 3.70-3.61 (m, 1H), 3.03-2.98 (m, 1H), 2.87-2.77 (m, 1H), 2.71-2.65 (m, 3H), 1.63 (d, J=6.7 Hz, 1H), 1.50 (d, J=6.8 Hz, 2H). Regioisomers were tentatively assigned.

Examples 40A and 40B: (R)-(7-Chloro-1H-benzo[d]imidazol-2-yl)(6-methyl-3-(methylsulfonyl)-6,7-dihydroisothiazolo[4,3-c]pyridin-5(4H)-yl)methanone and (R)-(7-Chloro-1H-benzo[d]imidazol-2-yl)(4-methyl-3-(methylsulfonyl)-6,7-dihydroisothiazolo[4,3-c]pyridin-5(4H)-yl)methanone

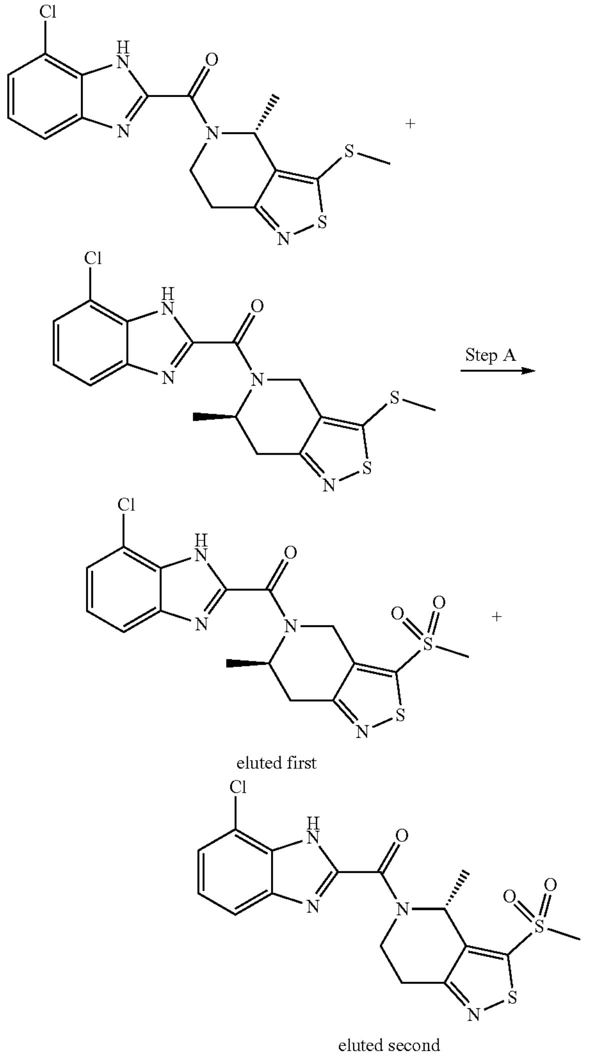

eluted first eluted second

Step A: A suspension of mixture of (R)-(7-chloro-1H-benzo[d]imidazol-2-yl)(6-methyl-3-(methylthio)-6,7-dihydroisothiazolo[4,3-c]pyridin-5(4H)-yl)methanone and (R)-

(7-chloro-1H-benzo[d]imidazol-2-yl)(4-methyl-3-(methylthio)-6,7-dihydroisothiazolo[4,3-c]pyridin-5(4H)-yl)methanone (25.0 mg, 0.0660 mmol) (products of Examples 39A and 39B, Step D) in THF (660 uL) and water (660 uL) was treated with oxone (324 mg, 0.528 mmol) and heated at 50° C. for 1 h. The mixture was cooled to room temperature, filtered through a PTFE filter and the filtrate was concentrated under reduced pressure to remove the THF. The aqueous solution was then re-partitioned into EtOAc. The organic layer was washed with brine, dried ($Na_2SO_4$), filtered and concentrated under reduced pressure. The residue was purified by flash column chromatography and then further purified by chiral-HPLC (Column: Chiral-Pak IC SFC, 5 m, 10×250 mm Cellulose tris(3,5-dichlorophenylcarbamate). Gradient: 30%-70% Eluents: A=iPrOH; B=supercritical CO2 Flow: 10 mL/min. Run Time: 12 min) to give (R)-(7-chloro-1H-benzo[d]imidazol-2-yl)(6-methyl-3-(methylsulfonyl)-6,7-dihydroisothiazolo[4,3-c]pyridin-5(4H)-yl)methanone and (R)-(7-chloro-1H-benzo[d]imidazol-2-yl)(4-methyl-3-(methylsulfonyl)-6,7-dihydroisothiazolo[4,3-c]pyridin-5(4H)-yl)methanone. (R)-(7-chloro-1H-benzo[d]imidazol-2-yl)(6-methyl-3-(methylsulfonyl)-6,7-dihydroisothiazolo[4,3-c]pyridin-5(4H)-yl)methanone: LC-MS: 411.4 $[M+H]^+$. $^1H$ NMR (400 MHz, DMSO-$d_6$) δ 13.55 (br s, 1H), 7.60-7.49 (m, 1H), 7.41-7.34 (m, 1H), 7.31 (t, J=7.8 Hz, 1H), 6.26-6.12 (m, 0.5H), 5.73 (d, J=18.9 Hz, 0.5H), 5.43-5.35 (m, 0.5H), 4.79 (d, J=17.8 Hz, 0.5H), 4.62 (d, J=18.7 Hz, 0.5H), 3.58 (d, J=5.5 Hz, 3H), 3.37-3.32 (m, 1H), 3.16 (dd, J=16.9, 6.0 Hz, 0.5H), 3.03 (t, J=18.0 Hz, 1H), 1.26 (d, J=7.0 Hz, 3H). (R)-(7-chloro-1H-benzo[d]imidazol-2-yl)(4-methyl-3-(methylsulfonyl)-6,7-dihydroisothiazolo[4,3-c]pyridin-5(4H)-yl)methanone: LC-MS: 379.4 $[M+H]^+$. $^1H$ NMR (400 MHz, DMSO-$d_6$) δ 13.54 (br s, 1H), 7.58-7.49 (m, 1H), 7.38-7.32 (m, 1H), 7.30 (t, J=7.9 Hz, 1H), 6.24 (d, J=6.7 Hz, 1H), 5.61 (br s, 1H), 4.79 (dd, J=13.8, 6.7 Hz, 1H), 3.83-3.73 (m, 0.7H), 3.56 (d, J=18.4 Hz, 3H), 3.59-3.52 (m, 0.3H), 3.19-3.13 (m, 1H), 3.03-2.93 (m, 1H), 1.72 (d, J=6.8 Hz, 1.5H), 1.65 (d, J=6.9 Hz, 1.5H). Regioisomers were tentatively assigned.

Examples 41A and 41B: (R)-(7-Chloro-4-fluoro-1H-benzo[d]imidazol-2-yl)(6-methyl-3-(methylthio)-6,7-dihydroisothiazolo[4,3-c]pyridin-5(4H)-yl)methanone and (R)-(7-Chloro-4-fluoro-1H-benzo[d]imidazol-2-yl)(4-methyl-3-(methylthio)-6,7-dihydroisothiazolo[4,3-c]pyridin-5(4H)-yl)methanone

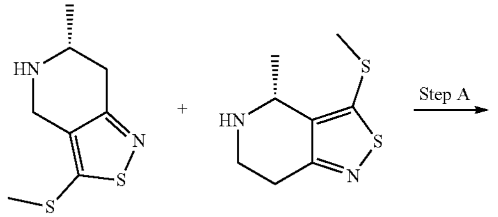

-continued

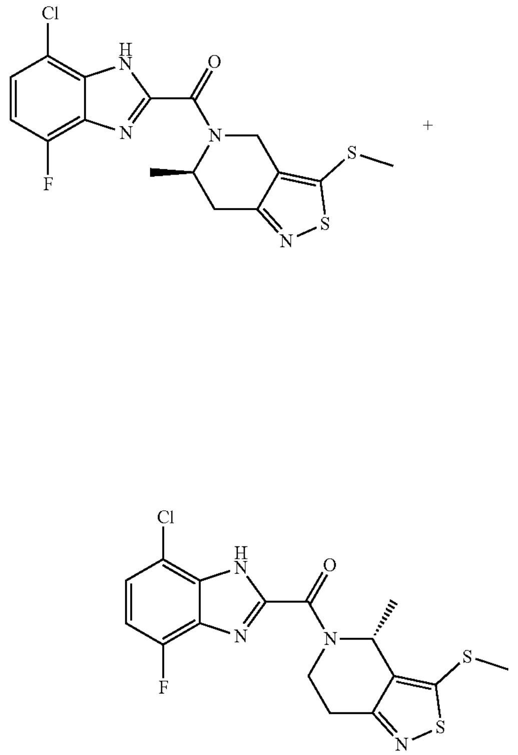

Step A: Prepared as in Examples 36A and 36B, Step E using 1:1 (R)-6-methyl-3-(methylthio)-4,5,6,7-tetrahydroisothiazolo[4,3-c]pyridine and (R)-4-methyl-3-(methylthio)-4,5,6,7-tetrahydroisothiazolo[4,3-c]pyridine (25.0 mg, 0.125 mmol) (product of Examples 39A and 39B, Step C) and 7-chloro-4-fluoro-1H-benzo[d]imidazole-2-carboxylic acid (product of Examples 38A and 38B, Step G) to afford (R)-(7-chloro-4-fluoro-1H-benzo[d]imidazol-2-yl)(6-methyl-3-(methylthio)-6,7-dihydroisothiazolo[4,3-c]pyridin-5(4H)-yl)methanone (3.84 mg, 7.8%) and (R)-(7-chloro-4-fluoro-1H-benzo[d]imidazol-2-yl)(4-methyl-3-(methylthio)-6,7-dihydroisothiazolo[4,3-c]pyridin-5(4H)-yl)methanone (4.12 mg, 8.3%). (R)-(7-chloro-4-fluoro-1H-benzo[d]imidazol-2-yl)(6-methyl-3-(methylthio)-6,7-dihydroisothiazolo[4,3-c]pyridin-5(4H)-yl)methanone: LC-MS: 397.3 $[M+H]^+$. $^1H$ NMR (400 MHz, DMSO-$d_6$) δ 7.20-7.14 (m, 1H), 7.01-6.93 (m, 1H), 5.85-5.78 (m, 0.5H), 5.45-5.36 (m, 1H), 5.36-5.32 (m, 0.5H), 5.25 (d, J=17.2 Hz, 1H), 4.43 (d, J=17.6 Hz, 0.5H), 4.13 (d, J=17.5 Hz, 1H), 3.02-2.99 (m, 0.5H), 2.82 (d, J=16.9 Hz, 1H), 2.70 (s, 2H), 2.60 (s, 1H), 1.22-1.14 (m, 3H). (R)-(7-chloro-4-fluoro-1H-benzo[d]imidazol-2-yl)(4-methyl-3-(methylthio)-6,7-dihydroisothiazolo[4,3-c]pyridin-5(4H)-yl)methanone: LC-MS: 397.3 $[M+H]^+$. $^1H$ NMR (400 MHz, DMSO-$d_6$) δ 7.34-7.25 (m, 1H), 7.10 (t, J=9.4 Hz, 1H), 6.29-6.19 (m, 0.5H), 5.68 (q, J=6.7 Hz, 0.5H), 5.07-5.00 (m, 0.5H), 4.74 (dd, J=13.5, 5.8 Hz, 0.5H), 3.65-3.58 (m, 0.5H), 3.41-3.39 (m, 0.5H), 3.06-2.95 (m, 2H), 2.93-2.77 (m, 1H), 2.71 (s, 2H), 2.62 (s, 1H), 1.61 (d, J=6.7 Hz, 1H), 1.50 (d, J=6.8 Hz, 2H). Regioisomers were tentatively assigned.

Examples 42A, 42B, 42C, and 42D: (R)-(7-Chloro-1H-benzo[d]imidazol-2-yl)(2,6-dimethyl-6,7-dihydro-2H-pyrazolo[4,3-c]pyridin-5(4H)-yl)methanone, (R)-(7-Chloro-1H-benzo[d]imidazol-2-yl)(1,6-dimethyl-6,7-dihydro-1H-pyrazolo[4,3-c]pyridin-5(4H)-yl)methanone, (R)-(7-Chloro-1H-benzo[d]imidazol-2-yl)(1,4-dimethyl-6,7-dihydro-1H-pyrazolo[4,3-c]pyridin-5(4H)-yl)methanone, and (R)-(7-Chloro-1H-benzo[d]imidazol-2-yl)(2,4-dimethyl-6,7-dihydro-2H-pyrazolo[4,3-c]pyridin-5(4H)-yl)methanone

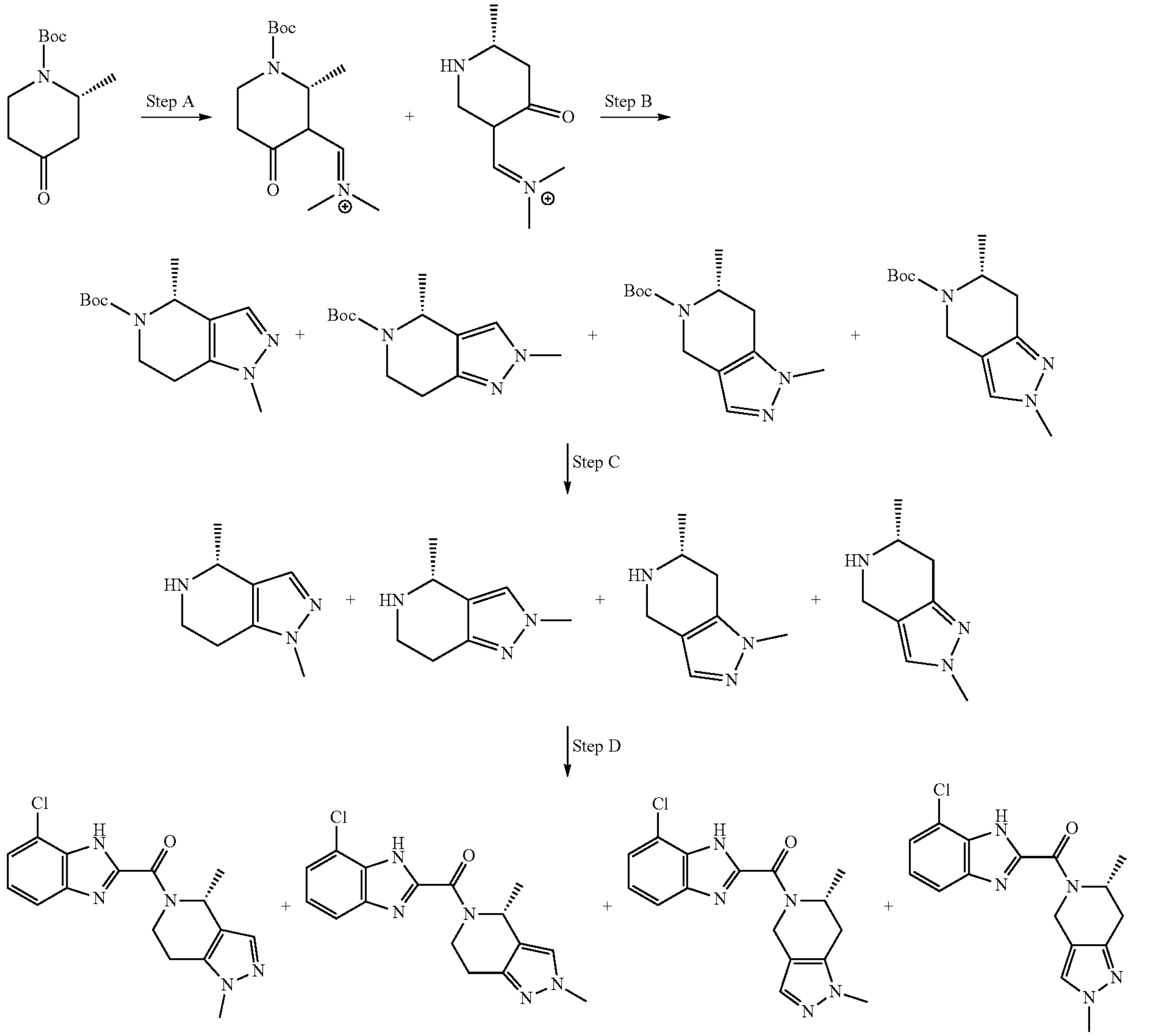

Step A: To a solution of (R)-tert-butyl 2-methyl-4-oxopiperidine-1-carboxylate (2.00 g, 9.10 mmol) in DMF (12.0 mL) was added N,N-dimethylformamide dimethyl acetal (1.40 mL, 10.0 mmol). The reaction mixture was stirred for 1 h at 90° C. The mixture was cooled to room temperature and concentrated under reduced pressure to obtain a mixture of N-(((2R)-1-(tert-butoxycarbonyl)-2-methyl-4-oxopiperidin-3-yl)methylene)-N-methylmethanaminium and N-(((6R)-1-(tert-butoxycarbonyl)-6-methyl-4-oxopiperidin-3-yl)methylene)-N-methylmethanaminium (1.23 g, 50%) and used the residue in the next step without purification.

Step B: To a solution of N-(((2R)-1-(tert-butoxycarbonyl)-2-methyl-4-oxopiperidin-3-yl)methylene)-N-methylmethanaminium and N-(((6R)-1-(tert-butoxycarbonyl)-6-methyl-4-oxopiperidin-3-yl)methylene)-N-methylmethanaminium (1.20 g, 4.46 mmol) in EtOH (12.0 mL) was added methylhydrazine (2.05 g, 44.6 mmol). The reaction mixture was heated at 90° C. for 90 minutes. The mixture was cooled to room temperature, concentrated under reduced pressure, and re-partitioned between EtOAc and water. The organic solution was washed with aq. sat. $NH_4Cl$, brine and dried ($Na_2SO_4$). The solution was filtered and concentrated under reduced pressure. The residue was purified by flash column to give a mixture of (R)-tert-butyl 1,4-dimethyl-6,7-dihydro-1H-pyrazolo[4,3-c]pyridine-5(4H)-carboxylate, (R)-tert-butyl 2,4-dimethyl-6,7-dihydro-2H-pyrazolo[4,3-c]pyridine-5(4H)-carboxylate, (R)-tert-butyl 1,6-dimethyl-6,7-dihydro-1H-pyrazolo[4,3-c]pyridine-5(4H)-carboxylate and (R)-tert-butyl 2,6-dimethyl-6,7-dihydro-2H-pyrazolo[4,3-c]pyridine-5(4H)-carboxylate (744 mg, 66%). LC-MS: 252.3 $[M+H]^+$.

Step C: Prepared as in Examples 36A and 36B, Step D starting from a mixture of (R)-tert-butyl 1,4-dimethyl-6,7-dihydro-1H-pyrazolo[4,3-c]pyridine-5(4H)-carboxylate, (R)-tert-butyl 2,4-dimethyl-6,7-dihydro-2H-pyrazolo[4,3-c]pyridine-5(4H)-carboxylate, (R)-tert-butyl 1,6-dimethyl-6,7-dihydro-1H-pyrazolo[4,3-c]pyridine-5(4H)-carboxylate and (R)-tert-butyl 2,6-dimethyl-6,7-dihydro-2H-pyrazolo[4,3-c]pyridine-5(4H)-carboxylate (243 mg, 0.967 mmol) to afford a mixture of (R)-1,4-dimethyl-4,5,6,7-tetrahydro-1H-pyrazolo[4,3-c]pyridine, (R)-2,4-dimethyl-4,5,6,7-tetrahydro-2H-pyrazolo[4,3-c]pyridine, (R)-1,6-dimethyl-4,5,6,7-tetrahydro-1H-pyrazolo[4,3-c]pyridine, (R)-2,6-dimethyl-4,5,6,7-tetrahydro-2H-pyrazolo[4,3-c]pyridine (146.2 mg, 100%), which was used without purification in the next step. LC-MS: 152.2 $[M+H]^+$.

Step D: To a mixture (R)-1,4-dimethyl-4,5,6,7-tetrahydro-1H-pyrazolo[4,3-c]pyridine, (R)-2,4-dimethyl-4,5,6,7-tetrahydro-2H-pyrazolo[4,3-c]pyridine, (R)-1,6-dimethyl-4,5,6,7-tetrahydro-1H-pyrazolo[4,3-c]pyridine, and (R)-2,6-dimethyl-4,5,6,7-tetrahydro-2H-pyrazolo[4,3-c]pyridine (97.4 mg, 0.644 mmol) in DMF (10.0 mL) and N,N-diisopropylethylamine (850 uL, 4.83 mmol) was added 7-chloro-1H-benzo[d]imidazole-2-carboxylic acid (209 mg, 1.06 mmol) and bis(2-oxo-3-oxazolidinyl)phosphinic chloride (279 mg, 1.06 mmol). The reaction mixture was stirred for 16 h at room temperature. The mixture was diluted with EtOAc and 10% aq. LiCl. The organic solution was washed with 10% aq. LiCl, and brine. The organic solution was then dried ($Na_2SO_4$), filtered and concentrated under reduced pressure. The residue was purified by flash column chromatography and then further separated to its constituent regioisomers (Pre-Column: XBridge BEH Prep C18, 5 μm, 19×10 mm. Column: Atlantis T3 Prep OBD, 5 μm, 19×150 mm. Gradient: 15% B for 2 mins, then 20 mins to 35% B, hold for 0.1 min, then 4 min at 100% B. Eluents: A=10 mM Ammonium Acetate (pH 6.7); B=MeCN. Solvent at 40° C. Flow: 30 mL/min. Run Time: 24 min) to provide (R)-(7-chloro-1H-benzo[d]imidazol-2-yl)(2,6-dimethyl-6,7-dihydro-2H-pyrazolo[4,3-c]pyridin-5(4H)-yl)methanone (9.73 mg, 27%), (R)-(7-chloro-1H-benzo[d]imidazol-2-yl)(1,6-dimethyl-6,7-dihydro-1H-pyrazolo[4,3-c]pyridin-5(4H)-yl)methanone (8.21 mg, 23%), (R)-(7-chloro-1H-benzo[d]imidazol-2-yl)(1,4-dimethyl-6,7-dihydro-1H-pyrazolo[4,3-c]pyridin-5(4H)-yl)methanone (14.9 mg, 41%) and (R)-(7-chloro-1H-benzo[d]imidazol-2-yl)(2,4-dimethyl-6,7-dihydro-2H-pyrazolo[4,3-c]pyridin-5(4H)-yl)methanone (2.68 mg, 7.4%). (R)-(7-chloro-1H-benzo[d]imidazol-2-yl)(2,6-dimethyl-6,7-dihydro-2H-pyrazolo[4,3-c]pyridin-5(4H)-yl)methanone: LC-MS: 330.1 $[M+H]^+$. $^1$H NMR (400 MHz, DMSO-$d_6$) δ 7.54 (d, J=9.7 Hz, 1H), 7.50 (d, J=10.8 Hz, 1H), 7.31-7.17 (m, 2H), 5.87-5.70 (m, 1H), 5.35-5.23 (m, 1H), 4.44 (d, J=15.3 Hz, 0.5H), 4.10 (d, J=16.3 Hz, 0.5H), 3.77 (app d, J=17.3 Hz, 3H), 3.01 (dd, J=15.2, 5.6 Hz, 0.5H), 2.88 (dd, J=15.7, 6.3 Hz, 0.5H), 2.58 (dd, J=15.6, 7.7 Hz, 1H), 1.20 (t, J=7.7 Hz, 3H). (R)-(7-chloro-1H-benzo[d]imidazol-2-yl)(1,6-dimethyl-6,7-dihydro-1H-pyrazolo[4,3-c]pyridin-5(4H)-yl)methanone: LC-MS: 330.1 $[M+H]^+$. $^1$H NMR (400 MHz, DMSO-$d_6$) δ 7.52-7.47 (m, 1H), 7.34 (s, 0.5H), 7.29-7.23 (m, 1.5H), 7.22-7.15 (m, 1H), 5.82-5.72 (m, 1H), 5.38-5.30 (m, 0.5H), 5.27 (d, J=16.3 Hz, 0.5H), 4.39 (d, J=16.7 Hz, 0.5H), 4.04 (d, J=15.6 Hz, 0.5H), 3.69 (app d, J=3.6 Hz, 3H), 3.05 (d, J=5.5 Hz, 0.5H), 2.92 (d, J=10.6 Hz, 0.5H), 2.70 (dd, J=16.4, 5.6 Hz, 1H), 1.22 (t, J=6.8 Hz, 3H). (R)-(7-chloro-1H-benzo[d]imidazol-2-yl)(1,4-dimethyl-6,7-dihydro-1H-pyrazolo[4,3-c]pyridin-5(4H)-yl)methanone: LC-MS: 330.2 $[M+H]^+$. $^1$H NMR (400 MHz, DMSO-$d_6$) δ 7.54 (s, 0.5H), 7.49-7.41 (m, 1.5H), 7.22-7.08 (m, 2H), 5.98-5.90 (m, 0.5H), 5.60 (q, J=7.2 Hz, 0.5H), 5.27-5.18 (m, 0.5H), 4.69 (dd, J=12.1, 4.4 Hz, 0.5H), 3.72 (app d, J=18.1 Hz, 3H), 3.13-3.09 (m, 1H), 2.80-2.71 (m, 1H), 2.66-2.61 (m, 1H), 1.48 (d, J=6.4 Hz, 1H), 1.37 (d, J=6.7 Hz, 2H). (R)-(7-chloro-1H-benzo[d]imidazol-2-yl)(2,4-dimethyl-6,7-dihydro-2H-pyrazolo[4,3-c]pyridin-5(4H)-yl)methanone: LC-MS: 330.2 $[M+H]^+$. $^1$H NMR (400 MHz, DMSO-$d_6$) δ 7.54-7.48 (m, 1H), 7.35 (s, 0.5H), 7.29-7.23 (m, 1.5H), 7.24-7.17 (m, 1H), 6.01-5.95 (m, 0.5H), 5.59 (q, J=6.4 Hz, 0.5H), 5.41-5.33 (m, 0.5H), 4.76 (dd, J=14.0, 5.2 Hz, 0.5H), 3.69 (app d, J=3.3 Hz, 3H), 3.19-3.15 (m, 1H), 2.86-2.81 (m, 1H), 2.74-2.63 (m, 1H), 1.53 (d, J=6.4 Hz, 1H), 1.41 (d, J=6.8 Hz, 2H). Regioisomers were tentatively assigned.

Example 43: (R)-(7-Chloro-4-fluoro-1H-benzo[d]imidazol-2-yl)(2-(difluoromethyl)-4-methyl-6,7-dihydro-2H-pyrazolo[4,3-c]pyridin-5(4H)-yl)methanone

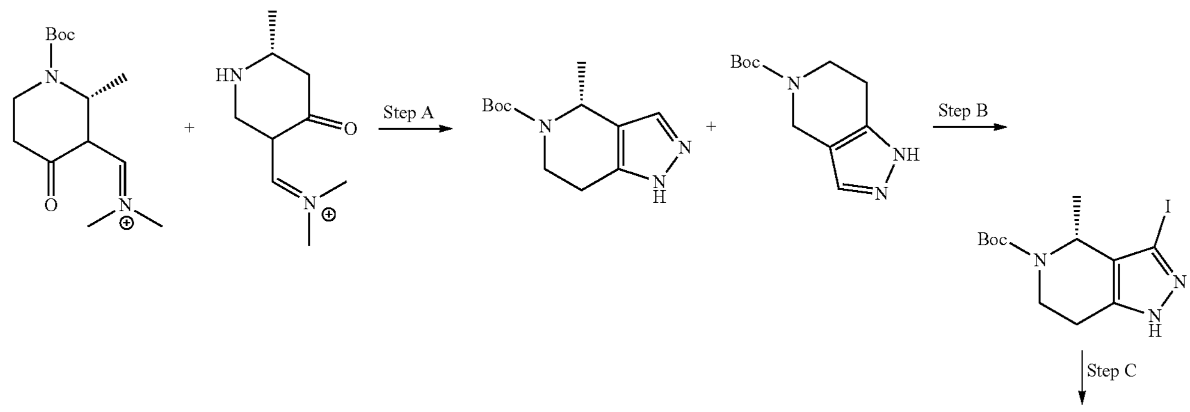

-continued

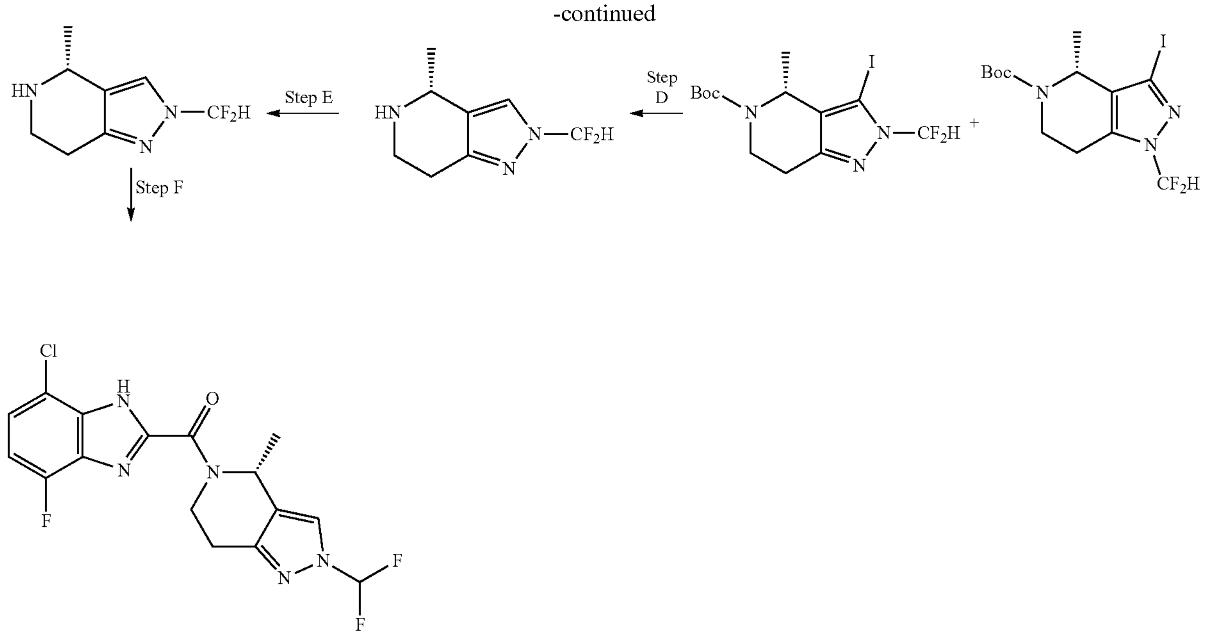

Step A: To a solution of N-(((2R)-1-(tert-butoxycarbonyl)-2-methyl-4-oxopiperidin-3-yl)methylene)-N-methylmethanaminium (1.23 g, 4.55 mmol) and N-(((6R)-1-(tert-butoxycarbonyl)-6-methyl-4-oxopiperidin-3-yl)methylene)-N-methylmethanaminium (product of Examples 42A, 42B, 42C and 42D, Step A) (1.23 g, 4.55 mmol) in EtOH (22.0 mL) was added hydrazine hydrate solution (1.44 mL, 45.5 mmol) and stirred overnight at 60° C. Cooled to room temperature and concentrated under reduced pressure, then re-partitioned between EtOAc and water and adjusted to pH 8 with aq. sat. $NaHCO_3$. Rinsed the organics with brine and dried ($Na_2SO_4$). Filtered and concentrated under reduced pressure to obtain a mixture of (R)-tert-butyl 4-methyl-6,7-dihydro-1H-pyrazolo[4,3-c]pyridine-5(4H)-carboxylate and (R)-tert-butyl 6-methyl-6,7-dihydro-1H-pyrazolo[4,3-c]pyridine-5(4H)-carboxylate (1.23 g). LC-MS: 238.3 $[M+H]^+$.

Step B: To a solution of (R)-tert-butyl 4-methyl-6,7-dihydro-1H-pyrazolo[4,3-c]pyridine-5(4H)-carboxylate and (R)-tert-butyl 6-methyl-6,7-dihydro-1H-pyrazolo[4,3-c]pyridine-5(4H)-carboxylate (220 mg, 0.927 mmol) in DMF (9.00 mL) was added finely-ground potassium hydroxide (490 mg, 7.42 mmol) followed by iodine (943 mg, 3.71 mmol). The reaction mixture was stirred for 1 h at room temperature and then overnight at 40° C. The mixture was diluted with EtOAc and water and adjusted to pH 7 with 1.0 M aq. HCl. The organic layer was successively washed with aq. sat. LiCl, $Na_2S_2O_3$, brine and then dried ($Na_2SO_4$). The organic solution was filtered and concentrated under reduced pressure. The residue was purified by flash column chromatography to give (R)-tert-butyl 3-iodo-4-methyl-6,7-dihydro-1H-pyrazolo[4,3-c]pyridine-5(4H)-carboxylate (202 mg, 60%). LC-MS: 364.1 $[M+H]^+$.

Step C: A solution of (R)-tert-butyl 3-iodo-4-methyl-6,7-dihydro-1H-pyrazolo[4,3-c]pyridine-5(4H)-carboxylate (204 mg, 0.562 mmol) in ACN (10.0 mL) was treated with diethyl (bromodifluoromethyl)phosphonate (104 uL, 0.562 mmol). The reaction was stirred for 16 h at room temperature. Another portion of diethyl (bromodifluoromethyl) phosphonate (104 uL, 0.562 mmol) was added and the reaction mixture was stirred for 24 h at room temperature. Finally, another portion of diethyl (bromodifluoromethyl) phosphonate (104 uL, 0.562 mmol) and the mixture was stirred for 3 h at room temperature. The mixture was concentrated under reduced pressure and re-partitioned between EtOAc and water. The organic solution was washed with brine, dried ($Na_2SO_4$), filtered and concentrated under reduced pressure. The residue was purified by flash column chromatography to give (R)-tert-butyl 2-(difluoromethyl)-3-iodo-4-methyl-6,7-dihydro-2H-pyrazolo[4,3-c]pyridine-5(4H)-carboxylate (47.7 mg, 21%) and (R)-tert-butyl 1-(difluoromethyl)-3-iodo-4-methyl-6,7-dihydro-1H-pyrazolo[4,3-c]pyridine-5(4H)-carboxylate (60.9 mg, 26%). P1: LC-MS: 314.0 $[M+H]^+$. P2: LC-MS: 314.3 $[M+H]^+$.

Step D: Prepared as in Examples 36A and 36B, Step C using (R)-tert-butyl 2-(difluoromethyl)-3-iodo-4-methyl-6,7-dihydro-2H-pyrazolo[4,3-c]pyridine-5(4H)-carboxylate (47.7 mg, 0.115 mmol) to obtain (R)-tert-butyl 2-(difluoromethyl)-4-methyl-6,7-dihydro-2H-pyrazolo[4,3-c]pyridine-5(4H)-carboxylate (7.80 mg, 24%). LC-MS: 188.2 $[M-Boc+H]^+$.

Step E: Prepared as in Examples 36A and 36B, Step D using (R)-tert-butyl 2-(difluoromethyl)-4-methyl-6,7-dihydro-2H-pyrazolo[4,3-c]pyridine-5(4H)-carboxylate (7.80 mg, 27.1 umol) to provide (R)-2-(difluoromethyl)-4-methyl-4,5,6,7-tetrahydro-2H-pyrazolo[4,3-c]pyridine (5.08 mg, 100%). LC-MS: 188.1 $[M+H]^+$.

Step F: Prepared as in Examples 42A and 42B, Step D using (R)-2-(difluoromethyl)-4-methyl-4,5,6,7-tetrahydro-2H-pyrazolo[4,3-c]pyridine (5.08 mg, 0.0271 mmol) and 7-chloro-4-fluoro-1H-benzo[d]imidazole-2-carboxylic acid (product of Examples 38A and 38B, Step G) to obtain (R)-(7-chloro-4-fluoro-1H-benzo[d]imidazol-2-yl)(2-(difluoromethyl)-4-methyl-6,7-dihydro-2H-pyrazolo[4,3-c]pyridin-5(4H)-yl)methanone (0.57 mg, 5.5%). LC-MS: 382.2 $[M+H]^+$. $^1H$ NMR (400 MHz, $CD_3OD$) δ 8.53 (br s, 1H), 7.70-7.41 (m, 2H), 7.37-7.25 (m, 1H), 7.07 (t, J=9.2 Hz, 1H), 5.73-5.65 (m, 0.5H), 5.49-5.40 (m, 0.5H), 4.63 (br s, 0.5H), 4.59 (br s, 1H), 4.22 (d, J=17.7 Hz, 0.5H), 3.41-3.36 (m, 0.5H), 3.23-3.14 (m, 0.5H), 3.03-2.89 (m, 1H), 1.42-1.27 (m, 3H).

Example 44: (R)-(7-Chloro-4-fluoro-1H-benzo[d]imidazol-2-yl)(1-(difluoromethyl)-4-methyl-6,7-dihydro-1H-pyrazolo[4,3-c]pyridin-5(4H)-yl)methanone

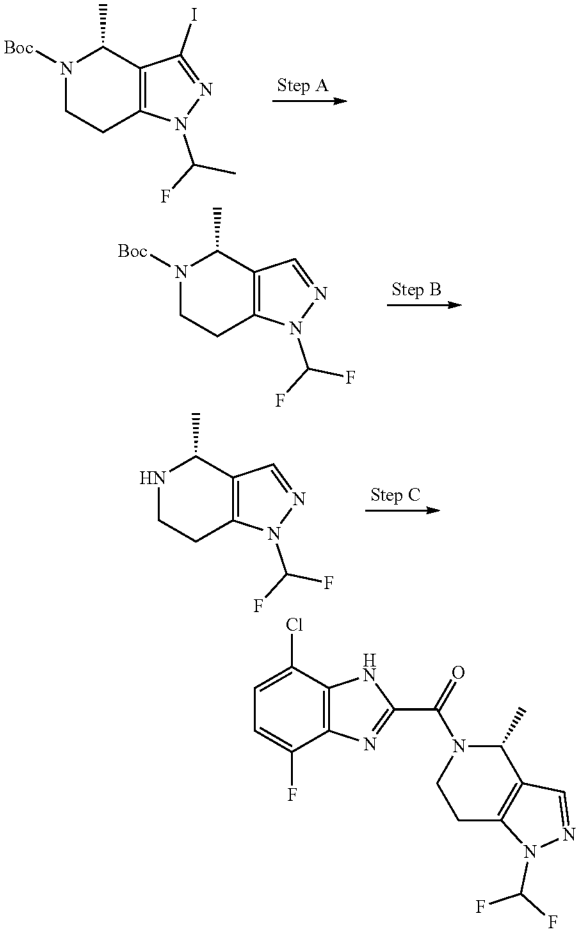

Step A: Prepared as in Examples 36A and 36B, Step C using (R)-tert-butyl 1-(difluoromethyl)-3-iodo-4-methyl-6,7-dihydro-1H-pyrazolo[4,3-c]pyridine-5(4H)-carboxylate (second product of Example 43, Step C) (60.9 mg, 0.147 mmol) to obtain (R)-tert-butyl 1-(difluoromethyl)-4-methyl-6,7-dihydro-1H-pyrazolo[4,3-c]pyridine-5(4H)-carboxylate (16.0 mg, 38%). LC-MS: 188.2 [M-Boc+H]$^+$.

Step B: Prepared as in Examples 36A and 36B, Step D using (R)-tert-butyl 1-(difluoromethyl)-4-methyl-6,7-dihydro-1H-pyrazolo[4,3-c]pyridine-5(4H)-carboxylate (16.0 mg, 55.7 umol) to provide (R)-1-(difluoromethyl)-4-methyl-4,5,6,7-tetrahydro-1H-pyrazolo[4,3-c]pyridine (10.4 mg, 100%). LC-MS: 188.1 [M+H]$^+$.

Step C: Prepared as in Examples 42A and 42B, Step D using (R)-1-(difluoromethyl)-4-methyl-4,5,6,7-tetrahydro-1H-pyrazolo[4,3-c]pyridine (10.4 mg, 0.0556 mmol) and 7-chloro-4-fluoro-1H-benzo[d]imidazole-2-carboxylic acid (product of Examples 38A and 38B, Step G) to obtain to obtain (R)-(7-chloro-4-fluoro-1H-benzo[d]imidazol-2-yl)(1-(difluoromethyl)-4-methyl-6,7-dihydro-1H-pyrazolo[4,3-c]pyridin-5(4H)-yl)methanone (0.390 mg, 1.8%). LC-MS: 382.2 [M+H]$^+$. H NMR (400 MHz, $CD_3OD$) δ 8.52 (br s, 1H), 7.97 (br s, 0.5H), 7.86 (br, s, 0.5H), 7.34 (t, J=60.0 Hz, 1H), 7.34-7.31 (m, 1H), 7.06 (t, J=9.4 Hz, 1H), 5.77 (d, J=17.6 Hz, 0.5H), 5.63-5.57 (m, 0.5H), 5.46 (d, J=16.8 Hz, 0.5H), 4.68 (d, J=16.8 Hz, 0.5H), 4.62-4.53 (m, 0.5H), 4.30 (d, J=16.7 Hz, 0.5H), 3.28-3.21 (m, 0.5H), 3.15-3.05 (m, 0.5H), 2.78 (t, J=14.0 Hz, 1H), 1.33 (d, J=6.8 Hz, 3H).

Examples 46A, 46B, and 46C: (R)-8-Methyl-3-(4-methyl-6,7-dihydrothiazolo[5,4-c]pyridin-5(4H)-yl)quinoxalin-2(1H)-one, (R)-8-Methyl-3-(6-methyl-6,7-dihydrothiazolo[5,4-c]pyridin-5(4H)-yl)quinoxalin-2(1H)-one, and (R)-5-Methyl-3-(4-methyl-6,7-dihydrothiazolo[5,4-c]pyridin-5(4H)-yl)quinoxalin-2(1H)-one

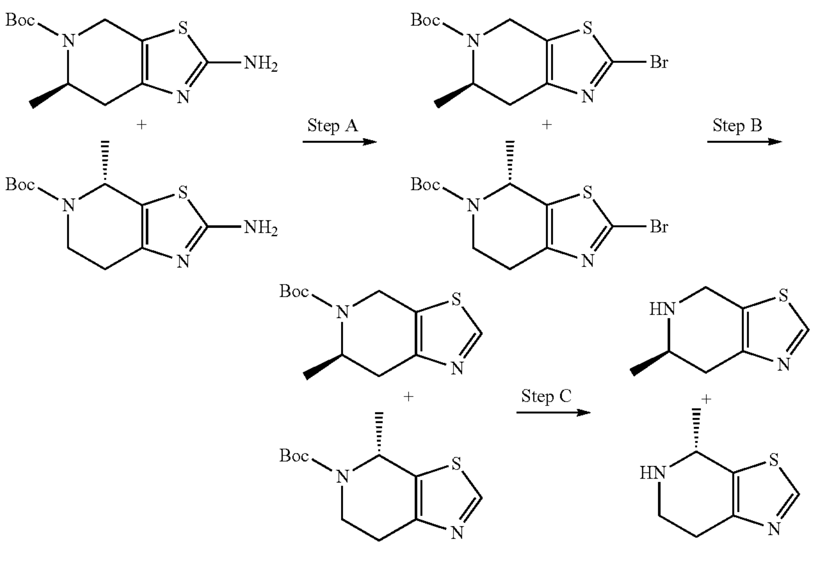

-continued

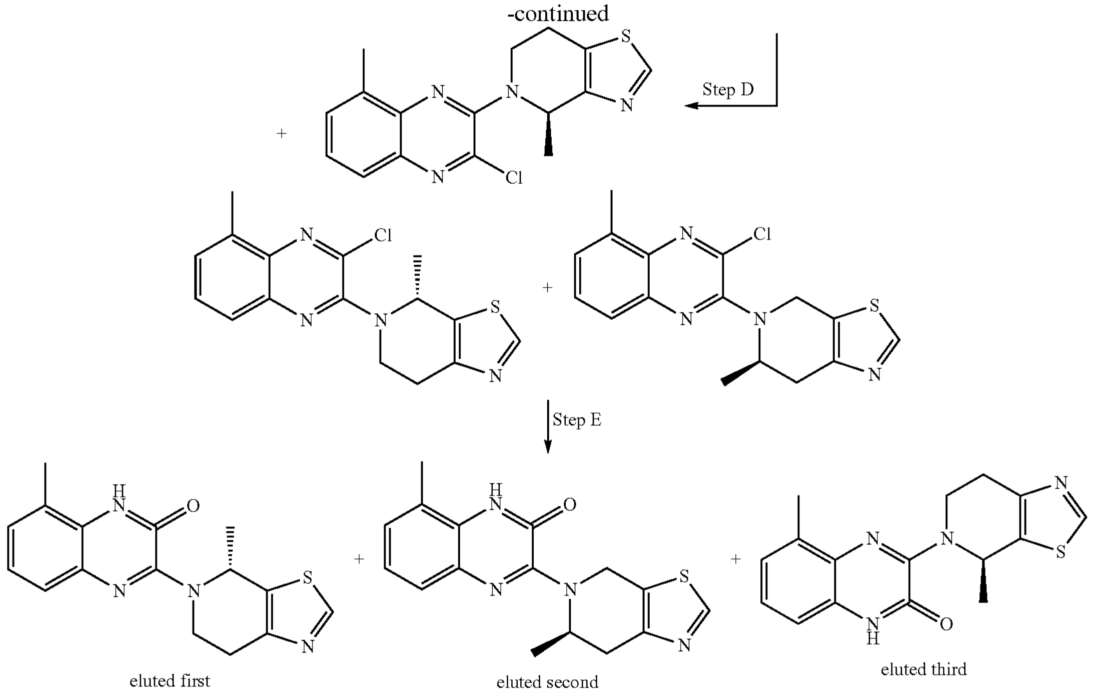

eluted first eluted second eluted third

Step A: Prepared as in Examples 36A and 36B, Step B using (R)-tert-butyl 2-amino-6-methyl-6,7-dihydrothiazolo[5,4-c]pyridine-5(4H)-carboxylate and (R)-tert-butyl 2-amino-4-methyl-6,7-dihydrothiazolo[5,4-c]pyridine-5(4H)-carboxylate (product of Examples 45A and 45B, Step A) (650 mg, 2.42 mmol) to afford a 1:3 mixture of (R)-tert-butyl 2-bromo-6-methyl-6,7-dihydrothiazolo[5,4-c]pyridine-5(4H)-carboxylate and (R)-tert-butyl 2-bromo-4-methyl-6,7-dihydrothiazolo[5,4-c]pyridine-5(4H)-carboxylate (300 mg, 75%). LC-MS: 333.3 $[M+H]^+$.

Step B: Prepared as in Examples 36A and 36B, Step C using (R)-tert-butyl 2-bromo-6-methyl-6,7-dihydrothiazolo[5,4-c]pyridine-5(4H)-carboxylate (25.0 mg, 0.0750 mmol) and (R)-tert-butyl 2-bromo-4-methyl-6,7-dihydrothiazolo[5,4-c]pyridine-5(4H)-carboxylate (75.0 mg, 0.225 mmol) to afford tert-butyl (R)-6-methyl-6,7-dihydrothiazolo[5,4-c]pyridine-5(4H)-carboxylate (19.1 mg, 100%) and tert-butyl (R)-4-methyl-6,7-dihydrothiazolo[5,4-c]pyridine-5(4H)-carboxylate (57.2 mg, 100%).

Step C: Prepared as in Examples 36A and 36B, Step D using tert-butyl (R)-6-methyl-6,7-dihydrothiazolo[5,4-c]pyridine-5(4H)-carboxylate (19.1 mg, 0.075 mmol) and tert-butyl (R)-4-methyl-6,7-dihydrothiazolo[5,4-c]pyridine-5(4H)-carboxylate (57.2 mg, 0.225 mmol) to afford (R)-6-methyl-4,5,6,7-tetrahydrothiazolo[5,4-c]pyridine (20.1 mg, 100%) and (R)-4-methyl-4,5,6,7-tetrahydrothiazolo[5,4-c]pyridine (60.4 mg, 100%).

Step D: To a solution containing a 9:1 ratio of (R)-4-methyl-4,5,6,7-tetrahydrothiazolo[5,4-c]pyridine hydrochloride and (R)-6-methyl-4,5,6,7-tetrahydrothiazolo[5,4-c]pyridine hydrochloride (150 mg, 0.787 mmol) in MeCN (1.56 mL) was added N,N-diisopropylethylamine (415 uL, 2.36 mmol) and 2,3-dichloro-5-methylquinoxaline (168 mg, 0.787 mmol) and stirred for 16 h at 70° C. The reaction mixture was then heated at 100° C. for an additional 72 h. The reaction mixture was cooled and concentrated under reduced pressure. The residue was then re-dissolved in NMP (1.00 mL). Another portion of 9:1 (R)-4-methyl-4,5,6,7-tetrahydrothiazolo[5,4-c]pyridine hydrochloride and (R)-6-methyl-4,5,6,7-tetrahydrothiazolo[5,4-c]pyridine hydrochloride (100 mg, 0.525 mmol) and N,N-diisopropylethylamine (415 uL, 2.36 mmol) were added to the reaction mixture and heated for 2 h at 150° C. via microwave irradiation and then the temperature was raise to 180° C. and heated for an additional 4 h. Diluted with EtOAc and rinsed the organics with 10% aq. LiCl, brine and dried ($Na_2SO_4$). Filtered and concentrated under reduced pressure, then purified by flash column chromatography (0-100% EtOAc/heptanes). Concentrated under reduced pressure to obtain a mixture of (R)-5-(3-chloro-5-methylquinoxalin-2-yl)-6-methyl-4,5,6,7-tetrahydrothiazolo[5,4-c]pyridine, (R)-5-(3-chloro-8-methylquinoxalin-2-yl)-4-methyl-4,5,6,7-tetrahydrothiazolo[5,4-c]pyridine and (R)-5-(3-chloro-5-methylquinoxalin-2-yl)-4-methyl-4,5,6,7-tetrahydrothiazolo[5,4-c]pyridine (90 mg, 34%). LC-MS: [MH]=331.2.

Step E: A solution of (R)-5-(3-chloro-5-methylquinoxalin-2-yl)-4-methyl-4,5,6,7-tetrahydrothiazolo[5,4-c]pyridine, (R)-5-(3-chloro-8-methylquinoxalin-2-yl)-4-methyl-4,5,6,7-tetrahydrothiazolo[5,4-c]pyridine and (R)-5-(3-chloro-5-methylquinoxalin-2-yl)-6-methyl-4,5,6,7-tetrahydrothiazolo[5,4-c]pyridine (90.0 mg, 0.272 mmol), tris(dibenzylideneacetone)-dipalladium(0) (12.5 mg, 0.0136 mmol) and 2.0M aq. potassium hydroxide (680 uL, 1.36 mmol) in dioxane (1.40 mL) was sparged with $N_2$ for 5 minutes. The reaction mixture was heated overnight at 80° C., cooled to room temperature, concentrated under reduced pressure, and re-dissolved in EtOAc. The mixture was filtered through a PTFE frit (0.45 micron) and the filtrate was rinsed with aq. sat. $NaHCO_3$, brine and dried ($Na_2SO_4$). The solution was filtered and concentrated under reduced pressure. The residue was purified by flash column chromatography and then further purified by prep-HPLC-MS (Column: CSH Prep C18 OBD, 5 μm, 30x75 mm. Gradient: isocratic at 30% B for 1 min, 20% to 40% B in 8 min, 50% to 100% B in 0.1 min, hold 100% B for 2.9 min. Eluents:

A=Milli Q H2O+10 mM AmF pH=3.8; B=MeCN. Solvent at 40° C. Flow: 45 mL/min. Run Time: 12 min) to give (R)-8-methyl-3-(4-methyl-6,7-dihydrothiazolo[5,4-c]pyridin-5(4H)-yl)quinoxalin-2(1H)-one (14.7 mg, 35%, third eluent), (R)-8-methyl-3-(6-methyl-6,7-dihydrothiazolo[5,4-c]pyridin-5(4H)-yl)quinoxalin-2(1H)-one (1.05 mg, 2.5%, first eluent), and (R)-5-methyl-3-(4-methyl-6,7-dihydrothiazolo[5,4-c]pyridin-5(4H)-yl)quinoxalin-2(1H)-one (1.15 mg, 2.7%, second eluent). Third eluted: LC-MS: 314.3 $[M+H]^+$. $^1H$ NMR (500 MHz, DMSO-$d_6$) δ 12.08 (br s, 1H), 8.97 (s, 1H), 7.08 (t, J=7.5 Hz, 1H), 7.05-7.01 (m, 2H), 6.20-6.13 (m, 1H), 5.10-4.97 (m, 1H), 3.43-3.37 (m, 2H), 3.16-3.08 (m, J=32.8 Hz, 1H), 2.89-2.84 (m, J=18.9 Hz, 1H), 2.48 (s, 3H), 1.62 (d, J=6.7 Hz, 3H). First eluted: LC-MS: 314.4 $[M+H]^+$. $^1H$ NMR (500 MHz, DMSO-$d_6$) δ 8.99 (s, 1H), 7.32-7.27 (m, 1H), 7.09-7.04 (m, 2H), 5.67 (s, 1H), 5.53 (d, J=17.2 Hz, 1H), 4.49 (d, J=17.6 Hz, 1H), 3.24-3.21 (m, 1H), 2.78 (d, J=16.1 Hz, 1H), 2.39 (s, 3H), 1.16 (d, J=6.9 Hz, 3H). Second eluted: LC-MS: 314.4 $[M+H]^+$. $^1H$ NMR (500 MHz, DMSO-$d_6$) δ 12.08 (br s, 0.8H), 8.99 (s, 1H), 8.50 (s, 0.2H), 7.11 (t, J=7.6 Hz, 1H), 7.07-7.00 (m, 2H), 5.72-5.56 (m, 2H), 4.48 (d, J=17.6 Hz, 1H), 3.28-3.23 (m, 1H), 2.79 (d, J=16.2 Hz, 1H), 2.49 (s, 3H), 1.19 (d, J=6.9 Hz, 3H). Regioisomers were tentatively assigned.

Examples 47A and 47B: (S)-3-(5-(Difluoromethyl)-7,8-dihydro-1,6-naphthyridin-6(5H)-yl)-5-methylquinoxalin-2(1H)-one and (S)-3-(5-(Difluoromethyl)-7,8-dihydro-1,6-naphthyridin-6(5H)-yl)-8-methylquinoxalin-2(1H)-one

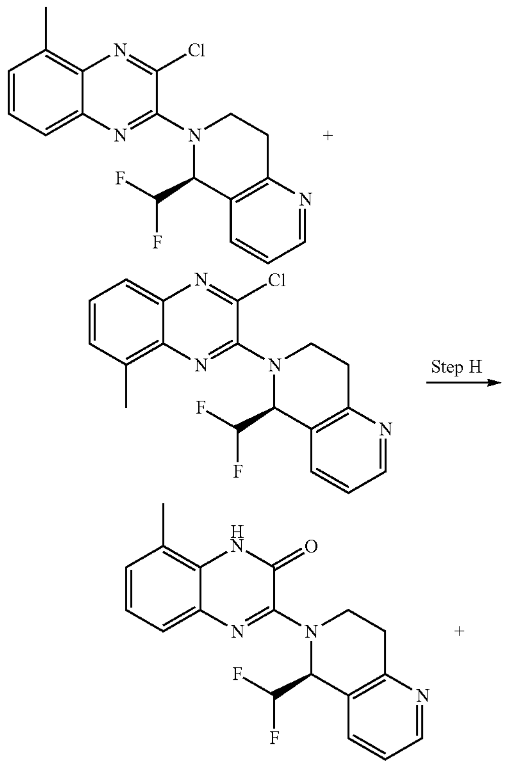

eluted second

-continued

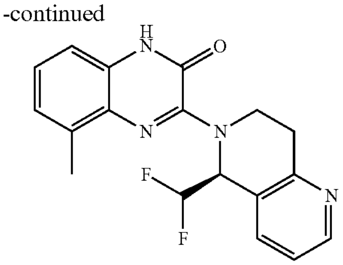

eluted first

Step A: To a −78° C. solution of 2-chloropyridine (833 uL, 8.72 mmol) in anhydrous THF (87.2 mL) under argon was added dropwise lithium diisopropylamide (5.23 mL, 10.5 mmol). After stirring for 1 h, ethyl difluoroacetate (1.43 mL, 13.1 mmol) was added and the reaction stirred for 2 h. The reaction was quenched at −78° C. by addition of aqueous saturated ammonium chloride and brought to room temperature. The mixture was diluted with ethyl acetate, the organic washed with water, brine, dried ($Na_2SO_4$) and concentrated to give 1-(2-chloropyridin-3-yl)-4,4,4-trifluorobutane-1,3-dione (1.67 g, 100%) which was used in the next step without further purification. LC-MS: 190.3 [M−H].

Step B: 1-(2-Chloropyridin-3-yl)-4,4,4-trifluorobutane-1,3-dione (1.50 g, 7.83 mmol), (S)-(−)-t-butylsulfinamide (1.07 g, 8.61 mmol) and titanium isopropoxide (3.58 mL, 11.7 mmol) were dissolved in THF (40.0 mL) and heated at 70° C. for 16 h. The crude reaction was cooled, diluted with citric acid solution (10%, aq.) and EtOAc and the layers were separated. The aq. solution was washed again with EtOAc, the combined organics washed with brine, dried over $Na_2SO_4$ and the solvent evaporated to afford (S,Z)—N-(1-(2-chloropyridin-3-yl)-2,2-difluoroethylidene)-2-methylpropane-2-sulfinamide (2.31 g, 100%) which was used in the next step without further purification LC-MS: 295.0 $[M+H]^+$.

Step C: A flame-dried vessel was charged with (S,Z)—N-(1-(2-chloropyridin-3-yl)-2,2-difluoroethylidene)-2-methylpropane-2-sulfinamide (2.31 g, 7.83 mmol) and THF (40.0 mL) at −78° C. under nitrogen, L-Selectride (658 uL, 0.658 mmol) was added dropwise over ten minutes, and the reaction stirred for an additional 5 min. The reaction was quenched with $NH_4OAc$ (aq.), diluted with EtOAc, and the organic layer removed. The aqueous solution was washed again with EtOAc, the combined organics dried over $Na_2SO_4$, and concentrated onto silica. The crude material was purified by flash chromatography on silica gel to give (S)—N—((S)-1-(2-chloropyridin-3-yl)-2,2-difluoroethyl)-2-methylpropane-2-sulfinamide (505 mg, 22%) and (S)—N—((R)-1-(2-chloropyridin-3-yl)-2,2-difluoroethyl)-2-methylpropane-2-sulfinamide (307 mg, 13%). Major diastereomer: LC-MS: 297.1 $[M+H]^+$. Minor diastereomer: LC-MS: 297.1 $[M+H]^+$.

Step D: (S)—N—((S)-1-(2-Chloropyridin-3-yl)-2,2-difluoroethyl)-2-methylpropane-2-sulfinamide (405 mg, 1.36 mmol), trans-2-ethoxyvinylboronic acid pinacol ester (1.52 g, 6.82 mmol), 1,1'-bis(diphenylphosphino)ferrocene dichloropalladium (II) (100 mg, 0.136 mmol) and cesium carbonate (1.36 g, 4.09 mmol) were dissolved in nitrogen-sparged water (4.00 mL) and dioxane (20.0 mL), and stirred at 100° C. for 36 h. The crude reaction was diluted with water and EtOAc, the organic layer removed, and the aqueous washed again with EtOAc. The combined organics were dried over $Na_2SO_4$ and concentrated onto silica. The crude material was purified by flash chromatography on silica gel to give (S)—N—((S)-1-(2-((E)-2-ethoxyvinyl)pyridin-3-yl)-2,2-difluoroethyl)-2-methylpropane-2-sulfinamide (172 mg, 38%). LC-MS: 333.2 $[M+H]^+$.

Step E: (S)—N—((S)-1-(2-((E)-2-Ethoxyvinyl)pyridin-3-yl)-2,2-difluoroethyl)-2-methylpropane-2-sulfinamide (86.0 mg, 0.259 mmol) was dissolved in DCM (5.00 mL) under nitrogen at room temperature, and hydrochloric acid (4M in dioxane, 647 μL, 2.59 mmol) was added. The reaction was stirred for 30 min, after which an additional 10 eq. of HCl were added to solution, and the mixture was stirred for an additional 30 min. The reaction was neutralized with 1 mL of $NaHCO_3$ solution (aq. sat) and concentrated to dryness to afford (S)-5-(difluoromethyl)-5,8-dihydro-1,6-naphthyridine (47.1 mg, 100%). LC-MS: 183.1 $[M+H]^+$.

Step F: (S)-5-(Difluoromethyl)-5,8-dihydro-1,6-naphthyridine (47.1 mg, 0.259 mmol) was dissolved under nitrogen in MeOH (10.0 mL), and sodium cyanoborohydride (33.2 mg, 0.517 mmol) was added. The reaction was stirred for 16 hours at room temperature, after which the reaction was concentrated, dissolved in water and loaded directly onto a C18 column for purification using 1:1 MeOH:ACN in 10 mM ammonium bicarbonate (0 to 100% over 12 CV). Lyophilization of the relevant fractions afforded (S)-5-(difluoromethyl)-5,6,7,8-tetrahydro-1,6-naphthyridine (18.0 mg, 38%) as a colourless solid. LC-MS: 185.1 $[M+H]^+$.

Step G: To a solution of (S)-5-(difluoromethyl)-5,6,7,8-tetrahydro-1,6-naphthyridine hydrochloride (100 mg, 0.453 mmol) in NMP (450 uL) was added N,N-diisopropylethylamine (399 uL, 2.27 mmol) and 2,3-dichloro-5-methylquinoxaline (112 mg, 0.524 mmol). The reaction mixture was heated for 4 h at 150° C. via microwave irradiation, and then 2 h at 180° C. The mixture was cooled to room temperature and diluted with EtOAc. The organic layer was washed with 10% aq. LiCl and brine. The organic solution was dried ($Na_2SO_4$), filtered and concentrated under reduced pressure. The residue was purified by flash column chromatography to give a 1:2 mixture of (S)-2-chloro-3-(5-(difluoromethyl)-7,8-dihydro-1,6-naphthyridin-6(5H)-yl)-5-methylquinoxaline and (S)-3-chloro-2-(5-(difluoromethyl)-7,8-dihydro-1,6-naphthyridin-6(5H)-yl)-5-methylquinoxaline (54.0 mg, 33%). LC-MS: 361.3 $[M+H]^+$.

Step H: Prepared as in Examples 46A, 46B, and 46C, Step E from (S)-3-chloro-2-(5-(difluoromethyl)-7,8-dihydro-1,6-naphthyridin-6(5H)-yl)-5-methylquinoxaline and (S)-2-chloro-3-(5-(difluoromethyl)-7,8-dihydro-1,6-naphthyridin-6(5H)-yl)-5-methylquinoxaline (54.0 mg, 0.148 mmol) to afford (S)-3-(5-(difluoromethyl)-7,8-dihydro-1,6-naphthyridin-6(5H)-yl)-5-methylquinoxalin-2(1H)-one (2.52 mg, 15%, first eluted) and (S)-3-(5-(difluoromethyl)-7,8-dihydro-1,6-naphthyridin-6(5H)-yl)-8-methylquinoxalin-2(1H)-one (8.74 mg, 26%, second eluted). Eluted second: LC-MS: 343.2 $[M+H]^+$. $^1H$ NMR (500 MHz, DMSO-$d_6$) δ 8.50 (dd, J=4.7, 1.5 Hz, 1H), 8.45 (br s, 1H), 7.81 (d, J=7.7 Hz, 1H), 7.33-7.29 (m, 2H), 7.11-7.07 (m, 2H), 6.63 (d, J=34.9 Hz, 1H), 6.69-6.46 (m, 1H), 5.00-4.94 (m, 1H), 3.66-3.60 (m, 1H), 3.16-3.09 (m, 1H), 2.99 (ddd, J=17.3, 4.1, 2.5 Hz, 1H), 2.40 (s, 3H). Eluted first: LC-MS: 343.2 $[M+H]^+$. $^1H$ NMR (500 MHz, DMSO-$d_6$) δ 12.12 (br s, 1H), 8.50 (dd, J=4.7, 1.6 Hz, 1H), 7.79 (d, J=7.9 Hz, 1H), 7.31 (dd, J=7.8, 4.8 Hz, 1H), 7.13 (t, J=7.6 Hz, 1H), 7.09-7.04 (m, 2H), 6.72-6.48 (m, 1H), 6.64-6.55 (m, 1H), 5.03-4.95 (m, 1H), 3.68-3.62 (m, 1H), 3.19-3.13 (m, 1H), 3.00 (ddd, J=17.1, 4.1, 2.7 Hz, 1H), 2.49 (s, 3H). Regioisomers were tentatively assigned.

Examples 48A and 48B: (R) or (S)-(7-Chloro-4-fluoro-1H-benzo[d]imidazol-2-yl)(1,4-dimethyl-1,4-dihydropyrido[2,3-d]pyrimidin-3(2H)-yl)methanone and (R) or (S)-(7-Chloro-4-fluoro-1H-benzo[d]imidazol-2-yl)(1,4-dimethyl-1,4-dihydropyrido[2,3-d]pyrimidin-3(2H)-yl)methanone

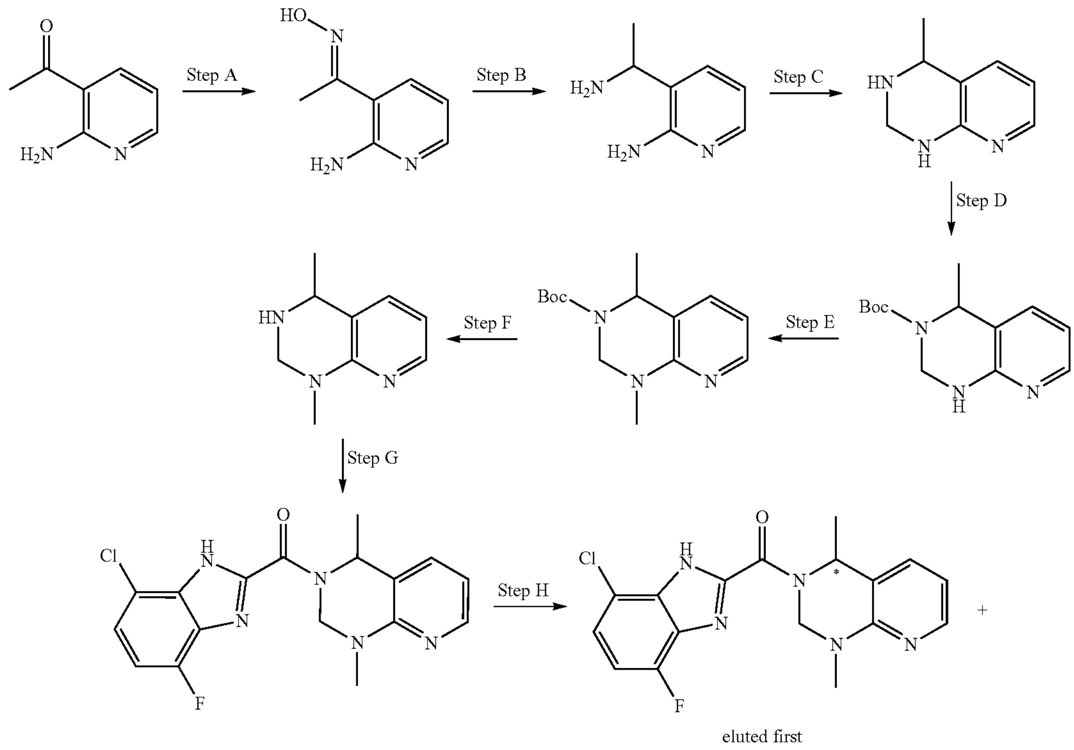

-continued

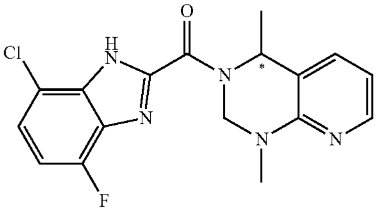

eluted second

Step A: To a solution of 1-(2-amino-3-pyridyl)ethanone (5.00 g, 7.34 mmol) in pyridine (40.0 mL) was added hydroxylamine hydrochloride (3.83 g, 11.0 mmol). The reaction was stirred at 80° C. for 4 h. The reaction was concentrated in vacuum to give a residue which was washed with Petroleum ether/EtOAc (v/v)=3/1 (150 ml) and the filter cake was dried under vacuum to give (E)-1-(2-amino-pyridin-3-yl)ethan-1-one oxime (7.90 g). LC-MS: 152.2 $[M+H]^+$.

Step B: To a mixture of (E)-1-(2-aminopyridin-3-yl) ethan-1-one oxime (1.00 g, 6.62 mmol) in concentrated HCl (15.0 mL) was added Zn (1.73 g, 26.5 mmol). The mixture was stirred at 90° C. for 12 h. The reaction mixture was allowed to cool to room temperature and adjusted pH to 9-10 with 2 M NaOH aqueous and extracted with DCM/MeOH (v/v)=10:1 (20.0 mL×2). The combined organic layers were dried over $Na_2SO_4$ and concentrated under vacuum to give 3-(1-aminoethyl)pyridin-2-amine (733 mg, 81%). LC-MS: 138.2 $[M+H]^+$.

Step C: To a solution of 3-(1-aminoethyl)pyridin-2-amine (670 mg, 4.88 mmol) in EtOH (20.0 mL) was added NaOH (430 mg, 10.7 mmol) and 37 w/w % formaldehyde aqueous solution (1.46 g, 18.0 mmol). The mixture was stirred at 25° C. for 12 h. The resulting precipitate was filtered and the filtrate was poured into $H_2O$ (10.0 mL) and adjusted pH 2~3 with 1M HCl aqueous. The product was extracted with EtOAc (10.0 mL×3). The combined organic layers were dried over $Na_2SO_4$, filtered, and concentrated under vacuum to give 4-methyl-1,2,3,4-tetrahydropyrido[2,3-d]pyrimidine (1.30 g, crude). LC-MS: 150.2 $[M+H]^+$.

Step D: To a solution of 4-methyl-1,2,3,4-tetrahydro-pyrido[2,3-d]pyrimidine (581 mg, 3.13 mmol) in DCM (10.0 mL) was added di-tert-butyl dicarbonate (751 mg, 3.44 mmol) and TEA (633 mg, 6.26 mmol). The mixture was stirred at 25° C. for 2 h. The mixture was concentrated under vacuum to give a residue which was purified by flash silica gel chromatography to give tert-butyl 4-methyl-1,4-dihydro-pyrido[2,3-d]pyrimidine-3(2H)-carboxylate (240 mg, 31%). LC-MS: 250.2 $[M+H]^+$.

Step E: To a solution of tert-butyl 4-methyl-1,4-dihydro-pyrido[2,3-d]pyrimidine-3(2H)-carboxylate (200 mg, 0.802 mmol) in MeOH (10.0 mL) was added 37 w/w % formal-dehyde aqueous solution (3.26 g, 40.1 mmol) and acetic acid (2.41 g, 40.1 mmol). Then sodium cyanoborohydride (504 mg, 8.02 mmol) was added. The reaction mixture was stirred at 25° C. for 1 h. The reaction mixture was concentrated under vacuum to give a residue which was poured into $H_2O$ (5.00 mL) and extracted with EtOAc (5.00 mL×4). The combined organic layers were dried over $Na_2SO_4$, filtered and concentrated under vacuum to give a residue which was purified by preparative TLC to give tert-butyl 1,4-dimethyl-1,4-dihydropyrido[2,3-d]pyrimidine-3(2H)-carboxylate (200 mg, 95%). LC-MS: 264.2 $[M+H]^+$.

Step F: A solution of tert-butyl 1,4-dimethyl-1,4-dihydro-pyrido[2,3-d]pyrimidine-3(2H)-carboxylate (170 mg, 0.646 mmol) in HCl/EtOAc (2.00 M, 5.67 mL) was stirred at 20° C. for 2 h. The mixture was concentrated under vacuum to give 1,4-dimethyl-1,2,3,4-tetrahydropyrido[2,3-d]pyrimi-dine hydrochloride (120 mg). LC-MS: 164.3 $[M+H]^+$.

Step G: A mixture of 1,4-dimethyl-1,2,3,4-tetrahydro-pyrido[2,3-d]pyrimidine (120 mg, 0.601 mmol), 7-chloro-4-fluoro-1H-benzimidazole-2-carboxylic acid (129 mg, 0.601 mmol), HATU (229 mg, 0.601 mmol) and DIEA (233 mg, 1.80 mmol) in DMF (3.00 mL) was stirred at 25° C. for 2 h. The reaction mixture was poured into $H_2O$ (6.00 mL) and extracted with DCM (6.00 mL×4). The combined organic layers were dried over $Na_2SO_4$, filtered, and con-centrated under vacuum to give a residue which was purified by preparative HPLC (Phenomenex Luna C18 column (100×40 mm, 5 μm); flow rate: 60 mL/min; gradient: 35%-65% B over 8 min; mobile phase A: 0.04% aqueous HCl, mobile phase B: acetonitrile) to give (7-chloro-4-fluoro-1H-benzo[d]imidazol-2-yl)(1,4-dimethyl-1,4-dihydropyrido[2,3-d]pyrimidin-3(2H)-yl)methanone (45.0 mg, 21%). LC-MS: 360.1 $[M+H]^+$.

Step H: (7-Chloro-4-fluoro-1H-benzo[d]imidazol-2-yl) (1,4-dimethyl-1,4-dihydropyrido[2,3-d]pyrimidin-3(2H)-yl) methanone (45.0 mg) was further separated by chiral SFC DAICEL CHIRALPAK IG (250×30 mm, 10 μm); flow rate: 80 mL/min; gradient: 50% B over 66 min; mobile phase A: heptane, mobile phase B: $CO_2$-EtOH (0.1% $NH_3H_2O$) to afford a first eluted compound (14.3 mg) and a second eluted compound (12.0 mg). First eluted compound (Example 48A): LC-MS: 360.1 $[M+H]^+$. $^1H$ NMR (400 MHz, DMSO-$d_6$) δ 14.54-13.82 (m, 1H), 8.23-7.88 (m, 1H), 7.56 (d, J=7.0 Hz, 1H), 7.40 (br d, J=5.5 Hz, 1H), 7.27-7.08 (m, 1H), 6.79-6.60 (m, 1H), 6.56-5.71 (m, 1H), 5.68-5.49 (m, 1H), 4.78-4.40 (m, 1H), 3.18-2.91 (m, 3H), 1.80-1.42 (m, 3H). Second eluted compound (Example 48B): LC-MS: 360.1 $[M+H]^+$. $^1H$ NMR (400 MHz, DMSO-$d_6$) δ 14.41-13.79 (m, 1H), 8.20-7.85 (m, 1H), 7.62-7.34 (m, 2H), 7.28-7.13 (m, 1H), 6.78-6.57 (m, 1H), 6.54-5.77 (m, 1H), 5.72-5.48 (m, 1H), 4.84-4.36 (m, 1H), 3.20-2.94 (m, 3H), 1.74-1.50 (m, 3H). The absolute stereochemistry for the first and second eluted compounds was not determined.

Examples 49A and 49B: (R) or (S)-(7-Chloro-4-fluoro-1H-benzo[d]imidazol-2-yl)(4-methyl-1,4-dihydropyrido[2,3-d]pyrimidin-3(2H)-yl)methanone and (R) or (S)-(7-chloro-4-fluoro-1H-benzo[d]imidazol-2-yl)(4-methyl-1,4-dihydropyrido[2,3-d]pyrimidin-3(2H)-yl)methanone

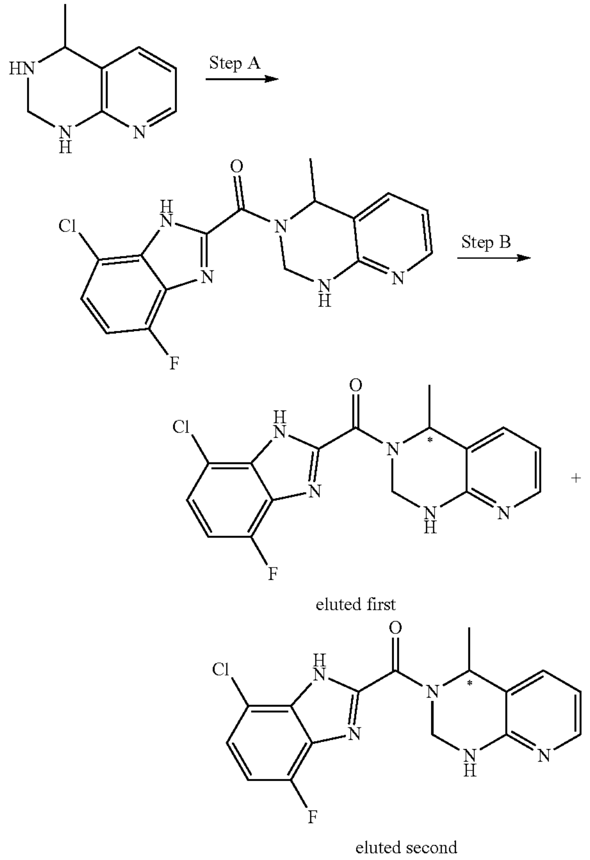

Step A: A mixture of 7-chloro-4-fluoro-1H-benzimidazole-2-carboxylic acid (150 mg, 0.699 mmol), 4-methyl-1,2,3,4-tetrahydropyrido[2,3-d]pyrimidine (137 mg, 0.699 mmol), HATU (266 mg, 0.699 mmol) and DIEA (271 mg, 2.10 mmol) in DMF (3.00 mL) was stirred at 22° C. for 2 h. The reaction mixture was poured into $H_2O$ (6.00 mL) and extracted with DCM (6.00 mL×4). The combined organic layers were dried over $Na_2SO_4$, filtered, and concentrated under vacuum to give a residue which was purified by preparative HPLC (Phenomenex Luna C18 column (100×40 mm, 5 μm); flow rate: 60 mL/min; gradient: 25%-55% B over 8 min; mobile phase A: 0.04% aqueous HCl, mobile phase B: acetonitrile) to afford (7-chloro-4-fluoro-1H-benzo[d]imidazol-2-yl)(4-methyl-1,4-dihydropyrido[2,3-d]pyrimidin-3(2H)-yl)methanone (39.5 mg, 16%). LC-MS: 346.1 $[M+H]^+$.

Step B: (7-Chloro-4-fluoro-1H-benzo[d]imidazol-2-yl)(4-methyl-1,4-dihydropyrido[2,3-d]pyrimidin-3(2H)-yl)methanone (37.0 mg) was further separated by chiral SFC DAICEL CHIRALPAK IG (250×30 mm, 10 μm); flow rate: 80 mL/min; gradient: 40% B over 66 min; mobile phase A: heptane, mobile phase B: $CO_2$-EtOH (0.1% $NH_3H_2O$) to afford a first eluted compound (13.2 mg) and a second eluted compound (10.3 mg). First eluted compound (Example 49A): LC-MS: 346.1 $[M+H]^+$. $^1$H NMR (400 MHz, DMSO-$d_6$) δ 14.58-13.72 (m, 1H), 8.07-7.79 (m, 1H), 7.60 (br d, J=7.3 Hz, 1H), 7.51-7.30 (m, 2H), 7.28-7.09 (m, 2H), 6.83-5.78 (m, 2H), 5.74-4.32 (m, 2H), 1.72-1.53 (m, 3H). Second eluted compound (Example 49B): LC-MS: 346.1 $[M+H]^+$. $^1$H NMR (400 MHz, DMSO-$d_6$) δ 14.44-13.90 (m, 1H), 7.94 (br d, J=4.9 Hz, 1H), 7.61 (br d, J=7.3 Hz, 1H), 7.51-7.31 (m, 2H), 7.29-7.07 (m, 2H), 6.80-5.76 (m, 2H), 5.71-4.39 (m, 2H), 1.70-1.53 (m, 3H). The absolute stereochemistry for the first and second eluted compounds was not determined.

Examples 50: 2-(7-Chloro-4-fluoro-1H-benzo[d]imidazole-2-carbonyl)-1-methyl-1,2,3,4-tetrahydro-6H-pyrido[1,2-a]pyrazin-6-one

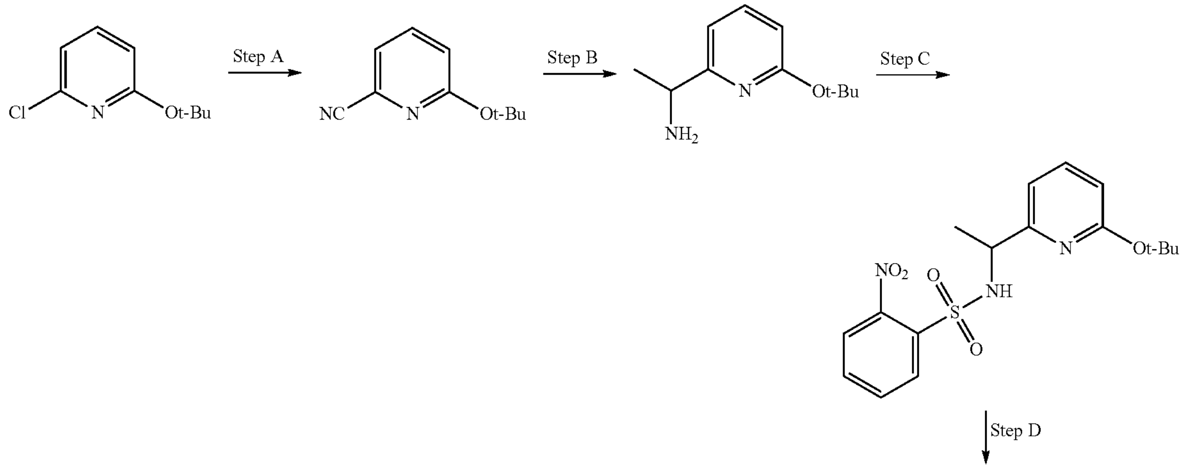

-continued

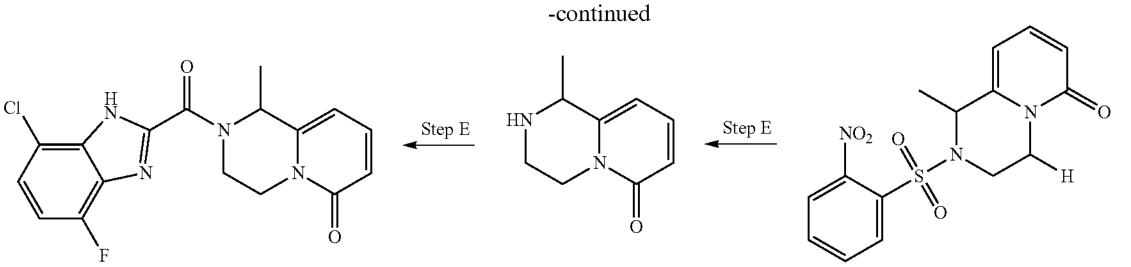

Step A: To a solution of 2-(tert-butoxy)-6-chloropyridine (5.00 g, 26.9 mmol) in dry DMF (50.0 mL) was added zinc cyanide (4.74 g, 40.4 mmol) and Tetrakis(triphenylphosphine)palladium(0) (3.11 g, 2.69 mmol) at 20° C. The reaction mixture was degassed and purged with N2 for three times. The resulting mixture was stirred at 100° C. for 2 h. The reaction mixture was quenched by saturated $NaHCO_3$ solution (50.0 mL) and extracted with EtOAc (30.0 mL×3). The combined organic layers were dried over $Na_2SO_4$, filtered and concentrated under vacuum to give a residue which was purified by flash silica gel chromatography to give 6-(tert-butoxy)picolinonitrile (2.50 g, 51%). LC-MS: 121.0 $[M-56+H]^+$.

Step B: To a solution of 6-(tert-butoxy)picolinonitrile (1.40 g, 7.94 mmol) in THF (14.0 mL) was added 3.0 M methylmagnesium bromide solution in diethyl ether (5.30 mL) at 0° C. under nitrogen. The reaction mixture was stirred at 0° C. for 0.5 h under nitrogen. Then MeOH (14.0 mL) and sodium borohydride (601 mg, 15.8 mmol) were added at 20° C. under nitrogen. The resulting mixture was stirred at 20° C. for 10 h under nitrogen. The reaction mixture was adjusted to pH 9 with 2M NaOH aqueous. The aqueous phase was extracted with EtOAc (30.0 mL×3). The combined organic layers were dried over $Na_2SO_4$, filtered and concentrated under vacuum to give a residue, which was purified by flash silica gel chromatography to give 1-(6-(tert-butoxy)pyridin-2-yl)ethan-1-amine (544 mg, 35%). LC-MS: 195.1 $[M+H]^+$.

Step C: To a solution of 1-(6-(tert-butoxy)pyridin-2-yl)ethan-1-amine (544 mg, 2.80 mmol) in DCM (5.00 mL) was added 2-nitrobenzenesulfonyl chloride (744 mg, 3.36 mmol) and DIEA (542 mg, 4.20 mmol). The reaction mixture was stirred at 20° C. for 1 h. The reaction mixture was quenched by saturated $NaHCO_3$ solution (20.0 mL) and the aqueous phase was extracted with DCM (20.0 mL×3). The combined organic layers were dried over anhydrous $Na_2SO_4$, filtered and concentrated in vacuum to give a residue, which was purified by flash silica gel chromatography to give N-(1-(6-(tert-butoxy)pyridin-2-yl)ethyl)-2-nitrobenzenesulfonamide (480 mg, 45%). LC-MS: 324.0 $[M-56+H]^+$.

Step D: To a solution of N-(1-(6-(tert-butoxy)pyridin-2-yl)ethyl)-2-nitrobenzenesulfonamide (480 mg, 1.27 mmol) in DMF (10.0 mL) was added cesium carbonate (8.24 g, 25.3 mmol) and 1,2-dibromoethane (2.38 g, 12.6 mmol) at 20° C. The reaction mixture was stirred at 60° C. for 2 h under nitrogen. The reaction mixture was concentrated in vacuum to give a residue, which was diluted with $H_2O$ (30.0 mL) and extracted with EtOAc (30.0 mL×3). The combined organic layers were dried over $Na_2SO_4$, filtered and the filtrate was concentrated to give a residue, which was purified by flash silica gel chromatography to give 1-methyl-2-((2-nitrophenyl)sulfonyl)-1,2,3,4-tetrahydro-6H-pyrido[1,2-a]pyrazin-6-one (280 mg, 63%). LC-MS: 350.1 $[M+H]^+$.

Step E: To a solution of 1-methyl-2-((2-nitrophenyl)sulfonyl)-1,2,3,4-tetrahydro-6H-pyrido[1,2-a]pyrazin-6-one (180 mg, 0.515 mmol) in $CH_3CN$ (5.00 mL) was added thiophenol (85.15 mg, 0.772 mmol) and potassium carbonate (213 mg, 1.55 mmol) at 20° C. The reaction mixture was stirred at 50° C. for 3 h. The reaction mixture was filtered and the filtrate was concentrated to give a residue, which was adjusted to pH 11 with saturated $Na_2CO_3$ aqueous. The aqueous phase was extracted with EtOAc (15.0 mL×3). The combined organic layers were dried over anhydrous $Na_2SO_4$, filtered and concentrated in vacuum to give 1-methyl-1,2,3,4-tetrahydro-6H-pyrido[1,2-a]pyrazin-6-one (200 mg). LC-MS: 165.1 $[M+H]^+$.

Step F: To a solution of 1-methyl-1,2,3,4-tetrahydro-6H-pyrido[1,2-a]pyrazin-6-one (80.0 mg, 0.480 mmol) in EtOAc (8.00 mL) was added DIEA (188 mg, 1.46 mmol), 7-chloro-4-fluoro-1H-benzo[d]imidazole-2-carboxylic acid (104 mg, 0.487 mmol) and propylphosphonic anhydride ethyl acetate solution (702 mg, 0.974 mmol, 50% purity). The reaction mixture was stirred at 20° C. for 1 h. The reaction mixture was concentrated to give a residue, which was purified by preparative HPLC (Phenomenex Gemini C18 column (150×40×70 um); flow rate: 60 mL/min; gradient: 15%-50% B over 8 min; mobile phase A: $H_2O$ (10 mM $NH_4HCO_3$), mobile phase B: acetonitrile to give 2-(7-chloro-4-fluoro-1H-benzo[d]imidazole-2-carbonyl)-1-methyl-1,2,3,4-tetrahydro-6H-pyrido[1,2-a]pyrazin-6-one (27.0 mg, 13%). LC-MS: 361.1 $[M+H]^+$. $^1H$ NMR (400 MHz, DMSO-$d_6$) δ 14.41-13.88 (m, 1H), 7.56-7.30 (m, 2H), 7.19 (br s, 1H), 6.51-6.16 (m, 2H), 5.57 (q, J=6.7 Hz, 1H), 4.56-4.22 (m, 2H), 4.20-3.79 (m, 2H), 1.59 (d, J=6.8 Hz, 3H).

Examples 50A and 50B: (R)-2-(7-Chloro-4-fluoro-1H-benzo[d]imidazole-2-carbonyl)-1-methyl-1,2,3,4-tetrahydro-6H-pyrido[1,2-a]pyrazin-6-one and (S)-2-(7-Chloro-4-fluoro-1H-benzo[d]imidazole-2-carbonyl)-1-methyl-1,2,3,4-tetrahydro-6H-pyrido[1,2-a]pyrazin-6-one

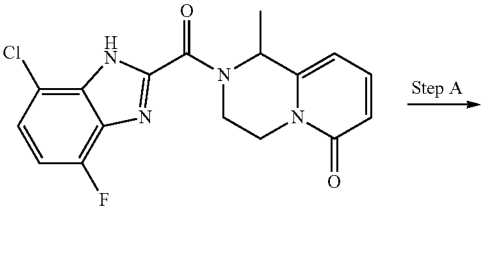

-continued

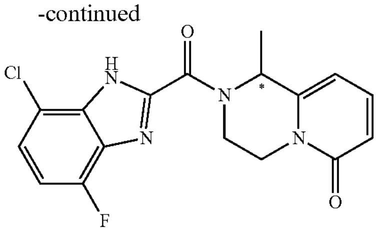

eluted first

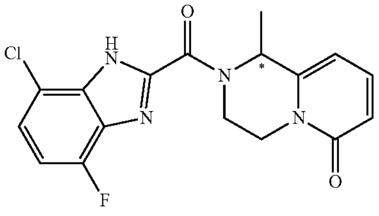

eluted second

Step A: 2-(7-Chloro-4-fluoro-1H-benzo[d]imidazole-2-carbonyl)-1-methyl-1,2,3,4-tetrahydro-6H-pyrido[1,2-a]pyrazin-6-one (product of Example 50) (40.0 mg, 0.111 mmol) was purified by chiral SFC (column: DAICEL CHIRALPAK IG, 250×30 mm, 10 um; mobile phase: [$CO_2$-EtOH]; B %: 50%, isocratic elution mode) to afford a first eluted compound (11.75 mg) and a second eluted compound (11.32 mg). First eluted compound (Example 50A): LC-MS: 361.1 $[M+H]^+$. $^1H$ NMR (400 MHz, DMSO-$d_6$) δ 14.48-13.83 (m, 1H), 7.56-7.03 (m, 3H), 6.55-5.45 (m, 3H), 4.81-4.25 (m, 2H), 4.16-3.68 (m, 2H), 1.85-1.46 (m, 3H). Second eluted compound (Example 50B): LC-MS: 361.1 $[M+H]^+$. $^1H$ NMR (400 MHz, DMSO-$d_6$) δ 14.48-13.84 (m, 1H), 7.58-7.07 (m, 3H), 5.57 (br d, J=6.9 Hz, 3H), 4.67-3.75 (m, 4H), 1.83-1.39 (m, 3H). The absolute stereochemistry for the first and second eluted compounds was not determined.

Examples 51A and 51B: (R) or (S)-(7-Chloro-4-fluoro-1H-benzo[d]imidazol-2-yl)(4-hydroxy-5-methyl-7,8-dihydro-1,6-naphthyridin-6(5H)-yl)methanone and (R) or (S)-(7-Chloro-4-fluoro-1H-benzo[d]imidazol-2-yl)(4-hydroxy-5-methyl-7,8-dihydro-1,6-naphthyridin-6(5H)-yl)methanone

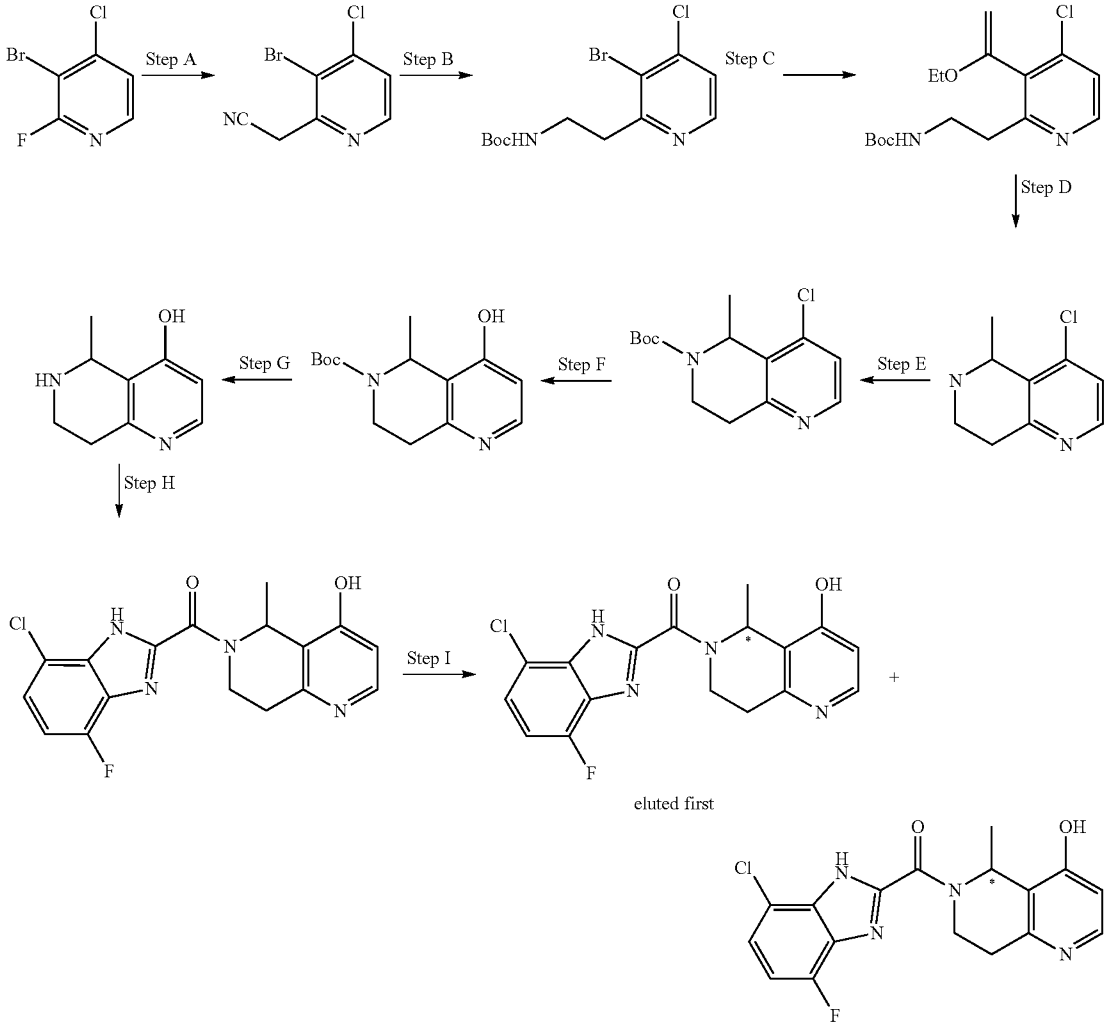

eluted second

Step A: To a solution of LiHMDS (1 M in THF, 19.0 mL) in THF (40.0 mL) was added dropwise acetonitrile (780 mg, 19.0 mmol) at −78° C. under $N_2$. After addition, the mixture was stirred at this temperature for 1 h, and then 3-bromo-4-chloro-2-fluoropyridine (2.00 g, 9.50 mmol) in THF (4.00 mL) was added dropwise at −78° C. for 1 h. The resulting mixture was stirred at 20° C. for 1 h under $N_2$. The reaction mixture was added into saturated $NH_4Cl$ aqueous (50.0 mL) and extracted with EtOAc (50.0 mL×3). The combined organic layers were dried over $Na_2SO_4$, and concentrated under reduced pressure to give a residue which was purified by flash silica gel chromatography to give 2-(3-bromo-4-chloropyridin-2-yl)acetonitrile (1.6 g, 73%). LC-MS: 231.0 $[M+H]^+$.

Step B: To a solution of Raney-Ni (0.426 mg, 4.97 mmol) in MeOH (20.0 mL) was added 2-(3-bromo-4-chloropyridin-2-yl)acetonitrile (0.500 g, 2.16 mmol) and di-tert-butyl dicarbonate (0.519 mg, 2.38 mmol) at 20° C. Then the reaction mixture was stirred at 20° C. for 1 h under $H_2$ (15 Psi). The reaction mixture was filtered, and concentrated under vacuum to give a residue which was purified by flash silica gel chromatography to give tert-butyl (2-(3-bromo-4-chloropyridin-2-yl)ethyl)carbamate (150 mg, 21%). LC-MS: 335.0 $[M+H]^+$.

Step C: To a mixture of tert-butyl (2-(3-bromo-4-chloropyridin-2-yl)ethyl)carbamate (150 mg, 0.447 mmol), tributyl(1-ethoxyvinyl)stannane (323 mg, 0.894 mmol) in dioxane (8.00 mL) was added bis(triphenylphosphine)palladium(II) dichloride (31.4 mg, 0.045 mmol). The mixture was degassed and purged with $N_2$ for three times. The resulting mixture was stirred at 90° C. for 2 h under a $N_2$ atmosphere. The mixture was filtered, and concentrated under vacuum to give a residue which was purified by preparative TLC to give tert-butyl (2-(4-chloro-3-(1-ethoxyvinyl)pyridin-2-yl)ethyl)carbamate (120 mg, 82%). LC-MS: $[MH]^+$=327.2 $[M+H]^+$.

Step D: To a mixture of tert-butyl (2-(4-chloro-3-(1-ethoxyvinyl)pyridin-2-yl)ethyl)carbamate (120 mg, 0.367 mmol) in EtOAc (2.00 mL) was added HCl/EtOAc (4 M, 5.00 mL). The mixture was stirred at 20° C. for 1 h under a $N_2$ atmosphere. The mixture was concentrated under vacuum at 30° C. to give 4-chloro-5-methyl-7,8-dihydro-1,6-naphthyridine (120 mg, crude). LC-MS: 181.1 $[M+H]^+$.

Step E: To a solution of 4-chloro-5-methyl-7,8-dihydro-1,6-naphthyridine (120 mg, 0.553 mmol) in MeOH (5.00 mL) was added di-tert-butyl dicarbonate (181 mg, 0.829 mmol) and sodium borohydride (46.0 mg, 1.22 mmol) at 0° C. The mixture was stirred at 20° C. for 2 h under a $N_2$ atmosphere. The reaction mixture was quenched by saturated $NH_4Cl$ solution (5.00 mL) and extracted with EtOAc (5.00 mL×3). The combined organic layers were washed with brine (5.00 mL×1), dried over anhydrous $Na_2SO_4$, filtered and concentrated in vacuum to give a residue which was purified by preparative TLC to give tert-butyl 4-chloro-5-methyl-7,8-dihydro-1,6-naphthyridine-6(5H)-carboxylate (50 mg, 32%). LC-MS: 283.2 $[M+H]^+$.

Step F: To a solution of tert-butyl 4-chloro-5-methyl-7,8-dihydro-1,6-naphthyridine-6(5H)-carboxylate (100 mg, 0.354 mmol) in dioxane (5.00 mL) and $H_2O$ (1.00 mL) was added potassium hydroxide (61.3 mg, 1.09 mmol), $Pd(dba)_2$ (3.25 mg, 0.006 mmol) and t-BuXPhos (3.75 mg, 0.009 mmol). The mixture was stirred at 100° C. for 2 h under a $N_2$ atmosphere. The reaction mixture was poured into $H_2O$ (2.00 mL) and extracted with EtOAc (3.00 mL×3). The combined organic layers were dried over $Na_2SO_4$, filtered and concentrated under reduced pressure to give a residue which was purified by preparative TLC to give tert-butyl 4-hydroxy-5-methyl-7,8-dihydro-1,6-naphthyridine-6(5H)-carboxylate (40.0 mg, 43%). LC-MS: $[MH]^+$=265.2.

Step G: To a solution of tert-butyl 4-hydroxy-5-methyl-7,8-dihydro-1,6-naphthyridine-6(5H)-carboxylate (35.0 mg, 0.177 mmol) in EtOAc (0.500 mL) was added HCl/EtOAc (4 M, 3.10 mL). The resulting mixture was stirred at 20° C. for 1 h. The mixture was concentrated under reduced pressure to give 5-methyl-5,6,7,8-tetrahydro-1,6-naphthyridin-4-ol (30 mg). LC-MS: 165.2 $[M+H]^+$.

Step H: To a solution of 5-methyl-5,6,7,8-tetrahydro-1,6-naphthyridin-4-ol (25.0 mg, 0.125 mmol) in DMF (1.00 mL) was added 7-chloro-4-fluoro-1H-benzo[d]imidazole-2-carboxylic acid (26.7 mg, 0.125 mmol), DIEA (40.3 mg, 0.311 mmol) and HATU (23.7 mg, 0.062 mmol). The mixture was stirred at 20° C. for 1 h. The reaction mixture was poured into $H_2O$ (2.00 mL) and extracted with EtOAc (3.00 mL×3). The combined organic layers were dried over $Na_2SO_4$, filtered and concentrated under reduced pressure to give a residue which was purified by preparative HPLC (Phenomenex luna C18 column 150×40 mm×10 um); flow rate: 25 mL/min; gradient: 10%-45% B over 8 min; mobile phase A: 10 mM aqueous $NH_4HCO_3$, mobile phase B: acetonitrile) to give (7-chloro-4-fluoro-1H-benzo[d]imidazol-2-yl)(4-hydroxy-5-methyl-7,8-dihydro-1,6-naphthyridin-6(5H)-yl) methanone (15 mg, 33%). LC-MS: 361.0 $[M+H]^+$.

Step I: (7-Chloro-4-fluoro-1H-benzo[d]imidazol-2-yl)(4-hydroxy-5-methyl-7,8-dihydro-1,6-naphthyridin-6(5H)-yl) methanone (15.0 mg, 0.042 mmol) was further separated by chiral SFCDAICEL CHIRALPAK IH (250×30 mm, 10 μm); flow rate: 30 mL/min; gradient: 30% B over 14 min; mobile phase A: heptane, mobile phase B: $CO_2$—IPA (0.1% $NH_3H_2O$) to afford a first eluted compound (4.4 mg) and a second eluted compound (4.4 mg). First eluted compound (Example 51A): LC-MS: 361.0 $[M+H]^+$. $^1H$ NMR (400 MHz, DMSO-$d_6$) δ 14.33-13.50 (m, 1H), 11.45 (br d, J=1.1 Hz, 1H), 7.59 (br s, 1H), 7.41-7.09 (m, 2H), 6.14-5.77 (m, 1H), 5.67-4.44 (m, 2H), 3.70-3.49 (m, 1H), 3.05-2.60 (m, 2H), 1.59-1.30 (m, 3H). Second eluted compound (Example 51B): LC-MS: 361.0 $[M+H]^+$. $^1H$ NMR (400 MHz, DMSO-$d_6$) δ 14.30-13.50 (m, 1H), 11.44 (br s, 1H), 7.69-6.95 (m, 3H), 6.12-5.89 (m, 1H), 5.62-4.53 (m, 2H), 3.61 (br s, 1H), 2.98-2.64 (m, 2H), 1.41 (d, J=6.5 Hz, 3H). The absolute stereochemistry for the first and second eluted compounds was not determined.

Example 52: (7-Chloro-4-fluoro-1H-benzo[d]imidazol-2-yl)(4-methyl-1-(methylsulfonyl)-1,4-dihydropyrido[2,3-d]pyrimidin-3(2H)-yl)methanone

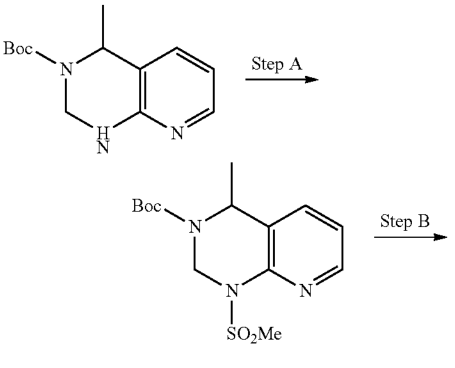

-continued

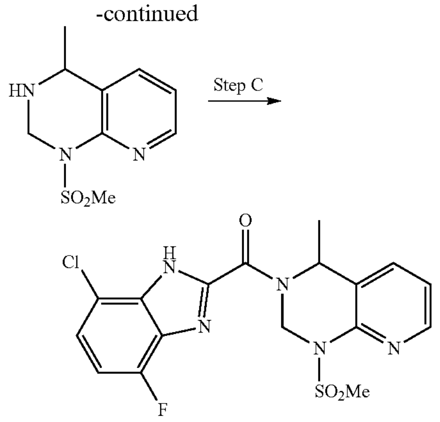

Step A: To a solution of tert-butyl 4-methyl-1,4-dihydropyrido[2,3-d]pyrimidine-3(2H)-carboxylate (product of Examples 48A and 48B Step D) (100 mg, 0.401 mmol) and TEA (89.3 mg, 0.882 mmol) in DCM (3.00 mL) at 0° C. was added methanesulfonyl chloride (59.7 mg, 0.521 mmol) dropwise. The resulting mixture was stirred at 25° C. for 1 h. The reaction mixture was poured into $H_2O$ (1.00 mL) and extracted with EtOAc (2.00 mL×4). The combined organic layers were dried over $Na_2SO_4$, filtered, and concentrated under vacuum to give a residue which was purified by prep-TLC to give tert-butyl 4-methyl-1-(methylsulfonyl)-1,4-dihydropyrido[2,3-d]pyrimidine-3(2H)-carboxylate (64 mg, 49%). LC-MS: 328.1 $[M+H]^+$.

Step B: A solution of tert-butyl 4-methyl-1-(methylsulfonyl)-1,4-dihydropyrido[2,3-d]pyrimidine-3(2H)-carboxylate (64.0 mg, 0.195 mmol) in HCl/EtOAc (2.00 M, 15.0 mL) was stirred at 25° C. for 6 h. The mixture was concentrated under vacuum to give 4-methyl-1-(methylsulfonyl)-1,2,3,4-tetrahydropyrido[2,3-d]pyrimidine (60.0 mg). LC-MS: 228.1 $[M+H]^+$.

Step C: A mixture of 4-methyl-1-methylsulfonyl-3,4-dihydro-2H-pyrido[2,3-d]pyrimidine (40.0 mg, 0.176 mmol), 7-chloro-4-fluoro-1H-benzimidazole-2-carboxylic acid (37.8 mg, 0.176 mmol), BOP—Cl (40.3 mg, 0.158 mmol) and TEA (17.8 mg, 0.176 mmol) in DCM (2.00 mL) was stirred at 25° C. for 12 h. The reaction mixture was poured into $H_2O$ (6.00 mL) and extracted with DCM (6.00 mL×4). The combined organic layers were dried over $Na_2SO_4$, filtered, and concentrated under vacuum to give a residue which was purified by preparative HPLC (Phenomenex Luna C18 column (100×40 mm, 5 μm); flow rate: 60 mL/min; gradient: 25%-55% B over 8 min; mobile phase A: 0.04% aqueous HCl, mobile phase B: acetonitrile) to give (7-chloro-4-fluoro-1H-benzo[d]imidazol-2-yl)(4-methyl-1-(methylsulfonyl)-1,4-dihydropyrido[2,3-d]pyrimidin-3(2H)-yl)methanone (2.98 mg, 58% yield). LC-MS: 424.0 $[M+H]^+$. $^1H$ NMR (400 MHz, DMSO-$d_6$) δ 14.67-13.86 (m, 1H), 8.44-8.25 (m, 1H), 8.07-7.77 (m, 1H), 7.45-7.36 (m, 1H), 7.30 (dd, J=4.8, 7.7 Hz, 1H), 7.25-7.09 (m, 2H), 6.64-5.70 (m, 1H), 5.18-4.61 (m, 1H), 3.61-3.46 (m, 3H), 1.88-1.48 (m, 3H).

Example 53: adRP HTS

The following assay protocol was followed: HEK293T cells were used for heterologous expression of the RHO P23H variant, a pathogenic mutation leading to protein misfolding and instability and causal for autosomal dominant retinitis pigmentosa. Rhodopsin plasma membrane expression was quantified using a HiBiT reporter assay, where a small luminescent HiBiT tag fused to the N-terminus of Rhodopsin reconstitutes luciferase activity upon addition of LgBiT to the extracellular media, producing a signal proportional to correctly folded and expressed protein on the cell surface.

Day 1—Seed Cells

1. Added 6 mL TrypLE select to T175 flask and incubated for 2-3 minutes
2. Added 12 mL DMEM+10% qFBS and collect cells in a 50 mL conical tube
3. Counted cells and transferred the desired amount to a new 50 mL conical tube
4. Centrifuged cells at 150×g for 3 minutes
5. Resuspended cells to 6e5 cells/mL in DMEM+10% qFBS
6. Dispensed 25 uL/well (15 k cells/well) into PLL: Collagen coated 384 well black plates
7. Pulsed spin plates
8. Incubated plates overnight at 37° C.

Day 2—Dox and Dose Cells

1. Prepared drug plates at 6× final screening concentration. Ensured the final DMSO concentration in the assay plate does not exceed 1%.
2. Prepared 6× Doxycycline media at 12 uM final concentration in Opti-MEM.
3. Dispensed 15 ul of Doxycycline Opti-MEM mixture into the drug plate.
4. Mixed wells thoroughly and stamp Sul of Opti-MEM drug mixture from drug plates into assay plates.
5. Pulsed spin plates
6. Incubated plates overnight at 37° C.

Day 3—Add Detection and Read

0. Prepared Nano-Glo HiBiT Extracellular Detection System (Promega) reagent
   a. Made fresh every time: 10 mL Extracellular Buffer with 100 μL of LgBiT protein and 200 uL Extracellular Substrate.
1. Mixed reagent 1:1 with OptiMEM
2. Flicked media and blotted on a dry kimwipe to remove residual liquid. Dispensed 30 μL of 1:1 Opti-MEM, HiBiT surface expression reagent into each well.
3. Shook plates at 300-500 rpm for 3-10 minutes.
4. Read Luminescence at an integration time of 500 ms $EC_{50}$ data according to the assay described above is provided in Table 1.

+=−4(log 10([M]))>$EC_{50}$≥−5(log 10([M])); ++=−5(log 10([M]))>$EC_{50}$≥−5.7(log 10([M]));

+++=$EC_{50}$<−5.7 (log 10([M])); ND=not active in top assay concentration tested (20 uM); *=absolute stereochemistry not determined

TABLE 1

| Example No. | $EC_{50}$ |
|---|---|
| 1A* | +++ |
| 1B* | ++ |
| 2A* | + |
| 2B* | +++ |
| 3 | +++ |
| 4A* | +++ |
| 4B* | ++ |
| 5 | +++ |
| 5A* | +++ |
| 5B* | ++ |
| 6 | +++ |
| 7A* | +++ |

TABLE 1-continued

| Example No. | $EC_{50}$ |
|---|---|
| 7B* | + |
| 8A* | +++ |
| 8B* | ++ |
| 9A* | +++ |
| 9B* | ++ |
| 10 | +++ |
| 11A* | +++ |
| 11B* | + |
| 12A | ++ |
| 12B | + |
| 13 | +++ |
| 14A* | +++ |
| 14B* | + |
| 15 | +++ |
| 16A* | ND |
| 16B* | +++ |
| 17 | +++ |
| 18 | +++ |
| 19A* | + |
| 19B* | +++ |
| 20A* | +++ |
| 20B* | ND |
| 21 | ND |
| 22 | ND |
| 23A* | + |
| 23B* | ND |
| 24 | ND |
| 25 | ND |
| 26 | +++ |
| 27A | +++ |
| 27B | ++ |
| 28 | ND |
| 29 | +++ |
| 30 | ND |
| 31 | ++ |
| 32A | ++ |
| 32B | ND |
| 32C | ND |
| 32D | ND |
| 33A | ++ |
| 33B | + |
| 34A* | +++ |
| 34B* | ND |
| 38A | ++ |
| 38B | + |
| 39A | ND |
| 39B | ND |
| 40A | + |
| 40B | ND |
| 41A | ND |
| 41B | + |
| 42A | ND |
| 42B | +++ |
| 42C | ++ |
| 42D | + |
| 43 | +++ |
| 44 | + |
| 46A | ND |
| 46B | + |
| 46C | + |
| 47A | +++ |
| 47B | ND |
| 48A* | +++ |
| 48B* | ++ |
| 49A* | +++ |
| 49B* | ND |
| 50 | +++ |
| 50A* | +++ |
| 50B* | + |
| 51A* | ND |
| 51B* | ND |
| 52 | ++ |

The examples and embodiments described herein are for illustrative purposes only and various modifications or changes suggested to persons skilled in the art are to be included within the spirit and purview of this application and scope of the appended claims.

What is claimed is:

1. A compound of Formula (I), or a pharmaceutically acceptable salt or solvate thereof:

Formula (I)

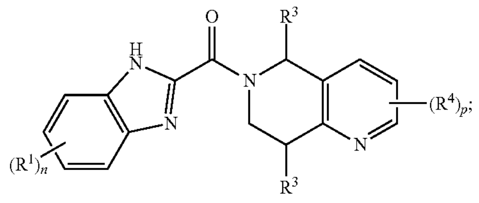

wherein:

each $R^1$ is independently selected from halogen, —CN, —OH, $C_{1-6}$alkyl, $C_{1-6}$haloalkyl, and $C_{1-6}$alkoxy;

$R^2$ is $C_{1-6}$alkyl or $C_{1-6}$haloalkyl;

$R^3$ is hydrogen, —CN, or $C_{1-6}$alkoxy, wherein if $R^3$ is hydrogen, then $R^2$ is $C_{1-6}$haloalkyl;

each $R^4$ is independently selected from halogen, —CN, $C_{1-6}$alkyl, and $C_{1-6}$haloalkyl;

n is 2, 3, or 4; and p is 0, 1, 2, or 3.

2. The compound of claim 1, or a pharmaceutically acceptable salt or solvate thereof, wherein $R^2$ is $C_{1-6}$haloalkyl.

3. The compound of claim 2, or a pharmaceutically acceptable salt or solvate thereof, wherein $R^2$ is —$CF_2H$.

4. The compound of compound 1, or a pharmaceutically acceptable salt or solvate thereof, wherein $R^2$ is $C_{1-6}$alkyl.

5. The compound of claim 4, or a pharmaceutically acceptable salt or solvate thereof, wherein $R^2$ is —$CH_3$.

6. The compound of claim 1, or a pharmaceutically acceptable salt or solvate thereof, wherein $R^3$ is hydrogen.

7. The compound of claim 1, or a pharmaceutically acceptable salt or solvate thereof, wherein $R^3$ is $C_{1-6}$alkoxy.

8. The compound of claim 7, or a pharmaceutically acceptable salt or solvate thereof, wherein $R^3$ is —$OCH_3$.

9. The compound of claim 1, or a pharmaceutically acceptable salt or solvate thereof, wherein $R^3$ is —CN.

10. The compound of claim 1, or a pharmaceutically acceptable salt or solvate thereof, wherein p is 0.

11. The compound of claim 1, or a pharmaceutically acceptable salt or solvate thereof, wherein each $R^1$ is independently selected from halogen, $C_{1-6}$alkyl, and $C_{1-6}$alkoxy.

12. The compound of claim 11, or a pharmaceutically acceptable salt or solvate thereof, wherein each $R^1$ is independently selected from halogen and $C_{1-6}$alkyl.

13. The compound of claim 1, or a pharmaceutically acceptable salt or solvate thereof, wherein n is 2.

14. The compound of claim 1, or a pharmaceutically acceptable salt or solvate thereof, wherein n is 3.

15. A compound, or a pharmaceutically acceptable salt or solvate thereof, selected from:

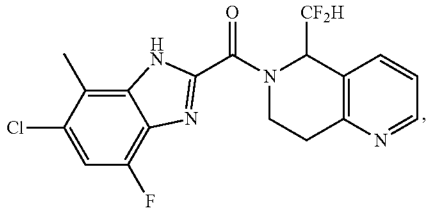

,

-continued
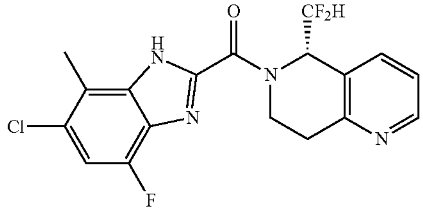,
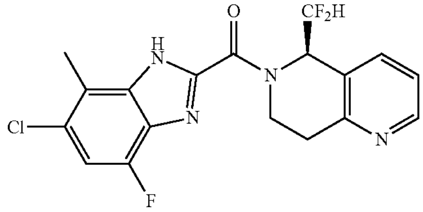,
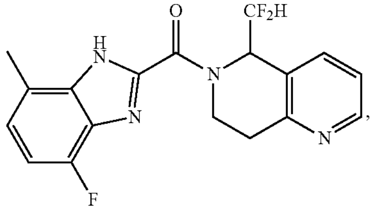,
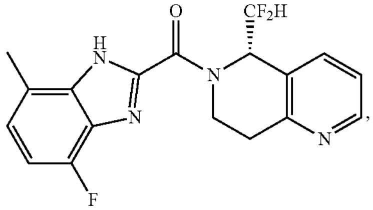,
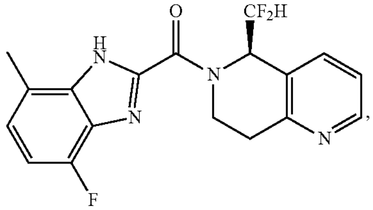,
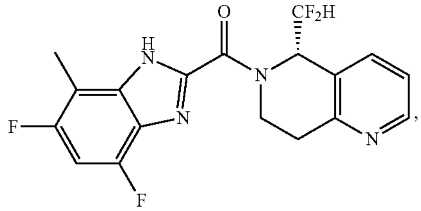,
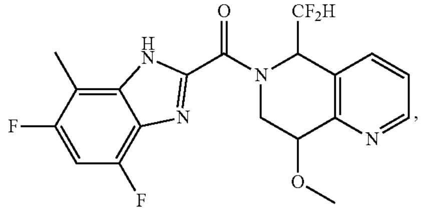,
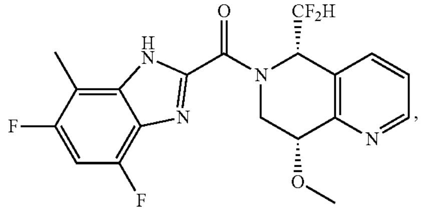,
-continued
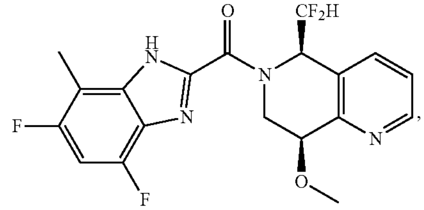,
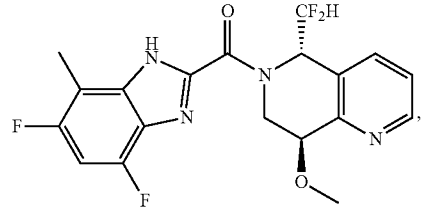,
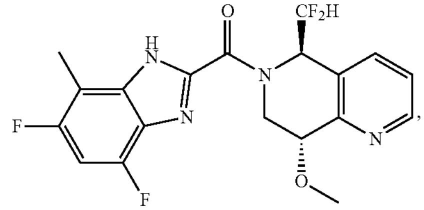,
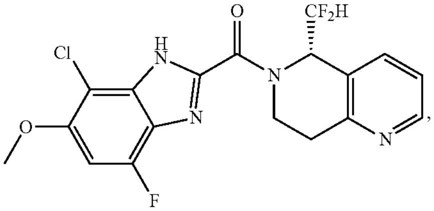,
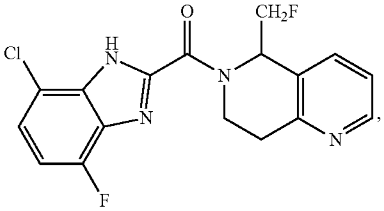,
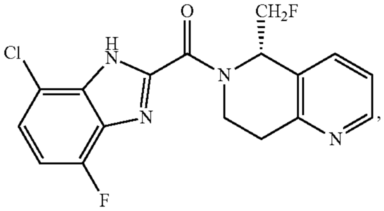,
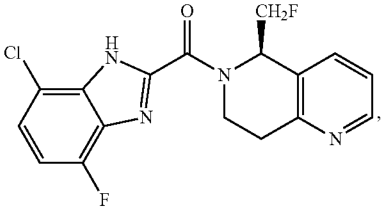,
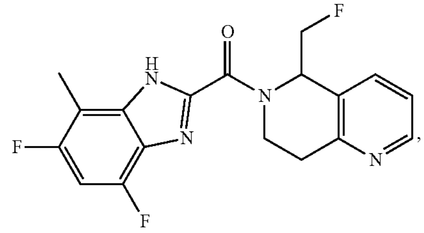, -continued
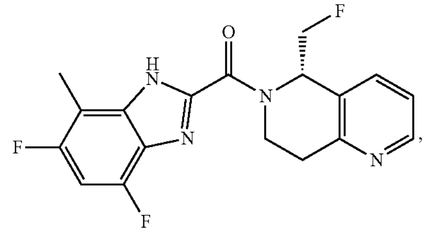
,
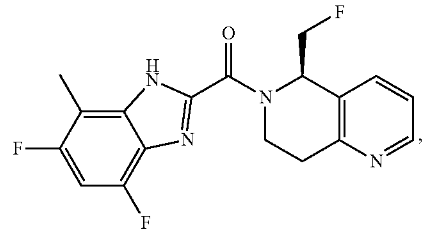
,
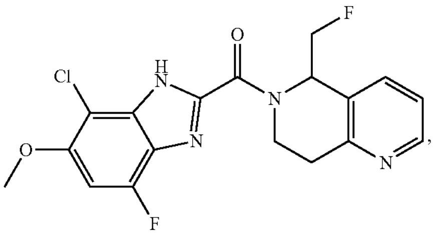
,
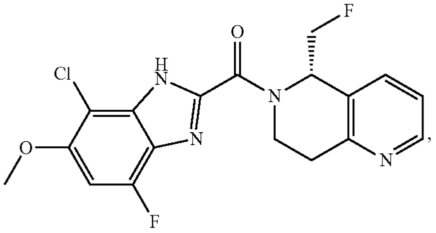
,
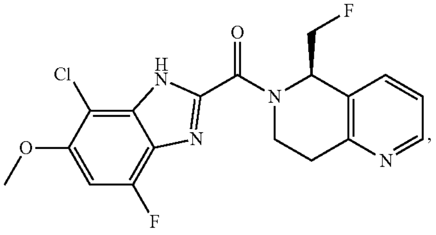
,
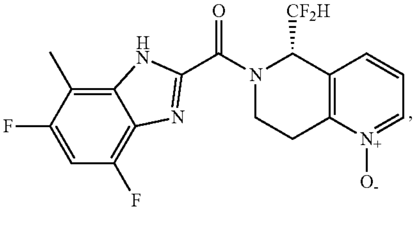
,
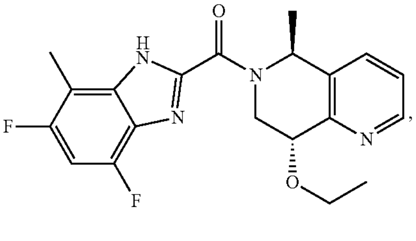
,
-continued
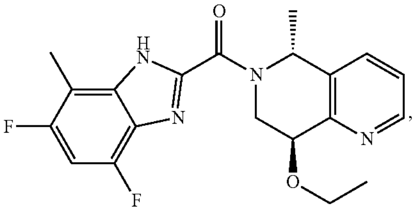
,
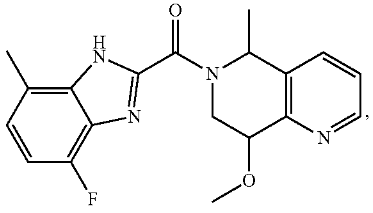
,
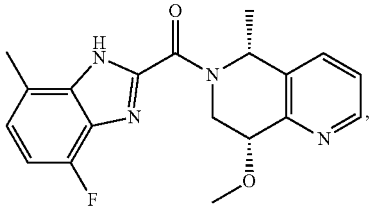
,
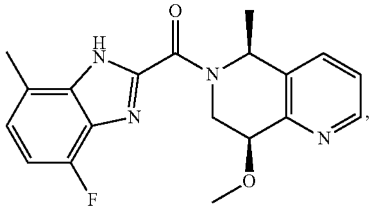
,
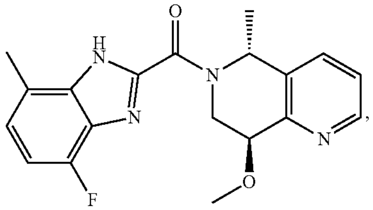
,
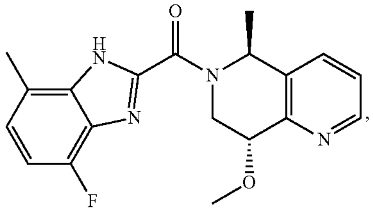
,
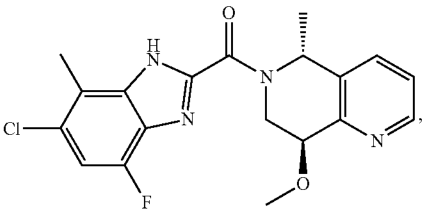
,
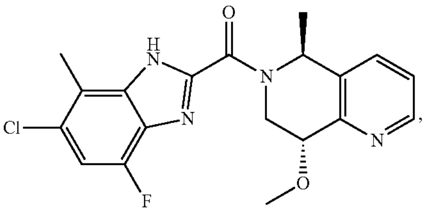
, -continued

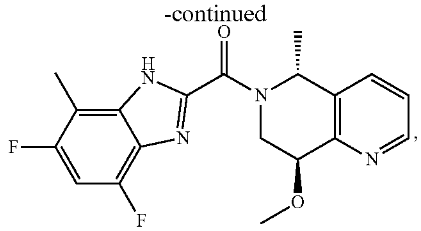

,

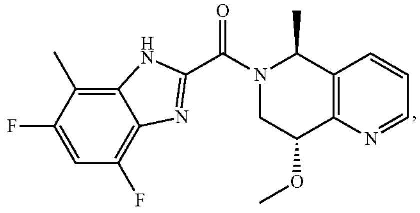

, and

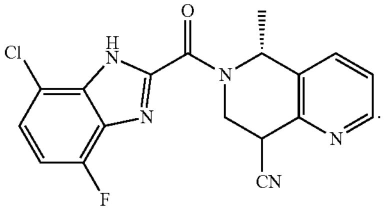

16. The compound of claim 1, or a pharmaceutically acceptable salt thereof, that is:

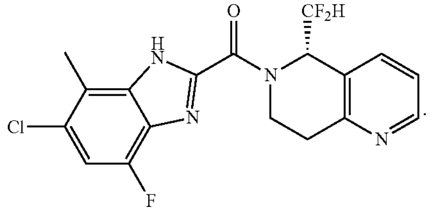 [SMILES: Cc1c(Cl)cc(F)c2nc(C(=O)N3CCc4ncccc4[C@H]3C(F)F)[nH]c12]

17. The compound of claim 1, or a pharmaceutically acceptable salt thereof, that is:

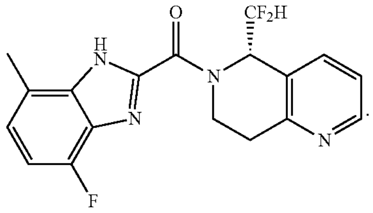 [SMILES: Cc1ccc(F)c2nc(C(=O)N3CCc4ncccc4[C@H]3C(F)F)[nH]c12]

18. The compound of claim 1, or a pharmaceutically acceptable salt thereof, that is:

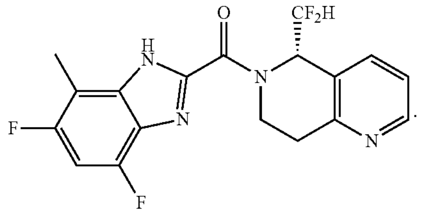 [SMILES: Cc1c(F)cc(F)c2nc(C(=O)N3CCc4ncccc4[C@H]3C(F)F)[nH]c12]

19. The compound of claim 1, or a pharmaceutically acceptable salt thereof, that is:

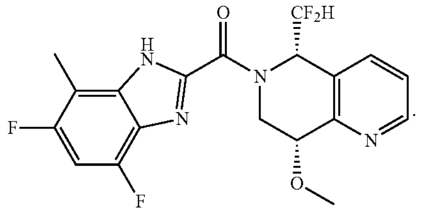 [SMILES: CO[C@@H]1CN(C(=O)c2nc3c(F)cc(F)c(C)c3[nH]2)[C@H](C(F)F)c2cccnc21]

20. The compound of claim 1, or a pharmaceutically acceptable salt thereof, that is:

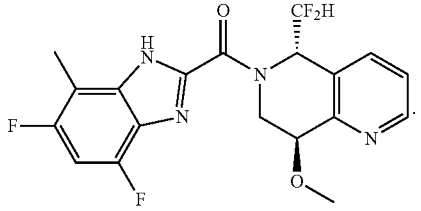 [SMILES: CO[C@H]1CN(C(=O)c2nc3c(F)cc(F)c(C)c3[nH]2)[C@H](C(F)F)c2cccnc21]

21. The compound of claim 1, or a pharmaceutically acceptable salt thereof, that is:

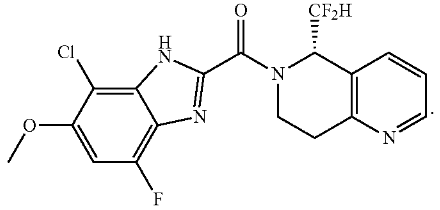 [SMILES: COc1cc(F)c2nc(C(=O)N3CCc4ncccc4[C@H]3C(F)F)[nH]c2c1Cl]

22. The compound of claim 1, or a pharmaceutically acceptable salt thereof, that is:

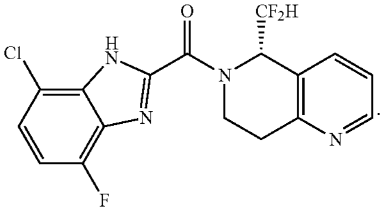 [SMILES: O=C(c1nc2c(F)ccc(Cl)c2[nH]1)N1CCc2ncccc2[C@H]1C(F)F]

23. The compound of claim 1, or a pharmaceutically acceptable salt thereof, that is:

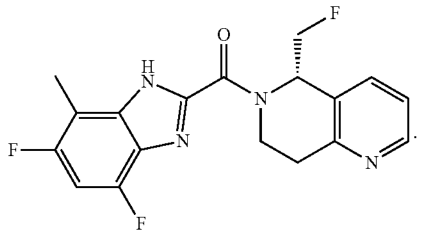 [SMILES: Cc1c(F)cc(F)c2nc(C(=O)N3CCc4ncccc4[C@H]3CF)[nH]c12]

24. The compound of claim 1, or a pharmaceutically acceptable salt thereof, that is:

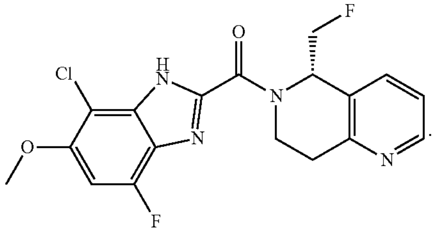 [SMILES: COc1cc(F)c2nc(C(=O)N3CCc4ncccc4[C@H]3CF)[nH]c2c1Cl]

25. The compound of claim 1, or a pharmaceutically acceptable salt thereof, that is:

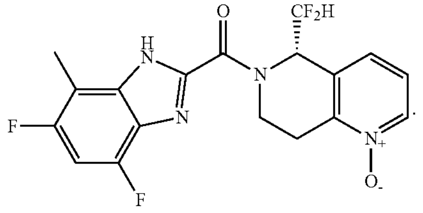

26. The compound of claim 1, or a pharmaceutically acceptable salt thereof, that is:

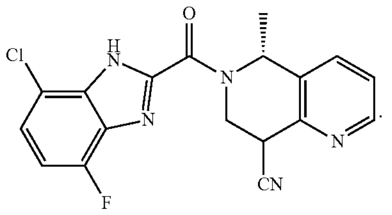 [SMILES: C[C@@H]1c2cccnc2C(C#N)CN1C(=O)c1nc2c(F)ccc(Cl)c2[nH]1]

27. A pharmaceutical composition comprising a compound of claim 1, or a pharmaceutically acceptable salt or solvate thereof, and at least one pharmaceutically acceptable excipient.

28. A method of treating autosomal dominant retinitis pigmentosa (adRP) in a subject in need thereof, comprising administering to the subject a compound of claim 1, or a pharmaceutically acceptable salt or solvate.

* * * * *